United States Patent
Weiner et al.

(10) Patent No.: US 11,464,841 B2
(45) Date of Patent: Oct. 11, 2022

(54) TERT IMMUNOGENIC COMPOSITIONS AND METHODS OF TREATMENT USING THE SAME

(71) Applicants: The Trustees of the University of Pennsylvania, Philadelphia, PA (US); THE WISTAR INSTITUTE OF ANATOMY AND BIOLOGY, Philadelphia, PA (US); INOVIO PHARMACEUTICALS, INC., Plymouth Meeting, PA (US)

(72) Inventors: David Weiner, Merion, PA (US); Jian Yan, Wallingford, PA (US)

(73) Assignees: The Trustees of the University of Pennsylvania, Philadelphia, PA (US); The Wistar Institute of Anatomy and Biology, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 0 days.

(21) Appl. No.: 16/337,637

(22) PCT Filed: Sep. 29, 2017

(86) PCT No.: PCT/US2017/054519
§ 371 (c)(1),
(2) Date: Mar. 28, 2019

(87) PCT Pub. No.: WO2018/064588
PCT Pub. Date: Apr. 5, 2018

(65) Prior Publication Data
US 2020/0030426 A1 Jan. 30, 2020

Related U.S. Application Data

(60) Provisional application No. 62/402,695, filed on Sep. 30, 2016, provisional application No. 62/468,124, filed on Mar. 7, 2017.

(51) Int. Cl.
*A61K 39/00* (2006.01)
*A61P 35/00* (2006.01)
*A61K 39/39* (2006.01)
*C12N 9/12* (2006.01)
*A61K 45/06* (2006.01)

(52) U.S. Cl.
CPC ...... *A61K 39/001157* (2018.08); *A61K 39/39* (2013.01); *A61P 35/00* (2018.01); *C12N 9/1276* (2013.01); *A61K 45/06* (2013.01); *A61K 2039/53* (2013.01); *A61K 2039/55538* (2013.01); *A61K 2039/572* (2013.01); *A61K 2039/575* (2013.01); *C12Y 207/07049* (2013.01)

(58) Field of Classification Search
CPC ......... A61K 39/00; C07H 21/02; C07H 21/04
USPC ........ 424/184.1, 185.1; 536/23.1, 23.2, 23.4, 536/23.5, 23.53
See application file for complete search history.

(56) References Cited

U.S. PATENT DOCUMENTS

| | | | |
|---|---|---|---|
| 7,851,591 B1 | 12/2010 | Nadler | |
| 9,290,546 B2 | 3/2016 | Weiner | |
| 2004/0106128 A1 | 6/2004 | Majumdar | |
| 2008/0090778 A1 | 4/2008 | Scarselli | |
| 2009/0074741 A1 | 3/2009 | Zanetti | |
| 2014/0056932 A1 | 2/2014 | Langlade-Demoyen | |
| 2015/0004194 A1* | 1/2015 | Wang | A61K 39/292 424/227.1 |

FOREIGN PATENT DOCUMENTS

| | | |
|---|---|---|
| WO | 2008014521 | 1/2008 |
| WO | 2014144885 | 9/2014 |
| WO | 2018204760 | 11/2018 |

OTHER PUBLICATIONS

ClinicalTrials.gov [Internet]. Bethesda (MD): National Library of Medicine (US). Feb. 29, 2000 -. Identifier NCT02960594 , hTERT Immunotherapy Alone or in Combination With IL-12 DNA Followed by Electroporation in Adults With Solid Tumors at High Risk of Relapse (TRT-001); Nov. 9, 2016.
Kotsakis et al., "Clinical outcome of patients with various advanced cancer types vaccinated with an optimized cryptic human telomerase reverse transcriptase (TERT) peptide: results of an expanded phase II study", Annals of Oncology, (Aug. 25, 2011), vol. 23, No. 2, pp. 442-449, XP002724182.
Lü et al., "hTERT-based therapy: A universal anticancer approach", Oncology Reports, (Sep. 17, 2012), vol. 28, pp. 1945-1952, XP055211187.
Yan et al., "Highly Optimized DNA Vaccine Targeting Human Telomerase Reverse Transcriptase Stimulates Potent Antitumor Immunity", Cancer Immunology Research, (Jul. 17, 2013), vol. 1, No. 3, pp. 179-189, XP055221286.

* cited by examiner

*Primary Examiner* — Gary B Nickol
*Assistant Examiner* — Jegatheesan Seharaseyon
(74) *Attorney, Agent, or Firm* — Riverside Law LLP

(57) ABSTRACT

Disclosed herein are compositions comprising optimized consensus TERT antigens and methods for treating cancer and in particular immunogenic compositions that treat and provide protection against tumor.

19 Claims, 31 Drawing Sheets
Specification includes a Sequence Listing.

pVax1 Immunized    pTyr Immunized

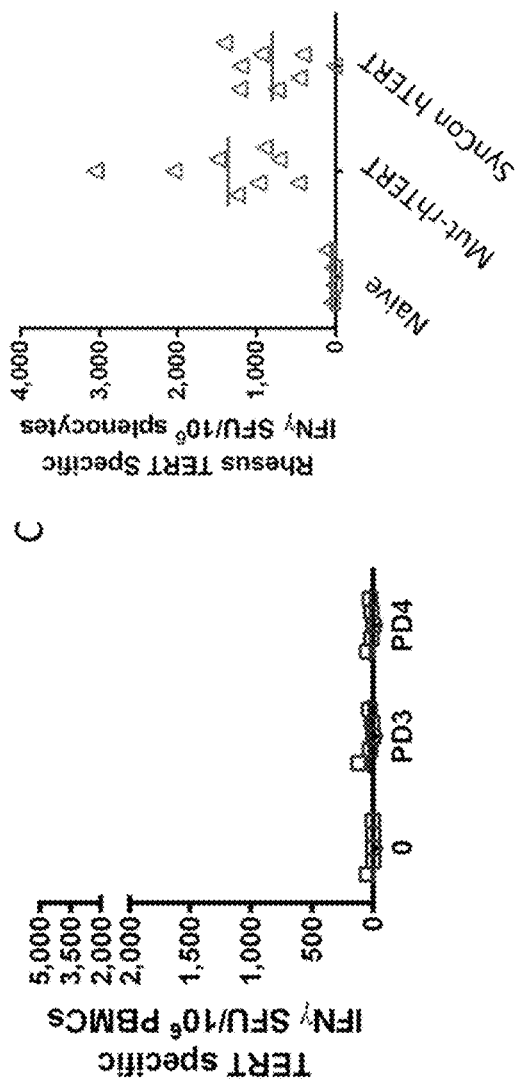
FIG. 24A – FIG. 24C

TERT IMMUNOGENIC COMPOSITIONS AND METHODS OF TREATMENT USING THE SAME

CROSS REFERENCE TO RELATED APPLICATIONS

This application is a U.S. national phase application filed under 35 U.S.C. § 371 claiming priority to International Patent Application No. PCT/US17/54519, filed Sep. 29, 2017, which is entitled to priority under 35 U.S.C. § 119(e) to U.S. Provisional Patent Application No. 62/468,124, filed Mar. 7, 2017, and to U.S. Provisional Patent Application No. 62/402,695, filed Sep. 30, 2016, the contents of each of which are incorporated by reference herein in their entireties.

TECHNICAL FIELD

Disclosed herein are compositions and methods for treating cancer and in particular, immunogenic compositions that treat and provide protection against tumor growth.

BACKGROUND

Cancer is among the leading causes of death worldwide, and in the United States, is the second most common cause of death, accounting for nearly 1 of every 4 deaths. Cancer arises from a single cell that has transformed from a normal cell into a tumor cell. Such a transformation is often a multistage process, progressing from a pre-cancerous lesion to malignant tumors. Multiple factors contribute this progression, including aging, genetic contributions, and exposure to external agents such as physical carcinogens (e.g., ultraviolet and ionizing radiation), chemical carcinogens (e.g., asbestos, components of tobacco smoke, etc.), and biological carcinogens (e.g., certain viruses, bacteria, and parasites).

Prevention, diagnosis and treatment of cancer may take many different forms. Prevention may include screening for pre-disposing factors (e.g., specific genetic variants), altering behavior (e.g., smoking, diet, and amount of physical activity), and vaccination against viruses (e.g., human papilloma virus hepatitis B virus). Treatment may include chemotherapy, radiation therapy, and surgical removal of a tumor or cancerous tissue. Despite the availability of numerous prevention and treatment methods, such methods often meet with limited success in effectively preventing and/or treating the cancer at hand.

Accordingly, a need exists for the identification and development of compositions and methods for the prevention and/or treatment of cancer to facilitate clinical management of protection against and progression of disease. Furthermore, more effective treatments are required to delay disease progression and/or decrease mortality in subjects suffering from cancer.

SUMMARY OF INVENTION

In one embodiment, the invention relates to an immunogenic composition comprising a nucleic acid molecule encoding a consensus Telomerase Reverse Transcriptase (TERT) antigen. In one embodiment, the consensus TERT antigen comprises an amino acid sequence selected from the group consisting of: a) an amino acid sequence selected from the group consisting of SEQ ID NO: 46, SEQ ID NO:48, SEQ ID NO:50, SEQ ID NO:52, SEQ ID NO:54, and SEQ ID NO:56, b) an amino acid sequence that is 95% identical or greater to an amino acid sequence selected from the group consisting of SEQ ID NO: 46, SEQ ID NO:48, SEQ ID NO:50, SEQ ID NO:52, SEQ ID NO:54, and SEQ ID NO:56, and c) a fragment of an amino acid sequence selected from the group consisting of SEQ ID NO: 46, SEQ ID NO:48, SEQ ID NO:50, SEQ ID NO:52, SEQ ID NO:54, and SEQ ID NO:56, wherein the fragment comprises at least 95% of the full length amino acid sequence.

In one embodiment, the immunogenic composition further comprises one or more nucleotide sequences encoding one or more amino acid sequence selected from the group consisting of: a) an amino acid sequence selected from the group consisting of: SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, SEQ ID NO:24, SEQ ID NO; 58, SEQ ID NO: 60, SEQ ID NO:62, SEQ ID NO:64, SEQ ID NO:66, SEQ ID NO:68, SEQ ID NO: 70; b) an amino acid sequence that is 95% identical or greater to the amino acid selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO: 18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, and c) a fragment of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, wherein the fragment comprises at least 95% of the full length amino acid sequence.

In one embodiment, the immunogenic composition further comprises a nucleotide sequence encoding one or more antigens selected from the group consisting of: MAGE A1, gp100, a viral antigen, and combinations thereof. In one embodiment, the viral antigen is an antigen from Hepatitis B virus (HBV), Hepatitis C virus (HCV), or Human Papilloma Virus (HPV). In one embodiment, the HBV antigen is an HBV core antigen or a HBV surface antigen, or a combination thereof. In one embodiment, the HCV antigen is an HCV NS34A antigen, an HCV NS5A antigen, an HCV NS5B antigen, an HCV NS4B antigen, or a combination thereof. In one embodiment, the HPV antigen is an HPV type 6 E6 antigen, an HPV type 6 E7 antigen, an HPV type 11 E6 antigen, an HPV type 11 E7 antigen, an HPV type 16 E6 antigen, an HPV type 16 E7 antigen, an HPV type 18 E6 antigen, an HPV type 18 E7 antigen, or a combination thereof.

In one embodiment, the immunogenic composition further comprises an immune checkpoint inhibitor.

In one embodiment, the nucleic acid molecule comprises a nucleotide sequence selected from the group consisting of a) a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, b) a nucleotide sequence that is 95% identical or greater to a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, and c) a fragment of a nucleotide sequence selected from the group consisting of SEQ ID NO: 45, SEQ ID NO: 47, SEQ ID NO:

49, SEQ ID NO: 51, SEQ ID NO: 53 and SEQ ID NO: 55, wherein the fragment comprises at least 95% of the full length nucleotide sequence.

In one embodiment, the immunogenic composition comprises one or more nucleotide sequences selected from the group consisting of: a) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69; b) a nucleotide sequence that is 95% identical or greater to a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, and c) a fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, wherein the fragment comprises at least 95% of the full length nucleotide sequence.

In one embodiment, the nucleic acid molecule is a plasmid.

In one embodiment, the immunogenic composition comprises one or more plasmids.

In one embodiment, the immunogenic composition further comprises an adjuvant. In one embodiment, the adjuvant is IL-12, IL-15, IL-28, or RANTES.

In one embodiment, the invention relates to a method of treating or preventing cancer in a subject in need thereof, the method comprising administering an immunogenic composition of comprising a nucleic acid molecule encoding a consensus TERT antigen to the subject. In one embodiment, the method of administration includes an electroporation step. In one embodiment, the method further comprises administering an immune checkpoint inhibitor to the subject.

In one embodiment, the immunogenic composition and immune checkpoint inhibitor are administered in a single formulation to the subject. In one embodiment, the immunogenic composition and immune checkpoint inhibitor are administered separately to the subject.

In one embodiment, the cancer is selected from the group consisting of: melanoma, head and neck cancer, prostate cancer, liver cancer, cervical cancer, recurrent respiratory papillomatosis (RRP), anal cancer, a blood cancer, ovarian cancer and a combination thereof.

In one embodiment, the invention relates to a nucleic acid molecule comprising one or more nucleotide sequences selected from the group consisting of: a) a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, b) a nucleotide sequence that is 95% identical or greater to a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, and c) a fragment of a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, wherein the fragment comprises at least 95% of the full length nucleotide sequence.

In one embodiment, the nucleic acid molecule further comprises one or more nucleotide sequences selected from the group consisting of: a) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69; b) a nucleotide sequence that is 95% identical or greater to a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, and c) a fragment of a nucleotide sequence selected from the group consisting of SEQ ID NO:1, SEQ ID NO: 3, SEQ ID NO: 5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, wherein the fragment comprises at least 95% of the full length nucleotide sequence.

In one embodiment, the nucleic acid molecule is a plasmid.

In one embodiment, the invention relates to an amino acid molecule comprising one or more amino acid sequence selected from the group consisting of: a) an amino acid sequence selected from the group consisting of SEQ ID NO: 46, SEQ ID NO:48, SEQ ID NO:50, SEQ ID NO:52, SEQ ID NO:54, and SEQ ID NO:56, b) an amino acid sequence that is 95% identical or greater to an amino acid sequence selected from the group consisting of SEQ ID NO: 46, SEQ ID NO:48, SEQ ID NO:50, SEQ ID NO:52, SEQ ID NO:54, and SEQ ID NO:56, and c) a fragment of an amino acid sequence selected from the group consisting of SEQ ID NO: 46, SEQ ID NO:48, SEQ ID NO:50, SEQ ID NO:52, SEQ ID NO:54, and SEQ ID NO:56, wherein the fragment comprises at least 95% of the full length amino acid sequence.

In one embodiment, the amino acid molecule further comprises one or more amino acid sequence selected from the group consisting of: a) an amino acid sequence selected from the group consisting of: SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70; b) an amino acid sequence that is 95% identical or greater to the amino acid selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, and c) a fragment of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, wherein the fragment comprises at least 95% of the full length amino acid sequence.

BRIEF DESCRIPTION OF THE DRAWINGS

FIG. 1, comprising

FIG. 2, comprising

FIG. 4, comprising

FIG. 5, comprising

FIG. 6, comprising

FIG. 8, comprising

FIG. 10, comprising

FIG. 11, comprising

FIG. 12, comprising

FIG. 17, comprising (FIG. 17A) Immunization schedule. Mice (n=8 per group) were immunized at weeks 0, 2 and 4 with Native RhTERT and synthetic consensus hTERT via IM/electroporation. (FIG. 17B) Frequency of TERT-specific IFN-γ spot-forming units (SFU) per million splenocytes isolated from vaccinated mice, determined by IFN-γ ELISpot assay using rhesus peptides.

FIG. 18, comprising (FIG. 18A) Immunization schedule. Rhesus macaque (n=5 per group) were immunized at weeks 0, 4, 8 and 12 with Native RhTERT or synthetic consensus hTERT as well as rhIL-12 via IM/electroporation. (FIG. 18B and FIG. 18C) Frequency of TERT-specific IFN-γ spot-forming units (SFU) per million splenocytes isolated from vaccinated mice, determined by IFN-γ ELISpot assay using native rhesus peptides and synthetic consensus hTERT peptide.

FIG. 21, comprising

FIG. 22, comprising FIG. 22A depicts an exemplary immunization schedule. FIG. 22B depicts a table demonstrating the constructs that were administered to the different groups. pGX1434: hTERT; pGX1406: Mut-hTERT; pGX1447: Mut-rhTERT; pGX1404: WT-1; pGX1108: PSMA; pGX6006:rhIL-12.

FIG. 23, comprising FIG. 23A depicts the results of experiments demonstrating that responses to native rhesus TERT were detected PD3 and PD4 in Group 1 animals. FIG. 23B depicts the results of experiments demonstrating that responses to native rhesus TERT were detected PD3 and PD4 in Group 2 animals.

FIG. 24, comprising FIG. 24A through FIG. 24C, depicts the results of experiments demonstrating that the SynCon design enables breaking self-tolerance. FIG. 24A depicts a table demonstrating the percent identity of the different constructs to the native sequences. FIG. 24B depicts the results of experiments demonstrating TERT specific IFNγ response. FIG. 24C depicts the results of experiments demonstrating Rhesus TERT specific IFNγ response.

FIG. 25, comprising FIG. 25A depicts the results of experiments demonstrating the TERT response generated using the combination of SynCon hTERT, PSMA, WT-1 and IL-12. FIG. 25B depicts the results of experiments demonstrating the TERT response generated using the combination of mut-hTERT, PSMA, WT-1 and IL-12.

FIG. 26, comprising FIG. 26A depicts the results of experiments demonstrating the TERT response generated using the combination of TERT, PSMA, WT-1 and IL-12. FIG. 26B depicts the results of experiments demonstrating the PSMA response generated using the combination of TERT, PSMA, WT-1 and IL-12. FIG. 26C depicts the results of experiments demonstrating the WT-1 response generated using the combination of TERT, PSMA, WT-1 and IL-12.

FIG. 27, comprising FIG. 27A depicts the immunization schedule used. FIG. 27B depicts the percentages of antigen specific T cells that were identified following immunization.

FIG. 28, comprising FIG. 28A depicts the immunization schedule used. FIG. 28B depicts the average tumor volume and % survival of animals immunized with a combination of WT1, PSMA and SynCon mTERT.

DETAILED DESCRIPTION

Figures 1A, 1B:
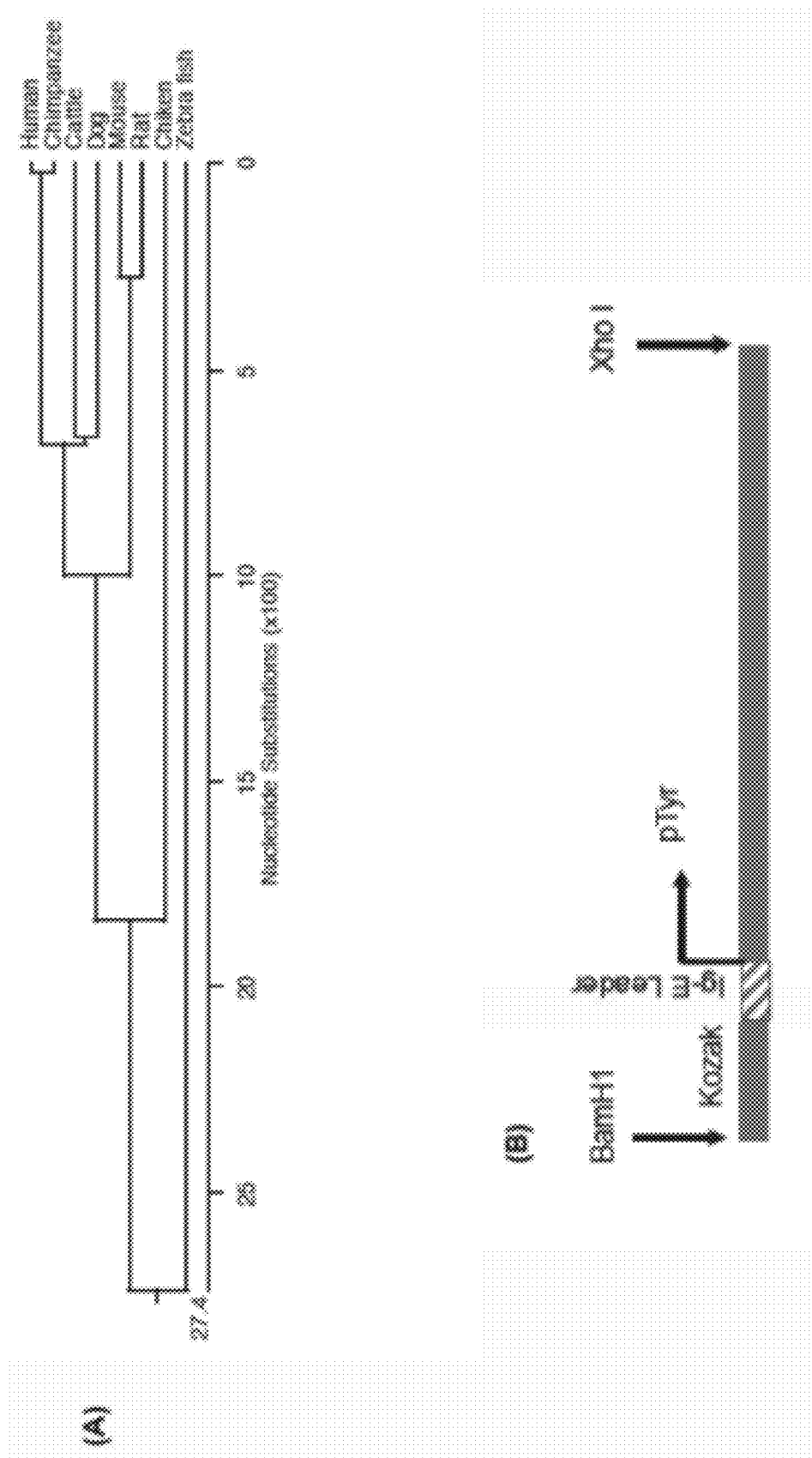
FIG. 1A through FIG. 1E, depicts the construction of pTyr.

The present invention is directed to immunogenic compositions comprising a synthetic consensus TERT antigen, alone or in combination with at least one additional cancer antigen or an inhibitor of an immune checkpoint protein, and method of use of the compositions for treating diseases or disorders. In one embodiment, the immounogenic composition comprises TERT and at least one additional cancer antigen consensus sequence. Cancer antigen consensus sequences that can be included in the immunogenic composition including, but are not limited to, tyrosinase (Tyr), preferentially expressed antigen in melanoma (PRAME), tyrosinase related protein 1 (Tyrp1), cancer testes antigen (NY-ESO-1), hepatitis B virus antigen, prostate specific antigen (PSA), prostate-specific membrane antigen (PSMA), six-transmembrane epithelial antigen of the prostate (STEAP), prostate stem cell antigen (PSCA), Fibroblast Activation Protein (FAP), follicle stimulating hormone receptor (FSHR) and Wilms tumor 1 antigen (WT-1). In one embodiment, the immunogenic composition of the invention can provide a combination of cancer antigens for the prevention or treatment of the cancer of a subject that is in need thereof.

One manner for designing the nucleic acid and corresponding encoded amino acid sequence of the recombinant cancer antigen is to introduce mutations that change particular amino acids in the overall amino acid sequence of the native cancer antigen. The introduction of mutations does not alter the cancer antigen so much that it cannot be universally applied across a mammalian subject, for example a human or dog subject, but changes the antigen enough that the resulting amino acid sequence breaks tolerance or is considered a foreign antigen in order to generate an immune response. Another manner may be creating a consensus recombinant cancer antigen that has at least 85% and up to 99% amino acid sequence identity, at least 90% and up to 98% sequence identity, at least 93% and up to 98% sequence identity, or at least 95% and up to 98% sequence identity to a corresponding native cancer antigen. In some instances the recombinant cancer antigen is 95%, 96%, 97%, 98%, or 99% amino acid sequence identity to a corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity; at least 90% and up to 98% sequence identity; at least 93% and up to 98% sequence identity; or at least 95% and up to 98% sequence identity to a corresponding native cancer antigen. In some instances the recombinant cancer antigen is 95%, 96%, 97%, 98%, or 99% amino acid sequence identity to a corresponding native cancer antigen. The aforementioned approaches can be combined so that the final recombinant cancer antigen has a percent similarity to a native cancer antigen amino acid sequence as discussed, above.

The recombinant cancer antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The immunogenic composition may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, by designing the cancer antigens to be recognized by the immune system helps to overcome other forms of immune suppression by tumor cells, and these immunogenic compositions can be used in combination with suppression or inhibition therapies (such as anti-PD-1 and anti-PDL-1 antibody therapies) to further increase T-cell and/or B-cell responses.

1. Definitions

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the immunogenic compositions described herein to enhance the immunogenicity of the antigens encoded by the Nucleic acid molecules and the encoding nucleic acid sequences described hereinafter.

"Antibody" as used herein means an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Immunogenic compositions comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein can facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described immunogenic compositions. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering an immunogenic composition of the present invention to an animal prior to onset of the disease. Suppressing the disease involves administering an immunogenic composition of the present invention to an animal after induction of the disease but before its clinical appearance. Repressing the disease involves administering an immunogenic composition of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and in one embodiment, is an expression plasmid. The vector can contain or include one or more heterologous nucleic acid sequences.

2. Synthetic Consensus TERT

The invention provides an optimized consensus sequence of a TERT antigen. In one embodiment, the antigen encoded by the optimized consensus sequence is capable of eliciting an immune response in a mammal. In one embodiment, the antigen encoded by the optimized consensus sequence can comprise an epitope(s) that makes it particularly effective as an immunogen against which an immune response can be induced.

The optimized consensus sequence can be a consensus sequence derived from two or more native TERT antigens. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The TERT antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The TERT antigen encoded by the optimized consensus sequence can be designed to elicit stronger cellular and/or humoral immune responses than a corresponding native antigen. The TERT antigen encoded by the optimized consensus sequence can be designed to break tolerance and synergize with anti-cancer immune therapy.

In one embodiment, an optimized consensus TERT is designed to break tolerance to native human TERT. In one embodiment, a human optimized consensus TERT encoding sequence is as set forth in SEQ ID NO:45, SEQ ID NO:47, SEQ ID NO:49, SEQ ID NO:51, SEQ ID NO:53 or SEQ ID NO:55. In one embodiment, a human optimized consensus TERT encoded antigen has an amino acid sequence as set forth in SEQ ID NO:46, SEQ ID NO:48, SEQ ID NO:50, SEQ ID NO:52, SEQ ID NO:54 or SEQ ID NO:56.

In one embodiment, an optimized consensus TERT is designed to break tolerance to native mouse TERT. In one embodiment, a mouse optimized consensus TERT encoding sequence is as set forth in SEQ ID NO:49 or SEQ ID NO:51. In one embodiment, a mouse optimized consensus TERT encoded antigen has an amino acid sequence as set forth in SEQ ID NO:50 or SEQ ID NO:52.

In one embodiment, an optimized consensus TERT is designed to break tolerance to native rhesus macaque TERT. In one embodiment, a rhesus macaque optimized consensus TERT encoding sequence is as set forth in SEQ ID NO:53 or SEQ ID NO:55. In one embodiment, a mouse optimized consensus TERT encoded antigen has an amino acid sequence as set forth in SEQ ID NO:54 or SEQ ID NO:56.

In one embodiment, an optimized consensus encoded TERT antigen is operably linked to one or more regulatory elements. In one embodiment, a regulatory element is a leader sequence. In one embodiment, the optimized consensus DNA sequence operably linked to an IgE leader encoding sequence is set forth in SEQ ID NO:45, SEQ ID NO:49 and SEQ ID NO:53. In one embodiment, the optimized consensus-encoded TERT antigen operably linked to an IgE leader sequence is as set forth in SEQ ID NO:46, SEQ ID NO:50 and SEQ ID NO:54.

In one embodiment, a regulatory element is a start codon. Therefore, in one embodiment, the invention relates to a nucleic acid sequence as set forth in SEQ ID NO:47, SEQ ID NO:51, SEQ ID NO:55, or a fragment or homolog thereof, operably linked to a nucleotide sequence comprising a start codon at the 5' terminus. In one embodiment, the invention relates to an amino acid sequence as set forth in SEQ ID NO:48, SEQ ID NO:52 or SEQ ID NO:56, or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleic acid sequence as set forth in SEQ ID NO:45, SEQ ID NO:47, SEQ ID NO:49, SEQ ID NO:51, SEQ ID NO:53 or SEQ ID NO:55 or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, the optimized consensus sequence encoding a TERT antigen can encode a peptide having the amino acid sequence set forth in SEQ ID NO:46, SEQ ID NO:48, SEQ ID NO:50, SEQ ID NO:52, SEQ ID NO:54 or SEQ ID NO:56. In one embodiment, the optimized consensus sequence can have the nucleotide sequence set forth in SEQ ID NO:45, SEQ ID NO:47, SEQ ID NO:49, SEQ ID NO:51, SEQ ID NO:53 or SEQ ID NO:55. In some embodiments, the sequence can be the nucleotide sequence having at least about 90%, 91%, 92%, 93%, 94%, 95%, 96%, 97%, 98%, 99% or 100% identity over an entire length of the nucleotide sequence set forth in SEQ ID NO:45, SEQ ID NO:47, SEQ ID NO:49, SEQ ID NO:51, SEQ ID NO:53 or SEQ ID NO:55. In other embodiments, sequence can be the nucleotide sequence that encodes the amino acid sequence having at least about 90%, 91%, 92%, 93%, 94%, 95%, 96%, 97%, 98%, 99%, or 100% identity over an entire length of the amino acid sequence set forth in SEQ ID NO:46, SEQ ID NO:48, SEQ ID NO:50, SEQ ID NO:52, SEQ ID NO:54 or SEQ ID NO:56.

In some embodiments, the optimized consensus TERT antigen can be encoded by an RNA that is a transcript from a DNA sequence having at least about 96%, 97%, 98%, 99% or 100% identity over an entire length of the nucleic acid sequence set forth in the SEQ ID NO:45, SEQ ID NO:47, SEQ ID NO:49, SEQ ID NO:51, SEQ ID NO:53 or SEQ ID NO:55. In some embodiments, the optimized consensus TERT antigen can be encoded by an RNA that encodes an amino acid sequence having at least about 96%, 97%, 98%, 99% or 100% identity over an entire length of the amino acid sequence set forth in SEQ ID NO:46, SEQ ID NO:48, SEQ ID NO:50, SEQ ID NO:52, SEQ ID NO:54 or SEQ ID NO:56.

The optimized consensus-encoded TERT antigen can be a peptide having the amino acid sequence set forth in SEQ ID NO:2, SEQ ID NO:4, SEQ ID NO:6 or SEQ ID NO:8. In some embodiments, the antigen can have an amino acid sequence having at least about 90%, 91%, 92%, 93%, 94%, 95%, 96%, 97%, 98%, 99%, or 100% identity over an entire length of the amino acid sequence set forth in SEQ ID NO:46, SEQ ID NO:48, SEQ ID NO:50, SEQ ID NO:52, SEQ ID NO:54 or SEQ ID NO:56.

Immunogenic fragments of proteins with amino acid sequences homologous to immunogenic fragments of SEQ ID NO:46, SEQ ID NO:48, SEQ ID NO:50, SEQ ID NO:52, SEQ ID NO:54 or SEQ ID NO:56, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:46, SEQ ID NO:48, SEQ ID NO:50, SEQ ID NO:52, SEQ ID NO:54 or SEQ ID NO:56. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of an optimized consensus TERT antigen encodes at least one immunodominant or sub-immunodominant epitope of a full length optimized consensus TERT antigen.

Some embodiments relate to immunogenic fragments of SEQ ID NO:45, SEQ ID NO:47, SEQ ID NO:49, SEQ ID NO:51, SEQ ID NO:53 or SEQ ID NO:55 comprising at least 60%, at least 65%, at least 70%, at least 75%, at least 80%, at least 85%, at least 90%, at least 95%, at least 96%, at least 97%, at least 98% or at least 99% of the full length of SEQ ID NO:45, SEQ ID NO:47, SEQ ID NO:49, SEQ ID NO:51, SEQ ID NO:53 or SEQ ID NO: 55. Immunogenic fragments can be at least 96%, at least 97% at least 98% or at least 99% homologous to fragments of SEQ ID NO:45, SEQ ID NO:47, SEQ ID NO:49, SEQ ID NO:51, SEQ ID NO:53 or SEQ ID NO:55. In some embodiments, immunogenic fragments include sequences that encode a leader sequence, such as for example an immunoglobulin leader, such as the IgE leader. In some embodiments, fragments are free of coding sequences that encode a leader sequence.

3. Immunogenic Composition

In one embodiment, the immunogenic composition of the present invention can comprise the synthetic consensus TERT antigen, a fragment thereof, or a variant thereof. In one embodiment, the TERT antigen is a human TERT antigen (hTERT). hTERT is a human telomerase reverse transcriptase that synthesizes a TTAGGG tag on the end of telomeres to prevent cell death due to chromosomal shortening. Hyperproliferative cells can have abnormally high expression of hTERT. Abnormal expression of hTERT can also occur in hyperproliferative cells infected with HCV and HPV. Thus, immunotherapy for both HPV and HCV may be enhanced by targeting cells that express hTERT at abnormal levels. HPV and HCV antigens are discussed below in more detail. In one aspect, the hTERT cancer antigen can further be defined by U.S. patent application Ser. No. 14/139,660, filed Dec. 23, 2013, which is incorporated by reference in its' entirety.

In one embodiment, the TERT antigen is a non-human TERT antigen. Non-human TERT antigens include, but are not limited to, mouse TERT (mTERT) and rhesus macaque TERT (rhTERT).

TERT expression in dendritic cells transfected with TERT genes can induce CD8$^+$ cytotoxic T cells and elicit CD4$^+$ T cells in an antigen-specific fashion. Therefore, use of hTERT expression within antigen presenting cells (APCs) to delay senescence and sustain their capacity to present the antigen of choice can be used in immunotherapeutic methods such as in the methods described herein.

The TERT antigen can be associated with or expressed by any number of cancers including, but not limited to, melanoma, prostate cancer, liver cancer, cervical cancer, recurrent respiratory papillomatosis (RRP), anal cancer, head and neck cancer, and blood cancers. Accordingly, the vaccine, when including the TERT antigen described herein, can be used for treating subjects suffering from any number of cancers including, but not limited to, melanoma, prostate cancer, liver cancer, cervical cancer, recurrent respiratory papillomatosis (RRP), anal cancer, head and neck cancer, and blood cancers.

The TERT antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The TERT antigen can comprise protein epitopes that make them particularly effective as immunogens against which anti-TERT immune responses can be induced. The TERT antigen can comprise the full length translation product, a variant thereof, a fragment thereof or a combination thereof. The TERT antigen can comprise a consensus protein.

The nucleic acid sequence encoding the TERT antigen or consensus TERT antigen can be optimized with regards to codon usage and corresponding RNA transcripts. The nucleic acid encoding the TERT antigen or consensus TERT antigen can be codon and RNA optimized for expression. In some embodiments, the nucleic acid sequence encoding the TERT antigen or consensus TERT antigen can include a Kozak sequence (e.g., GCC ACC) to increase the efficiency of translation. The nucleic acid encoding the TERT antigen or consensus TERT antigen can include multiple stop codons (e.g., TGA TGA) to increase the efficiency of translation termination.

The nucleic acid encoding the TERT antigen or consensus TERT antigen can also encode an immunoglobulin E (IgE) leader sequence. The nucleic acid encoding the TERT antigen or consensus TERT antigen can further encode the IgE leader sequence such that the amino acid sequence of the IgE leader sequence is linked to the amino acid sequence of the TERT antigen or consensus TERT antigen by a peptide bond, respectively. The nucleic encoding the TERT antigen or consensus TERT antigen can also include a nucleotide sequence encoding the IgE leader sequence. In some embodiments, the nucleic acid encoding the TERT antigen or consensus TERT antigen is free of or does not contain a nucleotide sequence encoding the IgE leader sequence.

In some embodiments, the nucleic acid encoding the TERT antigen or consensus TERT antigen can be a heterologous nucleic acid sequence and/or contain one or more heterologous nucleic acid sequences. The nucleic acid encoding the TERT antigen or consensus TERT antigen can be mutated relative to the wild-type TERT antigen such that one or more amino acids or residues in the amino acid sequence of the TERT antigen or consensus TERT antigen, respectively, is replaced or substituted with another amino acid or residue. The nucleic acid encoding the TERT antigen or consensus TERT antigen can be mutated relative to the wild-type TERT antigen such that one or more residues in the amino acid sequence of the TERT antigen or consensus TERT antigen, respectively, are replaced or substituted with another residue, thereby causing the immune system to no longer be tolerant of TERT in the mammal administered the nucleic acid encoding the TERT antigen or consensus TERT antigen, the TERT antigen or consensus TERT antigen, or combinations thereof. The nucleic acid encoding TERT antigen or consensus TERT antigen can be mutated relative to the wild-type TERT antigen such that arginine 589, aspartate 1005, or both arginine 589 and aspartate 1005 in the amino acid sequence of the TERT antigen or consensus TERT antigen is replaced or substituted by a tyrosine residue.

In one aspect, the TERT antigen can be the nucleic acid sequence SEQ ID NO:23 or SEQ ID NO:57, which encode for the amino acid sequence SEQ ID NO:24 and SEQ ID NO:58 respectively. SEQ ID NO:23 and SEQ ID NO:57 encode a TERT antigen linked to an IgE leader sequence. In one embodiment, the TERT antigen can be linked to the IgE leader sequence and an HA tag. In other embodiments, the TERT antigen can be free of or not linked to an IgE leader sequence and/or an HA tag.

In some embodiments, the TERT antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:23 or SEQ ID NO:57. In other embodiments, the TERT antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:24 or SEQ ID NO:58. The TERT antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:24 or SEQ ID NO:58.

Some embodiments relate to nucleic acid sequences encoding proteins homologous to the TERT antigen, immunogenic fragment of the TERT antigen, and immunogenic fragments of homologous proteins. Such nucleic acid molecules that encode immunogenic proteins that have up to 95% homology to a sequence, up to 96% homology to a sequence, up to 97% homology to a sequence, up to 98% homology to a sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length TERT antigen, immunogenic fragment of the TERT antigen, and immunogenic fragments of proteins having identity to the TERT antigen. Such nucleic acid molecules that encode immunogenic proteins that have up to 80% identity to a full length TERT sequence, up to 85% identity to a full length sequence, up to 90% identity to a full length TERT sequence, up to 91% identity to a full length TERT sequence, up to 92% identity to a full length TERT sequence, up to 93% identity to a full length TERT sequence, up to 94% identity to a full length TERT sequence, up to 95% identity to a full length TERT sequence, up to 96% identity to a full length TERT sequence, up to 97% identity to a full length TERT sequence, up to 98% identity to a full length TERT sequence, and up to 99% identity to a full length TERT sequence can be provided. Likewise, nucleic acid sequences encoding the immunogenic fragments set forth herein and the immunogenic fragments of proteins with similar percent identities as indicated above to the TERT antigens set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:23 or SEQ ID NO:57. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:23 or SEQ ID NO:57. Fragments can be at least 95%, at least 96%, at least 97%, at least 98%, or at least 99% homologous to fragments of SEQ ID NO:23 or SEQ ID NO:57. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:23 or SEQ ID NO:57. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the TERT antigen is SEQ ID NO:24 or SEQ ID NO:58. The amino acid sequence of the TERT antigen linked to an IgE leader is SEQ ID NO:24 or SEQ ID NO:58. The amino acid sequence of the TERT antigen linked to the IgE leader may be linked to HA tag.

Some embodiments relate to proteins that are homologous to SEQ ID NO:24 or SEQ ID NO:58. Some embodiments relate to immunogenic proteins that have 95% homology to the protein sequences as set forth in SEQ ID NO:24 or SEQ ID NO:58. Some embodiments relate to immunogenic proteins that have 96% homology to the protein sequences as set forth in SEQ ID NO:24 or SEQ ID NO:58. Some embodiments relate to immunogenic proteins that have 97% homology to the protein sequences as set forth in SEQ ID NO:24 or SEQ ID NO:58. Some embodiments relate to immunogenic proteins that have 98% homology to the protein sequences as set forth in SEQ ID NO:24 or SEQ ID NO:58. Some embodiments relate to immunogenic proteins that have 99% homology to the protein sequences as set forth in SEQ ID NO:24 or SEQ ID NO:58.

Some embodiments relate to proteins that are identical to SEQ ID NO:24 or SEQ ID NO:58. Some embodiments relate to immunogenic proteins that have an amino acid sequence that is 80% identical to the full length amino acid sequences as set forth in SEQ ID NO:24 or SEQ ID NO:58. Some embodiments relate to immunogenic proteins that have an amino acid sequence that is 85% identical to the full length amino acid sequences as set forth in SEQ ID NO:24 or SEQ ID NO:58. Some embodiments relate to immunogenic proteins that have an amino acid sequence that is 90% identical to the full length amino acid sequences as set forth in SEQ ID NO:24 or SEQ ID NO:58. Some embodiments relate to immunogenic proteins that have an amino acid sequence that is 91% identical to the full length amino acid sequences as set forth in SEQ ID NO:24 or SEQ ID NO:58. Some embodiments relate to immunogenic proteins that have an amino acid sequence that is 92% identical to the full length amino acid sequences as set forth in SEQ ID NO:24 or SEQ ID NO:58. Some embodiments relate to immunogenic proteins that have an amino acid sequence that is 93% identical to the full length amino acid sequences as set forth in SEQ ID NO:24 or SEQ ID NO:58. Some embodiments relate to immunogenic proteins that have an amino acid sequence that is 94% identical to the full length amino acid sequences as set forth in SEQ ID NO:24 or SEQ ID NO:58. Some embodiments relate to immunogenic proteins that have an amino acid sequence that is 95% identical to the full length amino acid sequences as set forth in SEQ ID NO:24 or SEQ ID NO:58. Some embodiments relate to immunogenic proteins that have an amino acid sequence that is 96% identical to the full length amino acid sequences as set forth in SEQ ID NO:24 or SEQ ID NO:58. Some embodiments relate to immunogenic proteins that have an amino acid sequence that is 97% identical to the full length amino acid sequences as set forth in SEQ ID NO:24 or SEQ ID NO:58. Some embodiments relate to immunogenic proteins that have an amino acid sequence that is 98% identical to the full length amino acid sequences as set forth in SEQ ID NO:24 or SEQ ID NO:58. Some embodiments relate to immunogenic proteins that have an amino acid sequence that is 99% identical to the full length amino acid sequences as set forth in SEQ ID NO:24 or SEQ ID NO:58.

In some embodiments, the protein is free of a leader sequence. In some embodiments, the protein is free of the IgE leader. Fragments of proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a protein. Immunogenic fragments of SEQ ID NO:24 or SEQ ID NO:58 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:24 or SEQ ID NO:58. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:24 or SEQ ID NO:58 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:18. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:24 or SEQ ID NO:58 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:24 or SEQ ID NO:58. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

Fragments of SEQ ID NO:23 or SEQ ID NO:57 may comprise 30 or more nucleotides, including sequences that encode an immunodominant epitope. In some embodiments, fragments of SEQ ID NO:23 or SEQ ID NO:57 may comprise 45 or more nucleotides, including sequences that encode an immunodominant epitope. In some embodiments, fragments of SEQ ID NO:23 or SEQ ID NO:57 may comprise 60 or more nucleotides, including sequences that encode an immunodominant epitope. In some embodiments, fragments of SEQ ID NO:23 or SEQ ID NO:57 may comprise 75 or more nucleotides, including sequences that encode an immunodominant epitope. In some embodiments, fragments of SEQ ID NO:23 or SEQ ID NO:57 may comprise 90 or more nucleotides, including sequences that encode an immunodominant epitope. In some embodiments, fragments of SEQ ID NO:23 or SEQ ID NO:57 may comprise 120 or more nucleotides, including sequences that encode an immunodominant epitope. In some embodiments, fragments of SEQ ID NO:23 or SEQ ID NO:57 may comprise 150 or more nucleotides, including sequences that encode an immunodominant epitope. In some embodiments, fragments of SEQ ID NO:23 or SEQ ID NO:57 may comprise 180 or more nucleotides, including sequences that encode an immunodominant epitope. In some embodiments, fragments of SEQ ID NO:23 or SEQ ID NO:57 may comprise 210 or more nucleotides, including sequences that encode an immunodominant epitope. In some embodiments, fragments of SEQ ID NO:23 or SEQ ID NO:57 may comprise 240 or more nucleotides, including sequences that encode an immunodominant epitope. In some embodiments, fragments of SEQ ID NO:23 or SEQ ID NO:57 may comprise 270 or more nucleotides, including sequences that encode an immunodominant epitope. In some embodiments, fragments of SEQ ID NO:23 or SEQ ID NO:57 may comprise 300 or more nucleotides, including sequences that encode an immunodominant epitope. In some embodiments, fragments of SEQ ID NO:23 or SEQ ID NO:57 may comprise 360 or more nucleotides, including sequences that encode an immunodominant epitope. In some embodiments, fragments of SEQ ID NO:23 or SEQ ID NO:57 may comprise 420 or more nucleotides, including sequences that encode an immunodominant epitope. In some embodiments, fragments of SEQ ID NO:23 or SEQ ID NO:57 may comprise 480 or more nucleotides, including sequences that encode an immunodominant epitope. In some embodiments, fragments of SEQ ID NO:23 or SEQ ID NO:57 may comprise 540 or more nucleotides, including sequences that encode an immunodominant epitope. In some embodiments, fragments of SEQ ID NO:23 or SEQ ID NO:57 may comprise 600 or more nucleotides, including sequences that encode an immunodominant epitope. In some embodiments, fragments of SEQ ID NO:23 or SEQ ID NO:57 may comprise 300 or more nucleotides, including sequences that encode an immunodominant epitope. In some embodiments, fragments of SEQ ID NO:23 or SEQ ID NO:57 may comprise 660 or more nucleotides, including sequences that encode an immunodominant epitope. In some embodiments, fragments of SEQ ID NO:23 or SEQ ID NO:57 may comprise 720 or more nucleotides, including sequences that encode an immunodominant epitope. In some embodiments, fragments of SEQ ID NO:23 or SEQ ID NO:57 may comprise 780 or more nucleotides, including sequences that encode an immunodominant epitope. In some embodiments, fragments of SEQ ID NO:23 or SEQ ID NO:57 may comprise 840 or more nucleotides, including sequences that encode an immunodominant epitope. In some embodiments, fragments of SEQ ID NO:23 or SEQ ID NO:57 may comprise 900 or more nucleotides, including sequences that encode an immunodominant epitope. In some embodiments, fragments of SEQ ID NO:23 or SEQ ID NO:57 may comprise 960 or more nucleotides, including sequences that encode an immunodominant epitope. In some embodiments, fragments of SEQ ID NO:23 or SEQ ID NO:57 may comprise 1020 or more nucleotides, including sequences that encode an immunodominant epitope. In some embodiments, fragments of SEQ ID NO:23 or SEQ ID NO:57 may comprise 1080 or more nucleotides, including sequences that encode an immunodominant epitope. In some embodiments, fragments of SEQ ID NO:23 or SEQ ID NO:57 may comprise 1140 or more nucleotides, including sequences that encode an immunodominant epitope. In some embodiments, fragments of SEQ ID NO:23 or SEQ ID NO:57 may comprise 1200 or more nucleotides, including sequences that encode an immunodominant epitope. In some embodiments, fragments of SEQ ID NO:23 or SEQ ID NO:57 may comprise 1260 or more nucleotides, including sequences that encode an immunodominant epitope. In some embodiments, fragments of SEQ ID NO:23 or SEQ ID NO:57 may comprise 1320 or more nucleotides, including sequences that encode an immunodominant epitope. In some embodiments, fragments of SEQ ID NO:23 or SEQ ID NO:57 may comprise 1380 or more nucleotides, including sequences that encode an immunodominant epitope. In some embodiments, fragments of SEQ ID NO:23 or SEQ ID NO:57 may comprise 1440 or more nucleotides, including sequences that encode an immunodominant epitope. In some embodiments, fragments of SEQ ID NO:23 or SEQ ID NO:57 may comprise 1500 or more nucleotides, including sequences that encode an immunodominant epitope. In some embodiments, fragments of SEQ ID NO:23 or SEQ ID NO:57 may comprise 1560 or more nucleotides, including sequences that encode an immunodominant epitope. In some embodiments, fragments of SEQ ID NO:23 or SEQ ID NO:57 may comprise 1620 or more nucleotides, including sequences that encode an immunodominant epitope. In some embodiments, fragments of SEQ ID NO:23 or SEQ ID NO:57 may comprise 1680 or more nucleotides, including sequences that encode an immunodominant epitope. In some embodiments, fragments of SEQ ID NO:23 or SEQ ID NO:57 may comprise 1740 or more nucleotides, including sequences that encode an immunodominant epitope. In some embodiments, fragments of SEQ ID NO:23 or SEQ ID NO:57 may comprise 1800 or more nucleotides, including sequences that encode an immunodominant epitope. In some embodiments, fragments of SEQ ID NO:23 or SEQ ID NO:57 may comprise 1860 or more nucleotides, including sequences that encode an immunodominant epitope. In some embodiments, fragments of SEQ ID NO:23 or SEQ ID NO:57 may comprise 1920 or more nucleotides, including sequences that encode an immunodominant epitope. In some embodiments, fragments of SEQ ID NO:23 or SEQ ID NO:57 may comprise 1980 or more nucleotides, including sequences that encode an immunodominant epitope. In some embodiments, fragments of SEQ ID NO:23 or SEQ ID NO:57 may comprise 2040 or more nucleotides, including sequences that encode an immunodominant epitope. In some embodiments, fragments of SEQ ID NO:23 or SEQ ID NO:57 may comprise 2100 or more nucleotides, including sequences that encode an immunodominant epitope. In some embodiments, fragments of SEQ ID NO:23 or SEQ ID NO:57 may comprise 2160 or more nucleotides, including sequences that encode an immunodominant epitope. In some embodiments, fragments of SEQ ID NO:23 or SEQ ID NO:57 may comprise 2220 or more nucleotides, including sequences that encode an immunodominant epitope. In some embodiments, fragments of SEQ ID NO:23 or SEQ ID NO:57 may comprise 2280 or more nucleotides, including sequences that encode an immunodominant epitope. In some embodiments, fragments of SEQ ID NO:23 or SEQ ID NO:57 may comprise 2340 or more nucleotides, including sequences that encode an immunodominant epitope. In some embodiments, fragments of SEQ ID NO:23 or SEQ ID NO:57 may comprise 2400 or more nucleotides, including sequences that encode an immunodominant epitope. In some embodiments, fragments of SEQ ID NO:23 or SEQ ID NO:57 may comprise 2460 or more nucleotides, including sequences that encode an immunodominant epitope. In some embodiments, fragments of SEQ ID NO:23 or SEQ ID NO:57 may comprise 2520 or more nucleotides, including sequences that encode an immunodominant epitope. In some embodiments, fragments of SEQ ID NO:23 or SEQ ID NO:57 may comprise 2580 or more nucleotides, including sequences that encode an immunodominant epitope. In some embodiments, fragments of SEQ ID NO:23 or SEQ ID NO:57 may comprise 2640 or more nucleotides, including sequences that encode an immunodominant epitope. In some embodiments, fragments of SEQ ID NO:23 or SEQ ID NO:57 may comprise 2700 or more nucleotides, including sequences that encode an immunodominant epitope. In some embodiments, fragments of SEQ ID NO:23 or SEQ ID NO:57 may comprise 2760 or more nucleotides, including sequences that encode an immunodominant epitope. In some embodiments, fragments of SEQ ID NO:23 or SEQ ID NO:57 may comprise 2820 or more nucleotides, including sequences that encode an immunodominant epitope. In some embodiments, fragments of SEQ ID NO:23 or SEQ ID NO:57 may comprise 2880 or more nucleotides, including sequences that encode an immunodominant epitope. In some embodiments, fragments of SEQ ID NO:23 or SEQ ID NO:57 may comprise 2940 or more nucleotides, including sequences that encode an immunodominant epitope. In some embodiments, fragments of SEQ ID NO:23 or SEQ ID NO:57 may comprise 3000 or more nucleotides, including sequences that encode an immunodominant epitope. In some embodiments, fragments of SEQ ID NO:23 or SEQ ID NO:57 may comprise 3060 or more nucleotides, including sequences that encode an immunodominant epitope. In some embodiments, fragments of SEQ ID NO:23 or SEQ ID NO:57 may comprise 3120 or more nucleotides, including sequences that encode an immunodominant epitope. In some embodiments, fragments of SEQ ID NO:23 or SEQ ID NO:57 may comprise 3180 or more nucleotides, including sequences that encode an immunodominant epitope. In some embodiments, fragments of SEQ ID NO:23 or SEQ ID NO:57 may comprise 3240 or more nucleotides, including sequences that encode an immunodominant epitope. In some embodiments, fragments of SEQ ID NO:23 or SEQ ID NO:57 may comprise 3300 or more nucleotides, including sequences that encode an immunodominant epitope. In some embodiments, fragments of SEQ ID NO:23 or SEQ ID NO:57 may comprise 3360 or more nucleotides, including sequences that encode an immunodominant epitope. In some embodiments, fragments of SEQ ID NO:23 or SEQ ID NO:57 may comprise 3420 or more nucleotides, including sequences that encode an immunodominant epitope. In some embodiments, fragments of SEQ ID NO:23 or SEQ ID NO:57 may comprise 3480 or more nucleotides, including sequences that encode an immunodominant epitope. In some embodiments, fragments of SEQ ID NO:23 or SEQ ID NO:57 may comprise coding sequences for the IgE leader sequences. In some embodiments, fragments of SEQ ID NO:23 or SEQ ID NO:57 do not comprise coding sequences for the IgE leader sequences.

Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, in some embodiments fewer than 1740 nucleotides, in some embodiments fewer than 1800 nucleotides, in some embodiments fewer than 1860 nucleotides, in some embodiments fewer than 1920 nucleotides, in some embodiments fewer than 1980 nucleotides, in some embodiments fewer than 2040 nucleotides, in some embodiments fewer than 2100 nucleotides, in some embodiments fewer than 2160 nucleotides, in some embodiments fewer than 2220 nucleotides, in some embodiments fewer than 2280 nucleotides, in some embodiments fewer than 2340 nucleotides, in some embodiments fewer than 2400 nucleotides, in some embodiments fewer than 2460 nucleotides, in some embodiments fewer than 2520 nucleotides, in some embodiments fewer than 2580 nucleotides, in some embodiments fewer than 2640 nucleotides, in some embodiments fewer than 2700 nucleotides, in some embodiments fewer than 2760 nucleotides, in some embodiments fewer than 2820 nucleotides, in some embodiments fewer than 2860 nucleotides, in some embodiments fewer than 2940 nucleotides, in some embodiments fewer than 3000 nucleotides, in some embodiments fewer than 3060 nucleotides, in some embodiments fewer than 3120 nucleotides, in some embodiments fewer than 3180 nucleotides, in some embodiments fewer than 3240 nucleotides, in some embodiments fewer than 3300 nucleotides, in some embodiments fewer than 3360 nucleotides, in some embodiments fewer than 3420 nucleotides, in some embodiments fewer than 3480 nucleotides, and in some embodiments fewer than 3510 nucleotides.

Fragments of SEQ ID NO:24 or SEQ ID NO:58 may comprise 15 or more amino acids, including sequences that encode an immunodominant epitope. In some embodiments, fragments of SEQ ID NO:24 or SEQ ID NO:58 may comprise 18 or more amino acids, including sequences that encode an immunodominant epitope. In some embodiments, fragments of SEQ ID NO:24 or SEQ ID NO:58 may comprise 21 or more amino acids, including sequences that encode an immunodominant epitope. In some embodiments, fragments of SEQ ID NO:24 or SEQ ID NO:58 may comprise 24 or more amino acids, including sequences that encode an immunodominant epitope. In some embodiments, fragments of SEQ ID NO:24 or SEQ ID NO:58 may comprise 30 or more amino acids, including sequences that encode an immunodominant epitope. In some embodiments, fragments of SEQ ID NO:24 or SEQ ID NO:58 may comprise 36 or more amino acids, including sequences that encode an immunodominant epitope. In some embodiments, fragments of SEQ ID NO:24 or SEQ ID NO:58 may comprise 42 or more amino acids, including sequences that encode an immunodominant epitope. In some embodiments, fragments of SEQ ID NO:24 or SEQ ID NO:58 may comprise 48 or more amino acids, including sequences that encode an immunodominant epitope. In some embodiments, fragments of SEQ ID NO:24 or SEQ ID NO:58 may comprise 54 or more amino acids, including sequences that encode an immunodominant epitope. In some embodiments, fragments of SEQ ID NO:24 or SEQ ID NO:58 may comprise 60 or more amino acids, including sequences that encode an immunodominant epitope. In some embodiments, fragments of SEQ ID NO:24 or SEQ ID NO:58 may comprise 66 or more amino acids, including sequences that encode an immunodominant epitope. In some embodiments, fragments of SEQ ID NO:24 or SEQ ID NO:58 may comprise 72 or more amino acids, including sequences that encode an immunodominant epitope. In some embodiments, fragments of SEQ ID NO:24 or SEQ ID NO:58 may comprise 90 or more amino acids, including sequences that encode an immunodominant epitope. In some embodiments, fragments of SEQ ID NO:24 or SEQ ID NO:58 may comprise 120 or more amino acids, including sequences that encode an immunodominant epitope. In some embodiments, fragments of SEQ ID NO:24 or SEQ ID NO:58 may comprise 150 or more amino acids, including sequences that encode an immunodominant epitope. In some embodiments, fragments of SEQ ID NO:24 or SEQ ID NO:58 may comprise 180 or more amino acids, including sequences that encode an immunodominant epitope. In some embodiments, fragments of SEQ ID NO:24 or SEQ ID NO:58 may comprise 210 or more amino acids, including sequences that encode an immunodominant epitope. In some embodiments, fragments of SEQ ID NO:24 or SEQ ID NO:58 may comprise 240 or more amino acids, including sequences that encode an immunodominant epitope. In some embodiments, fragments of SEQ ID NO:24 or SEQ ID NO:58 may comprise 270 or more amino acids, including sequences that encode an immunodominant epitope. In some embodiments, fragments of SEQ ID NO:24 or SEQ ID NO:58 may comprise 300 or more amino acids, including sequences that encode an immunodominant epitope. In some embodiments, fragments of SEQ ID NO:24 or SEQ ID NO:58 may comprise 330 or more amino acids, including sequences that encode an immunodominant epitope. In some embodiments, fragments of SEQ ID NO:24 or SEQ ID NO:58 may comprise 360 or more amino acids, including sequences that encode an immunodominant epitope. In some embodiments, fragments of SEQ ID NO:24 or SEQ ID NO:58 may comprise 390 or more amino acids, including sequences that encode an immunodominant epitope. In some embodiments, fragments of SEQ ID NO:24 or SEQ ID NO:58 may comprise 420 or more amino acids, including sequences that encode an immunodominant epitope. In some embodiments, fragments of SEQ ID NO:24 or SEQ ID NO:58 may comprise 450 or more amino acids, including sequences that encode an immunodominant epitope. In some embodiments, fragments of SEQ ID NO:24 or SEQ ID NO:58 may comprise 480 or more amino acids, including sequences that encode an immunodominant epitope. In some embodiments, fragments of SEQ ID NO:24 or SEQ ID NO:58 may comprise 510 or more amino acids, including sequences that encode an immunodominant epitope. In some embodiments, fragments of SEQ ID NO:24 or SEQ ID NO:58 may comprise 540 or more amino acids, including sequences that encode an immunodominant epitope. In some embodiments, fragments of SEQ ID NO:24 or SEQ ID NO:58 may comprise 570 or more amino acids, including sequences that encode an immunodominant epitope. In some embodiments, fragments of SEQ ID NO:24 or SEQ ID NO:58 may comprise 600 or more amino acids, including sequences that encode an immunodominant epitope. In some embodiments, fragments of SEQ ID NO:24 or SEQ ID NO:58 may comprise 630 or more amino acids, including sequences that encode an immunodominant epitope. In some embodiments, fragments of SEQ ID NO:24 or SEQ ID NO:58 may comprise 660 or more amino acids, including sequences that encode an immunodominant epitope. In some embodiments, fragments of SEQ ID NO:24 or SEQ ID NO:58 may comprise 690 or more amino acids, including sequences that encode an immunodominant epitope. In some embodiments, fragments of SEQ ID NO:24 or SEQ ID NO:58 may comprise 720 or more amino acids, including sequences that encode an immunodominant epitope. In some embodiments, fragments of SEQ ID NO:24 or SEQ ID NO:58 may comprise 750 or more amino acids, including sequences that encode an immunodominant epitope. In some embodiments, fragments of SEQ ID NO:24 or SEQ ID NO:58 may comprise 780 or more amino acids, including sequences that encode an immunodominant epitope. In some embodiments, fragments of SEQ ID NO:24 or SEQ ID NO:58 may comprise 810 or more amino acids, including sequences that encode an immunodominant epitope. In some embodiments, fragments of SEQ ID NO:24 or SEQ ID NO:58 may comprise 840 or more amino acids, including sequences that encode an immunodominant epitope. In some embodiments, fragments of SEQ ID NO:24 or SEQ ID NO:58 may comprise 870 or more amino acids, including sequences that encode an immunodominant epitope. In some embodiments, fragments of SEQ ID NO:24 or SEQ ID NO:58 may comprise 900 or more amino acids, including sequences that encode an immunodominant epitope. In some embodiments, fragments of SEQ ID NO:24 or SEQ ID NO:58 may comprise 930 or more amino acids, including sequences that encode an immunodominant epitope. In some embodiments, fragments of SEQ ID NO:24 or SEQ ID NO:58 may comprise 960 or more amino acids, including sequences that encode an immunodominant epitope. In some embodiments, fragments of SEQ ID NO:24 or SEQ ID NO:58 may comprise 990 or more amino acids, including sequences that encode an immunodominant epitope. In some embodiments, fragments of SEQ ID NO:24 or SEQ ID NO:58 may comprise 1020 or more amino acids, including sequences that encode an immunodominant epitope. In some embodiments, fragments of SEQ ID NO:24 or SEQ ID NO:58 may comprise 1050 or more amino acids, including sequences that encode an immunodominant epitope. In some embodiments, fragments of SEQ ID NO:24 or SEQ ID NO:58 may comprise 1080 or more amino acids, including sequences that encode an immunodominant epitope. In some embodiments, fragments of SEQ ID NO:24 or SEQ ID NO:58 may comprise 1110 or more amino acids, including sequences that encode an immunodominant epitope. In some embodiments, fragments of SEQ ID NO:24 or SEQ ID NO:58 may comprise 1140 or more amino acids, including sequences that encode an immunodominant epitope. In some embodiments, fragments of SEQ ID NO:24 or SEQ ID NO:58 may comprise 1170 or more amino acids, including sequences that encode an immunodominant epitope. In some embodiments, fragments of SEQ ID NO:24 or SEQ ID NO:58 may comprise 1200 or more amino acids, including sequences that encode an immunodominant epitope. In some embodiments, fragments of SEQ ID NO:24 or SEQ ID NO:58 may comprise 1230 or more amino acids, including sequences that encode an immunodominant epitope. In some embodiments, fragments of SEQ ID NO:24 or SEQ ID NO:58 may comprise 1260 or more amino acids, including sequences that encode an immunodominant epitope. In some embodiments, fragments of SEQ ID NO:24 or SEQ ID NO:58 may comprise 1290 or more amino acids, including sequences that encode an immunodominant epitope. In some embodiments, fragments of SEQ ID NO:24 or SEQ ID NO:58 may comprise 1320 or more amino acids, including sequences that encode an immunodominant epitope. In some embodiments, fragments of SEQ ID NO:24 or SEQ ID NO:58 may comprise 1350 or more amino acids, including sequences that encode an immunodominant epitope. In some embodiments, fragments of SEQ ID NO:24 or SEQ ID NO:58 may comprise 1380 or more amino acids, including sequences that encode an immunodominant epitope. In some embodiments, fragments of SEQ ID NO:24 or SEQ ID NO:58 may comprise 1410 or more amino acids, including sequences that encode an immunodominant epitope. In some embodiments, fragments of SEQ ID NO:24 or SEQ ID NO:58 may comprise 1440 or more amino acids, including sequences that encode an immunodominant epitope. In some embodiments, fragments of SEQ ID NO:24 or SEQ ID NO:58 may comprise 1470 or more amino acids, including sequences that encode an immunodominant epitope. In some embodiments, fragments of SEQ ID NO:24 or SEQ ID NO:58 may comprise 1500 or more amino acids, including sequences that encode an immunodominant epitope. In some embodiments, fragments of SEQ ID NO:24 or SEQ ID NO:58 may comprise coding sequences for the IgE leader sequences. In some embodiments, fragments of SEQ ID NO:24 or SEQ ID NO:58 do not comprise coding sequences for the IgE leader sequences.

Fragments may comprise fewer than 24 amino acids, in some embodiments fewer than 30 amino acids, in some embodiments fewer than 36 amino acids, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids in some embodiments fewer than 240 amino acids, in some embodiments fewer than 260 amino acids, in some embodiments fewer than 290 amino acids, in some embodiments fewer than 320 amino acids, in some embodiments fewer than 350 amino acids, in some embodiments fewer than 380 amino acids, in some embodiments fewer than 410 amino acids in some embodiments fewer than 440 amino acids, in some embodiments fewer than 470 amino acids in some embodiments fewer than 500 amino acids, in some embodiments fewer than 530 amino acids in some embodiments fewer than 560 amino acids, in some embodiments fewer than 590 amino acids, in some embodiments fewer than 620 amino acids, in some embodiments fewer than 650 amino acids, in some embodiments fewer than 680 amino acids, in some embodiments fewer than 710 amino acids, in some embodiments fewer than 740 amino acids, in some embodiments fewer than 770 amino acids, in some embodiments fewer than 800 amino acids, in some embodiments fewer than 830 amino acids, in some embodiments fewer than 860 amino acids, in some embodiments fewer than 890 amino acids, in some embodiments fewer than 920 amino acids, in some embodiments fewer than 950 amino acids, in some embodiments fewer than 980 amino acids, in some embodiments fewer than 1010 amino acids, in some embodiments fewer than 1040 amino acids, in some embodiments fewer than 1070 amino acids, in some embodiments fewer than 1200 amino acids, in some embodiments fewer than 1230 amino acids, in some embodiments fewer than 1260 amino acids, in some embodiments fewer than 1290 amino acids, in some embodiments fewer than 1320 amino acids, in some embodiments fewer than 1350 amino acids, in some embodiments fewer than 1380 amino acids, in some embodiments fewer than 1410 amino acids, in some embodiments fewer than 1440 amino acids, in some embodiments fewer than 1470 amino acids, and in some embodiments fewer than 1500 amino acids.

In one embodiment, the TERT antigen is a synthetic consensus TERT antigen. In certain embodiments, the synthetic consensus TERT comprise 1 or more, 2 or more, 3 or more, 4 or more, 5 or more, 6 or more, 7 or more, 8 or more 9 or more, 10 or more, 15 or more, 20 or more, 30 or more, or 50 or more amino acid mutations relative to a native TERT antigen.

In one embodiment, the consensus hTERT antigen can be the nucleic acid sequence SEQ ID NO:45, which encodes for the amino acid sequence SEQ ID NO:46. SEQ ID NO:45 encodes the consensus hTERT antigen linked to an IgE leader sequence. The consensus hTERT antigen can be linked to the IgE leader sequence and an HA tag. In other embodiments, the consensus hTERT antigen can be free of or not linked to an IgE leader sequence and/or an HA tag. In one embodiment, the consensus hTERT antigen can be the nucleic acid sequence SEQ ID NO:47, which encodes for the amino acid sequence SEQ ID NO:48. SEQ ID NO:47 encodes the consensus hTERT antigen free of or not linked to an IgE leader sequence and/or an HA tag.

In one embodiment, the consensus mTERT antigen can be the nucleic acid sequence SEQ ID NO:49, which encodes for the amino acid sequence SEQ ID NO:50. SEQ ID NO:49 encodes the consensus mTERT antigen linked to an IgE leader sequence. The consensus mTERT antigen can be linked to the IgE leader sequence and an HA tag. In other embodiments, the consensus mTERT antigen can be free of or not linked to an IgE leader sequence and/or an HA tag. In one embodiment, the consensus mTERT antigen can be the nucleic acid sequence SEQ ID NO:51, which encodes for the amino acid sequence SEQ ID NO:52. SEQ ID NO:51 encodes the consensus mTERT antigen free of or not linked to an IgE leader sequence and/or an HA tag.

In one embodiment, the consensus rhTERT antigen can be the nucleic acid sequence SEQ ID NO:53, which encodes for the amino acid sequence SEQ ID NO:54. SEQ ID NO:53 encodes the consensus rhTERT antigen linked to an IgE leader sequence. The consensus rhTERT antigen can be linked to the IgE leader sequence and an HA tag. In other embodiments, the consensus rhTERT antigen can be free of or not linked to an IgE leader sequence and/or an HA tag. In one embodiment, the consensus rhTERT antigen can be the nucleic acid sequence SEQ ID NO:55, which encodes for the amino acid sequence SEQ ID NO:56. SEQ ID NO:55 encodes the consensus rhTERT antigen free of or not linked to an IgE leader sequence and/or an HA tag.

In some embodiments, the consensus TERT antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO:45, SEQ ID NO:47, SEQ ID NO:49, SEQ ID NO:51, SEQ ID NO:53 or SEQ ID NO:55. In other embodiments, the consensus TERT antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:46, SEQ ID NO:48, SEQ ID NO:50, SEQ ID NO:52, SEQ ID NO:54 or SEQ ID NO:56. The consensus TERT antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:46, SEQ ID NO:48, SEQ ID NO:50, SEQ ID NO:52, SEQ ID NO:54 or SEQ ID NO:56.

Some embodiments relate to nucleic acid sequences encoding proteins homologous to the consensus TERT antigen, immunogenic fragment of the consensus TERT antigen, and immunogenic fragments of homologous proteins. Such nucleic acid molecules that encode immunogenic proteins that have up to 95% homology to a sequence, up to 96% homology to a sequence, up to 97% homology to a sequence, up to 98% homology to a sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length consensus TERT antigen, immunogenic fragment of the consensus TERT antigen, and immunogenic fragments of proteins having identity to the consensus TERT antigen. Such nucleic acid molecules that encode immunogenic proteins that have up to 80% identity to a full length consensus TERT sequence, up to 85% identity to a full length sequence, up to 90% identity to a full length consensus TERT sequence, up to 91% identity to a full length consensus TERT sequence, up to 92% identity to a full length consensus TERT sequence, up to 93% identity to a full length consensus TERT sequence, up to 94% identity to a full length consensus TERT sequence, up to 95% identity to a full length consensus TERT sequence, up to 96% identity to a full length consensus TERT sequence, up to 97% identity to a full length consensus TERT sequence, up to 98% identity to a full length consensus TERT sequence, and up to 99% identity to a full length consensus TERT sequence can be provided. Likewise, nucleic acid sequences encoding the immunogenic fragments set forth herein and the immunogenic fragments of proteins with similar percent identities as indicated above to the consensus TERT antigens set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:45, SEQ ID NO:47, SEQ ID NO:49, SEQ ID NO:51, SEQ ID NO:53 or SEQ ID NO:55. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:45, SEQ ID NO:47, SEQ ID NO:49, SEQ ID NO:51, SEQ ID NO:53 or SEQ ID NO:55. Fragments can be at least 95%, at least 96%, at least 97%, at least 98%, or at least 99% homologous to fragments of SEQ ID NO:45, SEQ ID NO:47, SEQ ID NO:49, SEQ ID NO:51, SEQ ID NO:53 or SEQ ID NO:55. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:45, SEQ ID NO:47, SEQ ID NO:49, SEQ ID NO:51, SEQ ID NO:53 or SEQ ID NO:55. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, in one embodiment, the amino acid sequence of the consensus TERT antigen is SEQ ID NO:46, SEQ ID NO:48, SEQ ID NO:50, SEQ ID NO:52, SEQ ID NO:54 or SEQ ID NO:56. The amino acid sequence of the consensus TERT antigen linked to an IgE leader is SEQ ID NO:46, SEQ ID NO:48, SEQ ID NO:50, SEQ ID NO:52, SEQ ID NO:54 or SEQ ID NO:56. The amino acid sequence of the consensus TERT antigen linked to the IgE leader may be linked to HA tag.

Some embodiments relate to proteins that are homologous to SEQ ID NO:46, SEQ ID NO:48, SEQ ID NO:50, SEQ ID NO:52, SEQ ID NO:54 or SEQ ID NO:56. Some embodiments relate to immunogenic proteins that have 95% homology to the protein sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have 96% homology to the protein sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have 97% homology to the protein sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have 98% homology to the protein sequences as set forth in SEQ ID NO:46. Some embodiments relate to immunogenic proteins that have 99% homology to the protein sequences as set forth in SEQ ID NO:46, SEQ ID NO:48, SEQ ID NO:50, SEQ ID NO:52, SEQ ID NO:54 or SEQ ID NO:56.

Some embodiments relate to proteins that are identical to SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 80% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 85% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 90% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 91% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 92% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 93% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 94% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 95% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 96% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 97% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 98% identical to the full length amino acid sequences as set forth in SEQ ID NO:46, SEQ ID NO:48, SEQ ID NO:50, SEQ ID NO:52, SEQ ID NO:54 or SEQ ID NO:56. Some embodiments relate to immunogenic proteins that have an amino acid sequence that is 99% identical to the full length amino acid sequences as set forth in SEQ ID NO:46, SEQ ID NO:48, SEQ ID NO:50, SEQ ID NO:52, SEQ ID NO:54 or SEQ ID NO:56.

In some embodiments, the protein is free of a leader sequence. In some embodiments, the protein is free of the IgE leader. Fragments of proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a protein. Immunogenic fragments of SEQ ID NO:46, SEQ ID NO:48, SEQ ID NO:50, SEQ ID NO:52, SEQ ID NO:54 or SEQ ID NO:56 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:46, SEQ ID NO:48, SEQ ID NO:50, SEQ ID NO:52, SEQ ID NO:54 or SEQ ID NO:56. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:46, SEQ ID NO:48, SEQ ID NO:50, SEQ ID NO:52, SEQ ID NO:54 or SEQ ID NO:56 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:46, SEQ ID NO:48, SEQ ID NO:50, SEQ ID NO:52, SEQ ID NO:54 or SEQ ID NO:56. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:46, SEQ ID NO:48, SEQ ID NO:50, SEQ ID NO:52, SEQ ID NO:54 or SEQ ID NO:56 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:46, SEQ ID NO:48, SEQ ID NO:50, SEQ ID NO:52, SEQ ID NO:54 or SEQ ID NO:56. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

Fragments of SEQ ID NO:45, SEQ ID NO:47, SEQ ID NO:49, SEQ ID NO:51, SEQ ID NO:53 or SEQ ID NO:55 may comprise 30 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 45 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 60 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 75 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 90 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 120 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 150 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 180 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 210 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 240 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 270 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 300 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 360 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 420 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 480 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 540 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 600 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 300 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 660 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 720 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 780 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 840 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 900 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 960 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1020 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1080 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1140 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1200 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1260 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1320 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1380 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1440 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1500 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1560 or more nucleotides, including sequences that encode an immunodominant epitope. In some embodiments, fragments SEQ ID NO:45, SEQ ID NO:47, SEQ ID NO:49, SEQ ID NO:51, SEQ ID NO:53 or SEQ ID NO:55 may comprise 1620 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1680 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1740 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1800 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1860 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1920 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 1980 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2040 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2100 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2160 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2220 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2280 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2340 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2400 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2460 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2520 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2580 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2640 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2700 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2760 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2820 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2880 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 2940 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3000 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3060 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3120 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3180 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3240 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3300 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3360 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3420 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise 3480 or more nucleotides, including sequences that encode an immunodominant epitope. In some embodiments, fragments of SEQ ID NO:45, SEQ ID NO:47, SEQ ID NO:49, SEQ ID NO:51, SEQ ID NO:53 or SEQ ID NO:55 may comprise coding sequences for the IgE leader sequences. In some embodiments, fragments of SEQ ID NO:45, SEQ ID NO:47, SEQ ID NO:49, SEQ ID NO:51, SEQ ID NO:53 or SEQ ID NO:55 do not comprise coding sequences for the IgE leader sequences.

Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides, in some embodiments fewer than 1020 nucleotides, in some embodiments fewer than 1080 nucleotides, in some embodiments fewer than 1140 nucleotides, in some embodiments fewer than 1200 nucleotides, in some embodiments fewer than 1260 nucleotides, in some embodiments fewer than 1320 nucleotides, in some embodiments fewer than 1380 nucleotides, in some embodiments fewer than 1440 nucleotides, in some embodiments fewer than 1500 nucleotides, in some embodiments fewer than 1560 nucleotides, in some embodiments fewer than 1620 nucleotides, in some embodiments fewer than 1680 nucleotides, in some embodiments fewer than 1740 nucleotides, in some embodiments fewer than 1800 nucleotides, in some embodiments fewer than 1860 nucleotides, in some embodiments fewer than 1920 nucleotides, in some embodiments fewer than 1980 nucleotides, in some embodiments fewer than 2040 nucleotides, in some embodiments fewer than 2100 nucleotides, in some embodiments fewer than 2160 nucleotides, in some embodiments fewer than 2220 nucleotides, in some embodiments fewer than 2280 nucleotides, in some embodiments fewer than 2340 nucleotides, in some embodiments fewer than 2400 nucleotides, in some embodiments fewer than 2460 nucleotides, in some embodiments fewer than 2520 nucleotides, in some embodiments fewer than 2580 nucleotides, in some embodiments fewer than 2640 nucleotides, in some embodiments fewer than 2700 nucleotides, in some embodiments fewer than 2760 nucleotides, in some embodiments fewer than 2820 nucleotides, in some embodiments fewer than 2860 nucleotides, in some embodiments fewer than 2940 nucleotides, in some embodiments fewer than 3000 nucleotides, in some embodiments fewer than 3060 nucleotides, in some embodiments fewer than 3120 nucleotides, in some embodiments fewer than 3180 nucleotides, in some embodiments fewer than 3240 nucleotides, in some embodiments fewer than 3300 nucleotides, in some embodiments fewer than 3360 nucleotides, in some embodiments fewer than 3420 nucleotides, in some embodiments fewer than 3480 nucleotides, and in some embodiments fewer than 3510 nucleotides.

Fragments of SEQ ID NO:46, SEQ ID NO:48, SEQ ID NO:50, SEQ ID NO:52, SEQ ID NO:54 or SEQ ID NO:56 may comprise 15 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 18 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 21 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 24 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 30 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 36 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 42 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 48 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 54 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 60 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 66 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 72 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 90 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 120 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 150 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 180 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 210 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 240 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 270 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 300 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 330 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 360 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 390 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 420 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 450 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 480 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 510 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 540 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 570 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 600 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 630 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 660 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 690 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 720 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 750 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 780 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 810 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 840 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 870 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 900 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 930 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 960 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 990 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1020 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1050 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1080 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1110 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1140 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1170 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1200 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1230 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1260 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1290 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1320 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1350 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1380 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1410 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1440 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1470 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise 1500 or more amino acids, including sequences that comprise an immunodominant epitope. In some embodiments, fragments of SEQ ID NO:46, SEQ ID NO:48, SEQ ID NO:50, SEQ ID NO:52, SEQ ID NO:54 or SEQ ID NO:56 may comprise coding sequences for the IgE leader sequences. In some embodiments, fragments of SEQ ID NO:46, SEQ ID NO:48, SEQ ID NO:50, SEQ ID NO:52, SEQ ID NO:54 or SEQ ID NO:56 do not comprise coding sequences for the IgE leader sequences.

Fragments may comprise fewer than 24 amino acids, in some embodiments fewer than 30 amino acids, in some embodiments fewer than 36 amino acids, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids in some embodiments fewer than 240 amino acids, in some embodiments fewer than 260 amino acids, in some embodiments fewer than 290 amino acids, in some embodiments fewer than 320 amino acids, in some embodiments fewer than 350 amino acids, in some embodiments fewer than 380 amino acids, in some embodiments fewer than 410 amino acids in some embodiments fewer than 440 amino acids, in some embodiments fewer than 470 amino acids in some embodiments fewer than 500 amino acids, in some embodiments fewer than 530 amino acids in some embodiments fewer than 560 amino acids, in some embodiments fewer than 590 amino acids, in some embodiments fewer than 620 amino acids, in some embodiments fewer than 650 amino acids, in some embodiments fewer than 680 amino acids, in some embodiments fewer than 710 amino acids, in some embodiments fewer than 740 amino acids, in some embodiments fewer than 770 amino acids, in some embodiments fewer than 800 amino acids, in some embodiments fewer than 830 amino acids, in some embodiments fewer than 860 amino acids, in some embodiments fewer than 890 amino acids, in some embodiments fewer than 920 amino acids, in some embodiments fewer than 950 amino acids, in some embodiments fewer than 980 amino acids, in some embodiments fewer than 1010 amino acids, in some embodiments fewer than 1040 amino acids, in some embodiments fewer than 1070 amino acids, in some embodiments fewer than 1200 amino acids, in some embodiments fewer than 1230 amino acids, in some embodiments fewer than 1260 amino acids, in some embodiments fewer than 1290 amino acids, in some embodiments fewer than 1320 amino acids, in some embodiments fewer than 1350 amino acids, in some embodiments fewer than 1380 amino acids, in some embodiments fewer than 1410 amino acids, in some embodiments fewer than 1440 amino acids, in some embodiments fewer than 1470 amino acids, and in some embodiments fewer than 1500 amino acids.

The present invention is directed to an anti-cancer immunogenic composition. The immunogenic composition can comprise one or more cancer antigens. The immunogenic composition can prevent tumor growth. The immunogenic composition can reduce tumor growth. The immunogenic composition can prevent metastasis of tumor cells. Depending upon the cancer antigen, the immunogenic composition can be targeted to treat cancers, including but not limited to, liver cancer, prostate cancer, melanomas, blood cancers, head and neck cancer, glioblastoma, recurrent respiratory papillomatosis, anal cancer, cervical cancer, and brain cancer.

The first step in development of the immunogenic composition is to identify a cancer antigen that is not recognized by the immune system and is a self-antigen. The cancer antigen identified is changed from a self-antigen to a foreign antigen in order to be recognized by the immune system. The redesign of the nucleic acid and amino acid sequence of the recombinant cancer antigen from a self to a foreign antigen breaks tolerance of antigen by the immune system. In order to break tolerance, several redesign measures can be applied to the cancer antigen as described below.

The recombinant cancer antigen of the immunogenic composition is not recognized as self, therefore breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

In a particular embodiment, the immunogenic composition can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8$^+$ (CTL) to attack and kill tumor cells; (3) increase T helper cell responses; (4) and increase inflammatory responses via IFN-γ and TFN-α or a combination of the aforementioned. The immunogenic composition can increase tumor free survival by 30%, 31%, 32%, 33%, 34%, 35%, 36%, 37%, 38%, 39%, 40%, 41%, 42%, 43%, 44%, and 45%. The immunogenic composition can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The immunogenic composition can prevent and block increases in monocyte chemoattractant protein 1 (MCP-1), a cytokine secreted by myeloid derived suppressor cells. The immunogenic composition can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55% 56%, 57%, 58%, 59%, and 60%.

The immunogenic composition can increase a cellular immune response in a subject administered the immunogenic composition by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the immunogenic composition. In some embodiments the immunogenic composition can increase the cellular immune response in the subject administered the immunogenic composition by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the immunogenic composition.

The immunogenic composition can increase interferon gamma (IFN-γ) levels in a subject administered the immunogenic composition by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the immunogenic composition. In some embodiments the immunogenic composition can increase IFN-γ levels in the subject administered the immunogenic composition by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the immunogenic composition.

The immunogenic composition can be a nucleic acid vaccine. In one embodiment, the nucleic acid vaccine is a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The immunogenic composition can be an RNA vaccine. The RNA vaccine can be introduced into the cell. The RNA vaccine can further comprise elements or reagents that inhibit it from integrating into the chromosome.

The immunogenic composition can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The immunogenic composition of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The immunogenic composition can accomplish some or all of these features by containing the cancer antigen as discussed below.

As described in more detail below, the immunogenic composition can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation. As also described below in more detail, the immunogenic composition may be combined further with antibodies to checkpoint inhibitors such as PD-1, PDL-1, CTLA4, TIM3 and LAG3 to increase the stimulation of both the cellular and humoral immune responses. Using antibodies directed to immune checkpoint proteins prevents the immune checkpoint protein from suppressing T-cell and/or B-cell responses.

The immunogenic composition can also comprise an antigen, or fragment or variant thereof. The antigen can be anything that induces an immune response in a subject. The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV).

Some antigens can induce a strong immune response. Other antigens can induce a weak immune response. The antigen can elicit a greater immune response when combined with the TERT antigen.

a. Cancer Antigen

The immunogenic composition can comprise one or more cancer antigens. The cancer antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the cancer antigen by a peptide bond. The amino acid sequence can be a protein, a peptide, a variant thereof, a fragment thereof, or a combination thereof. The cancer antigen can be a recombinant cancer antigen.

In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Cancer antigens, or tumor antigens, are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

The TERT antigen and optionally one or more antibody targeting one or more immune checkpoint proteins can be associated or combined with a tumor antigen or fragment or variant thereof. Cancer markers are known proteins that are present or upregulated vis-à-vis certain cancer cells. By methodology of generating antigens that represent such markers in a way to break tolerance to self, a cancer vaccine can be generated. Such cancer vaccines can include the TERT antigen and optionally one or more antibody targeting one or more immune checkpoint proteins to enhance the immune response and optionally one or more additional tumor antigens. The following are some exemplary tumor antigens:

(1) Tyrosinase (Tyr)

The immunogenic composition of the present invention can comprise the cancer antigen tyrosinase (Tyr), a fragment thereof, or a variant thereof. Tyrosinase is a copper-containing enzyme having tyrosine hydroxylase and dopa oxidase catalytic activities that can be found in microorganisms and plant and animal tissues. Specifically, tyrosinase catalyzes the production of melanin and other pigments by the oxidation of phenols such as tyrosine. Mutations in the TYR gene result in oculocutaneous albinism in mammals and non-pathological polymorphisms in the TYR gene contribute to variation in skin pigmentation.

Additionally, in cancer or tumors such as melanoma, tyrosinase can become unregulated, resulting in increased melanin synthesis. Accordingly, tyrosinase can be a cancer antigen associated with melanoma. In subjects suffering from melanoma, tyrosinase can be a target of cytotoxic T cell recognition. In some instances, however, the immune response to the cancer or tumor (including melanoma) can be suppressed, leading to a microenvironment that supports tumor formation and/or growth and thus, disease progression.

Immune suppression can be facilitated by myeloid derived suppressor cells (MDSCs), which are a mixed population of immature macrophages, granulocytes, dendritic cells, and myeloid cells. The myeloid cells can be a heterogenous population of myeloid progenitor cells and immature myeloid cells (IMCs). Markers of MDSCs can include expression of Gr-1 and CD11b (i.e., Gr-1$^+$ and CD11b$^+$ cells).

Circulation of MDSCs can increase due to chronic infection and expansion of MDSC populations can be associated with autoimmunity and inflammation. Particularly, MDSC expansion (or presence in the tumor or cancerous tissue) can facilitate tumor growth and escape from immune detection and/or regulation, and thus, MDSCs can affect immune responses to anticancer vaccines.

MDSCs can be regulated by Regulator of G-protein signaling 2 (Rgs2) and Rgs2 can be highly expressed in MDSCs derived from tumors. Rgs2 can also be widely expressed in a variety of cells, for example, myeloid cells. MDSCs derived from tumor bearing mice can function differently from MDSCs derived from non-tumor bearing mice. One such difference can be the up-regulation of the production of the chemokine MCP-1, which is secreted by MDSCs. MCP-1 can promote cell migration by signaling through CCR2, a G-protein coupled receptor (GPCR) found on monocytes, endothelial cells, and T cells. Accordingly, MCP-1 can cause migration of endothelial cells, thereby promoting vascularization. Blocking MCP-1 via neutralizing antibodies can inhibit angiogenesis, and thus, can lead to decreased tumor metastases and increased survival. As such, MCP-1 can be considered an angiogenic factor. Besides secreting MCP-1, MDSCs can secrete growth factors, thereby further contributing to tumor growth.

The Tyr antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-0, tumor associated macrophages, tumor associated fibroblasts, soluble factors produced by immune suppressor cells, CTLA-4, PD-1, MDSCs, MCP-1, and an immune checkpoint molecule, which is described below in more detail.

As demonstrated herein, the Tyr antigen induces antigen-specific T-cell and high titer antibody responses against cancerous or tumor cells (e.g., melanoma cells). Specifically, the Tyr antigen is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8$^+$ (CTL) to attack and kill tumor cells; (3) increase T helper cell responses; and (4) increase inflammatory responses via IFN-γ and TFN-α or a combination of the aforementioned. As such, a protective immune response is provided against tumor formation and tumor growth by immunogenic compositions comprising the Tyr antigen (e.g., the consensus Tyr antigen, which is described below in more detail) because these immunogenic compositions prevent immune suppression by decreasing the population of MDSCs found within the cancerous or tumor tissue and block vascularization of the cancerous or tumor tissue by reducing production or secretion of MCP-1. Accordingly, any user can design an immunogenic composition of the present invention to include a Tyr antigen to provide broad immunity against tumor formation, metastasis of tumors, and tumor growth.

The Tyr antigen can comprise protein epitopes that make them particularly effective as immunogens against which anti-Tyr immune responses can be induced. The Tyr antigen can comprise the full length translation product, a variant thereof, a fragment thereof or a combination thereof. The Tyr antigen can comprise a consensus protein.

The nucleic acid sequence encoding the consensus Tyr antigen can be optimized with regards to codon usage and corresponding RNA transcripts. The nucleic acid encoding the consensus Tyr antigen can be codon and RNA optimized for expression. In some embodiments, the nucleic acid sequence encoding the consensus Tyr antigen can include a Kozak sequence (e.g., GCC ACC) to increase the efficiency of translation. The nucleic acid encoding the consensus Tyr antigen can include multiple stop codons (e.g., TGA TGA) to increase the efficiency of translation termination.

The nucleic acid encoding the consensus Tyr antigen can also encode an immunoglobulin E (IgE) leader sequence. The nucleic acid encoding the consensus Tyr antigen can further encode the IgE leader sequence such that the amino acid sequence of the IgE leader sequence is linked to the amino acid sequence of the consensus Tyr antigen by a peptide bond. The nucleic encoding the consensus Tyr antigen can also include a nucleotide sequence encoding the IgE leader sequence. In some embodiments, the nucleic acid encoding the consensus Tyr antigen is free of or does not contain a nucleotide sequence encoding the IgE leader sequence.

The consensus Tyr antigen can be the nucleic acid sequence SEQ ID NO:1, which encodes for the amino acid sequence SEQ ID NO:2. SEQ ID NO:1 encodes the consensus Tyr protein linked to an IgE leader sequence. The consensus Tyr protein can be linked to the IgE leader sequence and an HA tag. In other embodiments, the consensus Tyr protein can be free of or not linked to an IgE leader sequence and/or an HA tag.

In some embodiments, the consensus Tyr antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO: 1. In other embodiments, the consensus Tyr antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. The consensus Tyr antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

Some embodiments relate to nucleic acid sequences encoding proteins homologous to the Tyr consensus protein, immunogenic fragment of the Tyr consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length Tyr consensus protein, immunogenic fragment of the Tyr consensus protein, and immunogenic fragments of proteins having identity to the Tyr consensus protein. Such nucleic acid molecules that encode immunogenic proteins that have up to 80% identity to a full length Tyr consensus sequence, up to 85% identity to a full length consensus sequence, up to 90% identity to a full length Tyr consensus sequence, up to 91% identity to a full length Tyr consensus sequence, up to 92% identity to a full length Tyr consensus sequence, up to 93% identity to a full length Tyr consensus sequence, up to 94% identity to a full length Tyr consensus sequence, up to 95% identity to a full length Tyr consensus sequence, up to 96% identity to a full length Tyr consensus sequence, up to 97% identity to a full length Tyr consensus sequence, up to 98% identity to a full length Tyr consensus sequence, and up to 99% identity to a full length Tyr consensus sequence can be provided. Likewise, nucleic acid sequences encoding the immunogenic fragments set forth herein and the immunogenic fragments of proteins with similar percent identities as indicated above to the Tyr proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:1. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:1. Fragments can be at least 95%, at least 96%, at least 97%, at least 98%, or at least 99% homologous to fragments of SEQ ID NO:1. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:1. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:2 comprises the amino acid sequence of the consensus Tyr protein. The amino acid sequence of the consensus Tyr protein linked to an IgE leader is SEQ ID NO:2. The amino acid sequence of the consensus Tyr protein linked to the IgE leader may be linked to HA tag.

Some embodiments relate to proteins that are homologous to SEQ ID NO:2. Some embodiments relate to immunogenic proteins that have 95% homology to the consensus protein sequences as set forth in SEQ ID NO:2. Some embodiments relate to immunogenic proteins that have 96% homology to the consensus protein sequences as set forth in SEQ ID NO:2. Some embodiments relate to immunogenic proteins that have 97% homology to the consensus protein sequences as set forth in SEQ ID NO:2. Some embodiments relate to immunogenic proteins that have 98% homology to the consensus protein sequences as set forth in SEQ ID NO:2. Some embodiments relate to immunogenic proteins that have 99% homology to the consensus protein sequences as set forth in SEQ ID NO:2.

Some embodiments relate to proteins that are identical to SEQ ID NO:2. Some embodiments relate to immunogenic proteins that have an amino acid sequence that is 80% identical to the full length consensus amino acid sequences as set forth in SEQ ID NO:2. Some embodiments relate to immunogenic proteins that have an amino acid sequence that is 85% identical to the full length consensus amino acid sequences as set forth in SEQ ID NO:2. Some embodiments relate to immunogenic proteins that have an amino acid sequence that is 90% identical to the full length consensus amino acid sequences as set forth in SEQ ID NO:2. Some embodiments relate to immunogenic proteins that have an amino acid sequence that is 91% identical to the full length consensus amino acid sequences as set forth in SEQ ID NO:2. Some embodiments relate to immunogenic proteins that have an amino acid sequence that is 92% identical to the full length consensus amino acid sequences as set forth in SEQ ID NO:2. Some embodiments relate to immunogenic proteins that have an amino acid sequence that is 93% identical to the full length consensus amino acid sequences as set forth in SEQ ID NO:2. Some embodiments relate to immunogenic proteins that have an amino acid sequence that is 94% identical to the full length consensus amino acid sequences as set forth in SEQ ID NO:2. Some embodiments relate to immunogenic proteins that have an amino acid sequence that is 95% identical to the full length consensus amino acid sequences as set forth in SEQ ID NO:2. Some embodiments relate to immunogenic proteins that have an amino acid sequence that is 96% identical to the full length consensus amino acid sequences as set forth in SEQ ID NO:2. Some embodiments relate to immunogenic proteins that have an amino acid sequence that is 97% identical to the full length consensus amino acid sequences as set forth in SEQ ID NO:2. Some embodiments relate to immunogenic proteins that have an amino acid sequence that is 98% identical to the full length consensus amino acid sequences as set forth in SEQ ID NO:2. Some embodiments relate to immunogenic proteins that have an amino acid sequence that is 99% identical to the full length consensus amino acid sequences as set forth in SEQ ID NO:2.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:2 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:2 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:2. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:2 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:2. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(2) Tyrosinase-Related Protein 1 (TYRP1)

The immunogenic composition of the present invention can comprise the cancer antigen tyrosinase-related Protein 1 (TYRP1), a fragment thereof, or a variant thereof. TYRP1, encoded by the TYRP1 gene, is a 75 kDa transmembrane glycoprotein and is expressed in both normal and malignant melanocytes and melanoma cells. Like tyrosinase, TYRP1 contains a modified termed M-box that can bind to the microphtalmia transcription factor (MITF), which plays a central role within the melanocyte in activating pigmentation, cell proliferation and differentiation. TYRP1 may help to stabilize tyrosinase and can form a heterodimer, which may prevent the premature death of melanocytes by attenuating tyrosinase-mediated cytotoxicity.

As described above for tyrosinase, tyrosinase-related protein 1 (TYRP-1) can also be involved in the synthesis of melanin and pigmentary machinery of the melanocyte, and can be recognized by the immune system in subjects suffering from melanoma. Accordingly, TYRP-1 can be antigen associated with melanoma.

The TRYP-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-$\gamma$) and/or tumor necrosis factor alpha (TNF-$\alpha$). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-$\beta$, tumor associated macrophages, tumor associated fibroblasts, soluble factors produced by immune suppressor cells, CTLA-4, PD-1, MDSCs, MCP-1, and an immune checkpoint molecule, which is described below in more detail.

The TYRP-1 antigen can comprise protein epitopes that make them particularly effective as immunogens against which anti-TYRP-1 immune responses can be induced. The TYRP-1 antigen can comprise the full length translation product, a variant thereof, a fragment thereof or a combination thereof. The TYRP-1 antigen can comprise a consensus protein.

The nucleic acid sequence encoding the consensus TYRP-1 antigen can be optimized with regards to codon usage and corresponding RNA transcripts. The nucleic acid encoding the consensus TYRP-1 antigen can be codon and RNA optimized for expression. In some embodiments, the nucleic acid sequence encoding the consensus TYRP-1 antigen can include a Kozak sequence (e.g., GCC ACC) to increase the efficiency of translation. The nucleic acid encoding the consensus TYRP-1 antigen can include multiple stop codons (e.g., TGA TGA) to increase the efficiency of translation termination.

The nucleic acid encoding the consensus TYRP-1 antigen can also encode an immunoglobulin E (IgE) leader sequence. The nucleic acid encoding the consensus TYRP-1 antigen can further encode the IgE leader sequence such that the amino acid sequence of the IgE leader sequence is linked to the amino acid sequence of the consensus TYRP-1 antigen by a peptide bond. The nucleic encoding the consensus TYRP-1 antigen can also include a nucleotide sequence encoding the IgE leader sequence. In some embodiments, the nucleic acid encoding the consensus TYRP-1 antigen is free of or does not contain a nucleotide sequence encoding the IgE leader sequence.

The consensus TYRP-1 antigen can be the nucleic acid sequence SEQ ID NO:3, which encodes for the amino acid sequence SEQ ID NO:4. SEQ ID NO:3 encodes the consensus TYRP-1 protein linked to an IgE leader sequence. The consensus TYRP-1 protein can be linked to the IgE leader sequence and an HA tag. In other embodiments, the consensus TYRP-1 protein can be free of or not linked to an IgE leader sequence and/or an HA tag.

In some embodiments, the consensus TYRP-1 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:3. In other embodiments, the consensus TYRP-1 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4. The consensus TYRP-1 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:4.

Some embodiments relate to nucleic acid sequences encoding proteins homologous to the TYRP-1 consensus protein, immunogenic fragment of the TYRP-1 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length TYRP-1 consensus protein, immunogenic fragment of the TYRP-1 consensus protein, and immunogenic fragments of proteins having identity to the TYRP-1 consensus protein. Such nucleic acid molecules that encode immunogenic proteins that have up to 80% identity to a full length TYRP-1 consensus sequence, up to 85% identity to a full length TYRP-1 consensus sequence, up to 90% identity to a full length TYRP-1 consensus sequence, up to 910% identity to a full length TYRP-1 consensus sequence, up to 92% identity to a full length TYRP-1 consensus sequence, up to 93% identity to a full length TYRP-1 consensus sequence, up to 94% identity to a full length TYRP-1 consensus sequence, up to 95% identity to a full length TYRP-1 consensus sequence, up to 96% identity to a full length TYRP-1 consensus sequence, up to 97% identity to a full length TYRP-1 consensus sequence, up to 98% identity to a full length TYRP-1 consensus sequence, and up to 99% identity to a full length TYRP-1 consensus sequence can be provided. Likewise, nucleic acid sequences encoding the immunogenic fragments set forth herein and the immunogenic fragments of proteins with similar percent identities as indicated above to the TYRP-1 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:3. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:3. Fragments can be at least 95%, at least 96%, at least 97%, at least 98%, or at least 99% homologous to fragments of SEQ ID NO:3. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:3. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:4 comprises the amino acid sequence of the consensus TYRP-1 protein. The amino acid sequence of the consensus TYRP-1 protein linked to an IgE leader is SEQ ID NO:4. The amino acid sequence of the consensus TYRP-1 protein linked to the IgE leader may be linked to HA tag.

Some embodiments relate to proteins that are homologous to SEQ ID NO:4. Some embodiments relate to immunogenic proteins that have 95% homology to the consensus protein sequences as set forth in SEQ ID NO:4. Some embodiments relate to immunogenic proteins that have 96% homology to the consensus protein sequences as set forth in SEQ ID NO:4. Some embodiments relate to immunogenic proteins that have 97% homology to the consensus protein sequences as set forth in SEQ ID NO:4. Some embodiments relate to immunogenic proteins that have 98% homology to the consensus protein sequences as set forth in SEQ ID NO:4. Some embodiments relate to immunogenic proteins that have 99% homology to the consensus protein sequences as set forth in SEQ ID NO:4.

Some embodiments relate to proteins that are identical to SEQ ID NO:4. Some embodiments relate to immunogenic proteins that have an amino acid sequence that is 80% identical to the full length consensus amino acid sequences as set forth in SEQ ID NO:4. Some embodiments relate to immunogenic proteins that have an amino acid sequence that is 85% identical to the full length consensus amino acid sequences as set forth in SEQ ID NO:4. Some embodiments relate to immunogenic proteins that have an amino acid sequence that is 90% identical to the full length consensus amino acid sequences as set forth in SEQ ID NO:4. Some embodiments relate to immunogenic proteins that have an amino acid sequence that is 91% identical to the full length consensus amino acid sequences as set forth in SEQ ID NO:4. Some embodiments relate to immunogenic proteins that have an amino acid sequence that is 92% identical to the full length consensus amino acid sequences as set forth in SEQ ID NO:4. Some embodiments relate to immunogenic proteins that have an amino acid sequence that is 93% identical to the full length consensus amino acid sequences as set forth in SEQ ID NO:4. Some embodiments relate to immunogenic proteins that have an amino acid sequence that is 94% identical to the full length consensus amino acid sequences as set forth in SEQ ID NO:4. Some embodiments relate to immunogenic proteins that have an amino acid sequence that is 95% identical to the full length consensus amino acid sequences as set forth in SEQ ID NO:4. Some embodiments relate to immunogenic proteins that have an amino acid sequence that is 96% identical to the full length consensus amino acid sequences as set forth in SEQ ID NO:4. Some embodiments relate to immunogenic proteins that have an amino acid sequence that is 97% identical to the full length consensus amino acid sequences as set forth in SEQ ID NO:4. Some embodiments relate to immunogenic proteins that have an amino acid sequence that is 98% identical to the full length consensus amino acid sequences as set forth in SEQ ID NO:4. Some embodiments relate to immunogenic proteins that have an amino acid sequence that is 99% identical to the full length consensus amino acid sequences as set forth in SEQ ID NO:4.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus TYRP-1 protein. Immunogenic fragments of SEQ ID NO:4 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:4. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:4 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:4. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:4 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:4. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(3) Tyrosinase-Related Protein 2 (TYRP2)

The immunogenic composition of the present invention can comprise the cancer antigen tyrosinase-related Protein 2 (TYRP2; also known as dopachrome tautomerase (DCT)), a fragment thereof, or a variant thereof. TYRP2/DCT, encoded by the TYRP2/DCT gene, is a protein comprised of 519 amino acids and is expressed in both normal and malignant melanocytes and melanoma cells. TYRP2/DCT is a well-characterized melanocyte-specific enzyme that, in conjunction with tyrosinase and TYRP1, functions in the conversion of L-tyrosine to melanin in melanocytes. DCT specifically catalyses the tautomerization of the melanin precursors L-DOPAchrome to 5,6-dihydroindole-2-carboxylic acid (DHICA), which is subsequently oxidized by TYRP1 (as discussed above) to form eumelanin. Studies have shown that TYRP2/DCT may be a mediator of drug resistance in melanoma cells, with specificity for DNA-damaging agents. Since TYRP2/DCT has frequently been reported to be highly expressed in melanomas, this melanocyte-specific enzyme plays an important role contributing to intrinsic resistance phenotype of melanomas to various anticancer DNA-damaging drugs.

As described above for tyrosinase, tyrosinase-related protein 2 (TYRP-2) can also be involved in the synthesis of melanin and recognized by the immune system in subjects suffering from melanoma. Additionally, TYRP-2 can mediate drug resistance in melanoma cells. Accordingly, TYRP-2 can be an antigen associated with melanoma.

The TRYP-2 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The TYRP2 antigen can comprise protein epitopes that make them particularly effective as immunogens against which anti-TYRP2 immune responses can be induced. The TYRP2 antigen can comprise the full length translation product, a variant thereof, a fragment thereof or a combination thereof. The TYRP2 antigen can comprise a consensus protein.

The nucleic acid sequence encoding the consensus TYRP2 antigen can be optimized with regards to codon usage and corresponding RNA transcripts. The nucleic acid encoding the consensus TYRP2 antigen can be codon and RNA optimized for expression. In some embodiments, the nucleic acid sequence encoding the consensus TYRP2 antigen can include a Kozak sequence (e.g., GCC ACC) to increase the efficiency of translation. The nucleic acid encoding the consensus TYRP2 antigen can include multiple stop codons (e.g., TGA TGA) to increase the efficiency of translation termination.

The nucleic acid encoding the consensus TYRP2 antigen can also encode an immunoglobulin E (IgE) leader sequence. The nucleic acid encoding the consensus TYRP2 antigen can further encode the IgE leader sequence such that the amino acid sequence of the IgE leader sequence is linked to the amino acid sequence of the consensus TYRP2 antigen by a peptide bond. The nucleic encoding the consensus TYRP2 antigen can also include a nucleotide sequence encoding the IgE leader sequence. In some embodiments, the nucleic acid encoding the consensus TYRP2 antigen is free of or does not contain a nucleotide sequence encoding the IgE leader sequence.

The consensus TYRP2 antigen can be the nucleic acid sequence SEQ ID NO:5, which encodes for the amino acid sequence SEQ ID NO:6. SEQ ID NO:5 encodes the consensus TYRP2 protein linked to an IgE leader sequence. The consensus TYRP2 protein can be linked to the IgE leader sequence and an HA tag. In other embodiments, the consensus TYRP2 protein can be free of or not linked to an IgE leader sequence and/or an HA tag.

In some embodiments, the consensus TYRP2 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:5. In other embodiments, the consensus TYRP2 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6. The consensus TYRP2 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:6.

Some embodiments relate to nucleic acid sequences encoding proteins homologous to the TYRP2 consensus protein, immunogenic fragment of the TYRP2 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length TYRP2 consensus protein, immunogenic fragment of the TYRP2 consensus protein, and immunogenic fragments of proteins having identity to the TYRP2 consensus protein. Such nucleic acid molecules that encode immunogenic proteins that have up to 80% identity to a full length TYRP2 consensus sequence, up to 85% identity to a full length consensus sequence, up to 90% identity to a full length TYRP2 consensus sequence, up to 91% identity to a full length TYRP2 consensus sequence, up to 92% identity to a full length TYRP2 consensus sequence, up to 93% identity to a full length TYRP2 consensus sequence, up to 94% identity to a full length TYRP2 consensus sequence, up to 95% identity to a full length TYRP2 consensus sequence, up to 96% identity to a full length TYRP2 consensus sequence, up to 97% identity to a full length TYRP2 consensus sequence, up to 98% identity to a full length TYRP2 consensus sequence, and up to 99% identity to a full length TYRP2 consensus sequence can be provided. Likewise, nucleic acid sequences encoding the immunogenic fragments set forth herein and the immunogenic fragments of proteins with similar percent identities as indicated above to the TYRP2 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:5. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:5. Fragments can be at least 95%, at least 96%, at least 97%, at least 98%, or at least 99% homologous to fragments of SEQ ID NO:5. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:5. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:6 comprises the amino acid sequence of the consensus TYRP2 protein. The amino acid sequence of the consensus TYRP2 protein linked to an IgE leader is SEQ ID NO:6. The amino acid sequence of the consensus TYRP2 protein linked to the IgE leader may be linked to HA tag.

Some embodiments relate to proteins that are homologous to SEQ ID NO:6. Some embodiments relate to immunogenic proteins that have 95% homology to the consensus protein sequences as set forth in SEQ ID NO:6. Some embodiments relate to immunogenic proteins that have 96% homology to the consensus protein sequences as set forth in SEQ ID NO:6. Some embodiments relate to immunogenic proteins that have 97% homology to the consensus protein sequences as set forth in SEQ ID NO:6. Some embodiments relate to immunogenic proteins that have 98% homology to the consensus protein sequences as set forth in SEQ ID NO:6. Some embodiments relate to immunogenic proteins that have 99% homology to the consensus protein sequences as set forth in SEQ ID NO:6.

Some embodiments relate to proteins that are identical to SEQ ID NO:6. Some embodiments relate to immunogenic proteins that have an amino acid sequence that is 80% identical to the full length consensus amino acid sequences as set forth in SEQ ID NO:6. Some embodiments relate to immunogenic proteins that have an amino acid sequence that is 85% identical to the full length consensus amino acid sequences as set forth in SEQ ID NO:6. Some embodiments relate to immunogenic proteins that have an amino acid sequence that is 90% identical to the full length consensus amino acid sequences as set forth in SEQ ID NO:6. Some embodiments relate to immunogenic proteins that have an amino acid sequence that is 91% identical to the full length consensus amino acid sequences as set forth in SEQ ID NO:6. Some embodiments relate to immunogenic proteins that have an amino acid sequence that is 92% identical to the full length consensus amino acid sequences as set forth in SEQ ID NO:6. Some embodiments relate to immunogenic proteins that have an amino acid sequence that is 93% identical to the full length consensus amino acid sequences as set forth in SEQ ID NO:6. Some embodiments relate to immunogenic proteins that have an amino acid sequence that is 94% identical to the full length consensus amino acid sequences as set forth in SEQ ID NO:6. Some embodiments relate to immunogenic proteins that have an amino acid sequence that is 95% identical to the full length consensus amino acid sequences as set forth in SEQ ID NO:6. Some embodiments relate to immunogenic proteins that have an amino acid sequence that is 96% identical to the full length consensus amino acid sequences as set forth in SEQ ID NO:6. Some embodiments relate to immunogenic proteins that have an amino acid sequence that is 97% identical to the full length consensus amino acid sequences as set forth in SEQ ID NO:6. Some embodiments relate to immunogenic proteins that have an amino acid sequence that is 98% identical to the full length consensus amino acid sequences as set forth in SEQ ID NO:6. Some embodiments relate to immunogenic proteins that have an amino acid sequence that is 99% identical to the full length consensus amino acid sequences as set forth in SEQ ID NO:6.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:6 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:6 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:6. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:6 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(4) Melanoma-Associated Antigen 4 (MAGEA4)

The immunogenic composition of the present invention can comprise the cancer antigen Melanoma-associated Antigen 4 (MAGEA4), a fragment thereof, or a variant thereof. MAGEA4, encoded by the MAGEA4 gene, is a protein comprised of 317 amino acids and is expressed in male germ cells and tumor cells of various histological types such as gastrointestinal, esophageal and pulmonary carcinomas. MAGEA4 binds the oncoprotein, Gankyrin. This MAGEA4 specific binding is mediated by its C-terminus. Studies have shown that exogenous MAGEA4 can partly inhibit the adhesion-independent growth of Gankyrin-overexpressing cells in vitro and suppress the formation of migrated tumors from these cells in nude mice. This inhibition is dependent upon binding between MAGEA4 and Gankyrin, suggesting that interactions between Gankyrin and MAGEA4 inhibit Gankyrin-mediated carcinogenesis. It is likely that MAGE expression in tumor tissue is not a cause, but a result of tumor genesis, and MAGE genes take part in the immune process by targeting early tumor cells for destruction.

Melanoma-associated antigen 4 protein (MAGEA4) can be involved in embryonic development and tumor transformation and/or progression. MAGEA4 is normally expressed in testes and placenta. MAGEA4, however, can be expressed in many different types of tumors, for example, melanoma, head and neck squamous cell carcinoma, lung carcinoma, and breast carcinoma. Accordingly, MAGEA4 can be antigen associated with a variety of tumors.

The MAGEA4 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The MAGEA4 antigen can comprise protein epitopes that make them particularly effective as immunogens against which anti-MAGEA4 immune responses can be induced. The MAGEA4 antigen can comprise the full length translation product, a variant thereof, a fragment thereof or a combination thereof. The MAGEA4 antigen can comprise a consensus protein.

The nucleic acid sequence encoding the consensus MAGEA4 antigen can be optimized with regards to codon usage and corresponding RNA transcripts. The nucleic acid encoding the consensus MAGEA4 antigen can be codon and RNA optimized for expression. In some embodiments, the nucleic acid sequence encoding the consensus MAGEA4 antigen can include a Kozak sequence (e.g., GCC ACC) to increase the efficiency of translation. The nucleic acid encoding the consensus MAGEA4 antigen can include multiple stop codons (e.g., TGA TGA) to increase the efficiency of translation termination.

The nucleic acid encoding the consensus MAGEA4 antigen can also encode an immunoglobulin E (IgE) leader sequence. The nucleic acid encoding the consensus Tyr antigen can further encode the IgE leader sequence such that the amino acid sequence of the IgE leader sequence is linked to the amino acid sequence of the consensus MAGEA4 antigen by a peptide bond. The nucleic encoding the consensus MAGEA4 antigen can also include a nucleotide sequence encoding the IgE leader sequence. In some embodiments, the nucleic acid encoding the consensus MAGEA4 antigen is free of or does not contain a nucleotide sequence encoding the IgE leader sequence.

The consensus MAGEA4 antigen can be the nucleic acid sequence SEQ ID NO:7, which encodes for the amino acid sequence SEQ ID NO:8. SEQ ID NO:7 encodes the consensus MAGEA4 protein linked to an IgE leader sequence. The consensus MAGEA4 protein can be linked to the IgE leader sequence and an HA tag. In other embodiments, the consensus MAGEA4 protein can be free of or not linked to an IgE leader sequence and/or an HA tag.

In some embodiments, the consensus MAGEA4 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:7. In other embodiments, the consensus MAGEA4 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8. The consensus MAGEA4 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:8.

Some embodiments relate to nucleic acid sequences encoding proteins homologous to the MAGEA4 consensus protein, immunogenic fragment of the MAGEA4 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length MAGEA4 consensus protein, immunogenic fragment of the MAGEA4 consensus protein, and immunogenic fragments of proteins having identity to the MAGEA4 consensus protein. Such nucleic acid molecules that encode immunogenic proteins that have up to 80% identity to a full length MAGEA4 consensus sequence, up to 85% identity to a full length consensus sequence, up to 90% identity to a full length MAGEA4 consensus sequence, up to 91% identity to a full length MAGEA4 consensus sequence, up to 92% identity to a full length MAGEA4 consensus sequence, up to 93% identity to a full length MAGEA4 consensus sequence, up to 94% identity to a full length MAGEA4 consensus sequence, up to 95% identity to a full length MAGEA4 consensus sequence, up to 96% identity to a full length MAGEA4 consensus sequence, up to 97% identity to a full length MAGEA4 consensus sequence, up to 98% identity to a full length MAGEA4 consensus sequence, and up to 99% identity to a full length MAGEA4 consensus sequence can be provided. Likewise, nucleic acid sequences encoding the immunogenic fragments set forth herein and the immunogenic fragments of proteins with similar percent identities as indicated above to the MAGEA4 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:7. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:7. Fragments can be at least 95%, at least 96%, at least 97%, at least 98%, or at least 99% homologous to fragments of SEQ ID NO:7. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:7. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:8 comprises the amino acid sequence of the consensus MAGEA4 protein. The amino acid sequence of the consensus MAGEA4 protein linked to an IgE leader is SEQ ID NO:8. The amino acid sequence of the consensus MAGEA4 protein linked to the IgE leader may be linked to HA tag.

Some embodiments relate to proteins that are homologous to SEQ ID NO:8. Some embodiments relate to immunogenic proteins that have 95% homology to the consensus protein sequences as set forth in SEQ ID NO:8. Some embodiments relate to immunogenic proteins that have 96% homology to the consensus protein sequences as set forth in SEQ ID NO:8. Some embodiments relate to immunogenic proteins that have 97% homology to the consensus protein sequences as set forth in SEQ ID NO:8. Some embodiments relate to immunogenic proteins that have 98% homology to the consensus protein sequences as set forth in SEQ ID NO:8. Some embodiments relate to immunogenic proteins that have 99% homology to the consensus protein sequences as set forth in SEQ ID NO:8.

Some embodiments relate to proteins that are identical to SEQ ID NO:8. Some embodiments relate to immunogenic proteins that have an amino acid sequence that is 80% identical to the full length consensus amino acid sequences as set forth in SEQ ID NO:8. Some embodiments relate to immunogenic proteins that have an amino acid sequence that is 85% identical to the full length consensus amino acid sequences as set forth in SEQ ID NO:8. Some embodiments relate to immunogenic proteins that have an amino acid sequence that is 90% identical to the full length consensus amino acid sequences as set forth in SEQ ID NO:8. Some embodiments relate to immunogenic proteins that have an amino acid sequence that is 91% identical to the full length consensus amino acid sequences as set forth in SEQ ID NO:8. Some embodiments relate to immunogenic proteins that have an amino acid sequence that is 92% identical to the full length consensus amino acid sequences as set forth in SEQ ID NO:8. Some embodiments relate to immunogenic proteins that have an amino acid sequence that is 93% identical to the full length consensus amino acid sequences as set forth in SEQ ID NO:8. Some embodiments relate to immunogenic proteins that have an amino acid sequence that is 94% identical to the full length consensus amino acid sequences as set forth in SEQ ID NO:8. Some embodiments relate to immunogenic proteins that have an amino acid sequence that is 95% identical to the full length consensus amino acid sequences as set forth in SEQ ID NO:8. Some embodiments relate to immunogenic proteins that have an amino acid sequence that is 96% identical to the full length consensus amino acid sequences as set forth in SEQ ID NO:8. Some embodiments relate to immunogenic proteins that have an amino acid sequence that is 97% identical to the full length consensus amino acid sequences as set forth in SEQ ID NO:8. Some embodiments relate to immunogenic proteins that have an amino acid sequence that is 98% identical to the full length consensus amino acid sequences as set forth in SEQ ID NO:8. Some embodiments relate to immunogenic proteins that have an amino acid sequence that is 99% identical to the full length consensus amino acid sequences as set forth in SEQ ID NO:8.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:8 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:8. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:8 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:8. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:8 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:8. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(5) Growth Hormone Releasing Hormone (GHRH)

The immunogenic composition of the present invention can comprise the cancer antigen growth hormone releasing hormone (GHRH; also known as growth-hormone-releasing factor (GRF or GHRF) or somatocrinin), a fragment thereof, or a variant thereof. GHRH is a 44 amino acid peptide hormone produced in the arcuate nucleus of the hypothalamus. GHRH is secreted by the hypothalamus and stimulates the release of growth hormone, a regulator of growth, metabolism, and body structure, from the pituitary gland. GHRH also stimulates the product of growth hormone. Antagonists of GHRH can inhibit the growth of a variety of cancers, for example, osteosarcomas, glioblastomas, prostate cancer, renal cancer, pancreatic cancer, colorectal cancer, and breast cancer. Accordingly, GHRH can be an antigen associated with a variety of tumors.

The GHRH antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The GHRH antigen can comprise protein epitopes that make them particularly effective as immunogens against which anti-GHRH immune responses can be induced. The GHRH antigen can comprise the full length translation product, a variant thereof, a fragment thereof or a combination thereof. The GHRH antigen can comprise a consensus protein.

The nucleic acid sequence encoding the consensus GHRH antigen can be optimized with regards to codon usage and corresponding RNA transcripts. The nucleic acid encoding the consensus GHRH antigen can be codon and RNA optimized for expression. In some embodiments, the nucleic acid sequence encoding the consensus GHRH antigen can include a Kozak sequence (e.g., GCC ACC) to increase the efficiency of translation. The nucleic acid encoding the consensus GHRH antigen can include multiple stop codons (e.g., TGA TGA) to increase the efficiency of translation termination.

The nucleic acid encoding the consensus GHRH antigen can also encode an immunoglobulin E (IgE) leader sequence. The nucleic acid encoding the consensus GHRH antigen can further encode the IgE leader sequence such that the amino acid sequence of the IgE leader sequence is linked to the amino acid sequence of the consensus GHRH antigen by a peptide bond. The nucleic encoding the consensus GHRH antigen can also include a nucleotide sequence encoding the IgE leader sequence. In some embodiments, the nucleic acid encoding the consensus GHRH antigen is free of or does not contain a nucleotide sequence encoding the IgE leader sequence.

The consensus GHRH antigen can be the nucleic acid sequence SEQ ID NO:9, which encodes for the amino acid sequence SEQ ID NO:10. SEQ ID NO:9 encodes the consensus GHRH protein linked to an IgE leader sequence. The consensus GHRH protein can be linked to the IgE leader sequence and an HA tag. In other embodiments, the consensus GHRH protein can be free of or not linked to an IgE leader sequence and/or an HA tag.

In some embodiments, the consensus GHRH antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:9. In other embodiments, the consensus GHRH antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10. The consensus GHRH antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:10.

Some embodiments relate to nucleic acid sequences encoding proteins homologous to the GHRH consensus protein, immunogenic fragment of the GHRH consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length GHRH consensus protein, immunogenic fragment of the GHRH consensus protein, and immunogenic fragments of proteins having identity to the GHRH consensus protein. Such nucleic acid molecules that encode immunogenic proteins that have up to 80% identity to a full length GHRH consensus sequence, up to 85% identity to a full length consensus sequence, up to 90% identity to a full length GHRH consensus sequence, up to 91% identity to a full length GHRH consensus sequence, up to 92% identity to a full length GHRH consensus sequence, up to 93% identity to a full length GHRH consensus sequence, up to 94% identity to a full length GHRH consensus sequence, up to 95% identity to a full length GHRH consensus sequence, up to 96% identity to a full length GHRH consensus sequence, up to 97% identity to a full length GHRH consensus sequence, up to 98% identity to a full length GHRH consensus sequence, and up to 99% identity to a full length GHRH consensus sequence can be provided. Likewise, nucleic acid sequences encoding the immunogenic fragments set forth herein and the immunogenic fragments of proteins with similar percent identities as indicated above to the GHRH proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:9. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:9. Fragments can be at least 95%, at least 96%, at least 97%, at least 98%, or at least 99% homologous to fragments of SEQ ID NO:9. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:9. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:10 comprises the amino acid sequence of the consensus GHRH protein. The amino acid sequence of the consensus GHRH protein linked to an IgE leader is SEQ ID NO:10. The amino acid sequence of the consensus GHRH protein linked to the IgE leader may be linked to HA tag.

Some embodiments relate to proteins that are homologous to SEQ ID NO:10. Some embodiments relate to immunogenic proteins that have 95% homology to the consensus protein sequences as set forth in SEQ ID NO:10. Some embodiments relate to immunogenic proteins that have 96% homology to the consensus protein sequences as set forth in SEQ ID NO:10. Some embodiments relate to immunogenic proteins that have 97% homology to the consensus protein sequences as set forth in SEQ ID NO:10. Some embodiments relate to immunogenic proteins that have 98% homology to the consensus protein sequences as set forth in SEQ ID NO:10. Some embodiments relate to immunogenic proteins that have 99% homology to the consensus protein sequences as set forth in SEQ ID NO:10.

Some embodiments relate to proteins that are identical to SEQ ID NO:10. Some embodiments relate to immunogenic proteins that have an amino acid sequence that is 80% identical to the full length consensus amino acid sequences as set forth in SEQ ID NO: 10. Some embodiments relate to immunogenic proteins that have an amino acid sequence that is 85% identical to the full length consensus amino acid sequences as set forth in SEQ ID NO: 10. Some embodiments relate to immunogenic proteins that have an amino acid sequence that is 90% identical to the full length consensus amino acid sequences as set forth in SEQ ID NO: 10. Some embodiments relate to immunogenic proteins that have an amino acid sequence that is 91% identical to the full length consensus amino acid sequences as set forth in SEQ ID NO:10. Some embodiments relate to immunogenic proteins that have an amino acid sequence that is 92% identical to the full length consensus amino acid sequences as set forth in SEQ ID NO: 10. Some embodiments relate to immunogenic proteins that have an amino acid sequence that is 93% identical to the full length consensus amino acid sequences as set forth in SEQ ID NO: 10. Some embodiments relate to immunogenic proteins that have an amino acid sequence that is 94% identical to the full length consensus amino acid sequences as set forth in SEQ ID NO: 10. Some embodiments relate to immunogenic proteins that have an amino acid sequence that is 95% identical to the full length consensus amino acid sequences as set forth in SEQ ID NO:10. Some embodiments relate to immunogenic proteins that have an amino acid sequence that is 96% identical to the full length consensus amino acid sequences as set forth in SEQ ID NO: 10. Some embodiments relate to immunogenic proteins that have an amino acid sequence that is 97% identical to the full length consensus amino acid sequences as set forth in SEQ ID NO: 10. Some embodiments relate to immunogenic proteins that have an amino acid sequence that is 98% identical to the full length consensus amino acid sequences as set forth in SEQ ID NO: 10. Some embodiments relate to immunogenic proteins that have an amino acid sequence that is 99% identical to the full length consensus amino acid sequences as set forth in SEQ ID NO:10.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:10 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO: 10. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:10 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO: 10. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:10 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO: 10. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(6) MART-1/Melan-A

The immunogenic composition of the present invention can comprise the cancer antigen MART-1 (also known as Melan-A), a fragment thereof, or a variant thereof. MART-1, encoded by MLANA gene, is a 118-amino acid protein containing a single transmembrane domain and is expressed in most melanoma cells. MART-1 forms a complex with a structural protein and affects its expression, stability, trafficking and processing which is required for melanosome structure and maturation. Accordingly, MART-1 is indispensable for regulating mammalian pigmentation. Defects in melanosome maturation have been linked to susceptibility to cancer. MART-1 may be expressed in numerous cancers, including, but not limited to, melanomas.

Melan-A, also known as melanoma antigen recognized by T cells (MART-1) is a melanocyte differentiation antigen and can be found in normal skin, retina, and melanocytes. Melan-a can be associated with the endoplasmic reticulum and melanosomes. Melan-A can be recognized by cytotoxic T cells as an antigen on melanoma cells, but can also be associated with other tumors having melanocytic origin or differentiation (i.e., cells have melansomes), for example, clear cell sarcoma and melanotic neurofibroma. Accordingly, Melan-A can be antigen associated with a variety of tumors derived from cells having melanosomes.

The Melan-A antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The Melan-A antigen can comprise protein epitopes that make them particularly effective as immunogens against which anti-Melan-A immune responses can be induced. The Melan-A antigen can comprise the full length translation product, a variant thereof, a fragment thereof or a combination thereof. The Melan-A antigen can comprise a consensus protein.

The nucleic acid sequence encoding the consensus Melan-A antigen can be optimized with regards to codon usage and corresponding RNA transcripts. The nucleic acid encoding the consensus Melan-A antigen can be codon and RNA optimized for expression. In some embodiments, the nucleic acid sequence encoding the consensus Melan-A antigen can include a Kozak sequence (e.g., GCC ACC) to increase the efficiency of translation. The nucleic acid encoding the consensus Melan-A antigen can include multiple stop codons (e.g., TGA TGA) to increase the efficiency of translation termination.

The nucleic acid encoding the consensus Melan-A antigen can also encode an immunoglobulin E (IgE) leader sequence. The nucleic acid encoding the consensus Melan-A antigen can further encode the IgE leader sequence such that the amino acid sequence of the IgE leader sequence is linked to the amino acid sequence of the consensus Melan-A antigen by a peptide bond. The nucleic encoding the consensus Melan-A antigen can also include a nucleotide sequence encoding the IgE leader sequence. In some embodiments, the nucleic acid encoding the consensus Melan-A antigen is free of or does not contain a nucleotide sequence encoding the IgE leader sequence.

The consensus Melan-A antigen can be the nucleic acid sequence SEQ ID NO: 11, which encodes for the amino acid sequence SEQ ID NO:12. SEQ ID NO:11 encodes the consensus MELAN-A protein linked to an IgE leader sequence. The consensus Melan-A protein can be linked to the IgE leader sequence and an HA tag. In other embodiments, the consensus Melan-A protein can be free of or not linked to an IgE leader sequence and/or an HA tag.

In some embodiments, the consensus Melan-A antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:11. In other embodiments, the consensus Melan-A antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12. The consensus Melan-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:12.

Some embodiments relate to nucleic acid sequences encoding proteins homologous to the Melan-A consensus protein, immunogenic fragment of the Melan-A consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length Melan-A consensus protein, immunogenic fragment of the Melan-A consensus protein, and immunogenic fragments of proteins having identity to the Melan-A consensus protein. Such nucleic acid molecules that encode immunogenic proteins that have up to 80% identity to a full length Melan-A consensus sequence, up to 85% identity to a full length Melan-A consensus sequence, up to 90% identity to a full length Melan-A consensus sequence, up to 91% identity to a full length Melan-A consensus sequence, up to 92% identity to a full length Melan-A consensus sequence, up to 93% identity to a full length Melan-A consensus sequence, up to 94% identity to a full length Melan-A consensus sequence, up to 95% identity to a full length Melan-A consensus sequence, up to 96% identity to a full length Melan-A consensus sequence, up to 97% identity to a full length Melan-A consensus sequence, up to 98% identity to a full length Melan-A consensus sequence, and up to 99% identity to a full length Melan-A consensus sequence can be provided. Likewise, nucleic acid sequences encoding the immunogenic fragments set forth herein and the immunogenic fragments of proteins with similar percent identities as indicated above to the Melan-A proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:11. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 11. Fragments can be at least 95%, at least 96%, at least 97%, at least 98%, or at least 99% homologous to fragments of SEQ ID NO:11. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:11. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:12 comprises the amino acid sequence of the consensus Melan-A protein. The amino acid sequence of the consensus Melan-A protein linked to an IgE leader is SEQ ID NO:12. The amino acid sequence of the consensus Melan-A protein linked to the IgE leader may be linked to HA tag.

Some embodiments relate to proteins that are homologous to SEQ ID NO:12. Some embodiments relate to immunogenic proteins that have 95% homology to the consensus protein sequences as set forth in SEQ ID NO:12. Some embodiments relate to immunogenic proteins that have 96% homology to the consensus protein sequences as set forth in SEQ ID NO:12. Some embodiments relate to immunogenic proteins that have 97% homology to the consensus protein sequences as set forth in SEQ ID NO:12. Some embodiments relate to immunogenic proteins that have 98% homology to the consensus protein sequences as set forth in SEQ ID NO:12. Some embodiments relate to immunogenic proteins that have 99% homology to the consensus protein sequences as set forth in SEQ ID NO:12.

Some embodiments relate to proteins that are identical to SEQ ID NO:12. Some embodiments relate to immunogenic proteins that have an amino acid sequence that is 80% identical to the full length consensus amino acid sequences as set forth in SEQ ID NO: 12. Some embodiments relate to immunogenic proteins that have an amino acid sequence that is 85% identical to the full length consensus amino acid sequences as set forth in SEQ ID NO: 12. Some embodiments relate to immunogenic proteins that have an amino acid sequence that is 90% identical to the full length consensus amino acid sequences as set forth in SEQ ID NO: 12. Some embodiments relate to immunogenic proteins that have an amino acid sequence that is 91% identical to the full length consensus amino acid sequences as set forth in SEQ ID NO: 12. Some embodiments relate to immunogenic proteins that have an amino acid sequence that is 92% identical to the full length consensus amino acid sequences as set forth in SEQ ID NO: 12. Some embodiments relate to immunogenic proteins that have an amino acid sequence that is 93% identical to the full length consensus amino acid sequences as set forth in SEQ ID NO: 12. Some embodiments relate to immunogenic proteins that have an amino acid sequence that is 94% identical to the full length consensus amino acid sequences as set forth in SEQ ID NO: 12. Some embodiments relate to immunogenic proteins that have an amino acid sequence that is 95% identical to the full length consensus amino acid sequences as set forth in SEQ ID NO: 12. Some embodiments relate to immunogenic proteins that have an amino acid sequence that is 96% identical to the full length consensus amino acid sequences as set forth in SEQ ID NO: 12. Some embodiments relate to immunogenic proteins that have an amino acid sequence that is 97% identical to the full length consensus amino acid sequences as set forth in SEQ ID NO: 12. Some embodiments relate to immunogenic proteins that have an amino acid sequence that is 98% identical to the full length consensus amino acid sequences as set forth in SEQ ID NO: 12. Some embodiments relate to immunogenic proteins that have an amino acid sequence that is 99% identical to the full length consensus amino acid sequences as set forth in SEQ ID NO:12.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:12 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO: 12. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:12 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:12. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:12 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO: 12. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(7) NY-ESO-1

The immunogenic composition of the present invention can comprise the cancer antigen New York-esophageal cancer-1 (NY-ESO-1; also called CTAG1), a fragment thereof, or a variant thereof. NY-ESO-1, encoded by the CTAG1B gene, is a 180 amino-acid long protein, with a glycine-rich N-terminal region and an extremely hydrophobic C-terminal region. NY-ESO-1 has restricted expression in normal tissues but frequent occurrence in cancer. NY-ESO-1 may be expressed in numerous cancers including, but not limited to, bladder, colorectal, esophagus, gastric, hepatocarcinoma, head and neck, melanoma, non-small cell lung, ovarian, pancreatic, synovial carcinoma and prostate cancers.

Cancer-testis antigen (NY-ESO-1) can be expressed in the testis and ovary. NY-ESO-1 can be associated with a variety of cancers and can induce humoral immune responses. Subjects suffering from cancer or tumors can develop immunogenicity to NY-ESO-1. Accordingly, NY-ESO-1 can be an antigen associated with a variety of tumors.

The NY-ESO-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The NY-ESO-1 antigen can increase a cellular immune response in a subject administered the NY-ESO-1 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the NY-ESO-1 antigen. In some embodiments the NY-ESO-1 antigen can increase the cellular immune response in the subject administered the NY-ESO-1 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the NY-ESO-1 antigen.

The NY-ESO-1 antigen can increase interferon gamma (IFN-γ) levels in a subject administered the NY-ESO-1 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the NY-ESO-1 antigen. In some embodiments, the NY-ESO-1 antigen can increase IFN-γ levels in the subject administered the NY-ESO-1 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the NY-ESO-1 antigen.

The NY-ESO-1 antigen can comprise protein epitopes that make them particularly effective as immunogens against which anti-NY-ESO-1 immune responses can be induced. The NY-ESO-1 antigen can comprise the full length translation product, a variant thereof, a fragment thereof or a combination thereof. The NY-ESO-1 antigen can comprise a consensus protein.

The nucleic acid sequence encoding the consensus NY-ESO-1 antigen can be optimized with regards to codon usage and corresponding RNA transcripts. The nucleic acid encoding the consensus NY-ESO-1 antigen can be codon and RNA optimized for expression. In some embodiments, the nucleic acid sequence encoding the consensus NY-ESO-1 antigen can include a Kozak sequence (e.g., GCC ACC) to increase the efficiency of translation. The nucleic acid encoding the consensus NY-ESO-1 antigen can include multiple stop codons (e.g., TGA TGA) to increase the efficiency of translation termination.

The nucleic acid encoding the consensus NY-ESO-1 antigen can also encode an immunoglobulin E (IgE) leader sequence. The nucleic acid encoding the consensus NY-ESO-1 antigen can further encode the IgE leader sequence such that the amino acid sequence of the IgE leader sequence is linked to the amino acid sequence of the consensus NY-ESO-1 antigen by a peptide bond. The nucleic encoding the consensus NY-ESO-1 antigen can also include a nucleotide sequence encoding the IgE leader sequence. In some embodiments, the nucleic acid encoding the consensus NY-ESO-1 antigen is free of or does not contain a nucleotide sequence encoding the IgE leader sequence.

The consensus NY-ESO-1 antigen can be the nucleic acid sequence SEQ ID NO: 13, which encodes for the amino acid sequence SEQ ID NO:14. SEQ ID NO:13 encodes the consensus NY-ESO-1 protein linked to an IgE leader sequence. The consensus NY-ESO-1 protein can be linked to the IgE leader sequence and an HA tag. In other embodiments, the consensus NY-ESO-1 protein can be free of or not linked to an IgE leader sequence and/or an HA tag.

In some embodiments, the consensus NY-ESO-1 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:13. In other embodiments, the consensus NY-ESO-1 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:14. The consensus NY-ESO-1 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:14.

Some embodiments relate to nucleic acid sequences encoding proteins homologous to the NY-ESO-1 consensus protein, immunogenic fragment of the NY-ESO-1 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length NY-ESO-1 consensus protein, immunogenic fragment of the NY-ESO-1 consensus protein, and immunogenic fragments of proteins having identity to the NY-ESO-1 consensus protein. Such nucleic acid molecules that encode immunogenic proteins that have up to 80% identity to a full length NY-ESO-1 consensus sequence, up to 85% identity to a full length consensus sequence, up to 90% identity to a full length NY-ESO-1 consensus sequence, up to 91% identity to a full length NY-ESO-1 consensus sequence, up to 92% identity to a full length NY-ESO-1 consensus sequence, up to 93% identity to a full length NY-ESO-1 consensus sequence, up to 94% identity to a full length NY-ESO-1 consensus sequence, up to 95% identity to a full length NY-ESO-1 consensus sequence, up to 96% identity to a full length NY-ESO-1 consensus sequence, up to 97% identity to a full length NY-ESO-1 consensus sequence, up to 98% identity to a full length NY-ESO-1 consensus sequence, and up to 99% identity to a full length NY-ESO-1 consensus sequence can be provided. Likewise, nucleic acid sequences encoding the immunogenic fragments set forth herein and the immunogenic fragments of proteins with similar percent identities as indicated above to the NY-ESO-1 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:13. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 13. Fragments can be at least 95%, at least 96%, at least 97%, at least 98%, or at least 99% homologous to fragments of SEQ ID NO:13. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:13. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:14 comprises the amino acid sequence of the consensus NY-ESO-1. The amino acid sequence of the consensus NY-ESO-1 protein linked to an IgE leader is SEQ ID NO: 14. The amino acid sequence of the consensus NY-ESO-1 protein linked to the IgE leader may be linked to HA tag.

Some embodiments relate to proteins that are homologous to SEQ ID NO:14. Some embodiments relate to immunogenic proteins that have 95% homology to the consensus protein sequences as set forth in SEQ ID NO:14. Some embodiments relate to immunogenic proteins that have 96% homology to the consensus protein sequences as set forth in SEQ ID NO:14. Some embodiments relate to immunogenic proteins that have 97% homology to the consensus protein sequences as set forth in SEQ ID NO:14. Some embodiments relate to immunogenic proteins that have 98% homology to the consensus protein sequences as set forth in SEQ ID NO:14. Some embodiments relate to immunogenic proteins that have 99% homology to the consensus protein sequences as set forth in SEQ ID NO:14.

Some embodiments relate to proteins that are identical to SEQ ID NO:14. Some embodiments relate to immunogenic proteins that have an amino acid sequence that is 80% identical to the full length consensus amino acid sequences as set forth in SEQ ID NO: 14. Some embodiments relate to immunogenic proteins that have an amino acid sequence that is 85% identical to the full length consensus amino acid sequences as set forth in SEQ ID NO: 14. Some embodiments relate to immunogenic proteins that have an amino acid sequence that is 90% identical to the full length consensus amino acid sequences as set forth in SEQ ID NO: 14. Some embodiments relate to immunogenic proteins that have an amino acid sequence that is 91% identical to the full length consensus amino acid sequences as set forth in SEQ ID NO: 14. Some embodiments relate to immunogenic proteins that have an amino acid sequence that is 92% identical to the full length consensus amino acid sequences as set forth in SEQ ID NO: 14. Some embodiments relate to immunogenic proteins that have an amino acid sequence that is 93% identical to the full length consensus amino acid sequences as set forth in SEQ ID NO: 14. Some embodiments relate to immunogenic proteins that have an amino acid sequence that is 94% identical to the full length consensus amino acid sequences as set forth in SEQ ID NO: 14. Some embodiments relate to immunogenic proteins that have an amino acid sequence that is 95% identical to the full length consensus amino acid sequences as set forth in SEQ ID NO:14. Some embodiments relate to immunogenic proteins that have an amino acid sequence that is 96% identical to the full length consensus amino acid sequences as set forth in SEQ ID NO: 14. Some embodiments relate to immunogenic proteins that have an amino acid sequence that is 97% identical to the full length consensus amino acid sequences as set forth in SEQ ID NO: 14. Some embodiments relate to immunogenic proteins that have an amino acid sequence that is 98% identical to the full length consensus amino acid sequences as set forth in SEQ ID NO: 14. Some embodiments relate to immunogenic proteins that have an amino acid sequence that is 99% identical to the full length consensus amino acid sequences as set forth in SEQ ID NO:14.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:14 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:14. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:14 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:14. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:14 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO: 14. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(8) NY-ESO-2

The immunogenic composition of the present invention can comprise the cancer antigen New York-esophageal cancer-2 (NY-ESO-2; also known as cancer/testis antigen 2, ESO2, and LAGE1), a fragment thereof, or a variant thereof. NY-ESO-2 is an autoimmunogenic tumor antigen that belongs to the ESO/LAGE family of cancer-testis antigens. NY-ESO-2 can be expressed in a variety of cancers including melanoma, breast cancer, bladder cancer and prostate cancer and is normally expressed in testis tissue. Additionally, NY-ESO-2 can be observed in 25-50% of tumor samples of melanomas, non-small-cell lung carcinomas, bladder, prostate and head and neck cancers. The gene encoding NY-ESO-2 also contains an alternative open reading frame that encodes the protein named CAMEL, a tumor antigen that is recognized by melanoma-specific cytotoxic T-lymphocytes.

Similar to NY-ESO-1, NY-ESO-2 can be expressed in the testis and ovary. NY-ESO-2 can also be associated with a variety of cancers and immunogenic in subjects suffering from cancer or tumors. Accordingly, NY-ESO-2 can be an antigen associated with numerous tumors.

The NY-ESO-2 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The NY-ESO-2 antigen can increase a cellular immune response in a subject administered the NY-ESO-2 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the NY-ESO-2 antigen. In some embodiments the NY-ESO-2 antigen can increase the cellular immune response in the subject administered the NY-ESO-2 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the NY-ESO-2 antigen.

The NY-ESO-2 antigen can increase interferon gamma (IFN-γ) levels in a subject administered the NY-ESO-2 antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the NY-ESO-2 antigen. In some embodiments, the NY-ESO-2 antigen can increase IFN-γ levels in the subject administered the NY-ESO-2 antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the NY-ESO-2 antigen.

The NY-ESO-2 antigen can comprise protein epitopes that make them particularly effective as immunogens against which anti-NY-ESO-2 immune responses can be induced. The NY-ESO-2 antigen can comprise the full length translation product, a variant thereof, a fragment thereof or a combination thereof. The NY-ESO-2 antigen can comprise a consensus protein.

The nucleic acid sequence encoding the consensus NY-ESO-2 antigen can be optimized with regards to codon usage and corresponding RNA transcripts. The nucleic acid encoding the consensus NY-ESO-2 antigen can be codon and RNA optimized for expression. In some embodiments, the nucleic acid sequence encoding the consensus NY-ESO-2 antigen can include a Kozak sequence (e.g., GCC ACC) to increase the efficiency of translation. The nucleic acid encoding the consensus NY-ESO-2 antigen can include multiple stop codons (e.g., TGA TGA) to increase the efficiency of translation termination.

The nucleic acid encoding the consensus NY-ESO-2 antigen can also encode an immunoglobulin E (IgE) leader sequence. The nucleic acid encoding the consensus NY-ESO-2 antigen can further encode the IgE leader sequence such that the amino acid sequence of the IgE leader sequence is linked to the amino acid sequence of the consensus NY-ESO-2 antigen by a peptide bond. The nucleic encoding the consensus NY-ESO-2 antigen can also include a nucleotide sequence encoding the IgE leader sequence. In some embodiments, the nucleic acid encoding the consensus NY-ESO-2 antigen is free of or does not contain a nucleotide sequence encoding the IgE leader sequence.

The consensus NY-ESO-2 antigen can be the nucleic acid sequence SEQ ID NO: 15, which encodes for the amino acid sequence SEQ ID NO:16. SEQ ID NO:1 encodes the consensus NY-ESO-2 protein linked to an IgE leader sequence. The consensus NY-ESO-2 protein can be linked to the IgE leader sequence and an HA tag. In other embodiments, the consensus NY-ESO-2 protein can be free of or not linked to an IgE leader sequence and/or an HA tag.

In some embodiments, the consensus NY-ESO-2 antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:15. In other embodiments, the consensus NY-ESO-2 antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:16. The consensus NY-ESO-2 antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:16.

Some embodiments relate to nucleic acid sequences encoding proteins homologous to the NY-ESO-2 consensus protein, immunogenic fragment of the NY-ESO-2 consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length NY-ESO-2 consensus protein, immunogenic fragment of the NY-ESO-2 consensus protein, and immunogenic fragments of proteins having identity to the NY-ESO-2 consensus protein. Such nucleic acid molecules that encode immunogenic proteins that have up to 80% identity to a full length NY-ESO-2 consensus sequence, up to 85% identity to a full length consensus sequence, up to 90% identity to a full length NY-ESO-2 consensus sequence, up to 91% identity to a full length NY-ESO-2 consensus sequence, up to 92% identity to a full length NY-ESO-2 consensus sequence, up to 93% identity to a full length NY-ESO-2 consensus sequence, up to 94% identity to a full length NY-ESO-2 consensus sequence, up to 95% identity to a full length NY-ESO-2 consensus sequence, up to 96% identity to a full length NY-ESO-2 consensus sequence, up to 97% identity to a full length NY-ESO-2 consensus sequence, up to 98% identity to a full length NY-ESO-2 consensus sequence, and up to 99% identity to a full length NY-ESO-2 consensus sequence can be provided. Likewise, nucleic acid sequences encoding the immunogenic fragments set forth herein and the immunogenic fragments of proteins with similar percent identities as indicated above to the NY-ESO-2 proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:15. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO: 15. Fragments can be at least 95%, at least 96%, at least 97%, at least 98%, or at least 99% homologous to fragments of SEQ ID NO:15. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:15. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:16 comprises the amino acid sequence of the consensus NY-ESO-2 protein. The amino acid sequence of the consensus NY-ESO-2 protein linked to an IgE leader is SEQ ID NO:16. The amino acid sequence of the consensus NY-ESO-2 protein linked to the IgE leader may be linked to HA tag.

Some embodiments relate to proteins that are homologous to SEQ ID NO:16. Some embodiments relate to immunogenic proteins that have 95% homology to the consensus protein sequences as set forth in SEQ ID NO:16. Some embodiments relate to immunogenic proteins that have 96% homology to the consensus protein sequences as set forth in SEQ ID NO:16. Some embodiments relate to immunogenic proteins that have 97% homology to the consensus protein sequences as set forth in SEQ ID NO:16. Some embodiments relate to immunogenic proteins that have 98% homology to the consensus protein sequences as set forth in SEQ ID NO:16. Some embodiments relate to immunogenic proteins that have 99% homology to the consensus protein sequences as set forth in SEQ ID NO:16.

Some embodiments relate to proteins that are identical to SEQ ID NO:16. Some embodiments relate to immunogenic proteins that have an amino acid sequence that is 80% identical to the full length consensus amino acid sequences as set forth in SEQ ID NO: 16. Some embodiments relate to immunogenic proteins that have an amino acid sequence that is 85% identical to the full length consensus amino acid sequences as set forth in SEQ ID NO: 16. Some embodiments relate to immunogenic proteins that have an amino acid sequence that is 90% identical to the full length consensus amino acid sequences as set forth in SEQ ID NO: 16. Some embodiments relate to immunogenic proteins that have an amino acid sequence that is 91% identical to the full length consensus amino acid sequences as set forth in SEQ ID NO:16. Some embodiments relate to immunogenic proteins that have an amino acid sequence that is 92% identical to the full length consensus amino acid sequences as set forth in SEQ ID NO: 16. Some embodiments relate to immunogenic proteins that have an amino acid sequence that is 93% identical to the full length consensus amino acid sequences as set forth in SEQ ID NO: 16. Some embodiments relate to immunogenic proteins that have an amino acid sequence that is 94% identical to the full length consensus amino acid sequences as set forth in SEQ ID NO: 16. Some embodiments relate to immunogenic proteins that have an amino acid sequence that is 95% identical to the full length consensus amino acid sequences as set forth in SEQ ID NO:16. Some embodiments relate to immunogenic proteins that have an amino acid sequence that is 96% identical to the full length consensus amino acid sequences as set forth in SEQ ID NO: 16. Some embodiments relate to immunogenic proteins that have an amino acid sequence that is 97% identical to the full length consensus amino acid sequences as set forth in SEQ ID NO:16. Some embodiments relate to immunogenic proteins that have an amino acid sequence that is 98% identical to the full length consensus amino acid sequences as set forth in SEQ ID NO: 16. Some embodiments relate to immunogenic proteins that have an amino acid sequence that is 99% identical to the full length consensus amino acid sequences as set forth in SEQ ID NO:16.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:16 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO: 16. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:16 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO: 16. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:16 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO: 16. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(9) PRAME

The immunogenic composition of the present invention can comprise the cancer antigen PRAME, a fragment thereof, or a variant thereof. PRAME, encoded by the PRAME gene, is a protein comprised of 509 amino acids and is expressed in testis, placenta, endometrium, ovary, adrenals, and in tissues derived from melanoma, lung, kidney, and head and neck carcinomas. PRAME is also expressed in adult and pediatric acute leukemias, and multiple myeloma. PRAME contains an immunogenic nonapeptide able to elicit a cytotoxic response when presented by HLA-A24. Studies show that overexpression of PRAME in cultured cells induces a caspace-independent cell death responsible for a slower proliferation rate. Other studies demonstrate that overexpression of PRAME also confers growth or survival advantages by antagonizing retinoic acid receptor (RAR) signaling, and is causally involved in the tumorigenic process. Interference of RAR signaling leads to a loss in regulating cellular proliferation, development and differentiation.

PRAME can have an expression pattern similar to the cancer-testis antigens MAGE, BAGE, and GAGE, namely expression in the testis. PRAME, however, can be expressed in human melanomas and acute leukemias. PRAME can be recognized by cytolytic T lymphocytes. Accordingly, PRAME can be an antigen associated with melanoma and leukemias.

The PRAME antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PRAME antigen can increase a cellular immune response in a subject administered the PRAME antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the PRAME antigen. In some embodiments the PRAME antigen can increase the cellular immune response in the subject administered the PRAME antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the PRAME antigen.

The PRAME antigen can increase interferon gamma (IFN-γ) levels in a subject administered the PRAME antigen by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the PRAME antigen. In some embodiments, the PRAME antigen can increase IFN-γ levels in the subject administered the PRAME antigen by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the PRAME antigen.

The PRAME antigen can comprise protein epitopes that make them particularly effective as immunogens against which anti-PRAME immune responses can be induced. The PRAME antigen can comprise the full length translation product, a variant thereof, a fragment thereof or a combination thereof. The PRAME antigen can comprise a consensus protein.

The nucleic acid sequence encoding the consensus PRAME antigen can be optimized with regards to codon usage and corresponding RNA transcripts. The nucleic acid encoding the consensus PRAME antigen can be codon and RNA optimized for expression. In some embodiments, the nucleic acid sequence encoding the consensus PRAME antigen can include a Kozak sequence (e.g., GCC ACC) to increase the efficiency of translation. The nucleic acid encoding the consensus PRAME antigen can include multiple stop codons (e.g., TGA TGA) to increase the efficiency of translation termination.

The nucleic acid encoding the consensus PRAME antigen can also encode an immunoglobulin E (IgE) leader sequence. The nucleic acid encoding the consensus PRAME antigen can further encode the IgE leader sequence such that the amino acid sequence of the IgE leader sequence is linked to the amino acid sequence of the consensus PRAME antigen by a peptide bond. The nucleic encoding the consensus PRAME antigen can also include a nucleotide sequence encoding the IgE leader sequence. In some embodiments, the nucleic acid encoding the consensus PRAME antigen is free of or does not contain a nucleotide sequence encoding the IgE leader sequence.

The consensus PRAME antigen can be the nucleic acid sequence SEQ ID NO: 17, which encodes for the amino acid sequence SEQ ID NO:18. SEQ ID NO:17 encodes the consensus PRAME protein linked to an IgE leader sequence. The consensus PRAME protein can be linked to the IgE leader sequence and an HA tag. In other embodiments, the consensus PRAME protein can be free of or not linked to an IgE leader sequence and/or an HA tag.

In some embodiments, the consensus PRAME antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:17. In other embodiments, the consensus PRAME antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:18. The consensus PRAME antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:18.

Some embodiments relate to nucleic acid sequences encoding proteins homologous to the PRAME consensus protein, immunogenic fragment of the PRAME consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length PRAME consensus protein, immunogenic fragment of the PRAME consensus protein, and immunogenic fragments of proteins having identity to the PRAME consensus protein. Such nucleic acid molecules that encode immunogenic proteins that have up to 80% identity to a full length PRAME consensus sequence, up to 85% identity to a full length consensus sequence, up to 90% identity to a full length PRAME consensus sequence, up to 91% identity to a full length PRAME consensus sequence, up to 92% identity to a full length PRAME consensus sequence, up to 93% identity to a full length PRAME consensus sequence, up to 94% identity to a full length PRAME consensus sequence, up to 95% identity to a full length PRAME consensus sequence, up to 96% identity to a full length PRAME consensus sequence, up to 97% identity to a full length PRAME consensus sequence, up to 98% identity to a full length PRAME consensus sequence, and up to 99% identity to a full length PRAME consensus sequence can be provided. Likewise, nucleic acid sequences encoding the immunogenic fragments set forth herein and the immunogenic fragments of proteins with similar percent identities as indicated above to the PRAME proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:17. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:17. Fragments can be at least 95%, at least 96%, at least 97%, at least 98%, or at least 99% homologous to fragments of SEQ ID NO:17. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:17. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:18 comprises the amino acid sequence of the consensus PRAME protein. The amino acid sequence of the consensus PRAME protein linked to an IgE leader is SEQ ID NO:18. The amino acid sequence of the consensus PRAME protein linked to the IgE leader may be linked to HA tag.

Some embodiments relate to proteins that are homologous to SEQ ID NO:18. Some embodiments relate to immunogenic proteins that have 95% homology to the consensus protein sequences as set forth in SEQ ID NO:18. Some embodiments relate to immunogenic proteins that have 96% homology to the consensus protein sequences as set forth in SEQ ID NO:18. Some embodiments relate to immunogenic proteins that have 97% homology to the consensus protein sequences as set forth in SEQ ID NO:18. Some embodiments relate to immunogenic proteins that have 98% homology to the consensus protein sequences as set forth in SEQ ID NO:18. Some embodiments relate to immunogenic proteins that have 99% homology to the consensus protein sequences as set forth in SEQ ID NO:18.

Some embodiments relate to proteins that are identical to SEQ ID NO:18. Some embodiments relate to immunogenic proteins that have an amino acid sequence that is 80% identical to the full length consensus amino acid sequences as set forth in SEQ ID NO: 18. Some embodiments relate to immunogenic proteins that have an amino acid sequence that is 85% identical to the full length consensus amino acid sequences as set forth in SEQ ID NO: 18. Some embodiments relate to immunogenic proteins that have an amino acid sequence that is 90% identical to the full length consensus amino acid sequences as set forth in SEQ ID NO: 18. Some embodiments relate to immunogenic proteins that have an amino acid sequence that is 91% identical to the full length consensus amino acid sequences as set forth in SEQ ID NO:18. Some embodiments relate to immunogenic proteins that have an amino acid sequence that is 92% identical to the full length consensus amino acid sequences as set forth in SEQ ID NO: 18. Some embodiments relate to immunogenic proteins that have an amino acid sequence that is 93% identical to the full length consensus amino acid sequences as set forth in SEQ ID NO: 18. Some embodiments relate to immunogenic proteins that have an amino acid sequence that is 94% identical to the full length consensus amino acid sequences as set forth in SEQ ID NO: 18. Some embodiments relate to immunogenic proteins that have an amino acid sequence that is 95% identical to the full length consensus amino acid sequences as set forth in SEQ ID NO: 18. Some embodiments relate to immunogenic proteins that have an amino acid sequence that is 96% identical to the full length consensus amino acid sequences as set forth in SEQ ID NO: 18. Some embodiments relate to immunogenic proteins that have an amino acid sequence that is 97% identical to the full length consensus amino acid sequences as set forth in SEQ ID NO:18. Some embodiments relate to immunogenic proteins that have an amino acid sequence that is 98% identical to the full length consensus amino acid sequences as set forth in SEQ ID NO: 18. Some embodiments relate to immunogenic proteins that have an amino acid sequence that is 99% identical to the full length consensus amino acid sequences as set forth in SEQ ID NO:18.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:18 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO: 18. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:18 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:18. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:18 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO: 18. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

(10) PSA

The immunogenic composition of the present invention can comprise the cancer antigen prostate specific antigen (PSA; also known as gamma-seminoprotein or kallikrein-3 (KLK3)), a fragment thereof, or a variant thereof. PSA is an androgen-regulated serine protease produced by prostate epithelial cells and prostate cancer cells and encoded by the KLK3 gene. PSA is often used as a serum marker for prostate cancer. PSA is a member of the tissue kallikrein family and cleaves semenogelins in seminal coagulum after cleavage of the proenzyme to release the active enzyme, thereby liquefying semen to allow sperm to swim freely. Additionally, PSA enzymatic activity is regulated by zinc concentration, namely high zinc concentrations inhibit enzymatic activity of PSA.

The PSA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSA antigen can comprise protein epitopes that make them particularly effective as immunogens against which anti-PSA immune responses can be induced. The PSMA antigen can comprise the full length translation product, a variant thereof, a fragment thereof or a combination thereof. The PSA antigen can comprise a consensus protein.

The consensus PSA antigen can be the nucleic acid sequence SEQ ID NO:63, which encodes for the amino acid sequence SEQ ID NO:64. The consensus PSA protein can be linked to the IgE leader sequence and an HA tag. In other embodiments, the consensus PSA protein can be free of or not linked to an IgE leader sequence and/or an HA tag. The consensus PSA sequence can be operably linked to a regulatory sequence including, but not limited to, a start codon and at least one stop codon.

In some embodiments, the consensus PSA antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:63. In other embodiments, the consensus PSA antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:64. The consensus PSA antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:64.

Some embodiments relate to nucleic acid sequences encoding proteins homologous to the PSA consensus protein, immunogenic fragment of the PSA consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length PSA consensus protein, immunogenic fragment of the PSA consensus protein, and immunogenic fragments of proteins having identity to the PSA consensus protein. Such nucleic acid molecules that encode immunogenic proteins that have up to 80% identity to a full length PSA consensus sequence, up to 85% identity to a full length consensus sequence, up to 90% identity to a full length PSA consensus sequence, up to 91% identity to a full length PSA consensus sequence, up to 92% identity to a full length PSA consensus sequence, up to 93% identity to a full length PSA consensus sequence, up to 94% identity to a full length PSA consensus sequence, up to 95% identity to a full length PSA consensus sequence, up to 96% identity to a full length PSA consensus sequence, up to 97% identity to a full length PSA consensus sequence, up to 98% identity to a full length PSA consensus sequence, and up to 99% identity to a full length PSA consensus sequence can be provided. Likewise, nucleic acid sequences encoding the immunogenic fragments set forth herein and the immunogenic fragments of proteins with similar percent identities as indicated above to the PSA proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:63. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:63. Fragments can be at least 95%, at least 96%, at least 97%, at least 98%, or at least 99% homologous to fragments of SEQ ID NO:63. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:63. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:64 comprises the amino acid sequence of the consensus PSA protein. The amino acid sequence of the consensus PSA protein linked to an IgE leader is SEQ ID NO:64. The amino acid sequence of the consensus PSA protein linked to the IgE leader may be linked to HA tag.

Some embodiments relate to proteins that are homologous to SEQ ID NO:64. Some embodiments relate to immunogenic proteins that have 95% homology to the consensus protein sequences as set forth in SEQ ID NO:64. Some embodiments relate to immunogenic proteins that have 96% homology to the consensus protein sequences as set forth in SEQ ID NO:64. Some embodiments relate to immunogenic proteins that have 97% homology to the consensus protein sequences as set forth in SEQ ID NO:64. Some embodiments relate to immunogenic proteins that have 98% homology to the consensus protein sequences as set forth in SEQ ID NO:64. Some embodiments relate to immunogenic proteins that have 99% homology to the consensus protein sequences as set forth in SEQ ID NO:64.

Some embodiments relate to proteins that are identical to SEQ ID NO:64. Some embodiments relate to immunogenic proteins that have an amino acid sequence that is 80% identical to the full length consensus amino acid sequences as set forth in SEQ ID NO:64. Some embodiments relate to immunogenic proteins that have an amino acid sequence that is 85% identical to the full length consensus amino acid sequences as set forth in SEQ ID NO:64. Some embodiments relate to immunogenic proteins that have an amino acid sequence that is 90% identical to the full length consensus amino acid sequences as set forth in SEQ ID NO:64. Some embodiments relate to immunogenic proteins that have an amino acid sequence that is 91% identical to the full length consensus amino acid sequences as set forth in SEQ ID NO:64. Some embodiments relate to immunogenic proteins that have an amino acid sequence that is 92% identical to the full length consensus amino acid sequences as set forth in SEQ ID NO:64. Some embodiments relate to immunogenic proteins that have an amino acid sequence that is 93% identical to the full length consensus amino acid sequences as set forth in SEQ ID NO:64. Some embodiments relate to immunogenic proteins that have an amino acid sequence that is 94% identical to the full length consensus amino acid sequences as set forth in SEQ ID NO:64. Some embodiments relate to immunogenic proteins that have an amino acid sequence that is 95% identical to the full length consensus amino acid sequences as set forth in SEQ ID NO:64. Some embodiments relate to immunogenic proteins that have an amino acid sequence that is 96% identical to the full length consensus amino acid sequences as set forth in SEQ ID NO:64. Some embodiments relate to immunogenic proteins that have an amino acid sequence that is 97% identical to the full length consensus amino acid sequences as set forth in SEQ ID NO:64. Some embodiments relate to immunogenic proteins that have an amino acid sequence that is 98% identical to the full length consensus amino acid sequences as set forth in SEQ ID NO:64. Some embodiments relate to immunogenic proteins that have an amino acid sequence that is 99% identical to the full length consensus amino acid sequences as set forth in SEQ ID NO:64.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:64 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:64. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:64 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:64. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:64 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:64. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

The nucleic acid sequence encoding the consensus PSA antigen can be optimized with regards to codon usage and corresponding RNA transcripts. The nucleic acid encoding the consensus PSA antigen can be codon and RNA optimized for expression. In some embodiments, the nucleic acid sequence encoding the consensus PSA antigen can include a Kozak sequence (e.g., GCC ACC) to increase the efficiency of translation. The nucleic acid encoding the consensus PSA antigen can include multiple stop codons (e.g., TGA TGA) to increase the efficiency of translation termination.

The nucleic acid encoding the consensus PSA antigen can also encode an immunoglobulin E (IgE) leader sequence. The nucleic acid encoding the consensus PSA antigen can further encode the IgE leader sequence such that the amino acid sequence of the IgE leader sequence is linked to the amino acid sequence of the consensus PSA P antigen by a peptide bond. The nucleic encoding the consensus PSA antigen can also include a nucleotide sequence encoding the IgE leader sequence. In some embodiments, the nucleic acid encoding the consensus PSA antigen is free of or does not contain a nucleotide sequence encoding the IgE leader sequence.

In some embodiments, the nucleic acid encoding the consensus PSA antigen can be a heterologous nucleic acid sequence and/or contain one or more heterologous nucleic acid sequences.

(11) PSMA

The immunogenic composition of the present invention can comprise the cancer antigen prostate specific membrane antigen (PSMA; also known as Glutamate carboxypeptidase II (GCPII), N-acetyl-L-aspartyl-L-glutamate peptidase I (NAALADase I), and NAAG peptidase), a fragment thereof, or a variant thereof. PSMA is encoded by the folate hydrolase 1 (FOLH1) gene. PSMA is a zinc metalloenzyme found residing in membranes and the extracellular space. PSMA is highly expressed in the human prostate and is upregulated in prostate cancer. PSMA is also found to be overexpressed in other cancers such as solid tumors of the kidney, breast, and colon.

The PSMA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSMA antigen can comprise protein epitopes that make them particularly effective as immunogens against which anti-PSMA immune responses can be induced. The PSMA antigen can comprise the full length translation product, a variant thereof, a fragment thereof or a combination thereof. The PSMA antigen can comprise a consensus protein.

The consensus PSMA antigen can be the nucleic acid sequence SEQ ID NO:65, which encodes for the amino acid sequence SEQ ID NO:66. The consensus PSMA protein can be linked to the IgE leader sequence and an HA tag. In other embodiments, the consensus PSMA protein can be free of or not linked to an IgE leader sequence and/or an HA tag. The consensus PSMA sequence can be operably linked to a regulatory sequence including, but not limited to, a start codon and at least one stop codon.

In some embodiments, the consensus PSMA antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:65. In other embodiments, the consensus PSMA antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:66. The consensus PSMA antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:66.

Some embodiments relate to nucleic acid sequences encoding proteins homologous to the PSMA consensus protein, immunogenic fragment of the PSMA consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length PSMA consensus protein, immunogenic fragment of the PSMA consensus protein, and immunogenic fragments of proteins having identity to the PSMA consensus protein. Such nucleic acid molecules that encode immunogenic proteins that have up to 80% identity to a full length PSMA consensus sequence, up to 85% identity to a full length consensus sequence, up to 90% identity to a full length PSMA consensus sequence, up to 91% identity to a full length PSMA consensus sequence, up to 92% identity to a full length PSMA consensus sequence, up to 93% identity to a full length PSMA consensus sequence, up to 94% identity to a full length PSMA consensus sequence, up to 95% identity to a full length PSMA consensus sequence, up to 96% identity to a full length PSMA consensus sequence, up to 97% identity to a full length PSMA consensus sequence, up to 98% identity to a full length PSMA consensus sequence, and up to 99% identity to a full length PSMA consensus sequence can be provided. Likewise, nucleic acid sequences encoding the immunogenic fragments set forth herein and the immunogenic fragments of proteins with similar percent identities as indicated above to the PSMA proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:65. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:65. Fragments can be at least 95%, at least 96%, at least 97%, at least 98%, or at least 99% homologous to fragments of SEQ ID NO:65. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:65. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:66 comprises the amino acid sequence of the consensus PSMA protein. The amino acid sequence of the consensus PSMA protein linked to an IgE leader is SEQ ID NO:66. The amino acid sequence of the consensus PSMA protein linked to the IgE leader may be linked to HA tag.

Some embodiments relate to proteins that are homologous to SEQ ID NO:66. Some embodiments relate to immunogenic proteins that have 95% homology to the consensus protein sequences as set forth in SEQ ID NO:66. Some embodiments relate to immunogenic proteins that have 96% homology to the consensus protein sequences as set forth in SEQ ID NO:66. Some embodiments relate to immunogenic proteins that have 97% homology to the consensus protein sequences as set forth in SEQ ID NO:66. Some embodiments relate to immunogenic proteins that have 98% homology to the consensus protein sequences as set forth in SEQ ID NO:66. Some embodiments relate to immunogenic proteins that have 99% homology to the consensus protein sequences as set forth in SEQ ID NO:66.

Some embodiments relate to proteins that are identical to SEQ ID NO:66. Some embodiments relate to immunogenic proteins that have an amino acid sequence that is 80% identical to the full length consensus amino acid sequences as set forth in SEQ ID NO:66. Some embodiments relate to immunogenic proteins that have an amino acid sequence that is 85% identical to the full length consensus amino acid sequences as set forth in SEQ ID NO:66. Some embodiments relate to immunogenic proteins that have an amino acid sequence that is 90% identical to the full length consensus amino acid sequences as set forth in SEQ ID NO:66. Some embodiments relate to immunogenic proteins that have an amino acid sequence that is 91% identical to the full length consensus amino acid sequences as set forth in SEQ ID NO:66. Some embodiments relate to immunogenic proteins that have an amino acid sequence that is 92% identical to the full length consensus amino acid sequences as set forth in SEQ ID NO:66. Some embodiments relate to immunogenic proteins that have an amino acid sequence that is 93% identical to the full length consensus amino acid sequences as set forth in SEQ ID NO:66. Some embodiments relate to immunogenic proteins that have an amino acid sequence that is 94% identical to the full length consensus amino acid sequences as set forth in SEQ ID NO:66. Some embodiments relate to immunogenic proteins that have an amino acid sequence that is 95% identical to the full length consensus amino acid sequences as set forth in SEQ ID NO:66. Some embodiments relate to immunogenic proteins that have an amino acid sequence that is 96% identical to the full length consensus amino acid sequences as set forth in SEQ ID NO:66. Some embodiments relate to immunogenic proteins that have an amino acid sequence that is 97% identical to the full length consensus amino acid sequences as set forth in SEQ ID NO:66. Some embodiments relate to immunogenic proteins that have an amino acid sequence that is 98% identical to the full length consensus amino acid sequences as set forth in SEQ ID NO:66. Some embodiments relate to immunogenic proteins that have an amino acid sequence that is 99% identical to the full length consensus amino acid sequences as set forth in SEQ ID NO:66.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:66 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:66. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:66 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:66. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:66 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:66. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

The nucleic acid sequence encoding the consensus PSMA antigen can be optimized with regards to codon usage and corresponding RNA transcripts. The nucleic acid encoding the consensus PSMA antigen can be codon and RNA optimized for expression. In some embodiments, the nucleic acid sequence encoding the consensus PSMA antigen can include a Kozak sequence (e.g., GCC ACC) to increase the efficiency of translation. The nucleic acid encoding the consensus PSMA antigen can include multiple stop codons (e.g., TGA TGA) to increase the efficiency of translation termination.

The nucleic acid encoding the consensus PSMA antigen can also encode an immunoglobulin E (IgE) leader sequence. The nucleic acid encoding the consensus PSMA antigen can further encode the IgE leader sequence such that the amino acid sequence of the IgE leader sequence is linked to the amino acid sequence of the consensus PSMA P antigen by a peptide bond. The nucleic encoding the consensus PSMA antigen can also include a nucleotide sequence encoding the IgE leader sequence. In some embodiments, the nucleic acid encoding the consensus PSMA antigen is free of or does not contain a nucleotide sequence encoding the IgE leader sequence.

In some embodiments, the nucleic acid encoding the consensus PSMA antigen can be a heterologous nucleic acid sequence and/or contain one or more heterologous nucleic acid sequences.

(12) STEAP

The immunogenic composition of the present invention can comprise the cancer antigen six-transmembrane epithelial antigen of the prostate antigen (STEAP), a fragment thereof, or a variant thereof. STEAP is a metalloreductase encoded by the STEAP1 gene. STEAP is largely expressed in prostate tissues and is upregulated in cancer cells. STEAP is predicted to be a six-transmembrane protein and is a cell surface antigen found at cell-cell junctions.

The STEAP antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The STEAP antigen can comprise protein epitopes that make them particularly effective as immunogens against which anti-STEAP immune responses can be induced. The STEAP antigen can comprise the full length translation product, a variant thereof, a fragment thereof or a combination thereof. The STEAP antigen can comprise a consensus protein.

The consensus STEAP antigen can be the nucleic acid sequence SEQ ID NO:67, which encodes for the amino acid sequence SEQ ID NO:68. The consensus STEAP protein can be linked to the IgE leader sequence and an HA tag. In other embodiments, the consensus STEAP protein can be free of or not linked to an IgE leader sequence and/or an HA tag. The consensus STEAP sequence can be operably linked to a regulatory sequence including, but not limited to, a start codon and at least one stop codon.

In some embodiments, the consensus STEAP antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:67. In other embodiments, the consensus STEAP antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:68. The consensus STEAP antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:68.

Some embodiments relate to nucleic acid sequences encoding proteins homologous to the STEAP consensus protein, immunogenic fragment of the STEAP consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length STEAP consensus protein, immunogenic fragment of the STEAP consensus protein, and immunogenic fragments of proteins having identity to the STEAP consensus protein. Such nucleic acid molecules that encode immunogenic proteins that have up to 80% identity to a full length STEAP consensus sequence, up to 85% identity to a full length consensus sequence, up to 90% identity to a full length STEAP consensus sequence, up to 91% identity to a full length STEAP consensus sequence, up to 92% identity to a full length STEAP consensus sequence, up to 93% identity to a full length STEAP consensus sequence, up to 94% identity to a full length STEAP consensus sequence, up to 95% identity to a full length STEAP consensus sequence, up to 96% identity to a full length STEAP consensus sequence, up to 97% identity to a full length STEAP consensus sequence, up to 98% identity to a full length STEAP consensus sequence, and up to 99% identity to a full length STEAP consensus sequence can be provided. Likewise, nucleic acid sequences encoding the immunogenic fragments set forth herein and the immunogenic fragments of proteins with similar percent identities as indicated above to the STEAP proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:67. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:67. Fragments can be at least 95%, at least 96%, at least 97%, at least 98%, or at least 99% homologous to fragments of SEQ ID NO:67. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:67. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:68 comprises the amino acid sequence of the consensus STEAP protein. The amino acid sequence of the consensus STEAP protein linked to an IgE leader is SEQ ID NO:68. The amino acid sequence of the consensus STEAP protein linked to the IgE leader may be linked to HA tag.

Some embodiments relate to proteins that are homologous to SEQ ID NO:68. Some embodiments relate to immunogenic proteins that have 95% homology to the consensus protein sequences as set forth in SEQ ID NO:68. Some embodiments relate to immunogenic proteins that have 96% homology to the consensus protein sequences as set forth in SEQ ID NO:68. Some embodiments relate to immunogenic proteins that have 97% homology to the consensus protein sequences as set forth in SEQ ID NO:68. Some embodiments relate to immunogenic proteins that have 98% homology to the consensus protein sequences as set forth in SEQ ID NO:68. Some embodiments relate to immunogenic proteins that have 99% homology to the consensus protein sequences as set forth in SEQ ID NO:68.

Some embodiments relate to proteins that are identical to SEQ ID NO:68. Some embodiments relate to immunogenic proteins that have an amino acid sequence that is 80% identical to the full length consensus amino acid sequences as set forth in SEQ ID NO:68. Some embodiments relate to immunogenic proteins that have an amino acid sequence that is 85% identical to the full length consensus amino acid sequences as set forth in SEQ ID NO:68. Some embodiments relate to immunogenic proteins that have an amino acid sequence that is 90% identical to the full length consensus amino acid sequences as set forth in SEQ ID NO:68. Some embodiments relate to immunogenic proteins that have an amino acid sequence that is 91% identical to the full length consensus amino acid sequences as set forth in SEQ ID NO:68. Some embodiments relate to immunogenic proteins that have an amino acid sequence that is 92% identical to the full length consensus amino acid sequences as set forth in SEQ ID NO:68. Some embodiments relate to immunogenic proteins that have an amino acid sequence that is 93% identical to the full length consensus amino acid sequences as set forth in SEQ ID NO:68. Some embodiments relate to immunogenic proteins that have an amino acid sequence that is 94% identical to the full length consensus amino acid sequences as set forth in SEQ ID NO:68. Some embodiments relate to immunogenic proteins that have an amino acid sequence that is 95% identical to the full length consensus amino acid sequences as set forth in SEQ ID NO:68. Some embodiments relate to immunogenic proteins that have an amino acid sequence that is 96% identical to the full length consensus amino acid sequences as set forth in SEQ ID NO:68. Some embodiments relate to immunogenic proteins that have an amino acid sequence that is 97% identical to the full length consensus amino acid sequences as set forth in SEQ ID NO:68. Some embodiments relate to immunogenic proteins that have an amino acid sequence that is 98% identical to the full length consensus amino acid sequences as set forth in SEQ ID NO:68. Some embodiments relate to immunogenic proteins that have an amino acid sequence that is 99% identical to the full length consensus amino acid sequences as set forth in SEQ ID NO:68.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:68 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:68. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:68 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:68. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:68 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:68. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

The nucleic acid sequence encoding the consensus STEAP antigen can be optimized with regards to codon usage and corresponding RNA transcripts. The nucleic acid encoding the consensus STEAP antigen can be codon and RNA optimized for expression. In some embodiments, the nucleic acid sequence encoding the consensus STEAP antigen can include a Kozak sequence (e.g., GCC ACC) to increase the efficiency of translation. The nucleic acid encoding the consensus STEAP antigen can include multiple stop codons (e.g., TGA TGA) to increase the efficiency of translation termination.

The nucleic acid encoding the consensus STEAP antigen can also encode an immunoglobulin E (IgE) leader sequence. The nucleic acid encoding the consensus STEAP antigen can further encode the IgE leader sequence such that the amino acid sequence of the IgE leader sequence is linked to the amino acid sequence of the consensus STEAP antigen by a peptide bond. The nucleic encoding the consensus STEAP antigen can also include a nucleotide sequence encoding the IgE leader sequence. In some embodiments, the nucleic acid encoding the consensus STEAP antigen is free of or does not contain a nucleotide sequence encoding the IgE leader sequence.

In some embodiments, the nucleic acid encoding the consensus STEAP antigen can be a heterologous nucleic acid sequence and/or contain one or more heterologous nucleic acid sequences.

(13) PSCA

The immunogenic composition of the present invention can comprise the cancer antigen prostate specific stem cell antigen (PSCA), a fragment thereof, or a variant thereof. PSCA is a glycosylphosphatidylinositol (GPI)-anchored cell surface protein and is encoded by an androgen-responsive gene. PSCA is a member of the Thy-1/Ly-6 family of GPI-anchored cell surface antigens. PSCA is upregulated in many cancers including prostate, bladder, and pancreatic cancers.

The PSCA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSCA antigen can comprise protein epitopes that make them particularly effective as immunogens against which anti-PSCA immune responses can be induced. The PSCA antigen can comprise the full length translation product, a variant thereof, a fragment thereof or a combination thereof. The PSCA antigen can comprise a consensus protein.

The consensus PSCA antigen can be the nucleic acid sequence SEQ ID NO:69, which encodes for the amino acid sequence SEQ ID NO:70. The consensus PSCA protein can be linked to the IgE leader sequence and an HA tag. In other embodiments, the consensus PSCA protein can be free of or not linked to an IgE leader sequence and/or an HA tag. The consensus PSCA sequence can be operably linked to a regulatory sequence including, but not limited to, a start codon and at least one stop codon.

In some embodiments, the consensus PSCA antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:69. In other embodiments, the consensus PSCA antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:70. The consensus PSCA antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:70.

Some embodiments relate to nucleic acid sequences encoding proteins homologous to the PSCA consensus protein, immunogenic fragment of the PSCA consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length PSCA consensus protein, immunogenic fragment of the PSCA consensus protein, and immunogenic fragments of proteins having identity to the PSCA consensus protein. Such nucleic acid molecules that encode immunogenic proteins that have up to 80% identity to a full length PSCA consensus sequence, up to 85% identity to a full length consensus sequence, up to 90% identity to a full length PSCA consensus sequence, up to 91% identity to a full length PSCA consensus sequence, up to 92% identity to a full length PSCA consensus sequence, up to 93% identity to a full length PSCA consensus sequence, up to 94% identity to a full length PSCA consensus sequence, up to 95% identity to a full length PSCA consensus sequence, up to 96% identity to a full length PSCA consensus sequence, up to 97% identity to a full length PSCA consensus sequence, up to 98% identity to a full length PSCA consensus sequence, and up to 99% identity to a full length PSCA consensus sequence can be provided. Likewise, nucleic acid sequences encoding the immunogenic fragments set forth herein and the immunogenic fragments of proteins with similar percent identities as indicated above to the PSCA proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:69. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:69. Fragments can be at least 95%, at least 96%, at least 97%, at least 98%, or at least 99% homologous to fragments of SEQ ID NO:69. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:69. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:70 comprises the amino acid sequence of the consensus PSCA protein. The amino acid sequence of the consensus PSCA protein linked to an IgE leader is SEQ ID NO:70. The amino acid sequence of the consensus PSCA protein linked to the IgE leader may be linked to HA tag.

Some embodiments relate to proteins that are homologous to SEQ ID NO:70. Some embodiments relate to immunogenic proteins that have 95% homology to the consensus protein sequences as set forth in SEQ ID NO:70. Some embodiments relate to immunogenic proteins that have 96% homology to the consensus protein sequences as set forth in SEQ ID NO:70. Some embodiments relate to immunogenic proteins that have 97% homology to the consensus protein sequences as set forth in SEQ ID NO:70. Some embodiments relate to immunogenic proteins that have 98% homology to the consensus protein sequences as set forth in SEQ ID NO:70. Some embodiments relate to immunogenic proteins that have 99% homology to the consensus protein sequences as set forth in SEQ ID NO:70.

Some embodiments relate to proteins that are identical to SEQ ID NO:70. Some embodiments relate to immunogenic proteins that have an amino acid sequence that is 80% identical to the full length consensus amino acid sequences as set forth in SEQ ID NO:70. Some embodiments relate to immunogenic proteins that have an amino acid sequence that is 85% identical to the full length consensus amino acid sequences as set forth in SEQ ID NO:70. Some embodiments relate to immunogenic proteins that have an amino acid sequence that is 90% identical to the full length consensus amino acid sequences as set forth in SEQ ID NO:70. Some embodiments relate to immunogenic proteins that have an amino acid sequence that is 91% identical to the full length consensus amino acid sequences as set forth in SEQ ID NO:70. Some embodiments relate to immunogenic proteins that have an amino acid sequence that is 92% identical to the full length consensus amino acid sequences as set forth in SEQ ID NO:70. Some embodiments relate to immunogenic proteins that have an amino acid sequence that is 93% identical to the full length consensus amino acid sequences as set forth in SEQ ID NO:70. Some embodiments relate to immunogenic proteins that have an amino acid sequence that is 94% identical to the full length consensus amino acid sequences as set forth in SEQ ID NO:70. Some embodiments relate to immunogenic proteins that have an amino acid sequence that is 95% identical to the full length consensus amino acid sequences as set forth in SEQ ID NO:70. Some embodiments relate to immunogenic proteins that have an amino acid sequence that is 96% identical to the full length consensus amino acid sequences as set forth in SEQ ID NO:70. Some embodiments relate to immunogenic proteins that have an amino acid sequence that is 97% identical to the full length consensus amino acid sequences as set forth in SEQ ID NO:70. Some embodiments relate to immunogenic proteins that have an amino acid sequence that is 98% identical to the full length consensus amino acid sequences as set forth in SEQ ID NO:70. Some embodiments relate to immunogenic proteins that have an amino acid sequence that is 99% identical to the full length consensus amino acid sequences as set forth in SEQ ID NO:70.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:70 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:70. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:70 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:70. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:70 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:70. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

The nucleic acid sequence encoding the consensus PSCA antigen can be optimized with regards to codon usage and corresponding RNA transcripts. The nucleic acid encoding the consensus PSCA antigen can be codon and RNA optimized for expression. In some embodiments, the nucleic acid sequence encoding the consensus PSCA antigen can include a Kozak sequence (e.g., GCC ACC) to increase the efficiency of translation. The nucleic acid encoding the consensus PSCA antigen can include multiple stop codons (e.g., TGA TGA) to increase the efficiency of translation termination.

The nucleic acid encoding the consensus PSCA antigen can also encode an immunoglobulin E (IgE) leader sequence. The nucleic acid encoding the consensus PSCA antigen can further encode the IgE leader sequence such that the amino acid sequence of the IgE leader sequence is linked to the amino acid sequence of the consensus PSCA antigen by a peptide bond. The nucleic encoding the consensus PSCA antigen can also include a nucleotide sequence encoding the IgE leader sequence. In some embodiments, the nucleic acid encoding the consensus PSCA antigen is free of or does not contain a nucleotide sequence encoding the IgE leader sequence.

In some embodiments, the nucleic acid encoding the consensus PSCA antigen can be a heterologous nucleic acid sequence and/or contain one or more heterologous nucleic acid sequences.

(14) MAGE A1

The immunogenic composition of the present invention can comprise the cancer antigen melanoma-associated antigen 1 (MAGE A1), a fragment thereof, or a variant thereof. MAGE A1, encoded by the MAGEA1 gene, is a 280-amino acid protein, and has been found only to be expressed by tumor cells and germ cells. MAGE A1 relies on DNA methylation for its repression in normal somatic tissues. These genes become activated in many types of tumors in the course of the genome-wide demethylation process, which often accompanies tumorgenesis. Specifically, during neoplastic transformation, these genes are activated, expressed, and may become antigenic targets that are recognized and attacked by the immune system. Therefore, MAGE genes take part in the immune process by targeting some early tumor cells for immune destruction. MAGE A1 may be expressed in numerous cancers, including, but not limited to, melanomas, lung carcenomas and esophageal squamous-cell carcinomas.

The MAGE A1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

(15) WT1

The immunogenic composition of the present invention can comprise the cancer antigen Wilm's tumor 1 (WT1), a fragment thereof, or a variant thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, Wilm's tumor or tumors expressing WT1. Wilm's tumor often forms in one or both kidneys before metastasizing to other tissues, for example, but not limited to, liver tissue, urinary tract system tissue, lymph tissue, and lung tissue. Accordingly, Wilm's tumor can be considered a metastatic tumor. Wilm's tumor usually occurs in younger children (e.g., less than 5 years old) and in both sporadic and hereditary forms. The WT1 cancer antigen can further be defined by PCT/US13/75141, filed Dec. 23, 2013, which are hereby incorporated by reference in its' entirety.

The WT-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

Accordingly, the immunogenic composition can be used for treating subjects suffering from Wilm's tumor. The immunogenic composition can be used for treating subjects suffering from any number of cancers including, but not limited to, melanoma, prostate cancer, liver cancer, cervical cancer, recurrent respiratory papillomatosis (RRP), anal cancer, head and neck cancer, and blood cancers. The immunogenic composition can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Accordingly, WT1 antigen sequences that differ from the native WT1 gene (i.e., mutated WT1 genes or sequences) are provided herein.

Transcripts of the native WT1 gene are processed into a variety of mRNAs, and the resulting proteins are not all of equal value for inducing an immune response. The mutated WT1 genes described herein avoid alternative processing, producing one full-length transcript and resulting in stronger induction of effector T and B cell responses. The first mutated WT1 sequence is referred to as CON WT1 with modified Zinc Fingers or ConWT1-L. SEQ ID NO: 19 is a nucleic acid sequence encoding the WT1 antigen CON WT1 with modified Zinc Fingers. SEQ ID NO:20 is the amino acid sequence of WT1 antigen CON WT1 with modified Zinc Fingers. The second mutated WT1 sequence is referred to as CON WT1 without Zinc Fingers or ConWT1-S. SEQ ID NO:21 is a nucleic acid sequence encoding the WT1 antigen CON WT1 without Zinc Fingers. SEQ ID NO:22 is the amino acid sequence of WT1 antigen CON WT1 without modified Zinc Fingers.

The WT1 antigen can be a consensus antigen (or immunogen) sequence derived from two or more species. The WT1 antigen can comprise a consensus sequence and/or modification(s) for improved expression. Modification can include codon optimization, RNA optimization, additional of a kozak sequence (e.g., GCC ACC) for increased translation initiation and/or the addition of an immunoglobulin leader sequence to increase the immunogenicity of the WT1 antigen. The WT1 antigen can comprise a signal peptide such as an immunoglobulin signal peptide, for example, but not limited to, an immunoglobulin E (IgE) or immunoglobulin G (IgG) signal peptide. In some embodiments, the WT1 consensus antigen can comprise a hemagglutinin (HA) tag. The WT1 consensus antigen can be designed to elicit stronger and broader cellular and/or humoral immune responses than a corresponding codon optimized WT1 antigen.

The WT1 consensus antigen can comprise one or more mutations in one or more zinc fingers, thereby eliciting stronger and broader cellular and/or humoral immune responses than a corresponding codon optimized WT1 antigen. The one or more mutations can be a substitution of one or more of the amino acids that coordinate the zinc ion in the one or more zinc fingers. The one or more amino acids that coordinate the zinc ion can be a CCHH motif. Accordingly, in some embodiments, the one or more mutations can replace 1, 2, 3, or all 4 amino acids of CCHH motif.

In other embodiments, the one or more mutations are such that residues 312, 317, 342, and 347 of SEQ ID NO:20 are any residue other than cysteine (C) and residues 330, 334, 360, and 364 of SEQ ID NO:20 are any residue other than histidine (H). In particular, the one or more mutations are such that residues 312, 317, 330, 334, 342, 347, 360, and 364 of SEQ ID NO:20 are glycine (G).

In other embodiments, one or more of the zinc fingers can be removed from the WT1 consensus antigen. One, two, three, or all four of the zinc fingers can be removed from the WT1 consensus antigen.

The WT1 consensus antigen can be the nucleic acid SEQ ID NO:19, which encodes SEQ ID NO:20. In some embodiments, the WT1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO:19. In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20.

In still other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 342, and 347 of SEQ ID NO:20 are any residue other than cysteine (C) and residues 330, 334, 360, and 364 of SEQ ID NO:20 are any residue other than histidine (H). In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 330, 334, 342, 347, 360, and 364 of SEQ ID NO:20 are glycine (G).

The WT1 consensus antigen can be the amino acid sequence SEQ ID NO:20. In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20. The WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:20, provided that residues 312, 317, 342, and 347 of SEQ ID NO:20 are any residue other than cysteine (C) and residues 330, 334, 360, and 364 of SEQ ID NO:20 are any residue other than histidine (H). In some embodiments, the WT1 consensus antigen can be the amino acid sequence having at least about 80%, 81%, 82%, 83%, 84%, 85%, 86%, 87%, 88%, 89%, 90%9, 91%, 92%, 93%, 94%, 95%, 96%, 97%, 98%, or 99% identity over an entire length of the amino acid sequence set forth in SEQ ID NO:20, provided that residues 312, 317, 330, 334, 342, 347, 360, and 364 of SEQ ID NO:20 are glycine (G).

The WT1 consensus antigen can be the nucleic acid SEQ ID NO:21, which encodes SEQ ID NO:22. In some embodiments, the WT1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO:21. In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:22.

The WT1 consensus antigen can be the amino acid sequence SEQ ID NO:22. In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:22.

Immunogenic fragments of SEQ ID NO:20 and SEQ ID NO:22 can be provided. Immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:20 and/or SEQ ID NO:22. In some embodiments, immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:20, provided that if residues 312, 317, 342, and 347 of SEQ ID NO:20 are present in the immunogenic fragment, then these residues are any residue other than cysteine (C), and provided that if residues 330, 334, 360, and 364 of SEQ ID NO:20 are present in the immunogenic fragment, then these residues are any residue other than histidine (H). In other embodiments, immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:20, provided that if residues 312, 317, 330, 334, 342, 347, 360, and 364 of SEQ ID NO:20 are present in the immunogenic fragment, then these residues are glycine (G).

In some embodiments, immunogenic fragments include a leader sequence, for example, an immunoglobulin leader sequence, such as the immunoglobulin E (IgE) leader sequence. In some embodiments, immunogenic fragments are free of a leader sequence.

Immunogenic fragments of proteins with amino acid sequences having identity to immunogenic fragments of SEQ ID NO:20 and 22 can be provided. Such fragments can comprise at least 60%, at least 65%, at least 70%, at least 75%, at least 75%, at least 80%, at least 85%, at least 90%, at least 95%, at least 96%, at least 97%, at least 98%, or at least 99% of proteins having 95% or greater identity to SEQ ID NO:20 and/or SEQ ID NO:22. Some embodiments relate to immunogenic fragments that have 96% or greater identity to the immunogenic fragments of WT1 protein sequences herein. Some embodiments relate to immunogenic fragments that have 97% or greater identity to the immunogenic fragments of WT1 protein sequences herein. Some embodiments relate to immunogenic fragments that have 98% or greater identity to the immunogenic fragments of WT1 protein sequences herein. Some embodiments relate to immunogenic fragments that have 99% or greater identity to the immunogenic fragments of WT1 protein sequences herein. In some embodiments, immunogenic fragments include a leader sequence, for example, an immunoglobulin leader sequence such as the IgE leader sequence. In some embodiments, the immunogenic fragments are free of a leader sequence.

Some embodiments relate to immunogenic fragments of SEQ ID NO:19 and SEQ ID NO:21. Immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:19 and/or SEQ ID NO:21. In some embodiments, immunogenic fragments include sequences that encode a leader sequence, for example, an immunoglobulin leader sequence such as the IgE leader sequence. In some embodiments, immunogenic fragments are free of coding sequences that encode a leader sequence.

Immunogenic fragments of nucleic acids with nucleotide sequences having identity to immunogenic fragments of SEQ ID NO:19 and SEQ ID NO:21 can be provided. Such fragments can comprise at least 60%, at least 65%, at least 70%, at least 75%, at least 75%, at least 80%, at least 85%, at least 90%, at least 95%, at least 96%, at least 97%, at least 98%, or at least 99% of nucleic acids having 95% or greater identity to SEQ ID NO:19 and/or SEQ ID NO:21. Some embodiments relate to immunogenic fragments that have 96% or greater identity to the immunogenic fragments of WT1 nucleic acid sequences herein. Some embodiments relate to immunogenic fragments that have 97% or greater identity to the immunogenic fragments of WT1 nucleic acid sequences herein. Some embodiments relate to immunogenic fragments that have 98% or greater identity to the immunogenic fragments of WT1 nucleic acid sequences herein. Some embodiments relate to immunogenic fragments that have 99% or greater identity to the immunogenic fragments of WT1 nucleic sequences herein. In some embodiments, immunogenic fragments include sequences that encode a leader sequence, for example, an immunoglobulin leader sequence such as the IgE leader sequence. In some embodiments, immunogenic fragments are free of coding sequences that encode a leader sequence.

(16) FAP

The immunogenic composition of the present invention can comprise the cancer antigen fibroblast activating protein (FAP), a fragment thereof, or a variant thereof. The FAP antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The FAP antigen can comprise protein epitopes that make them particularly effective as immunogens against which anti-FAP immune responses can be induced. The PSMA antigen can comprise the full length translation product, a variant thereof, a fragment thereof or a combination thereof. The FAP antigen can comprise a consensus protein.

The consensus FAP antigen can be the nucleic acid sequence SEQ ID NO:59, which encodes for the amino acid sequence SEQ ID NO:60. The consensus FAP protein can be linked to the IgE leader sequence and an HA tag. In other embodiments, the consensus FAP protein can be free of or not linked to an IgE leader sequence and/or an HA tag. The consensus FAP sequence can be operably linked to a regulatory sequence including, but not limited to, a start codon and at least one stop codon.

In some embodiments, the consensus FAP antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:59. In other embodiments, the consensus FAP antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:60. The consensus FAP antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:60.

Some embodiments relate to nucleic acid sequences encoding proteins homologous to the FAP consensus protein, immunogenic fragment of the FAP consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length FAP consensus protein, immunogenic fragment of the FAP consensus protein, and immunogenic fragments of proteins having identity to the FAP consensus protein. Such nucleic acid molecules that encode immunogenic proteins that have up to 80% identity to a full length FAP consensus sequence, up to 85% identity to a full length consensus sequence, up to 90% identity to a full length FAP consensus sequence, up to 91% identity to a full length FAP consensus sequence, up to 92% identity to a full length FAP consensus sequence, up to 93% identity to a full length FAP consensus sequence, up to 94% identity to a full length FAP consensus sequence, up to 95% identity to a full length FAP consensus sequence, up to 96% identity to a full length FAP consensus sequence, up to 97% identity to a full length FAP consensus sequence, up to 98% identity to a full length FAP consensus sequence, and up to 99% identity to a full length FAP consensus sequence can be provided. Likewise, nucleic acid sequences encoding the immunogenic fragments set forth herein and the immunogenic fragments of proteins with similar percent identities as indicated above to the FAP proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:59. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:59. Fragments can be at least 95%, at least 96%, at least 97%, at least 98%, or at least 99% homologous to fragments of SEQ ID NO:59. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:59. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus FAP protein is SEQ ID NO:60. The amino acid sequence of the consensus FAP protein linked to an IgE leader is SEQ ID NO:60. The amino acid sequence of the consensus FAP protein linked to the IgE leader may be linked to HA tag.

Some embodiments relate to proteins that are homologous to SEQ ID NO:60. Some embodiments relate to immunogenic proteins that have 95% homology to the consensus protein sequences as set forth in SEQ ID NO:60. Some embodiments relate to immunogenic proteins that have 96% homology to the consensus protein sequences as set forth in SEQ ID NO:60. Some embodiments relate to immunogenic proteins that have 97% homology to the consensus protein sequences as set forth in SEQ ID NO:60. Some embodiments relate to immunogenic proteins that have 98% homology to the consensus protein sequences as set forth in SEQ ID NO:60. Some embodiments relate to immunogenic proteins that have 99% homology to the consensus protein sequences as set forth in SEQ ID NO:60.

Some embodiments relate to proteins that are identical to SEQ ID NO:60. Some embodiments relate to immunogenic proteins that have an amino acid sequence that is 80% identical to the full length consensus amino acid sequences as set forth in SEQ ID NO:60. Some embodiments relate to immunogenic proteins that have an amino acid sequence that is 85% identical to the full length consensus amino acid sequences as set forth in SEQ ID NO:60. Some embodiments relate to immunogenic proteins that have an amino acid sequence that is 90% identical to the full length consensus amino acid sequences as set forth in SEQ ID NO:60. Some embodiments relate to immunogenic proteins that have an amino acid sequence that is 91% identical to the full length consensus amino acid sequences as set forth in SEQ ID NO:60. Some embodiments relate to immunogenic proteins that have an amino acid sequence that is 92% identical to the full length consensus amino acid sequences as set forth in SEQ ID NO:60. Some embodiments relate to immunogenic proteins that have an amino acid sequence that is 93% identical to the full length consensus amino acid sequences as set forth in SEQ ID NO:60. Some embodiments relate to immunogenic proteins that have an amino acid sequence that is 94% identical to the full length consensus amino acid sequences as set forth in SEQ ID NO:60. Some embodiments relate to immunogenic proteins that have an amino acid sequence that is 95% identical to the full length consensus amino acid sequences as set forth in SEQ ID NO:60. Some embodiments relate to immunogenic proteins that have an amino acid sequence that is 96% identical to the full length consensus amino acid sequences as set forth in SEQ ID NO:60. Some embodiments relate to immunogenic proteins that have an amino acid sequence that is 97% identical to the full length consensus amino acid sequences as set forth in SEQ ID NO:60. Some embodiments relate to immunogenic proteins that have an amino acid sequence that is 98% identical to the full length consensus amino acid sequences as set forth in SEQ ID NO:60. Some embodiments relate to immunogenic proteins that have an amino acid sequence that is 99% identical to the full length consensus amino acid sequences as set forth in SEQ ID NO:60.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:60 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:60. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:60 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:60. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:60 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:60. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

The nucleic acid sequence encoding the consensus FAP antigen can be optimized with regards to codon usage and corresponding RNA transcripts. The nucleic acid encoding the consensus FAP antigen can be codon and RNA optimized for expression. In some embodiments, the nucleic acid sequence encoding the consensus FAP antigen can include a Kozak sequence (e.g., GCC ACC) to increase the efficiency of translation. The nucleic acid encoding the consensus FAP antigen can include multiple stop codons (e.g., TGA TGA) to increase the efficiency of translation termination.

The nucleic acid encoding the consensus FAP antigen can also encode an immunoglobulin E (IgE) leader sequence. The nucleic acid encoding the consensus FAP antigen can further encode the IgE leader sequence such that the amino acid sequence of the IgE leader sequence is linked to the amino acid sequence of the consensus FAP P antigen by a peptide bond. The nucleic encoding the consensus FAP antigen can also include a nucleotide sequence encoding the IgE leader sequence. In some embodiments, the nucleic acid encoding the consensus FAP antigen is free of or does not contain a nucleotide sequence encoding the IgE leader sequence.

In some embodiments, the nucleic acid encoding the consensus FAP antigen can be a heterologous nucleic acid sequence and/or contain one or more heterologous nucleic acid sequences.

(17) FSHR

The immunogenic composition of the present invention can comprise the cancer antigen follicle stimulating hormone receptor (FSHR) a fragment thereof, or a variant thereof. The FSHR antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The FSHR antigen can comprise protein epitopes that make them particularly effective as immunogens against which anti-FSHR immune responses can be induced. The PSMA antigen can comprise the full length translation product, a variant thereof, a fragment thereof or a combination thereof. The FSHR antigen can comprise a consensus protein.

The consensus FSHR antigen can be the nucleic acid sequence SEQ ID NO:61, which encodes for the amino acid sequence SEQ ID NO:62. The consensus FSHR protein can be linked to the IgE leader sequence and an HA tag. In other embodiments, the consensus FSHR protein can be free of or not linked to an IgE leader sequence and/or an HA tag. The consensus FSHR sequence can be operably linked to a regulatory sequence including, but not limited to, a start codon and at least one stop codon.

In some embodiments, the consensus FSHR antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:61. In other embodiments, the consensus FSHR antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:62. The consensus FSHR antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:62.

Some embodiments relate to nucleic acid sequences encoding proteins homologous to the FSHR consensus protein, immunogenic fragment of the FSHR consensus protein, and immunogenic fragments of homologous proteins. Such nucleic acid molecules that encode immunogenic proteins that have up to 95% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length FSHR consensus protein, immunogenic fragment of the FSHR consensus protein, and immunogenic fragments of proteins having identity to the FSHR consensus protein. Such nucleic acid molecules that encode immunogenic proteins that have up to 80% identity to a full length FSHR consensus sequence, up to 85% identity to a full length consensus sequence, up to 90% identity to a full length FSHR consensus sequence, up to 91% identity to a full length FSHR consensus sequence, up to 92% identity to a full length FSHR consensus sequence, up to 93% identity to a full length FSHR consensus sequence, up to 94% identity to a full length FSHR consensus sequence, up to 95% identity to a full length FSHR consensus sequence, up to 96% identity to a full length FSHR consensus sequence, up to 97% identity to a full length FSHR consensus sequence, up to 98% identity to a full length FSHR consensus sequence, and up to 99% identity to a full length FSHR consensus sequence can be provided. Likewise, nucleic acid sequences encoding the immunogenic fragments set forth herein and the immunogenic fragments of proteins with similar percent identities as indicated above to the FSHR proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:61. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NO:61. Fragments can be at least 95%, at least 96%, at least 97%, at least 98%, or at least 99% homologous to fragments of SEQ ID NO:61. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NO:61. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of SEQ ID NO:62 comprises the amino acid sequence of the consensus FSHR protein. The amino acid sequence of the consensus FSHR protein linked to an IgE leader is SEQ ID NO:62. The amino acid sequence of the consensus FSHR protein linked to the IgE leader may be linked to HA tag.

Some embodiments relate to proteins that are homologous to SEQ ID NO:62. Some embodiments relate to immunogenic proteins that have 95% homology to the consensus protein sequences as set forth in SEQ ID NO:62. Some embodiments relate to immunogenic proteins that have 96% homology to the consensus protein sequences as set forth in SEQ ID NO:62. Some embodiments relate to immunogenic proteins that have 97% homology to the consensus protein sequences as set forth in SEQ ID NO:62. Some embodiments relate to immunogenic proteins that have 98% homology to the consensus protein sequences as set forth in SEQ ID NO:62. Some embodiments relate to immunogenic proteins that have 99% homology to the consensus protein sequences as set forth in SEQ ID NO:62.

Some embodiments relate to proteins that are identical to SEQ ID NO:62. Some embodiments relate to immunogenic proteins that have an amino acid sequence that is 80% identical to the full length consensus amino acid sequences as set forth in SEQ ID NO:62. Some embodiments relate to immunogenic proteins that have an amino acid sequence that is 85% identical to the full length consensus amino acid sequences as set forth in SEQ ID NO:62. Some embodiments relate to immunogenic proteins that have an amino acid sequence that is 90% identical to the full length consensus amino acid sequences as set forth in SEQ ID NO:62. Some embodiments relate to immunogenic proteins that have an amino acid sequence that is 91% identical to the full length consensus amino acid sequences as set forth in SEQ ID NO:62. Some embodiments relate to immunogenic proteins that have an amino acid sequence that is 92% identical to the full length consensus amino acid sequences as set forth in SEQ ID NO:62. Some embodiments relate to immunogenic proteins that have an amino acid sequence that is 93% identical to the full length consensus amino acid sequences as set forth in SEQ ID NO:62. Some embodiments relate to immunogenic proteins that have an amino acid sequence that is 94% identical to the full length consensus amino acid sequences as set forth in SEQ ID NO:62. Some embodiments relate to immunogenic proteins that have an amino acid sequence that is 95% identical to the full length consensus amino acid sequences as set forth in SEQ ID NO:62. Some embodiments relate to immunogenic proteins that have an amino acid sequence that is 96% identical to the full length consensus amino acid sequences as set forth in SEQ ID NO:62. Some embodiments relate to immunogenic proteins that have an amino acid sequence that is 97% identical to the full length consensus amino acid sequences as set forth in SEQ ID NO:62. Some embodiments relate to immunogenic proteins that have an amino acid sequence that is 98% identical to the full length consensus amino acid sequences as set forth in SEQ ID NO:62. Some embodiments relate to immunogenic proteins that have an amino acid sequence that is 99% identical to the full length consensus amino acid sequences as set forth in SEQ ID NO:62.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:62 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:62. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:62 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:62. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:62 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NO:62. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences.

The nucleic acid sequence encoding the consensus FSHR antigen can be optimized with regards to codon usage and corresponding RNA transcripts. The nucleic acid encoding the consensus FSHR antigen can be codon and RNA optimized for expression. In some embodiments, the nucleic acid sequence encoding the consensus FSHR antigen can include a Kozak sequence (e.g., GCC ACC) to increase the efficiency of translation. The nucleic acid encoding the consensus FSHR antigen can include multiple stop codons (e.g., TGA TGA) to increase the efficiency of translation termination.

The nucleic acid encoding the consensus FSHR antigen can also encode an immunoglobulin E (IgE) leader sequence. The nucleic acid encoding the consensus FSHR antigen can further encode the IgE leader sequence such that the amino acid sequence of the IgE leader sequence is linked to the amino acid sequence of the consensus FSHR P antigen by a peptide bond. The nucleic encoding the consensus FSHR antigen can also include a nucleotide sequence encoding the IgE leader sequence. In some embodiments, the nucleic acid encoding the consensus FSHR antigen is free of or does not contain a nucleotide sequence encoding the IgE leader sequence.

In some embodiments, the nucleic acid encoding the consensus FSHR antigen can be a heterologous nucleic acid sequence and/or contain one or more heterologous nucleic acid sequences.

(18) gp100

The immunogenic composition of the present invention can comprise the cancer antigen glycoprotein 100 (gp100; also known as Trp2 and premelanosome protein (PMEL)), a fragment thereof, or a variant thereof gp100 is encoded by the PMEL gene. It is a 70 kDa type 1 transmembrane glycoprotein, comprised of 661 amino acids that plays a central role in the biogenesis of melanosomes as it is involved in the maturation of melanosomes from stage I to II. gp100 drives the formation of striations from within multivesicular bodies and is directly involved in the biogenesis of premelanosomes. gp100 is enriched in premelanosomes relative to mature melanosomes, but overexpressed by proliferating neonatal melanocytes and during tumor growth. The gp100 protein includes a variety of immunogenic epitopes that are recognized by cytotoxic T lymphocytes from peripheral blood of melanoma patients and from tumor infiltrating lymphocytes.

The gp100 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

(19) Viral Antigens

The cancer antigen can be a viral antigen, a fragment thereof, or a variant thereof. The viral antigen can be antigen from a hepatitis B virus, a hepatitis C virus, or a human papilloma virus (HPV). The HPV can be HPV 6, HPV 11, HPV 16, or HPV 18 as discussed below.

The viral antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

(a) Hepatitis B Virus Antigen

The viral antigen can be an antigen from Hepatitis B virus (HBV), a fragment thereof, or a variant thereof. The HBV antigen can be associated with or cause liver cancer. In some embodiments, the HBV antigen can be a heterologous nucleic acid molecule(s), such as a plasmid(s), which encodes one or more of the antigens from HBV. The HBV antigen can be full-length or immunogenic fragments of full-length proteins.

The HBV antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus HBV antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The HBV antigen can be a HBV core protein, a HBV surface protein, a HBV DNA polymerase, a HBV protein encoded by gene X, fragment thereof, variant thereof, or combination thereof. The HBV antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The HBV antigen can be a consensus HBV core protein, or a consensus HBV surface protein.

In some embodiments, the HBV antigen can be a HBV genotype A consensus core nucleic acid sequence construct, an IgE leader sequence linked to a consensus sequence for HBV genotype A core protein, or a HBV genotype A consensus core protein sequence.

In other embodiments, the HBV antigen can be a HBV genotype B consensus core nucleic acid sequence construct, an IgE leader sequence linked to a consensus sequence for HBV genotype B core protein, or a HBV genotype B consensus core protein sequence.

In still other embodiments, the HBV antigen can be a HBV genotype C consensus core nucleic acid sequence construct, an IgE leader sequence linked to a consensus sequence for HBV genotype C core protein, or a HBV genotype C consensus core protein sequence.

In some embodiments, the HBV antigen can be a HBV genotype D consensus core nucleic acid sequence construct, an IgE leader sequence linked to a consensus sequence for HBV genotype D core protein, or a HBV genotype D consensus core protein sequence.

In other embodiments, the HBV antigen can be a HBV genotype E consensus core nucleic acid sequence construct, an IgE leader sequence linked to a consensus sequence for HBV genotype E core protein, or a HBV genotype E consensus core protein sequence.

In some embodiments, the HBV antigen can be a HBV genotype F consensus core nucleic acid sequence construct, an IgE leader sequence linked to a consensus sequence for HBV genotype F core protein, or a HBV genotype F consensus core protein sequence.

In other embodiments, the HBV antigen can be a HBV genotype G consensus core nucleic acid sequence construct, an IgE leader sequence linked to a consensus sequence for HBV genotype G core protein, or a HBV genotype G consensus core protein sequence.

In some embodiments, the HBV antigen can be a HBV genotype H consensus core nucleic acid sequence construct, an IgE leader sequence linked to a consensus sequence for HBV genotype H core protein, or a HBV genotype H consensus core protein sequence.

In still other embodiments, the HBV antigen can be a HBV genotype A consensus surface nucleic acid sequence construct, an IgE leader sequence linked to a consensus sequence for HBV genotype A surface protein, or a HBV genotype A consensus surface protein sequence.

In some embodiments, the HBV antigen can be a HBV genotype B consensus surface nucleic acid sequence construct, an IgE leader sequence linked to a consensus sequence for HBV genotype B surface protein, or a HBV genotype B consensus surface protein sequence.

In other embodiments, the HBV antigen can be a HBV genotype C consensus surface nucleic acid sequence construct, an IgE leader sequence linked to a consensus sequence for HBV genotype C surface protein, or a HBV genotype C consensus surface protein sequence.

In still other embodiments, the HBV antigen can be a HBV genotype D consensus surface nucleic acid sequence construct, an IgE leader sequence linked to a consensus sequence for HBV genotype D surface protein, or a HBV genotype D consensus surface protein sequence.

In some embodiments, the HBV antigen can be a HBV genotype E consensus surface nucleic acid sequence construct, an IgE leader sequence linked to a consensus sequence for HBV genotype E surface protein, or a HBV genotype E consensus surface protein sequence.

In other embodiments, the HBV antigen can be a HBV genotype F consensus surface nucleic acid sequence construct, an IgE leader sequence linked to a consensus sequence for HBV genotype F surface protein, or a HBV genotype F consensus surface protein sequence.

In still other embodiments, the HBV antigen can be a HBV genotype G consensus surface nucleic acid sequence construct, an IgE leader sequence linked to a consensus sequence for HBV genotype G surface protein, or a HBV genotype G consensus surface protein sequence.

In other embodiments, the HBV antigen can be a HBV genotype H consensus surface nucleic acid sequence construct, an IgE leader sequence linked to a consensus sequence for HBV genotype H surface protein, or a HBV genotype H consensus surface protein sequence.

(b) Hepatitis C Virus Antigen

The viral antigen can be an antigen from Hepatitis C virus (HCV), a fragment thereof, or a variant thereof. The HCV antigen can be associated with or cause liver cancer. In some embodiments, the HCV antigen can be a heterologous nucleic acid molecule(s), such as a plasmid(s), which encodes one or more of the antigens from HCV. The HCV antigen can be full-length or immunogenic fragments of full-length proteins.

The HCV antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus HCV antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The HCV antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

(c) Human Papilloma Virus

The viral antigen can be an antigen from HPV, a fragment thereof, or a variant thereof. The HPV antigen can be from HPV types 16, 18, 31, 33, 35, 45, 52, and 58, which cause cervical cancer, rectal cancer, and/or other cancers. The HPV antigen can be from HPV types 6 and/or 11, which cause genital warts, and are known to be causes of head and neck cancer. The HPV antigen can be from HPV types 16 and/or 18, which cause cervical cancer. The HPV antigen can be from HPV types 6, 11, and/or 16, which cause RRP and anal cancer. The HPV cancer antigen can further be defined by U.S. Pat. No. 8,168,769 filed Jul. 30, 2007, U.S. Pat. No. 8,389,706 filed Jan. 21, 2010, U.S. patent application Ser. No. 13/271,576 filed Oct. 21, 2011 and U.S. Patent Appl. No. 61/777,198, filed Mar. 12, 2013, each of which are incorporated by reference in their entirety.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 16 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(d) Herpes Viruses

The viral antigen may be a herpes viral antigen. The herpes viral antigen can be an antigen selected from the group consisting of CMV, HSV1, HSV2, VZV, CeHV1, EBV, roseolovirus, Kaposi's sarcoma-associated herpesvirus, and MuHV.

A consensus protein HCMV-gB (SEQ ID NO:26), a consensus protein HCMV-gM (SEQ ID NO:28), a consensus protein HCMV-gN (SEQ ID NO:30), a consensus protein HCMV-gH (SEQ ID NO:32), a consensus protein HCMV-gL (SEQ ID NO:34), a consensus protein HCMV-gO (SEQ ID NO:36), a consensus protein HCMV-UL128 (SEQ ID NO:38), a consensus protein HCMV-UL130 (SEQ ID NO:40), a consensus protein HCMV-UL-131A (SEQ ID NO:42), a consensus protein HCMV-UL-83 (pp65) (SEQ ID NO:44).

Nucleic acid sequences including sequences encoding SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44. Nucleic acid molecules encoding the consensus amino acid sequences were generated. Immunogenic compositions may comprise one or more nucleic acid sequences that encode one or more of the consensus versions of the immunogenic proteins selected from this group of sequences generated to optimize stability and expression in humans. Nucleic acid sequence encoding consensus protein HCMV-gB (SEQ ID NO:25), nucleic acid sequence encoding consensus protein HCMV-gM (SEQ ID NO:27), nucleic acid sequence encoding consensus protein HCMV-gN (SEQ ID NO:29), nucleic acid sequence encoding consensus protein HCMV-gH (SEQ ID NO:31), nucleic acid sequence encoding consensus protein HCMV-gL (SEQ ID NO:33), nucleic acid sequence encoding consensus protein HCMV-gO (SEQ ID NO:35), nucleic acid sequence encoding consensus protein HCMV-UL128 (SEQ ID NO:37), nucleic acid sequence encoding consensus protein HCMV-UL130 (SEQ ID NO:39), nucleic acid sequence encoding consensus protein HCMV-UL-131A (SEQ ID NO:41), nucleic acid sequence encoding consensus protein HCMV-UL-83 (pp65) (SEQ ID NO:43). The nucleic acid sequence can additionally have an encoding IgE leader linked to the 5' end.

In view of evolutionary divergence from clinical isolates and extensive genetic differences among prevalent circulating human strains consensus amino acid sequences for each of immunogenic proteins have been generated. Consensus amino acid sequences for gB, gM, gH, gL, gE, gI, gK, gC, gD, UL128, UL130, UL-131A and UL-83 (pp65) were based upon sequences from human clinical isolates. Due to the great evolutionary divergence of the gN protein, the consensus sequence was generated from only one (gN-4c) of seven serotypes that represents the most sero-prevalent (gN-4). Similarly, in the case gO, a consensus amino acid sequences was generated from one (gO-5) of eight serotypes due to that particular serotypes reported linkage with the gN-4c sero-type.

As described above, the herpes viral antigen may be a consensus herpes virus. The consensus herpes viral antigen may be provided with a signal peptide. In some embodiments, the IgE leader is linked to the N terminus. As described herein, when referring to a signal peptide linked to the N terminus of a consensus sequence, it is intended to specifically include embodiments in which the N terminal Xaa residue of the consensus sequences is replaced with a signal peptide. That is, as used herein Xaa is intended to refer to any amino acid or no amino acid. The proteins which comprise a consensus sequence set forth herein SEQ ID NOs: 26, 28, 30, 32, 34, 36, 38, 40, 42, 44 may comprise those sequences free of the N terminal Xaa.

Amino acid sequences were generated which comprised in each particular instance, the IgE leader sequence at the N terminus of the herpes virus immunogenic protein consensus sequences. In some embodiments, nucleic acid constructs are provided in which two or more herpes virus antigens are expressed as fusion proteins linked to each other by proteolytic cleavage sites. A furin proteolytic cleavage site is an example of a proteolytic cleavage site which may link herpes virus antigens in a fusion protein expressed by a construct. The viral cancer antigen of the herpes family may further be any antigen disclosed in U.S. patent application Ser. No. 13/982,457, the contents of which is incorporated by reference in its' entirety.

4. Immunogenic Composition in Combination with Immune Checkpoint Inhibitor

The immunogenic composition can further comprise one or more inhibitors of one or more immune checkpoint molecules (i.e., an immune checkpoint inhibitor). Immune check point molecules are described below in more detail. The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune check point inhibitor can be an antibody, a variant thereof, a fragment thereof, or a combination thereof.

a. Immune Checkpoint Molecule

The immune check point molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof. The immune checkpoint molecule may be an inhibitor of at least one immune checkpoint protein. Immune checkpoint proteins include, but are not limited to, PD-1, PD-L1, CTLA4, TIM3 and LAG3.

b. Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

(1) PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

(2) PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

(3) CTLA4 Antibody

The anti-immune checkpoint molecule antibody can be an anti-CTLA4 antibody (also referred to herein as "CTLA4 antibody"), a variant thereof, a fragment thereof, or a combination thereof. The anti-CTLA4 antibody can inhibit CTLA4 activity, thereby inducing, eliciting, or increasing an immune response against a tumor or cancer and decreasing tumor growth.

(4) TIM3 Antibody

The anti-immune checkpoint molecule antibody can be an anti-TIM3 antibody (also referred to herein as "TIM3 antibody"), a variant thereof, a fragment thereof, or a combination thereof. The anti-TIM3 antibody can inhibit TIM3 activity, thereby inducing, eliciting, or increasing an immune response against a tumor or cancer and decreasing tumor growth.

(5) LAG3 Antibody

The anti-immune checkpoint molecule antibody can be an anti-LAG3 antibody (also referred to herein as "LAG3 antibody"), a variant thereof, a fragment thereof, or a combination thereof. The anti-LAG3 antibody can inhibit LAG3 activity, thereby inducing, eliciting, or increasing an immune response against a tumor or cancer and decreasing tumor growth.

5. Constructs and Plasmids

The immunogenic composition can comprise nucleic acid constructs or plasmids that encode the above described antigens and/or antibodies. The nucleic acid constructs or plasmids can include or contain one or more heterologous nucleic acid sequences. Provided herein are genetic constructs that can comprise a nucleic acid sequence that encodes the above described antigens and/or antibodies. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic construct can be useful for transfecting cells with nucleic acid encoding the above described antigens and/or antibodies, which the transformed host cell is cultured and maintained under conditions wherein expression of the above described antigens and/or antibodies takes place.

Coding sequences can be optimized for stability and high levels of expression. In some instances, codons are selected to reduce secondary structure formation of the RNA such as that formed due to intramolecular bonding.

The genetic constructs can be in the form of plasmids expressing the above described antigens and/or antibodies in any order.

Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

RNA Vectors

In one embodiment, the nucleic acid is an RNA molecule. Accordingly, in one embodiment, the invention provides an RNA molecule encoding one or more MAYV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleotide sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be pcrM2. The LEC can be pcrNP. pcrNP and pcrMR can be derived from pNP (Puerto Rico/34) and pM2 (New Caledonia/99), respectively.

Promoter, Intron, Stop Codon, and Polyadenylation Signal

The vector can comprise heterologous nucleic acid encoding the above described antigens and/or antibodies and can further comprise an initiation codon, which can be upstream of the one or more cancer antigen coding sequence(s), and a stop codon, which can be downstream of the coding sequence(s) of the above described antigens and/or antibodies.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The initiation and termination codon can be in frame with the coding sequence(s) of the above described antigens and/or antibodies. The vector can also comprise a promoter that is operably linked to the coding sequence(s) of the above described antigens and/or antibodies. The promoter operably linked to the coding sequence(s) of the above described antigens and/or antibodies can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens and/or antibodies. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the above described antigens and/or antibodies. The enhancer can be necessary for expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for a single antigen. In one embodiment, the antigen is FAP. Immunogenic compositions may comprise nucleic acid molecules, such as plasmids, that collectively contain coding sequence for multiple antigens. As an example, in one embodiment, the antigens are multiple antigens selected from TERT and an additional cancer antigen. In one exemplary embodiment, the antigens are WT-1 and TERT. In one exemplary embodiment, the antigens are PSMA and TERT. In another exemplary embodiment, the antigens are TERT, WT-1 and PSMA. Immunogenic compositions may comprise nucleic acid molecules, such as plasmids, that collectively contain coding sequence for one or more antigen and one or more cancer antigen.

Origin of Replication

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>−2876 backbone, downstream of the Kanamycin gene

C>T 3277 in pUC origin of replication (On) high copy number mutation (see Nucleic Acid Research 1985)

G>C 3753 in very end of pUC On upstream of RNASeH site

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The one or more cancer antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

6. Pharmaceutical Compositions

The immunogenic composition can be in the form of a pharmaceutical composition. The pharmaceutical composition can comprise the immunogenic composition. The pharmaceutical compositions can comprise about 5 nanograms to about 10 mg of a nucleic acid molecule encoding an antigen of the invention. In some embodiments, pharmaceutical compositions according to the present invention comprise about 25 nanogram to about 5 mg of nucleic acid. In some embodiments, the pharmaceutical compositions contain about 50 nanograms to about 1 mg of nucleic acid. In some embodiments, the pharmaceutical compositions contain about 0.1 to about 500 micrograms of nucleic acid. In some embodiments, the pharmaceutical compositions contain about 1 to about 350 micrograms of nucleic acid. In some embodiments, the pharmaceutical compositions contain about 5 to about 250 micrograms of nucleic acid. In some embodiments, the pharmaceutical compositions contain about 10 to about 200 micrograms of nucleic acid. In some embodiments, the pharmaceutical compositions contain about 15 to about 150 micrograms of nucleic acid. In some embodiments, the pharmaceutical compositions contain about 20 to about 100 micrograms of nucleic acid. In some embodiments, the pharmaceutical compositions contain about 25 to about 75 micrograms of nucleic acid. In some embodiments, the pharmaceutical compositions contain about 30 to about 50 micrograms of nucleic acid. In some embodiments, the pharmaceutical compositions contain about 35 to about 40 micrograms of nucleic acid. In some embodiments, the pharmaceutical compositions contain about 100 to about 200 microgram of nucleic acid. In some embodiments, the pharmaceutical compositions comprise about 10 microgram to about 100 micrograms of nucleic acid. In some embodiments, the pharmaceutical compositions comprise about 20 micrograms to about 80 micrograms of nucleic acid. In some embodiments, the pharmaceutical compositions comprise about 25 micrograms to about 60 micrograms of nucleic acid. In some embodiments, the pharmaceutical compositions comprise about 30 nanograms to about 50 micrograms of nucleic acid. In some embodiments, the pharmaceutical compositions comprise about 35 nanograms to about 45 micrograms of nucleic acid. In some embodiments, the pharmaceutical compositions contain about 0.1 to about 500 micrograms of nucleic acid. In some embodiments, the pharmaceutical compositions contain about 1 to about 350 micrograms of nucleic acid. In some embodiments, the pharmaceutical compositions contain about 25 to about 250 micrograms of nucleic acid. In some embodiments, the pharmaceutical compositions contain about 100 to about 200 microgram nucleic acid.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of nucleic acid. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of nucleic acid. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of nucleic acid.

In other embodiments, the pharmaceutical composition can comprise up to and including 15, 20, 25, 30, 35, 40, 45, 50, 55, 60, 65, 70, 75, 80, 85, 90, 95 or 100 nanograms of nucleic acid. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms of nucleic acid. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of nucleic acid.

The pharmaceutical composition can further comprise other agents for formulation purposes according to the mode of administration to be used. In cases where pharmaceutical compositions are injectable pharmaceutical compositions, they are sterile, pyrogen free and particulate free. In one embodiment, an isotonic formulation is used. Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation.

The immunogenic composition can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate. In one embodiment, the poly-L-glutamate is present in the immunogenic composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the immunogenic composition can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In one embodiment, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the immunogenic composition. The adjuvant can be selected from the group consisting of α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, 0x40, 0x40 LIGAND, NKG2D, MICA, MICB, NKG2A, NKG2B, NKG2C, NKG2E, NKG2F, TAP1, TAP2 and functional fragments thereof.

7. Combinational Immunogenic Compositions for Treating Particular Cancers

The immunogenic composition can be in the form of various combinations of the TERT antigen with one or more cancer antigens as described above to treat particular cancer or tumors. Depending upon the combination of one or more cancer antigens, various cancers or other tumor types may be targeted with the immunogenic composition. These cancers can include melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

a. Melanoma

The immunogenic composition can combine a TERT antigen and one or more cancer antigens such as tyrosinase, PRAME, or GP100-Trp2 to treat or prevent melanoma. The immunogenic composition can further combine one or more cancer antigen tyrosinase, PRAME, or GP100-Trp2 with any one or more cancer antigens NY-ESO-1, MAGE-A1, or WT1 for treating or preventing melanoma. Other combinations of cancer antigens may also be applied for treating or preventing melanoma.

b. Head and Neck Cancer

The immunogenic composition can comprise can combine a TERT antigen and one or more cancer antigen HPV 16 E6/E7 to treat or prevent head and neck cancer. The immunogenic composition can further combine cancer antigen HPV 16 E6/E7 with any one or more cancer antigens NY-ESO-1, MAGE-A1, or WT1 for treating or preventing head and neck cancer. Other combinations of cancer antigens may also be applied for treating or preventing head and neck cancer.

c. Recurrent Respiratory Papillomatosis/Anal Cancer

The immunogenic composition can combine a TERT antigen and one or more cancer antigen one or more cancer antigens such as HPV 6, HPV11, or HPV 16 to treat or prevent recurrent respiratory papilloatosis or anal cancer. The immunogenic composition can further combine one or more cancer antigens HPV 6, HPV11 or HPV16 with one or more cancer antigens, NY-ESO-1, MAGE-A1, or WT1 for treating or preventing recurrent respiratory papilloatosis or anal cancer. Other combinations of cancer antigens may also be applied for treating or preventing recurrent respiratory papilloatosis or anal cancer.

d. Cervical Cancer

The immunogenic composition can combine a TERT antigen and one or more cancer antigen one or more cancer antigens such as HPV 16 E6/E7 or HPV 18 E6/E7 to treat or prevent cervical cancer. The immunogenic composition can further combine one or more cancer antigens such as HPV 16 E6/E7 or HPV 18 E6/E7 with one or more cancer antigens NY-ESO-1, MAGE-A1, or WT1 for treating or preventing cervical. Other combinations of cancer antigens may also be applied for treating or preventing cervical cancer.

e. Liver Cancer

The immunogenic composition can combine a TERT antigen and one or more cancer antigen such as HBV core antigen, HBV surface antigen, HCVNS34A, HCVNS5A, HCV NS5B, or HCVNS4B to treat or prevent liver cancer. The immunogenic composition can further combine one or more cancer antigens HBV core antigen, HBV surface antigen, HCVNS34A, HCVNS5A, HCV NS5B, or HCVNS4B with one or more of cancer antigens NY-ESO-1, MAGE-A1, or WT1 for treating or preventing liver cancer. Other combinations of cancer antigens may also be applied for treating or preventing liver cancer.

f. Glioblastoma

The immunogenic composition can comprise a TERT antigen and one or more cancer antigen CMV to treat or prevent glioblastoma. The immunogenic composition can further combine CMV with one or more of cancer antigens NY-ESO-1, MAGE-A1, or WT1 for treating or preventing glioblastoma. Other combinations of cancer antigens may also be applied for treating or preventing glioblastoma.

g. Prostate

The immunogenic composition can combine a TERT antigen and one or more cancer antigens such as PSA, PSMA, or STEAP to treat or prevent prostate cancer. The immunogenic composition can further combine one or more cancer antigens PSA, PSMA, or STEAP with one or more of cancer antigens NY-ESO-1, MAGE-A1, or WT1 for treating or preventing prostate cancer. Other combinations of cancer antigens may also be applied for treating or preventing prostate cancer.

h. Blood Cancers (e.g., Leukemia, Lymphoma, Myeloma)

The immunogenic composition can combine a TERT antigen and one or more cancer antigens such as PRAME and WT-1 to treat or prevent blood cancers such as leukemia, lymphoma and myeloma. The immunogenic composition can further combine one or more cancer antigens PRAME and WT-1 with one or more of cancer antigens NY-ESO-1, or MAGE-A1 for treating or preventing blood cancers such as leukemia, lymphoma and myeloma. Other combinations of cancer antigens may also be applied for treating or preventing blood cancers such as leukemia, lymphoma and myeloma cancer.

i. Ovarian Cancers

The immunogenic composition can combine a TERT antigen and one or more cancer antigens such as a follicle stimulating hormone receptor (FSHR) antigen to treat or prevent ovarian cancer. The immunogenic composition can further combine FSHR with one or more of cancer antigens NY-ESO-1, or MAGE-A1 for treating or preventing ovarian cancer. Other combinations of cancer antigens may also be applied for treating or preventing ovarian cancer.

j. Other Cancers

The immunogenic composition can combine a TERT antigen and one or more cancer antigens such as FAP to treat or prevent cancers. The immunogenic composition can further combine FAP with one or more of cancer antigens NY-ESO-1, or MAGE-A1 for treating or preventing cancers. Other combinations of cancer antigens may also be applied for treating or preventing cancers.

8. Method of Vaccination

Provided herein is a method for treating or prevent cancer using the pharmaceutical formulations for providing genetic constructs and proteins of the one or more cancer antigens as described above, which comprise epitopes that make them particular effective immunogens against which an immune response to the one or more cancer antigens can be induced. The method of administering the immunogenic composition, or vaccination, can be provided to induce a therapeutic and/or prophylactic immune response. The vaccination process can generate in the mammal an immune response against one or more of the cancer antigens as disclosed herein. The immunogenic composition can be administered to an individual to modulate the activity of the mammal's immune system and enhance the immune response. The administration of the immunogenic composition can be the transfection of the one or more cancer antigens as disclosed herein as a nucleic acid molecule that is expressed in the cell and thus, delivered to the surface of the cell upon which the immune system recognizes and induces a cellular, humoral, or cellular and humoral response. The administration of the immunogenic composition can be used to induce or elicit an immune response in mammals against one or more of the cancer antigens as disclosed herein by administering to the mammals the immunogenic composition as discussed herein.

Upon administration of the immunogenic composition to the mammal, and thereupon the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal administered the immunogenic composition discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses. The immunogenic composition can be administered to an individual to modulate the activity of the individual's immune system, thereby enhancing the immune response.

Methods of administering the immunogenic composition are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken.

The immunogenic composition dose can be between 1 µg to 10 mg active component/kg body weight/time and can be 20 µg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, 10, or more doses.

a. Method of Generating an Immune Response with the Immunogenic Composition

The immunogenic composition can be used to generate an immune response in a mammal, including therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which comprise administering to an individual the immunogenic composition. Some embodiments provide methods of prophylactically vaccinating an individual against a cancer or tumor expressing one or more of the cancer antigens as described above, which comprise administering the immunogenic composition. Some embodiments provide methods of therapeutically vaccinating an individual that has been suffering from the cancer or tumor expressing one or more of the cancer antigens, which comprise administering the immunogenic composition. Diagnosis of the cancer or tumor expressing the one or more cancer antigens as disclosed herein prior to administration of the immunogenic composition can be done routinely.

b. Method of Cancer Treatment with the Immunogenic Composition

The immunogenic composition can be used to generate or elicit an immune response in a mammal that is reactive or directed to a cancer or tumor (e.g., melanoma, head and neck, cervical, liver, prostate, blood cancers, esophageal squamous, gastric) of the mammal or subject in need thereof. The elicited immune response can prevent cancer or tumor growth.

The elicited immune response can prevent and/or reduce metastasis of cancerous or tumor cells. Accordingly, the immunogenic composition can be used in a method that treats and/or prevents cancer or tumors in the mammal or subject administered the immunogenic composition. Depending upon the antigen used in the immunogenic composition, the treated cancer or tumor based growth can be any type of cancer such as, but not limited to, melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

In some embodiments, the administered immunogenic composition can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-γ and TFN-α or a combination of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the immunogenic composition.

In some embodiments, the administered immunogenic composition can increase tumor free survival, reduce tumor mass, increase tumor survival, or a combination thereof in the subject. The administered immunogenic composition can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The administered immunogenic composition can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60, 61%, 62%, 63%, 64%, 65%, 66%, 67%, 68%, 69%, and 70% in the subject after immunization.

The administered immunogenic composition can prevent and block increases in monocyte chemoattractant protein 1 (MCP-1), a cytokine secreted by myeloid derived suppressor cells, in the subject. In some embodiments, the administered immunogenic composition can prevent and block increases in MCP-1 within the cancerous or tumor tissue in the subject, thereby reducing vascularization of the cancerous or tumor tissue in the subject.

The administered immunogenic composition can increase tumor survival by 20%, 21%, 22%, 23%, 24%, 25%, 26%, 27%, 28%, 29%, 30%, 31%, 32%, 33%, 34%, 35%, 36%, 37%, 38%, 39% 40%, 41%, 42%, 43%, 44%, 45%, 46%, 47%, 48%, 49%, 50%, 51%, 52%, 53%, 54%, 55%, 56%, %57%, 58%, 59%, 60%, 61%, 62%, 63%, 64%, 65%, 66%, 67%, 68%, 69%, and 70% in the subject. In some embodiments, the immunogenic composition can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the immunogenic composition.

The administered immunogenic composition can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered immunogenic composition can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered immunogenic composition can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered immunogenic composition can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The immunogenic composition dose can be between 1 μg to 10 mg active component/kg body weight/time and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

(1) Combinational Therapies with Immune Checkpoint Targeting Antibodies

The present invention is also directed to a method of increasing an immune response in a mammal using the immunogenic composition as described above. The immunogenic composition as described above can comprise the cancer antigen and a PD1 antibody and/or PDL1 antibody as described above. The combination can be in a single formulation or can be separate and administered in sequence (either cancer antigen first and then immune checkpoint antibody or immune checkpoint antibody first and then cancer antigen). In some embodiments, the cancer antigen can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the immune checkpoint antibody is administered to the subject. In other embodiments, the immune checkpoint antibody can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the cancer antigen is administered to the subject.

The combination of the cancer antigen and immune checkpoint antibody induces the immune system more efficiently than an immunogenic composition comprising the cancer antigen alone. This more efficient immune response provides increased efficacy in the treatment and/or prevention of a particular cancer. Depending upon the antigen used in the immunogenic composition combined with the immune checkpoint antibody, the treated cancer or tumor based growth can be any type of cancer such as, but not limited to, melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

In some embodiments, the immune response can be increased by about 0.5-fold to about 15-fold, about 0.5-fold to about 10-fold, or about 0.5-fold to about 8-fold. Alternatively, the immune response in the subject administered the immunogenic composition can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the immunogenic composition can be increased about 50% to about 1500%, about 50% to about 1000%, or about 50% to about 800%. In other embodiments, the immune response in the subject administered the immunogenic composition can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The immunogenic composition dose can be between 1 µg to 10 mg active component/kg body weight/time, and can be 20 µg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

(2) Cancer

The immunogenic composition can be used to generate or elicit an immune response in a mammal that is reactive or directed to a tumor in the mammal or subject in need thereof. The elicited immune response can prevent tumor growth. The elicited immune response can reduce tumor growth. The elicited immune response can prevent and/or reduce metastasis of cancerous or tumor cells. Accordingly, the immunogenic composition can be used in a method that treats and/or prevents cancer in the mammal or subject administered the immunogenic composition.

In some embodiments, the administered immunogenic composition can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing melanoma growth; (2) increase cytotoxic T lymphocyte such as $CD8^+$ (CTL) to attack and kill melanoma cells; (3) increase T helper cell responses; (4) and increase inflammatory responses via IFN-γ and TFN-α or a combination of the aforementioned.

In some embodiments, the administered immunogenic composition can increase tumor free survival, reduce tumor mass, increase tumor-free survival, or a combination thereof in the subject. The administered immunogenic composition can increase tumor-free survival by 30%, 31%, 32%, 33%, 34%, 35%, 36%, 37%, 38%, 39%, 40%, 41%, 42%, 43%, 44%, and 45% in the subject. The administered immunogenic composition can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject after immunization. The administered immunogenic composition can reduce vascularization of the tumor tissue in the subject. The administered immunogenic composition can increase tumor survival by 30%, 31%, 32%, 33%, 34%, 35%, 36%, 37%, 38%, 39% 40%, 41%, 42%, 43%, 44%, 45%, 46%, 47%, 48%, 49%, 50%, 51%, 52%, 53%, 54%, 55%, 56%, 57%, 58%, 59%, and 60% in the subject.

9. Routes of Administration

The immunogenic composition or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The immunogenic composition can be administered by traditional syringes, needleless injection devices, "microprojectile bombardment gone guns", or other physical methods such as electroporation ("EP"), "hydrodynamic method", or ultrasound.

The vector of the immunogenic composition can be administering to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The one or more cancer antigens of the immunogenic composition can be administered via DNA injection and along with in vivo electroporation.

a. Electroporation

The immunogenic composition or pharmaceutical composition can be administered by electroporation. Administration of the immunogenic composition via electroporation can be accomplished using electroporation devices that can be configured to deliver to a desired tissue of a mammal a pulse of energy effective to cause reversible pores to form in cell membranes. In one embodiment, the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate administration of the immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the include those provided in co-pending and co-owned U.S. patent application Ser. No. 11/874,072, filed Oct. 17, 2007, which claims the benefit under 35 USC 119(e) to U.S. Provisional application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deneurological system the biomolecule of choice) is also inserted completely into the target organ, and the injection is administered perpendicular to the target issue, in the area that is pre-delineated by the electrodes. In one embodiment, the electrodes are 20 mm long and 21 gauge, as described in U.S. Pat. No. 7,245,963 and U.S. Patent Pub. 2005/005263.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

10. Method of Preparing the Immunogenic Composition

Provided herein are methods for preparing nucleic acid molecules that comprise the immunogenic compositions discussed herein. The nucleic acid molecules can be used to inoculate a cell culture in a large scale fermentation tank, using known methods in the art.

The nucleic acid molecules for use with the EP devices of the present invention can be formulated or manufactured using a combination of known devices and techniques. In one embodiment, they are manufactured using an optimized plasmid manufacturing technique that is described in a US published application no. 20090004716, which was filed on May 23, 2007. In some examples, the nucleic acid molecules used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

11. Examples

Example 1

Construction of pTyr

Figure 9:
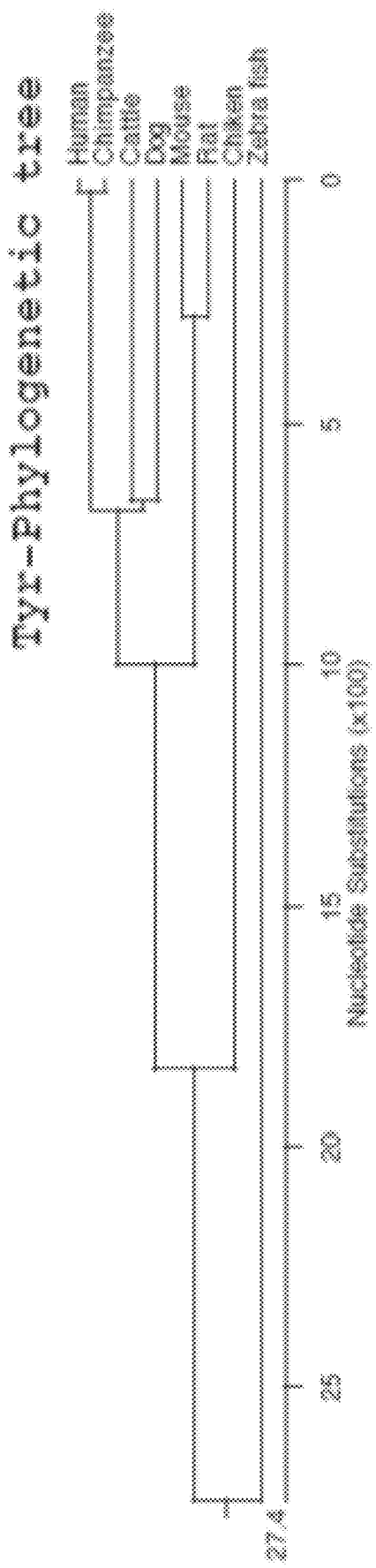
FIG. 9 depicts the results of experiments demonstrating the phylogenetic relationship of Tyr nucleotide sequences amongst the indicated organisms.

As shown in FIGS. 1A and 9, Tyrosinase (Tyr) can be found in many different organisms. Accordingly, a consensus Tyr was generated by aligning sequences corresponding to Tyr from the organisms shown in FIG. 1A, and choosing the most common amino acid and/or nucleotide for the consensus Tyr. The corresponding Tyr sequences for each organism were obtained from GenBank (NCBI). As such, the consensus Tyr reflected the conserved elements of Tyr sequences across species.

The nucleic acid sequence encoding the consensus Tyr was adapted to include the IgE leader sequence. Specifically, the IgE leader sequence was fused in frame upstream of the consensus Tyr nucleic acid sequence (FIG. 1B). The resulting sequence was then inserted into the pVax1 expression vector to create a Tyrosinase construct or plasmid (pTyr) such that a Kozak sequence preceded the nucleotide sequence encoding the IgE leader sequence and the consensus Tyr.

Figures 1C, 1D, 1E:
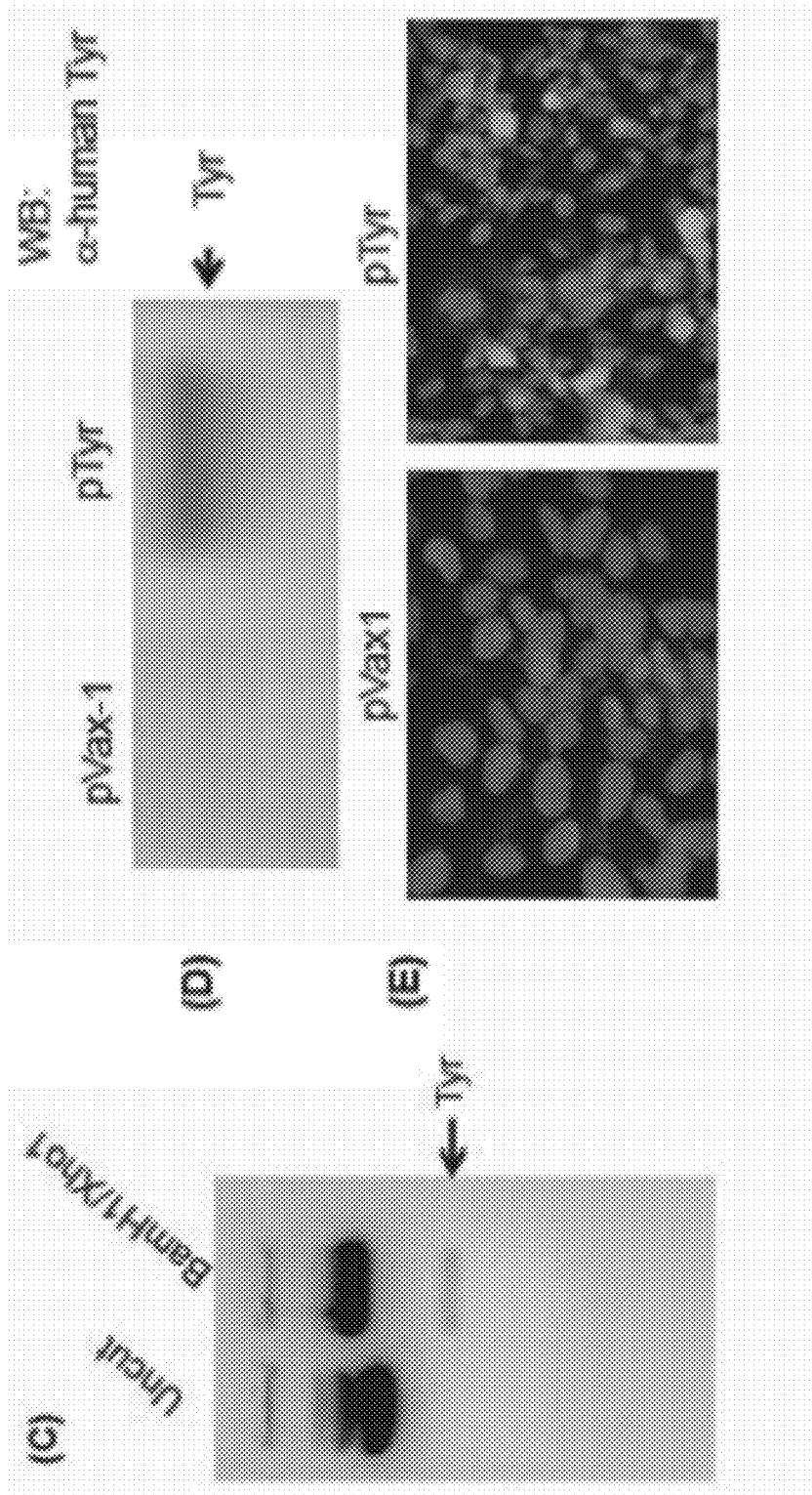

Insertion of the consensus Tyr nucleic acid sequence into pVax1 was confirmed by restriction enzyme analysis. As shown in FIG. 1C, the consensus Tyr nucleic acid sequence was separated from the pVax1 plasmid on a DNA agarose gel (i.e., the lane labeled BamH1/Xho1), thereby confirming that the pVax1 vector contained the consensus Tyr nucleic acid sequence.

Expression of the consensus Tyr was confirmed by transfecting HeLa cells with pTyr. Western blotting with a human anti-Tyr antibody confirmed expression of the consensus Tyr protein in HeLa cells (FIG. 1D). GPF staining further showed expression of the consensus Tyr protein in transfected HeLa cells (FIG. 1E). In both the western blotting and staining experiments, Example 2

Vaccination with pTyr Induced a Cell Mediated Immune Response

The above described pTyr was used to vaccinate mice to evaluate whether a cellular immune response was induced by pTyr. C57/B6 mice were immunized using the immunization strategy shown in FIG. 2A. Some mice were immunized with pVax1 while other mice were immunized with pTyr. The mice immunized with pTyr were further broken into the following groups: (1) 5 μg dosage of pTyr; (2) 20 μg dosage of pTyr; (3) 30 μg dosage of pTyr; and (4) 60 μg dosage of pTyr.

Figures 2A, 2B:
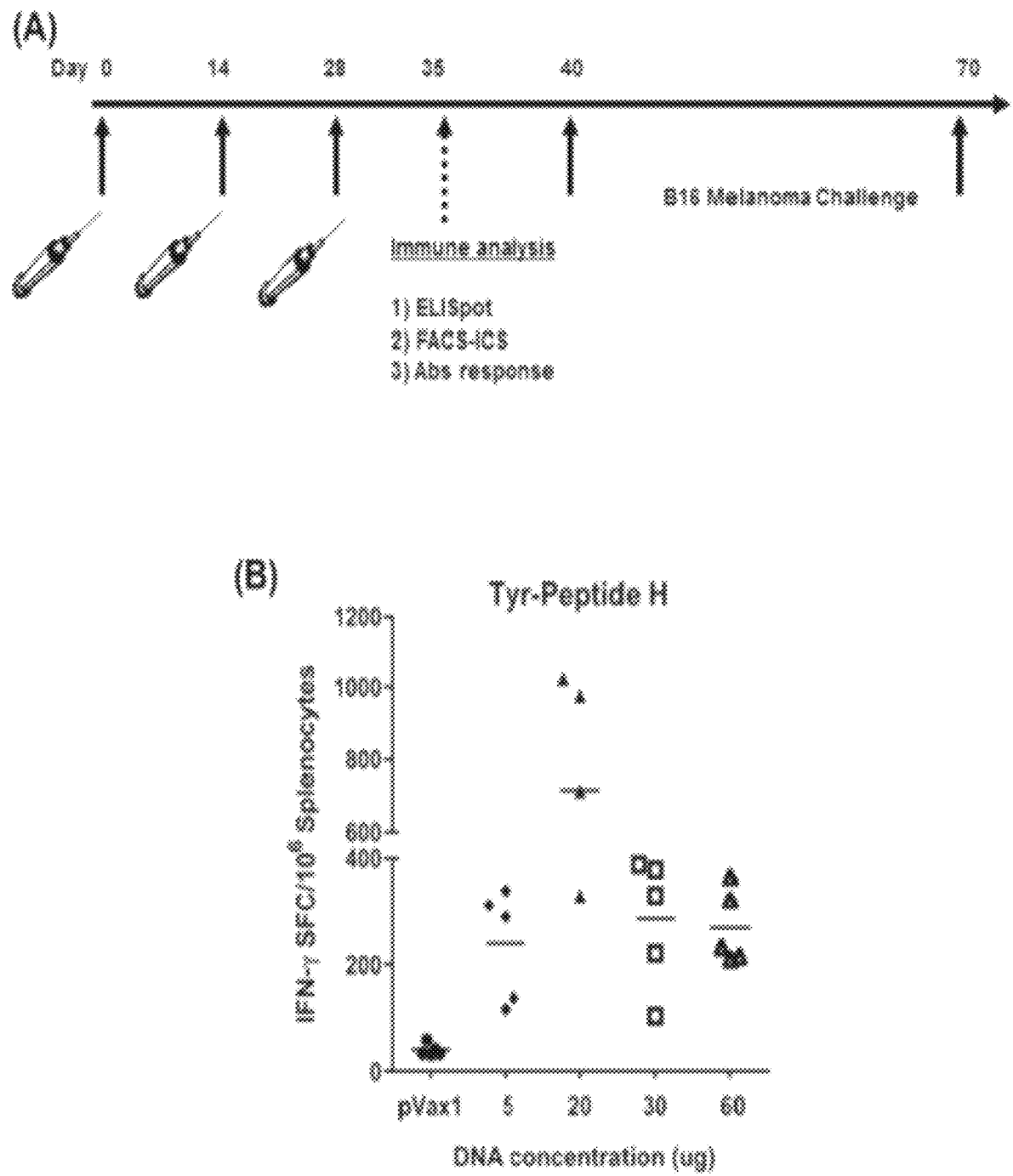
FIG. 2A through FIG. 2B, depicts the results of experiments demonstrating an immunization strategy and induction of cell mediated immune responses by Tyr DNA vaccination, respectively.

At day 35 of the immunization strategy, splenocytes were isolated from the C57B/6 mice and evaluated for induction of interferon-γ (IFN-γ) by IFN-γ ELISpot analysis. As shown in FIG. 2B, the 20 μg dosage of pTyr induced the highest levels of IFN-γ.

The cellular immune response to pTyr was further evaluated in immunized Balb/c and C57B/6 mice. Mice were immunized with either pVax1 or pTyr. Splenocytes were isolated two weeks after the third immunization and stimulated with the consensus Tyr peptide. After stimulation, the number of IFN-γ secreting splenocytes was calculated as the average number of spots in the triplicate stimulant wells. This assay indicated that C57/B6 mice were suitable for pTyr vaccination (data not shown).

Example 3 pTyr Vaccination Increased Cytokines IFN-γ and TNF-α

Figure 3:
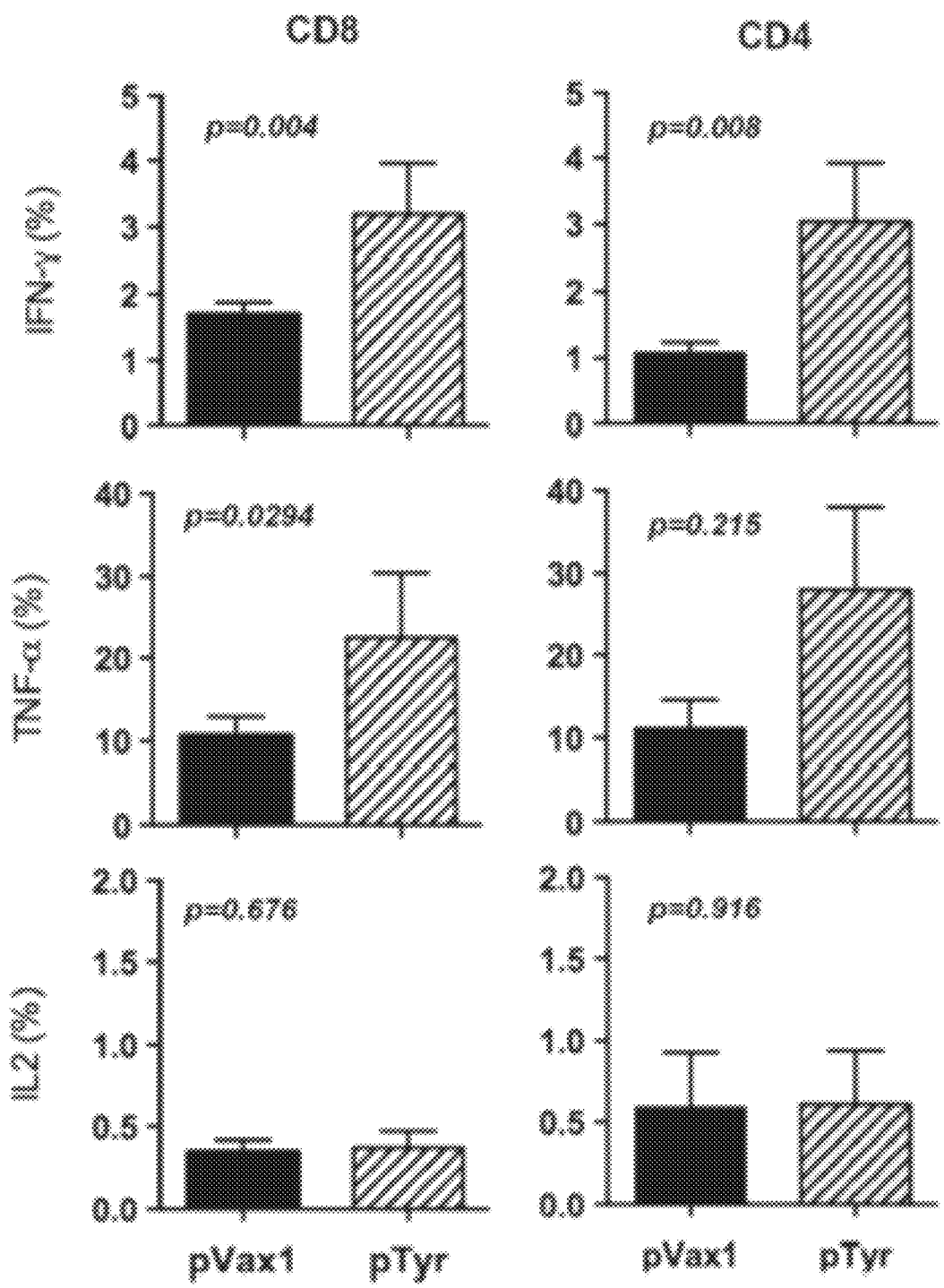
FIG. 3 depicts the results of experiments demonstrating flow fluorescence-activated cell sorting (FACS) of control and immunized mice.

Cytokine production was examined in mice immunized with pTyr and pVax1. Mice were immunized using the strategy shown in FIG. 2A. At day 35 of the immunization strategy, cells isolated from the immunized mice were stimulated overnight with Tyr peptides. After stimulation, analysis of the polyfunctional responses was measured by FACS. Specifically, the analysis examined CD8$^+$ and CD4$^+$ T cells. FACS allowed for the identification of T cells positive for the cytokines IL-2, TNF-α, and IFN-γ. Of the CD44 hi cells, a significant percentage of CD8$^+$ T cells produced IFN-γ in the mice immunized with pTyr as compared to mice immunized with pVax1 (FIG. 3).

Example 4

Tyr Specific Antibodies are Produced in Response to pTyr Vaccination

Figures 4A, 4B:
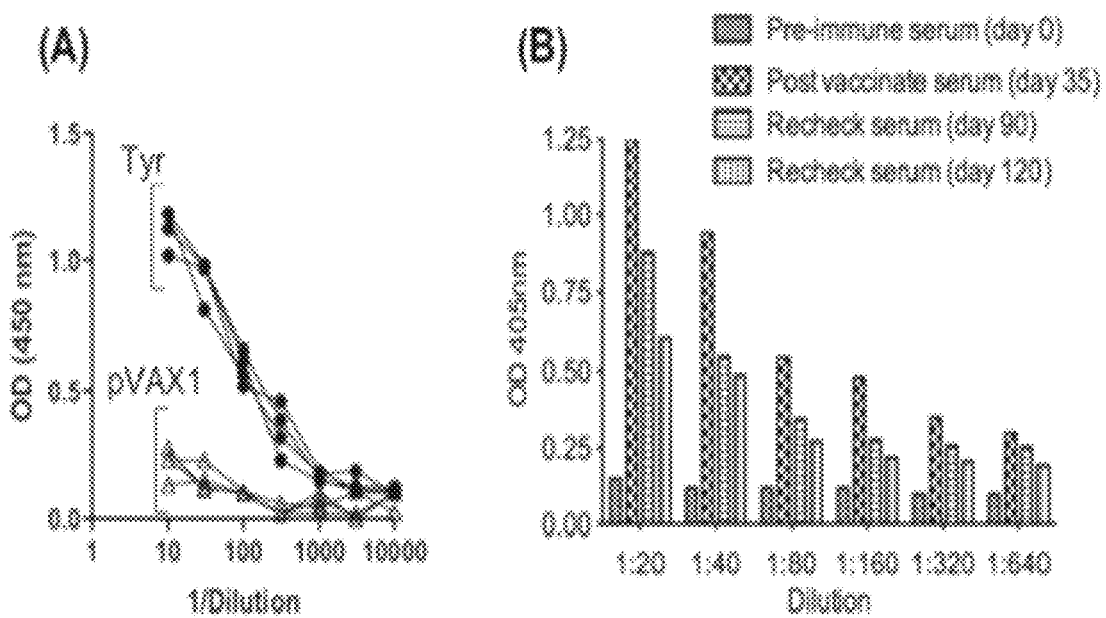
FIG. 4A through FIG. 4B, depicts the results of experiments demonstrating induction of tyrosinase-specific antibodies in immunized mice.

The humoral immune response was examined in mice vaccinated with pTyr. Specifically, C57BI/6 mice (n=4) were immunized three times at 2-week intervals with either pTyr or pVax1. Each immunization consisted of a 20 μg/intramuscular injection followed by electroporation with MID-EP. After the third immunization (i.e., day 35), serum was collected from the mice and antibody titers were measured by ELISA using total IgG-specific HRP labeled secondary antibodies. The sera were diluted as indicated in FIG. 4A. As shown in FIG. 4A, specific antibodies to Tyr were produced by the mice immunized with pTyr. Mice immunized with pTyr are represented by the filled circle in FIG. 4A while mice immunized with pVax1 are represented by the open triangle in FIG. 4A.

Additionally, the sera from the immunized mice were serially diluted at 1:20, 1:40, 1:80, 1:160, 1:320, and 1:640. Each serum dilution was added in triplicate to individual wells (50 μl/well) containing Tyr peptides. The peak increase in Tyr-specific titer, compared to the preimmune serum, was detected for all immunized groups of mice at recheck days 90 and 120. Representative results of three independent experiments at each serial dilution point are shown in FIG. 4B. These data further indicated that immunization with pTyr induced production of Tyr specific antibodies in mice immunized with pTyr.

Example 5

Mice Vaccinated with pTyr have Increased Survival to Tumor Challenge pTry was further analyzed to determine if pTyr vaccination could provide protection from tumors. Specifically, C57BI/6 mice (10 per group) were immunized at 2-week intervals with either pTyr or pVax1. Each immunization consisted of a 20 μg/intramuscular injection followed by electroporation with MID-EP. One week after the third immunization (i.e., day 35), the immunized mice were challenged intradermally with B16 melanoma until the tumor diameter exceeded 200 mm$^2$.

Figures 5A, 5B:
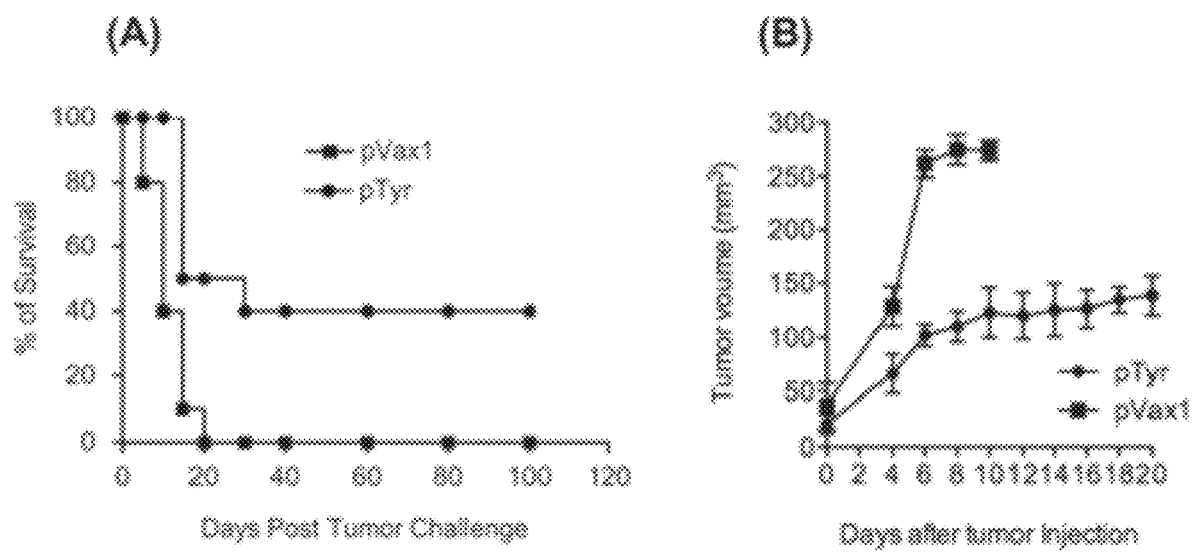
FIG. 5A through FIG. 5B, depicts the results of experiments demonstrating Kaplan-Meier survival curves and tumor volume curves, respectively, after tumor challenge in control and immunized mice.

Subsequently, tumor-free survival and tumor volume was evaluated in the immunized groups of mice. As shown in FIG. 5A (a Kaplan-Meier survival curve), mice immunized with pTyr were improved in tumor-free survival (i.e., 40% at days 40 and on after tumor challenge) as compared to mice vaccinated with pVax1 (p=0.05), which were all dead by day 20 after tumor challenge. Mice immunized with pTyr also had reduced tumor volume (i.e., about 50%) as compared to mice immunized with pVax1 (FIG. 5B). For both FIGS. 5A and 5B, mice immunized with pVax1 are represented by filled squares while mice immunized with pTyr are represented by filled circles. Accordingly, these data showed that pTyr vaccination provided protection against melanoma, namely increased tumor-free survival and reduction in tumor volume.

Example 6

MDSC Population is Reduced in Tumors from Mice Vaccinated with pTyr

MDSC populations were examined in mice immunized with pTyr and non-immunized mice to examine whether vaccination with pTyr altered levels of MDSCs in tumors from the respective groups of mice. Specifically, the percentage of Gr-1+ and CD11b+ cells were examined in the immunized and non-immunized mice.

Figure 6A:
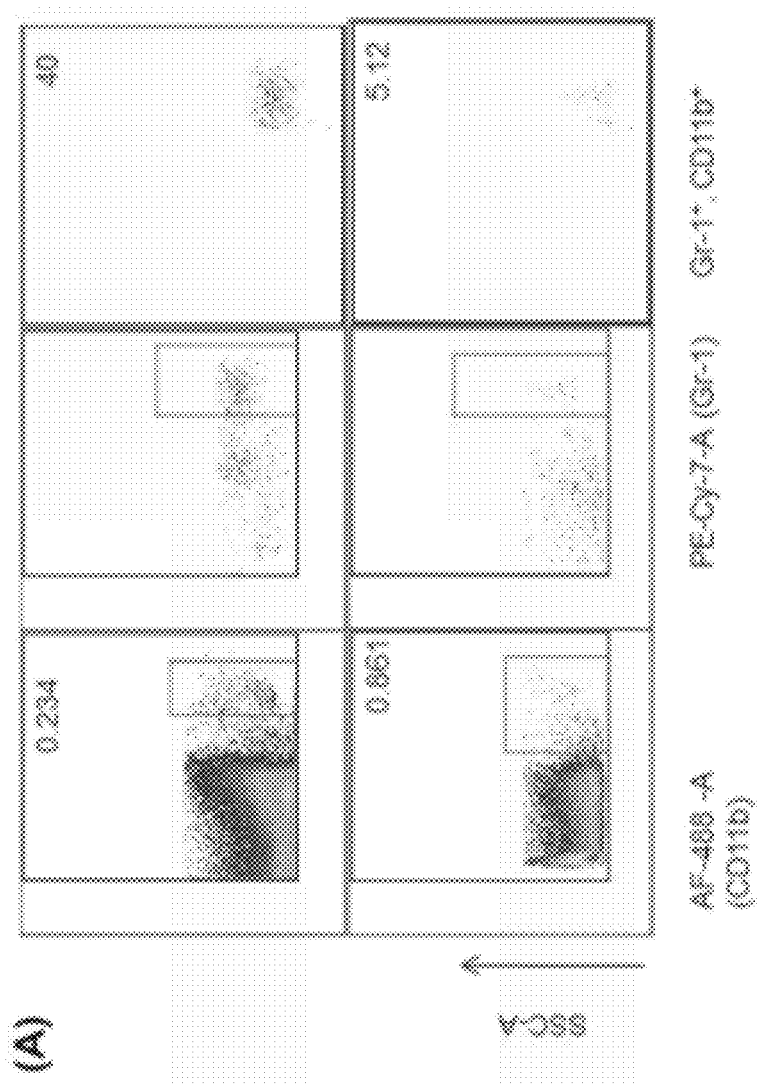
FIG. 6A through FIG. 6B, depicts the results of experiments demonstrating MDSC cell populations in immunized and non-immunized mice.
Figure 6B:
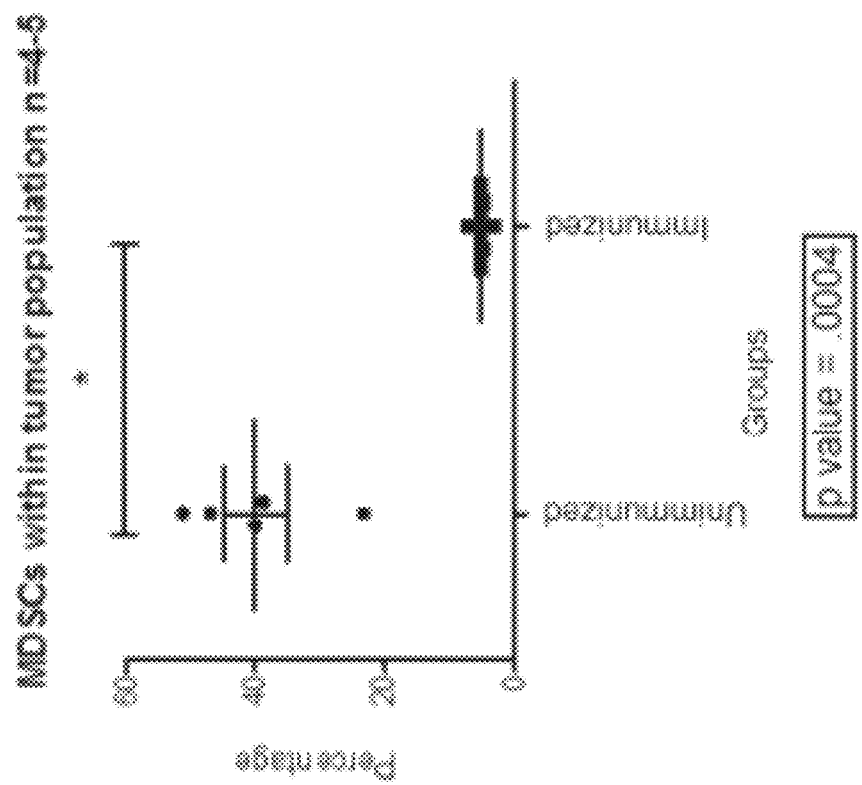
Figure 7:
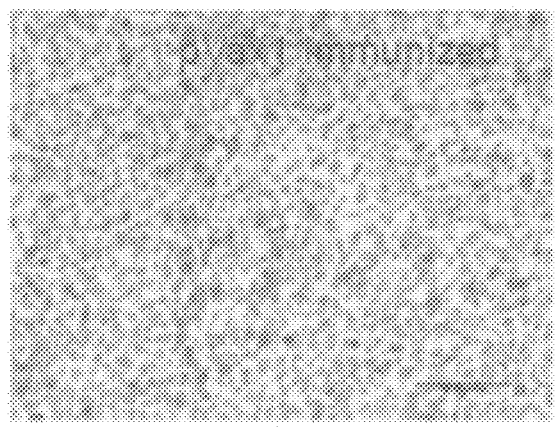
FIG. 7 depicts the results of experiments demonstrating staining for MDSCs in mice immunized with pVax1 and pTyr.
Figure 7:
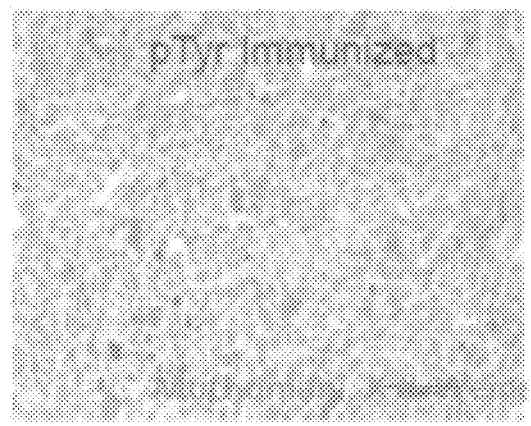

As shown in FIGS. 6 and 7, MDSC levels were significantly reduced within tumors from mice immunized with pTyr as compared to non-immunized mice (p=0.0004). The percentage of MDSC population in non-immunized mice was 40.00±4.826. The percentage of MDSC population in mice immunized with pTyr was 5.103±0.7718. Accordingly, these data showed that immunization with pTyr reduced MDSC populations within tumors of mice vaccinated with pTyr.

Example 7

MCP-1 Levels are Reduced by pTyr Vaccination

MDSCs can secrete the cytokine MCP-1, which promotes angiogenesis or vascularization by migration of endothelial cells. Given the above described effect of pTyr vaccination on MDSC levels in tumors, MCP-1 levels were examined after vaccination with pTyr.

Figure 8A:
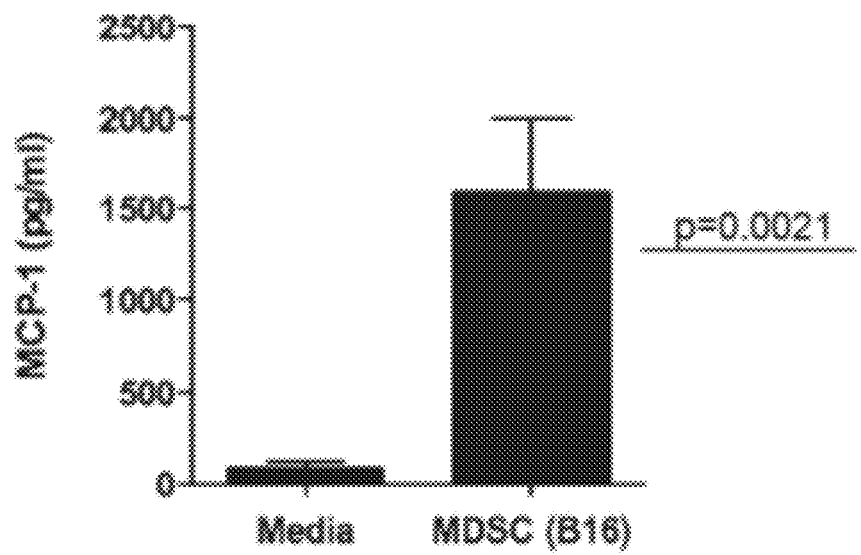
FIG. 8A through FIG. 8B, depicts the results of experiments demonstrating MCP-1 secretion by MDSCs.

As shown in FIG. 8A, MDSCs within the B16 melanoma can secrete MCP-1. As such, mice immunized with pTyr and mice immunized with pVax1 were challenged with the B16 melanoma to examine whether pTyr immunization altered MCP-1 levels. Naïve mice were included as a further control. After the challenge, MDSCs were isolated directly from the tumor tissue, and MCP-1 cytokine levels were analyzed ELISA. The experiment was performed in triplicate and repeated two times.

Figure 8B:
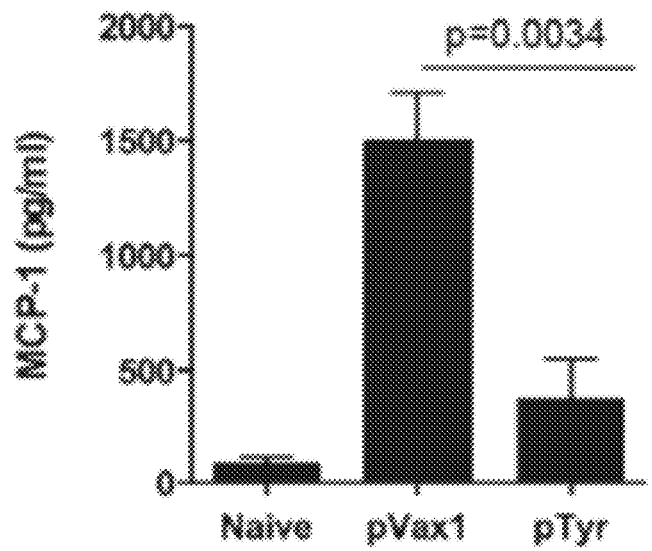

As shown in FIG. 8B, MDSCs within the B16 melanoma or tumor tissue significantly secreted MCP-1 (see pVax1 immunized mice). Mice immunized with pTyr, however, did not have a significant increase in MCP-1 levels. Rather, MCP-1 levels in mice immunized with pTyr were about 3-fold lower than mice immunized with pVax1. Accordingly, these data showed that pTyr vaccination reduced the level of MCP-1 secretion by MDSCs within tumors of mice immunized with pTyr.

Example 8

Construction of pPRAME

Figure 10A:
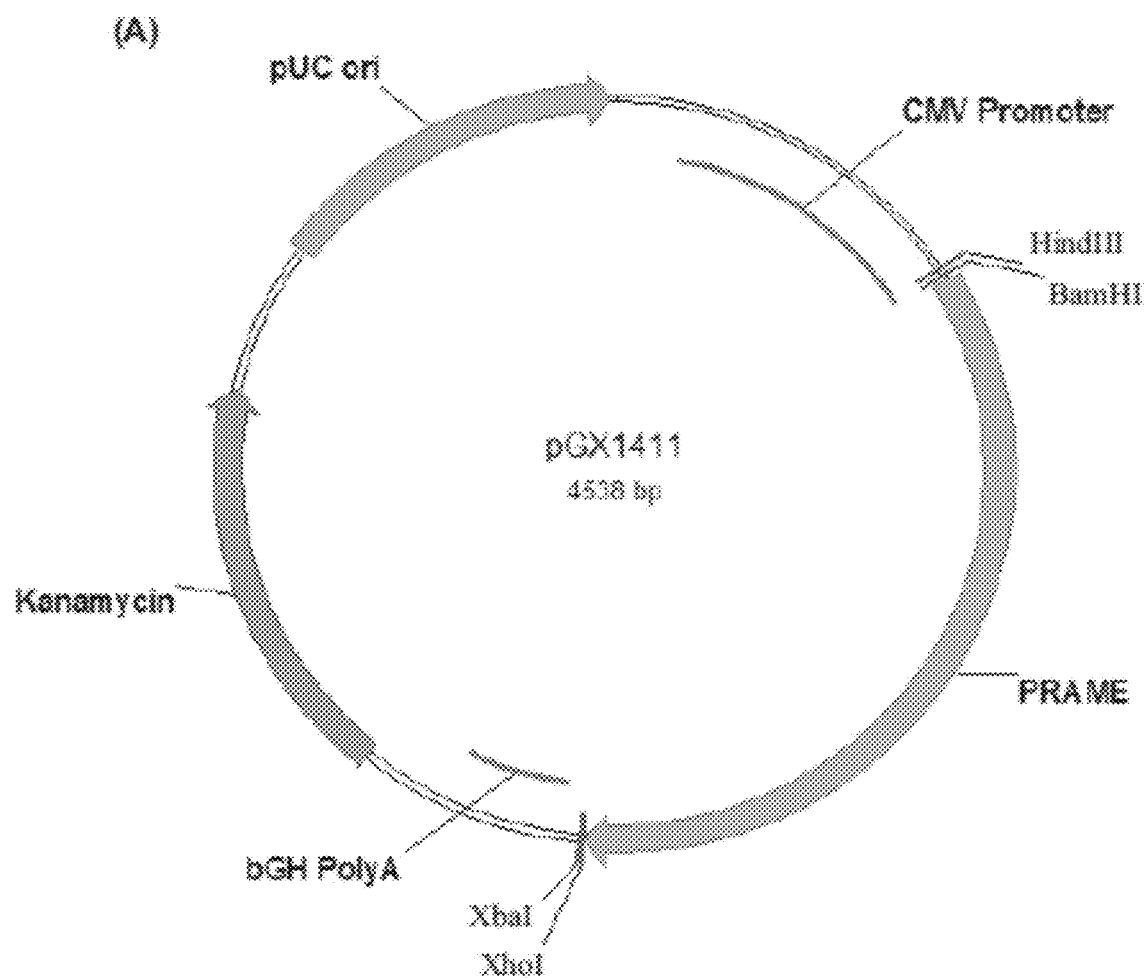
FIG. 10A through FIG. 10C, depicts the results of experiments demonstrating (A) a schematic illustrating a plasmid map of pPRAME (also known herein as pGX1411); (B) staining of RD and 293T cells for nuclei with DAPI and for the consensus PRAME antigen; and (C) western blotting for the consensus PRAME antigen in lysates from non-transfected cells ("control"), cells transfected with pVAX ("pVAX"), and cells transfected with pPRAME ("PRAME-pVAX").

A consensus sequence was generated for PRAME and the nucleotide sequence encoding the consensus PRAME antigen was inserted into the BamHI and XhoI restriction enzyme sites of the expression vector or plasmid pVAX (also known as pVAX1 herein) to yield pGX1411 (also known as pPRAME herein) (see FIG. 10A).

Figure 10B:
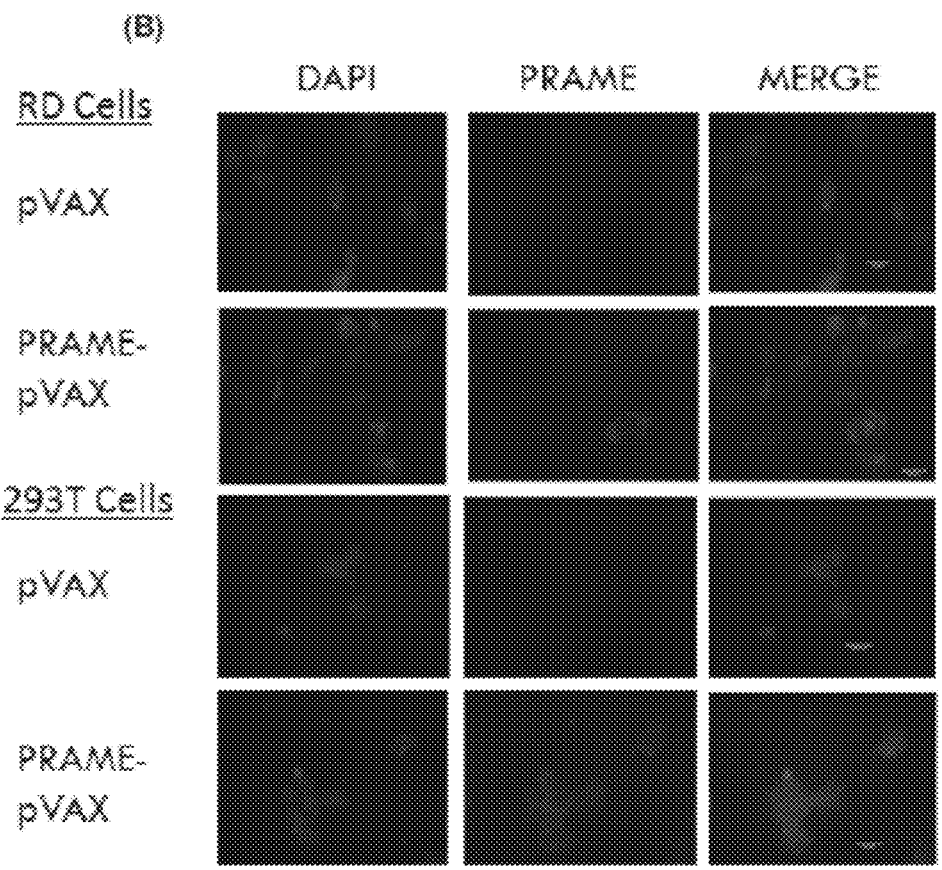

To confirm that pPRAME resulted in expression of the consensus PRAME antigen, pVAX and pPRAME were transfected into RD cells and 293T cells. DAPI was used to stain nuclei and the consensus PRAME antigen was also fluorescently stained. This staining, along with a merge of the DAPI and consensus PRAME antigen staining, are shown in FIG. 10B. These staining demonstrated that the PRAME consensus antigen was expressed from pPRAME and no consensus PRAME antigen was detected in the cells transfected with pVAX (i.e., negative control).

Figure 10C:
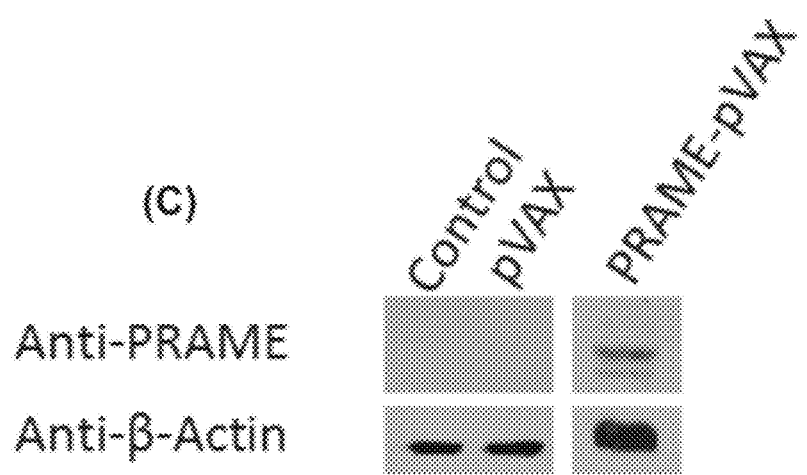

Additionally, western blotting analysis of lysates from the transfected cells was used to confirm expression of the consensus PRAME antigen in transfected cells (FIG. 10C). Non-transfected cells and cells transfected with pVAX were used as negative controls (see lanes labeled "control" and "pVAX," respectively in FIG. 10C). In FIG. 10C, beta-actin detection was used as a loading control. In summary, the staining of transfected cells and western blotting of lysates from transfected cells demonstrated that the vector pPRAME provided expression of the consensus PRAME antigen within cells.

Example 9

Interferon Gamma Response to Vaccination with pPRAME

The above described pPRAME was used to vaccinate mice to evaluate whether a cellular immune response was induced by pPRAME. C57BL/6 mice were separated into groups. A first group was naïve and did not receive pPRAME. Second, third, fourth, fifth, and sixth groups of mice received 5 µg, 10 µg, 15 µg, 25 g, and 50 µg of pPRAME, respectively.

Figures 11A, 11B:
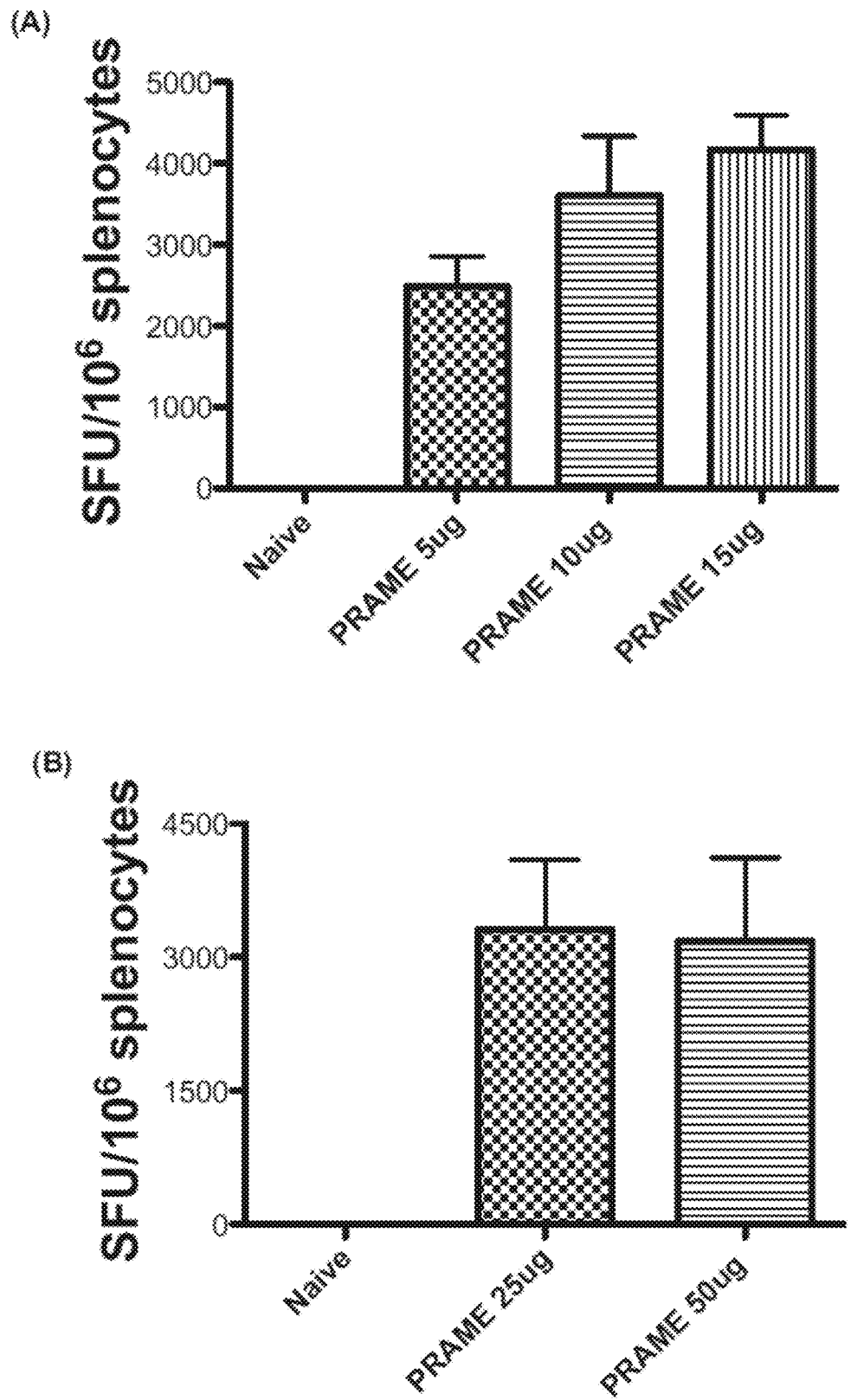
FIG. 11A through FIG. 11B, depicts the results of experiments demonstrating graphs plotting mouse group vs. spot forming units (SFU)/$10^6$ splenocytes for interferon gamma (IFN-γ).

After immunization, splenocytes were isolated from the C57BL/6 mice and evaluated for induction of interferon gamma (IFN-γ) by IFN-γ ELISpot analysis. As shown in FIGS. 11A and 11B, each dosage of pPRAME induced production or secretion of IFN-γ unlike the negative control naïve mice. In particular, the IFN-γ levels were increased by about 3000-fold to about 4500-fold in vaccinated mice as compared to non-vaccinated mice. Accordingly, these data demonstrated that vaccination with pPRAME, which encodes the consensus PRAME antigen, induced a cellular immune response as evidenced by increased IFN-γ levels as compared non-vaccination.

Example 10

Construction of pNY-ESO-1

Figure 12A:
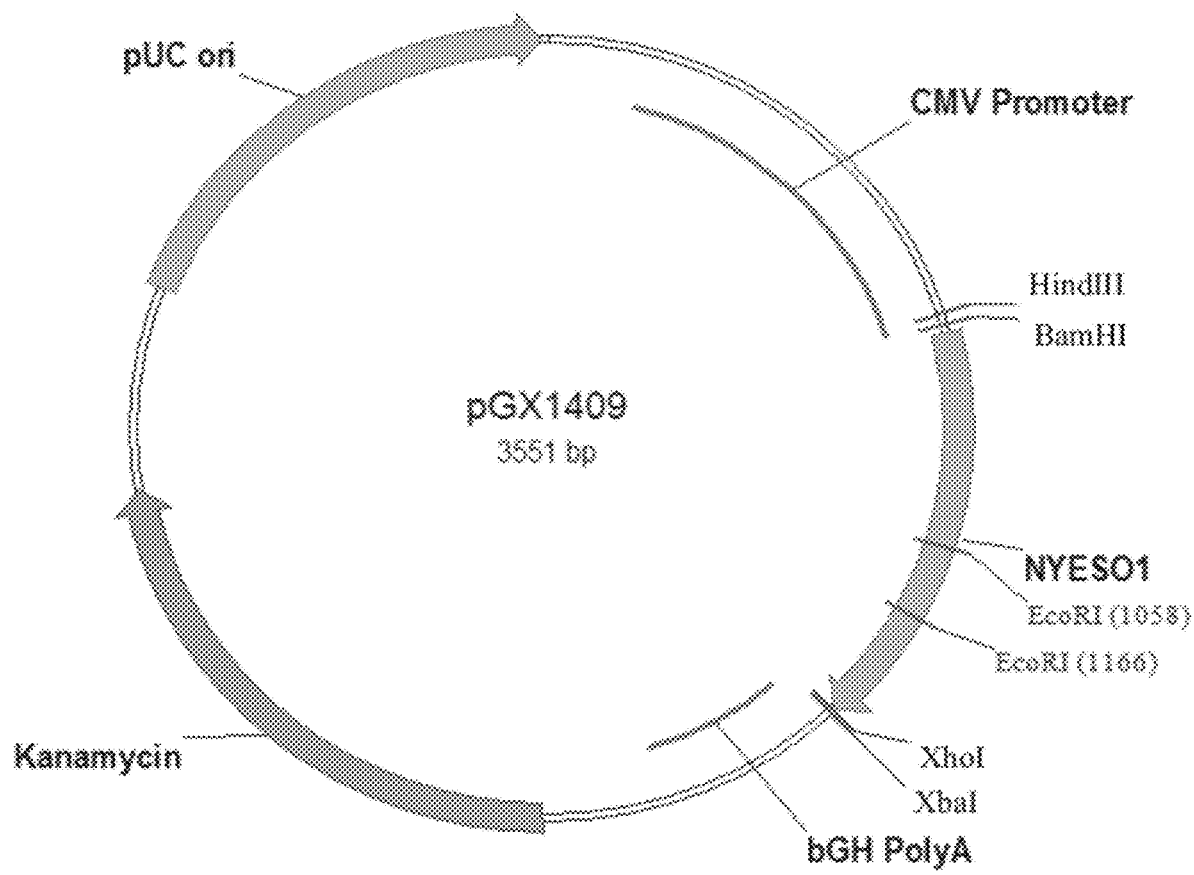
FIG. 12A through FIG. 12C, depicts the results of experiments demonstrating (A) a schematic illustrating a plasmid map of pNY-ESO-1 (also known herein as pGX1409); (B) staining of cells for nuclei with DAPI and for the consensus NY-ESO-1 antigen; and (C) western blotting for the consensus NY-ESO-1 antigen in RD and 293T lysates from non-transfected cells ("control"), cells transfected with pVAX ("pVAX"), and cells transfected with pNY-ESO-1 ("pNY-ESO-1").

A consensus sequence was generated for NY-ESO-1 and the nucleotide sequence encoding the consensus NY-ESO-1 antigen was inserted into the BamHI and XhoI restriction enzyme sites of the expression vector or plasmid pVAX (also known as pVAX1 herein) to yield pGX1409 (also known as pNY-ESO-1 herein) (see FIG. 12A).

Figures 12B, 12C:
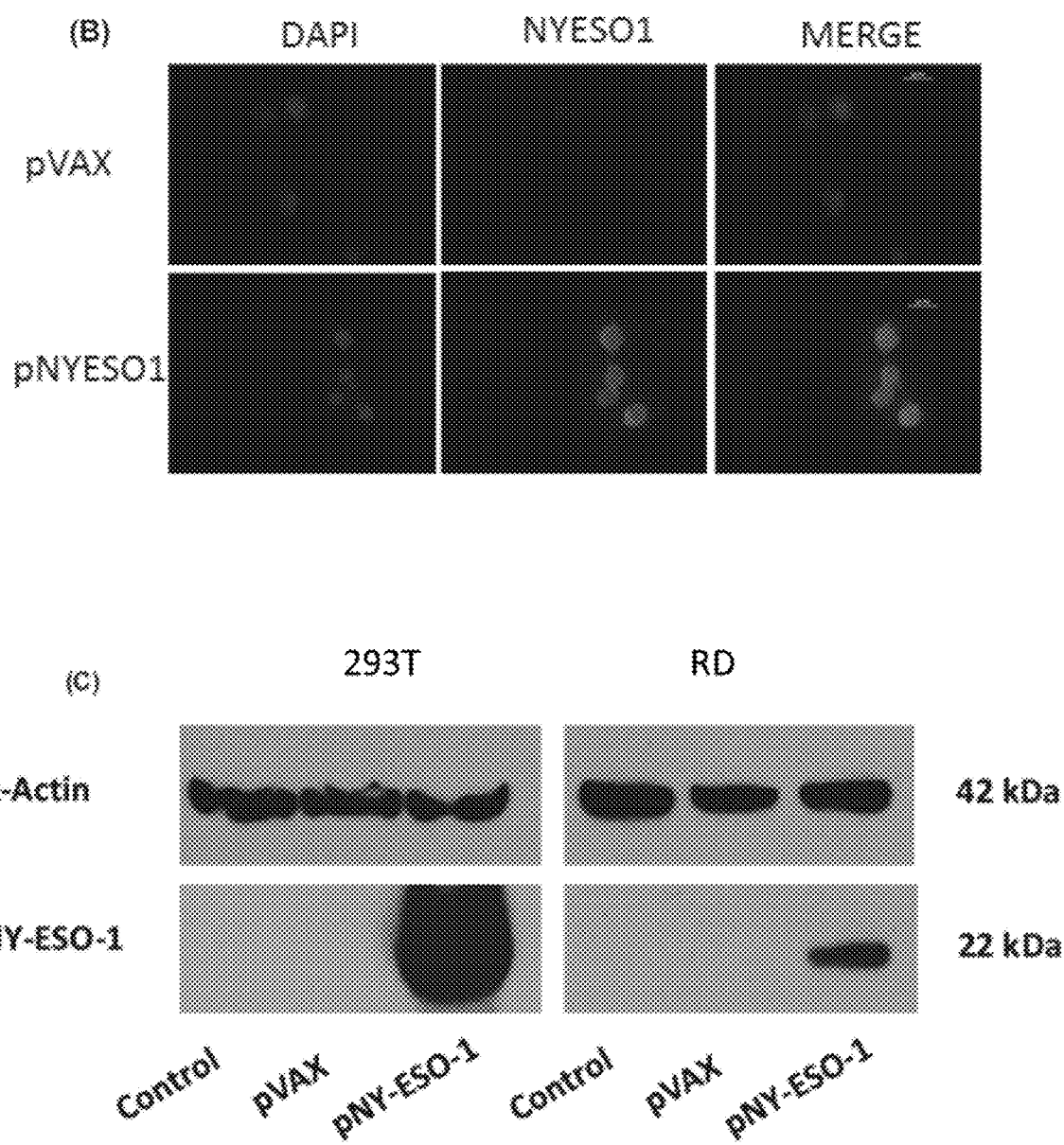

To confirm that pNY-ESO-1 resulted in expression of the consensus NY-ESO-1 antigen, pVAX and pNY-ESO-1 were transfected into cells. DAPI was used to stain nuclei and the consensus NY-ESO-1 antigen was also fluorescently stained. This staining, along with a merge of the DAPI and consensus NY-ESO-1 antigen staining, are shown in FIG. 12B. These staining demonstrated that the NY-ESO-1 consensus antigen was expressed from pNY-ESO-1 and no consensus NY-ESO-1 antigen was detected in the cells transfected with pVAX (i.e., negative control).

Additionally, western blotting analysis of lysates from 293T and RD transfected cells was used to confirm expression of the consensus NY-ESO-1 antigen in the transfected cells (FIG. 12C). Non-transfected cells and cells transfected with pVAX were used as negative controls (see lanes labeled "control" and "pVAX," respectively in FIG. 12C). In FIG. 12C, alpha-actin detection was used as a loading control. In summary, the staining of transfected cells and western blotting of lysates from the transfected cells demonstrated that the vector pNY-ESO-1 provided expression of the consensus NY-ESO-1 antigen within cells.

Example 11

Interferon Gamma Response to Vaccination with pNY-ESO-1 The above described pNY-ESO-1 was used to vaccinate mice to evaluate whether a cellular immune response was induced by pNY-ESO-1. C57BL/6 mice were separated into groups. A first group was naïve and did not receive pNY-ESO-1. Second and third groups of mice received 25 µg and 50 µg pNY-ESO-1, respectively.

Figure 13:
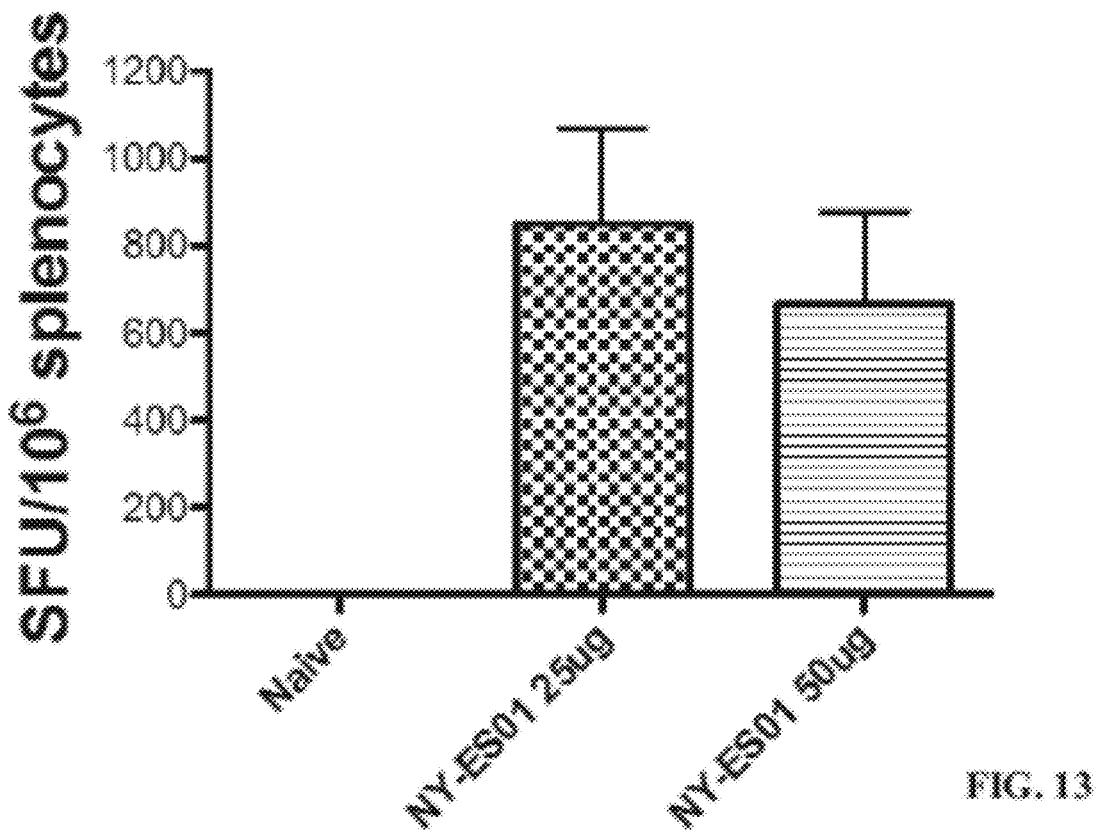
FIG. 13 depicts a graph plotting mouse group vs. spot forming units (SFU)/$10^6$ splenocytes for interferon gamma (IFN-γ).

After immunization, splenocytes were isolated from the C57BL/6 mice and evaluated for induction of interferon gamma (IFN-γ) by IFN-γ ELISpot analysis. As shown in FIG. 13, each dosage of pPRAME induced production or secretion of IFN-γ unlike the negative control naïve mice. In particular, the IFN-γ levels were increased by about 700-fold to about 1100-fold in vaccinated mice as compared to non-vaccinated mice. Accordingly, these data demonstrated that vaccination with pNY-ESO-1, which encodes the consensus NY-ESO-1 antigen, induced a cellular immune response as evidenced by increased IFN-γ levels as compared non-vaccination.

Example 12

Interferon Gamma Response to Vaccination with pNY-ESO-2

A consensus sequence was generated for NY-ESO-2 and the nucleotide sequence encoding the consensus NY-ESO-2 antigen was inserted into the multiple cloning site of the expression vector or plasmid pVAX (also known as pVAX1 herein) to yield pNY-ESO-2.

This pNY-ESO-2 was used to vaccinate mice to evaluate whether a cellular immune response was induced by pNY-ESO-2. C57BL/6 mice were separated into groups. A first group was naïve and did not receive pNY-ESO-2. Second and third groups of mice received 25 μg and 50 μg of pNY-ESO-2, respectively.

Figure 14:
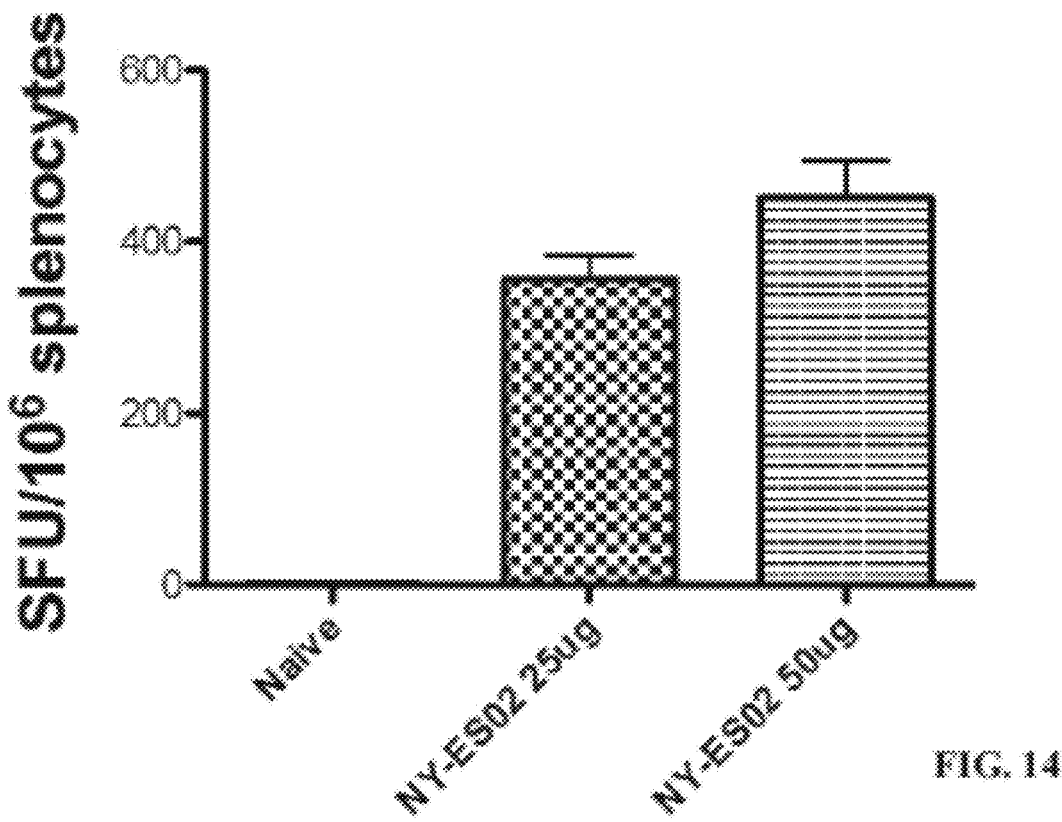
FIG. 14 depicts a graph plotting mouse group vs. spot forming units (SFU)/$10^6$ splenocytes for interferon gamma (IFN-γ).
Figure 15:
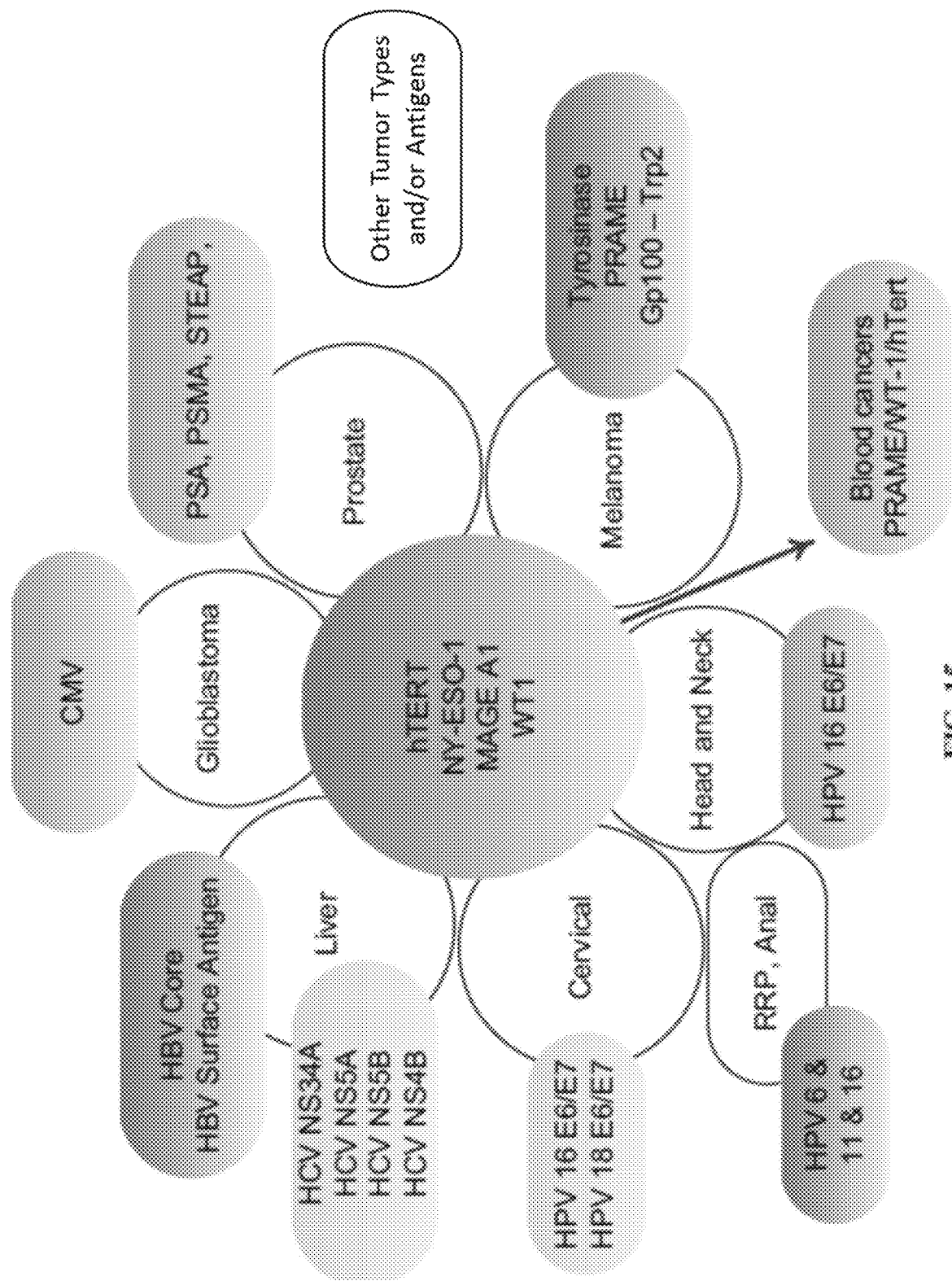
FIG. 15 depicts a schematic illustrating various cancers with some of their associated cancer antigen(s).

After immunization, splenocytes were isolated from the C57BL/6 mice and evaluated for induction of interferon gamma (IFN-γ) by IFN-γ ELISpot analysis. As shown in FIG. 14, each dosage of pNY-ESO-2 induced production or secretion of IFN-γ unlike the negative control naïve mice. In particular, the IFN-γ levels were increased by about 400-fold to about 500-fold in vaccinated mice as compared to non-vaccinated mice. Accordingly, these data demonstrated that vaccination with pNY-ESO-2, which encodes the consensus NY-ESO-2 antigen, induced a cellular immune response as evidenced by increased IFN-γ levels as compared non-vaccination.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Example 13

Synthetic Consensus hTERT

The experiments presented herein were designed to evaluate the ability of a synthetic consensus hTERT, designed and manufactured using methods described herein, to break tolerance in non-human primates. A synthetic consensus hTERT (pGX1434) that is approximately 96% identical to the rhesus macaque TERT was designed. Rhesus macaques were either immunized with a plasmid encoding synthetic consensus hTERT or a plasmid encoding native RhTERT in the presence of IL12 adjuvant. The nucleotide sequence which encodes the synthetic consensus hTERT (pGX1434) is provided by SEQ ID NO: 45. The amino acid sequence of the synthetic consensus hTERT (pGX1434) is provided by SEQ ID NO: 46. Monkeys were immunized four times and cellular immune responses were evaluated by ELISpot assay. It was observed that, compared to native RhTERT, immunization with synthetic consensus hTERT elicited stronger immune responses (1200 SFU/$10^6$ vs 400 SFU/$10^6$).

Figure 16:
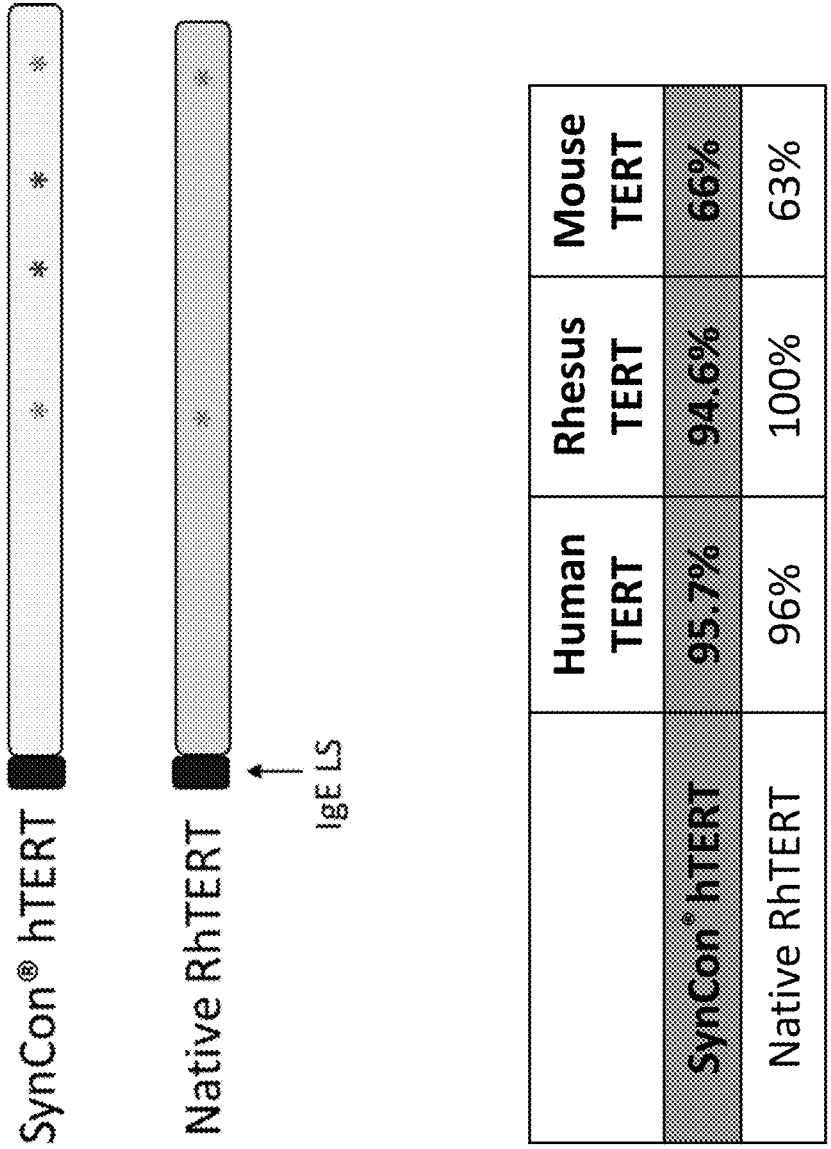
FIG. 16 depicts a schematic design of the TERT construct. Synthetic consensus hTERT was designed for human TERT with 5 mutations to abolish its function. Native RhTERT encode Rhesus TERT with 2 mutations. Both constructs were optimized. The Table shows the protein homology between the optimized TERT and native TERT identified in human, rhesus and mice.

A synthetic consensus hTERT was designed for human TERT with 5 mutations to abolish its function. Native RhTERT encode Rhesus TERT with 2 mutations. Both constructs were optimized. A schematic design of the TERT constructs are provided in FIG. 16 (top). FIG. 16 also shows the protein homology between the optimized TERT and native TERT identified in human, rhesus and mice (FIG. 16 (bottom)).

Figures 17A, 17B:
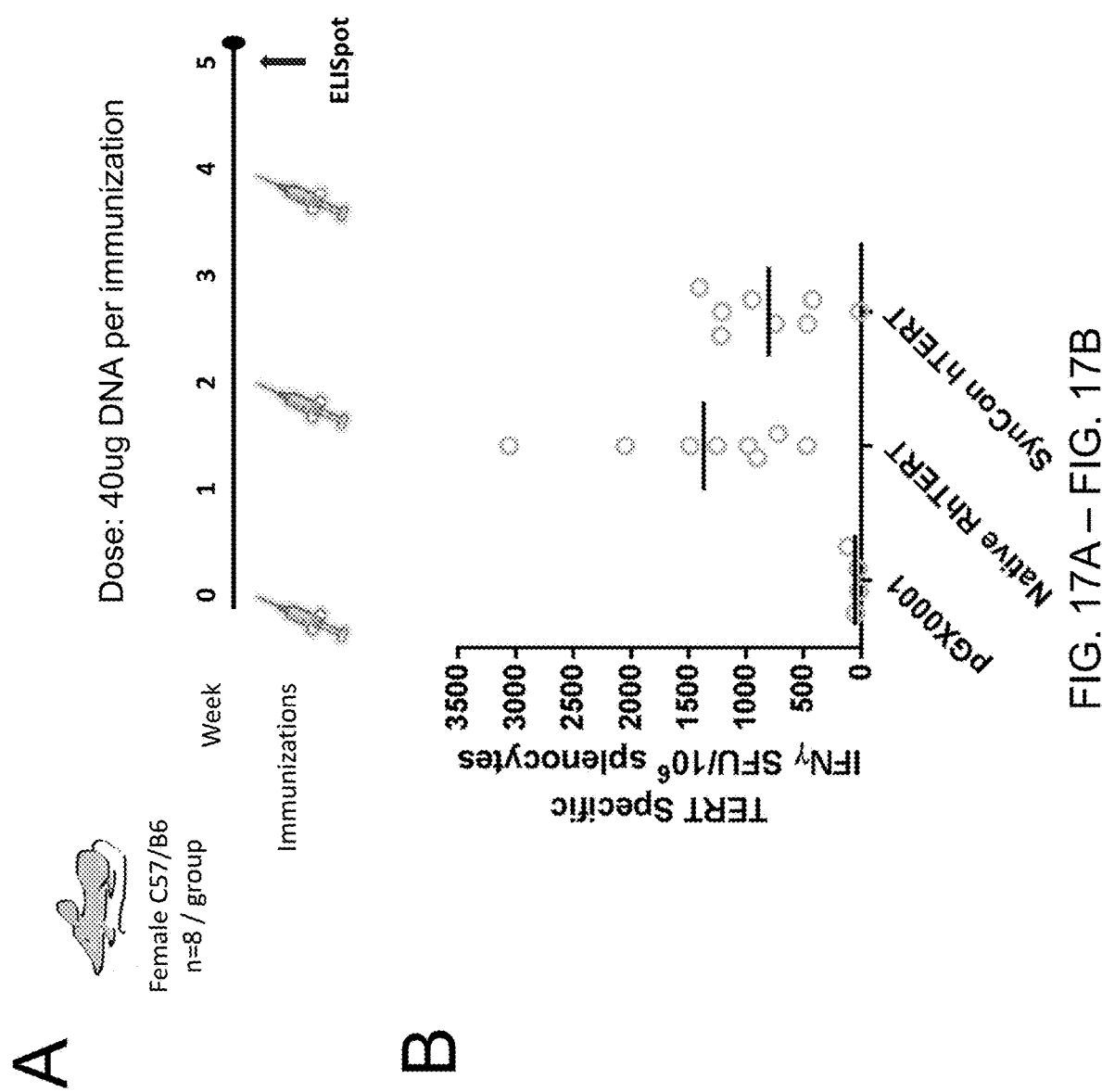
FIG. 17A through FIG. 17B, depicts the characterization of mouse TERT-specific IFN-γ responses against rhesus native peptides.

Experiments were done to characterize mouse TERT-specific IFN-γ responses against rhesus native peptides. Mice (n=8 per group) were immunized at weeks 0, 2 and 4 with native RhTERT and synthetic consensus hTERT via IM/electroporation. The DNA vaccine immunization schedule is shown in FIG. 17A. The frequency of TERT-specific IFN-γ spot-forming units (SFU) per million splenocytes isolated from vaccinated mice, was determined by IFN-γ ELISpot assay using rhesus peptides. It was observed that immunization with RhTERT and synthetic consensus hTERT elicited a robust cellular immune response (FIG. 17B).

Figure 18A:
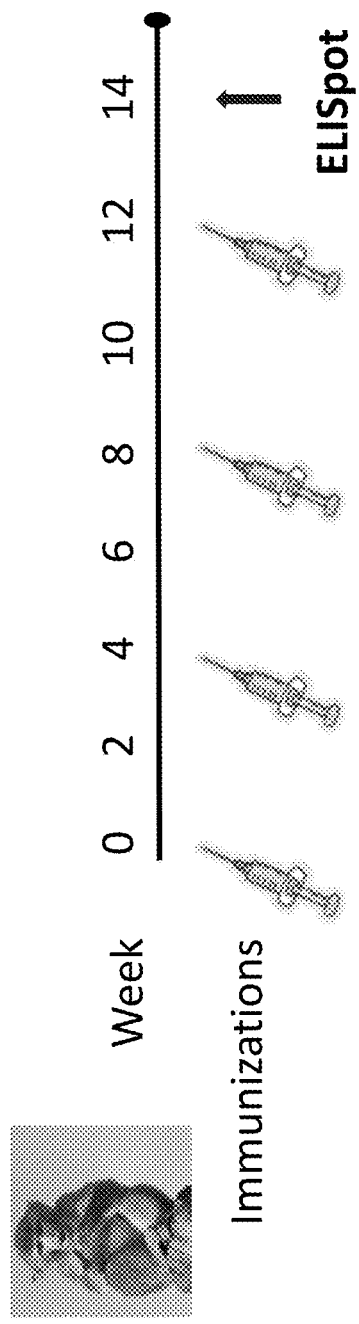
FIG. 18A through FIG. 18C, depicts the characterization of rhesus TERT-specific IFN-γ responses.
Figure 18B:
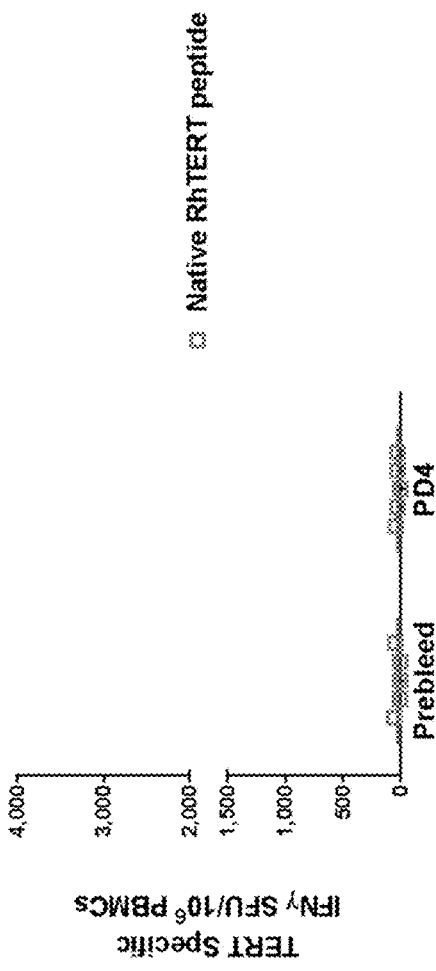
Figure 18C:
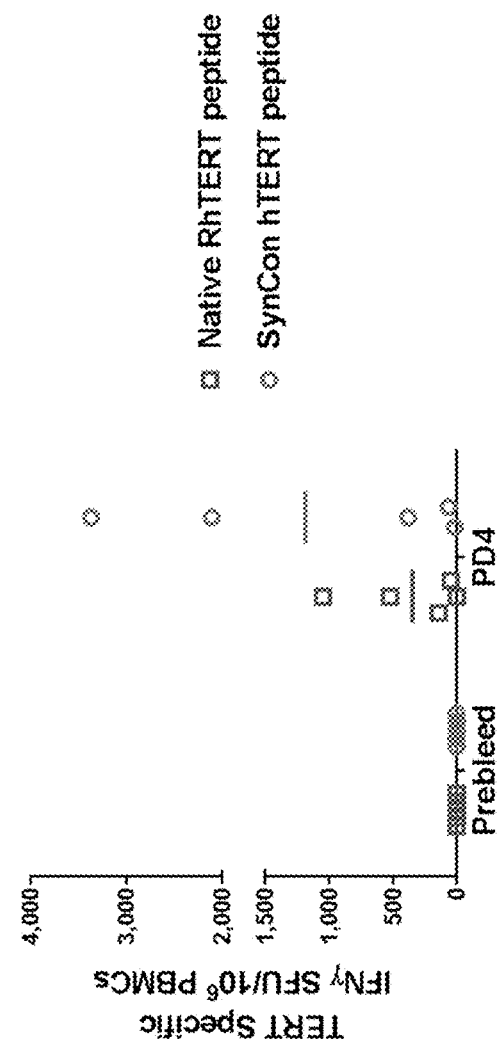

Experiments were conducted to characterize rhesus TERT-specific IFN-γ responses Rhesus macaque (n=5 per group) were immunized at weeks 0, 4, 8 and 12 with Native RhTERT or synthetic consensus hTERT as well as rhIL-12 via IM/electroporation. The DNA vaccine immunization schedule is provide in FIG. 18A. The frequency of TERT-specific IFN-γ spot-forming units (SFU) per million splenocytes isolated from vaccinated mice, was determined by IFN-γ ELISpot assay using native rhesus peptides and SynCon hTERT peptide. It was observed that synthetic consensus hTERT exhibits better ability to break tolerance in non-human primates, as compared to RhTERT (FIG. 18B and FIG. 18C).

Figure 19:
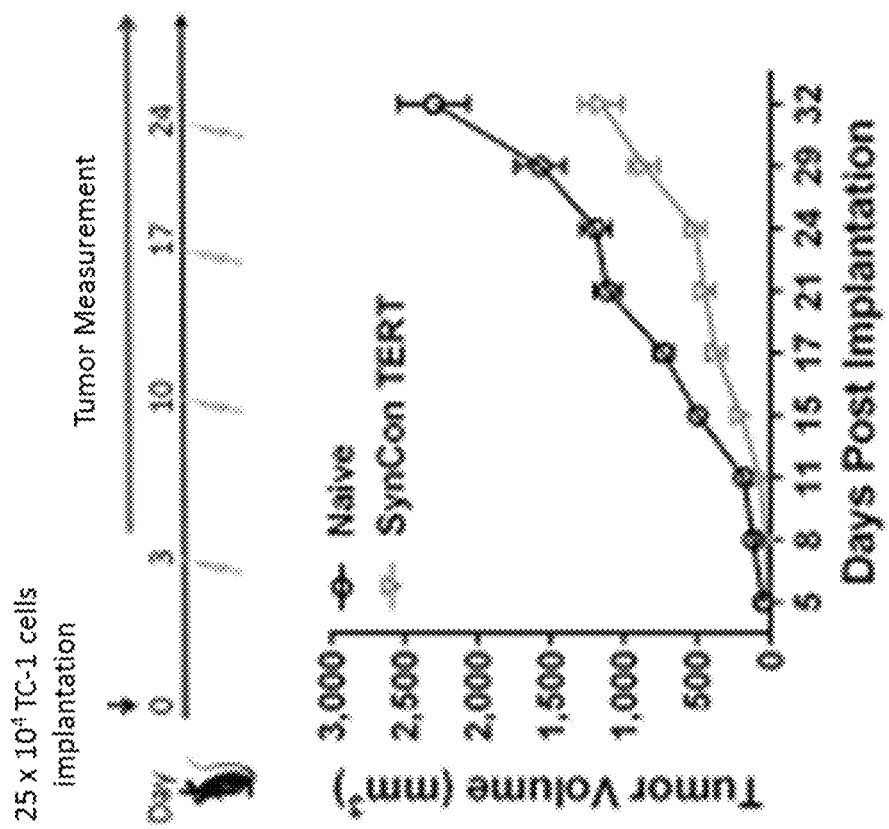
FIG. 19 depicts the results of experiments demonstrating that synthetic consensus hTERT (pGX1434) induces robust T cell responses in mice and slows TC-1 tumor growth. (left) Mice received 3 immunizations 2 weeks apart with 0, 20, 40, or 60 μg of pGX1434. T cell responses in the mice were evaluated at 5 weeks, demonstrating that pGX1434 induced a robust T cell response. (right) Mice were implanted with 25×$10^4$ TC-1 cells. Mice then received 4 immunizations 1 week apart with 25 μg of pGX1434. Tumor volume was measured over 32 days, demonstrating that mice treated with pGX1434 had decreased tumor volume as compared to naïve mice.
Figure 19:
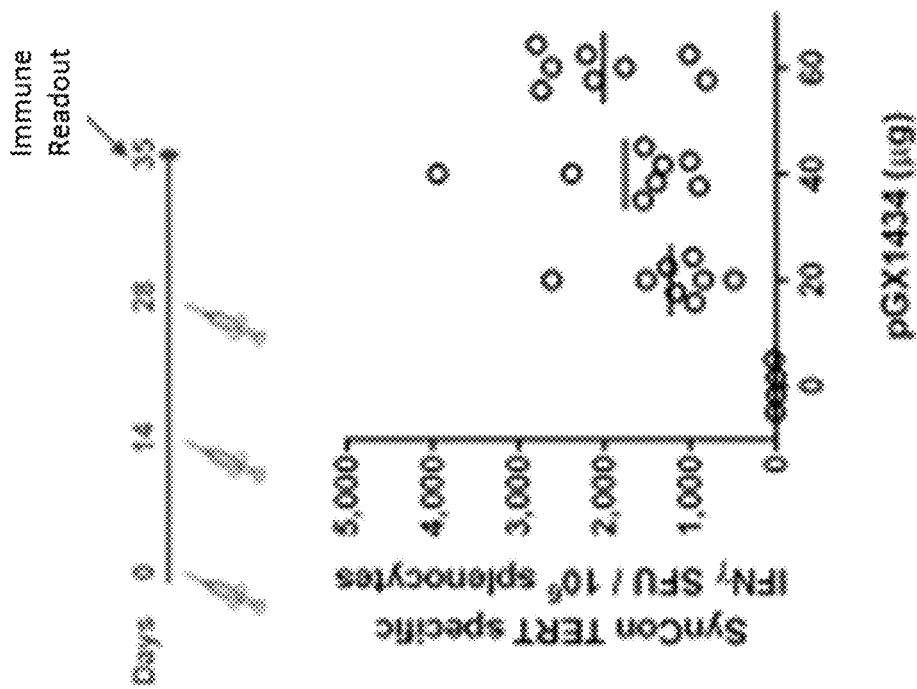
Figure 20:
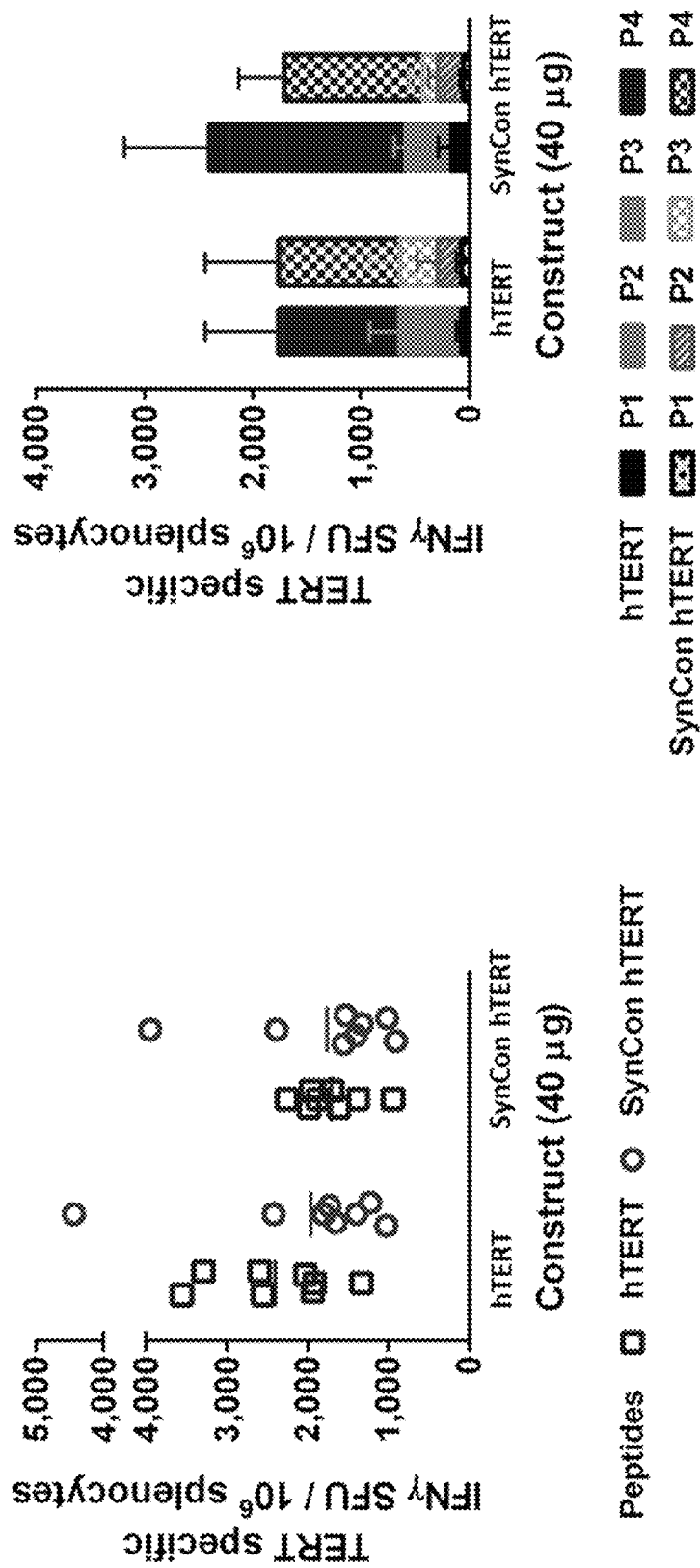
FIG. 20 depicts the results of experiments demonstrating the immunogenicity of SynCon hTERT (pGX1434) in mice.
Figures 21A, 21B:
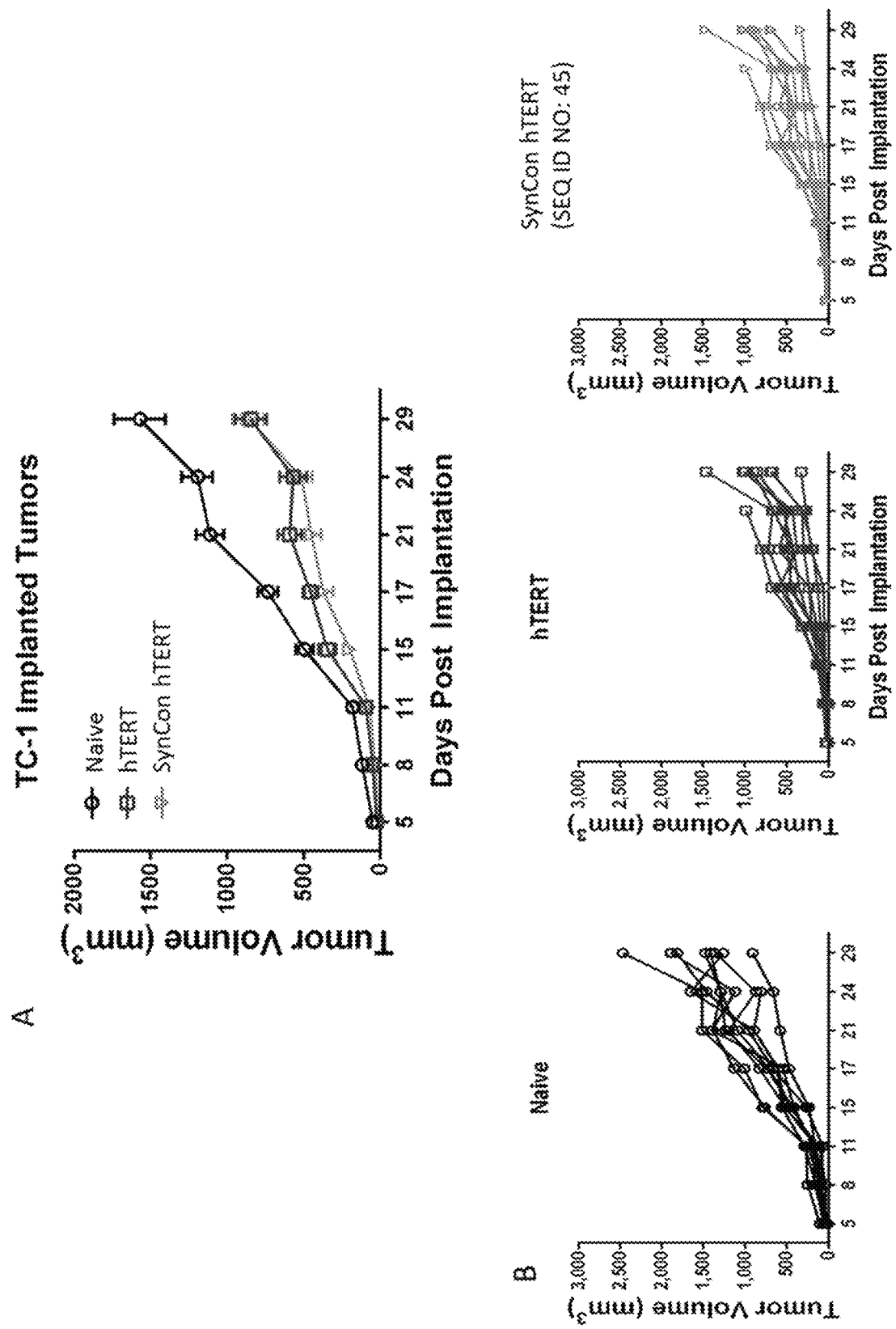
FIG. 21A through FIG. 21B, depicts the results of experiments demonstrating SynCon hTERT (pGX1434) and mut-hTERT (pGX1406) provide similar control of TC-1 tumor growth.

Further experiments were conducted to evaluate the effect of synthetic consensus hTERT (pGX1434) on T cell responses and tumor growth. Mice received 3 immunizations 2 weeks apart with 0, 20, 40, or 60 μg of pGX1434. T cell responses in the mice were evaluated at 5 weeks, demonstrating that pGX1434 induced a robust T cell response (FIG. 19 (left). To evaluate tumor growth, mice were implanted with 25×$10^4$ TC-1 cells. Mice then received 4 immunizations 1 week apart with 25 μg of pGX1434. Tumor volume was measured over 32 days, demonstrating that mice treated with pGX1434 had decreased tumor volume as compared to naïve mice (FIG. 19 (right), FIG. 20 and FIG. 21).

The experiments presented herein demonstrate that synthetic consensus hTERT was able to break tolerance, induce a strong cellular immune response, and reduce tumor growth. The synthetic consensus hTERT is superior to native self-antigen regarding the ability of eliciting a neo-antigen-like immune response to break tolerance.

Example 14

SynCon hTERT Breaks Tolerance in NHP

Figures 22A, 22B:
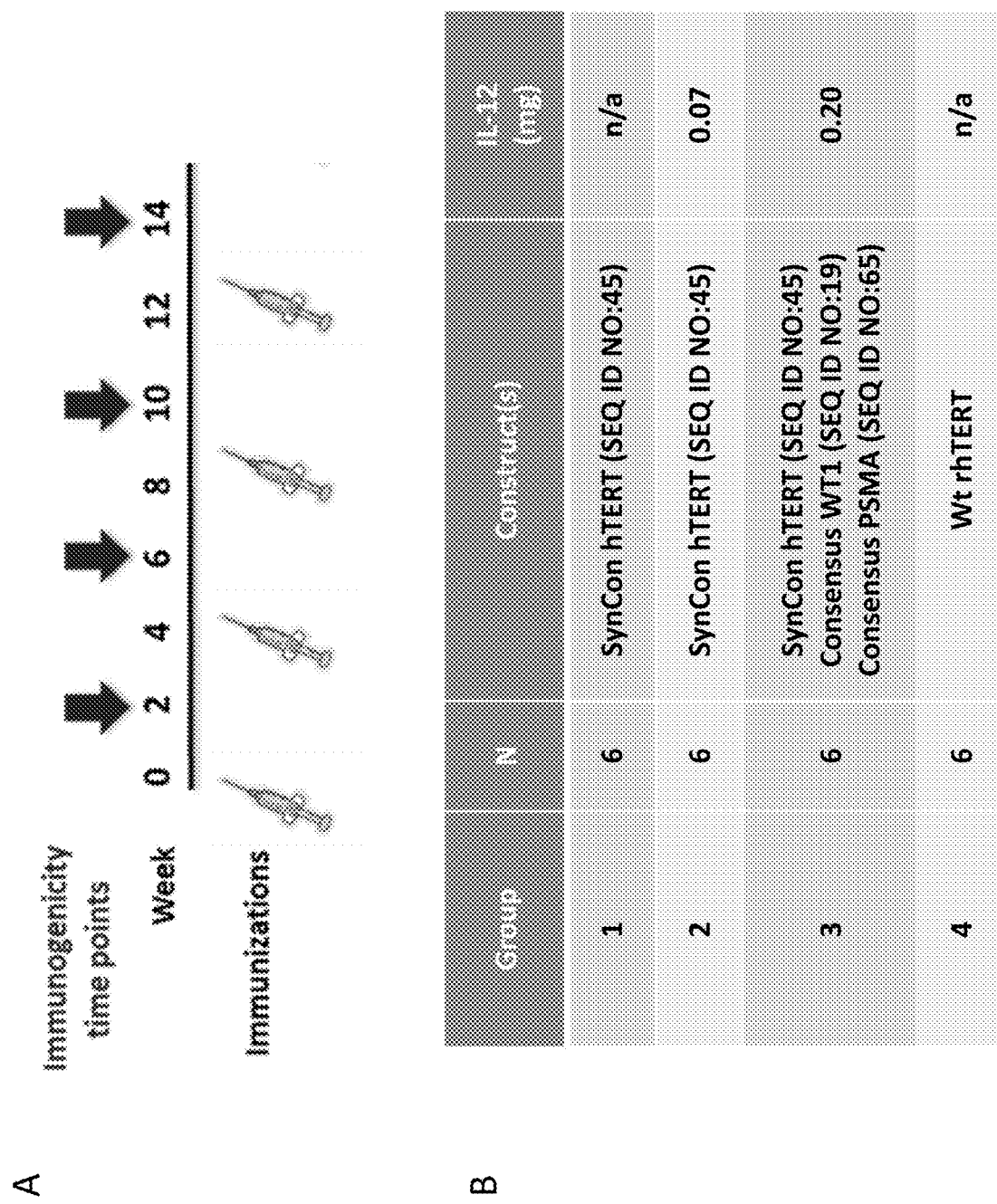
FIG. 22A through FIG. 22B, depicts the experimental design for experiments demonstrating hTERT immunogenicity in non-human primates (NHPs).
Figures 23A, 23B:
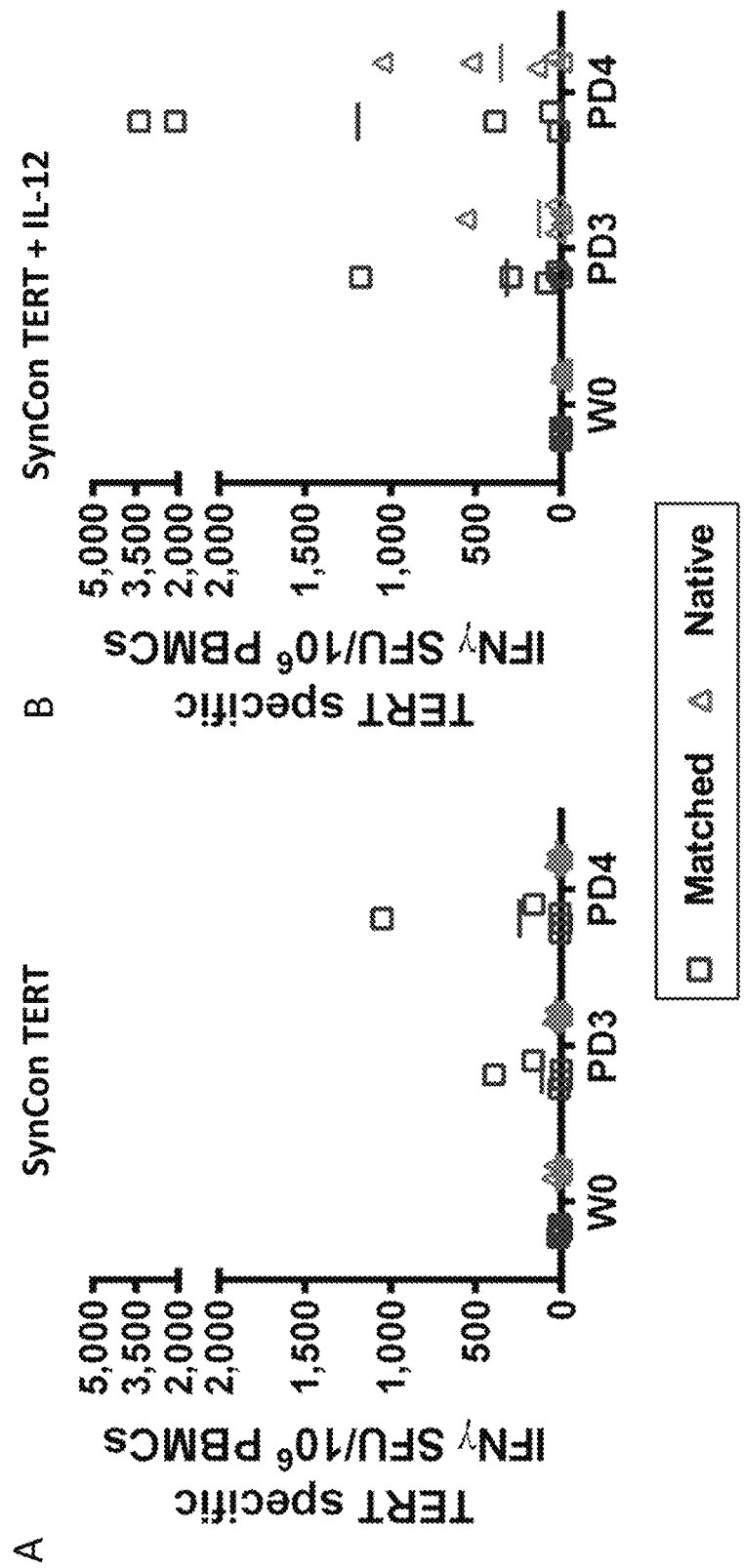
FIG. 23A through FIG. 23B, depicts the results of experiments demonstrating that SynCon hTERT breaks self-tolerance in NHPs.

Experiments were performed to assess immune responses induced by pGX1434 in NHPs+/−IL-12 (FIG. 22B, Groups 1 &2) and to evaluate immune responses induced by pGX1434 in the Wave 1 antigen combination (FIG. 22B, Group 3). Experiments were further designed to determine if SynCon design allows for breaking tolerance (FIG. 22B, Group 4) and to assess the ability of SynCon hTERT to break tolerance in NHPs (FIG. 22B, Groups 1-4).

The experimental design is provided in FIG. 22A. The formulation used for these experiments was: 3.0 mg/construct in 1.0 mL 20×SSC, with a 1 mL injection volume.

Figures 25A, 25B:
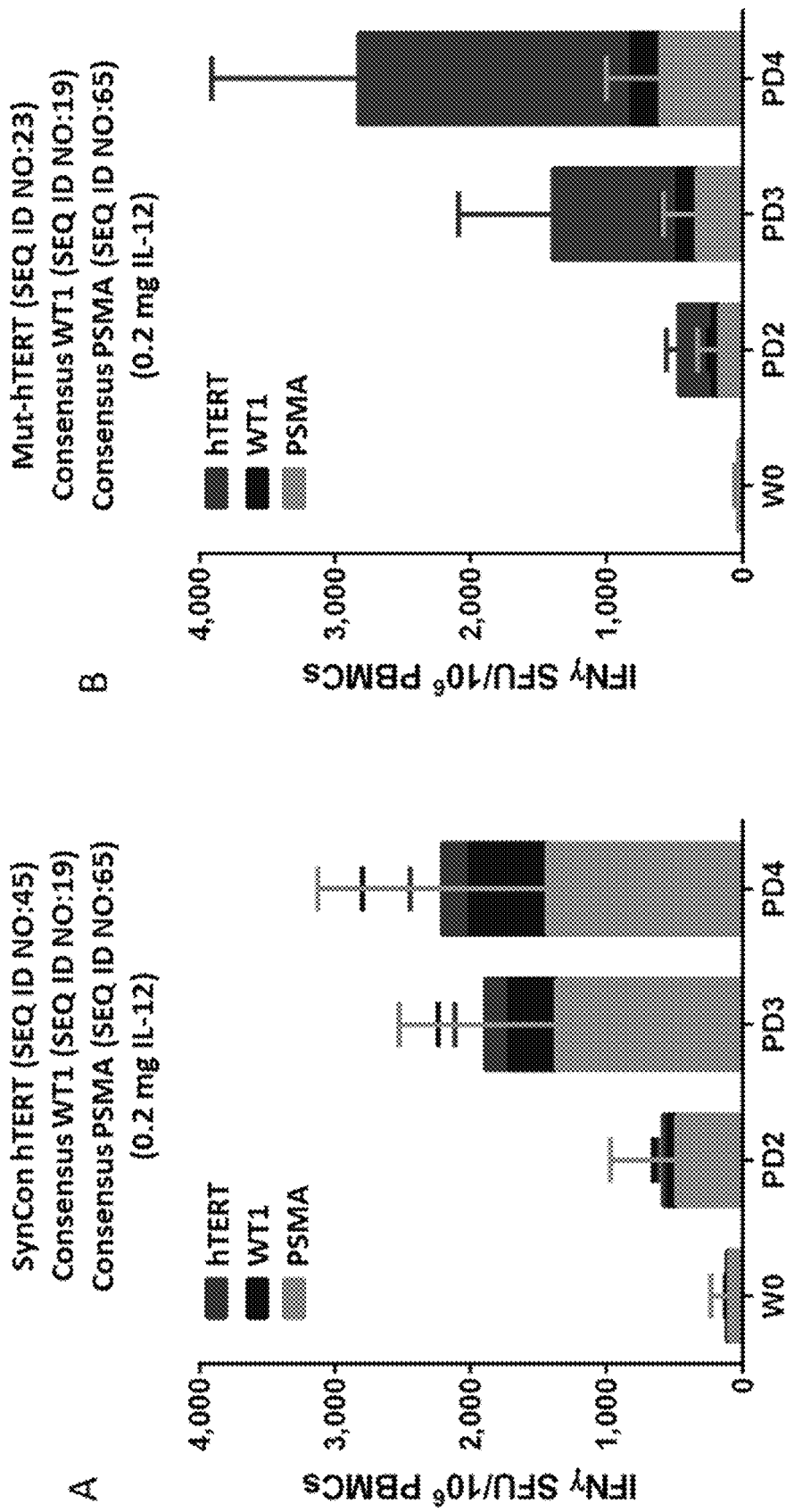
FIG. 25A through FIG. 25B, depicts the results of experiments demonstrating NHP immunogenicity of the SynCon hTERT.
Figures 26A, 26B, 26C:
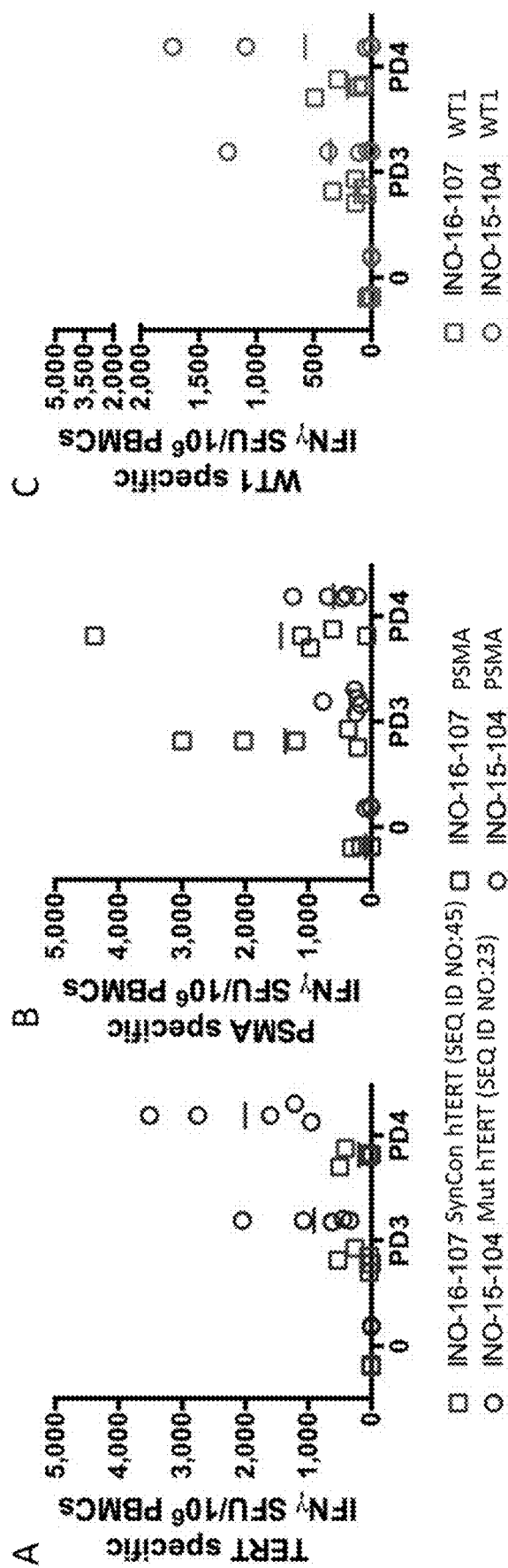
FIG. 26A through FIG. 26C, depicts the results of experiments demonstrating NHP immunogenicity of the SynCon hTERT.

The results from the experiments are provided in FIG. 23 through FIG. 26. Responses to native rhesus TERT were detected PD3 and PD4 in the pGX1434+pGX6006 group (FIG. 23). pGX1406 induces more robust TERT responses compared to pGX1434 when combined in the multivalent Wave 1 formulation with 0.20 mg pGX6006 (FIG. 25). SynCon PSMA and SynCon WT-1 specific responses PD4 are similar for groups containing pGX1434 and pGX1406.

Figures 27A, 27B:
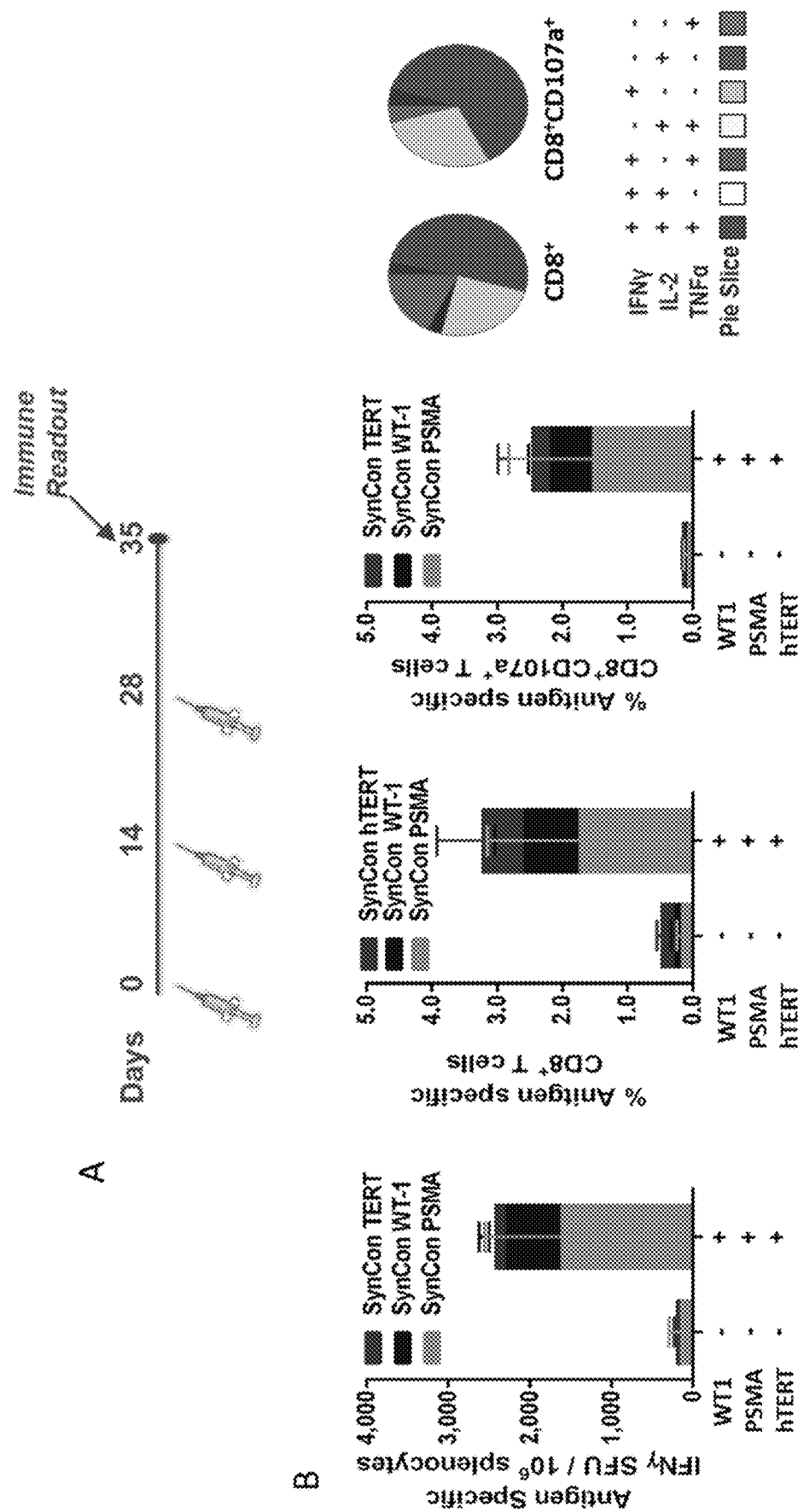
FIG. 27A through FIG. 27B, depicts the results of experiments demonstrating the breadth of the multivalent SynCon vaccines.
Figures 28A, 28B:
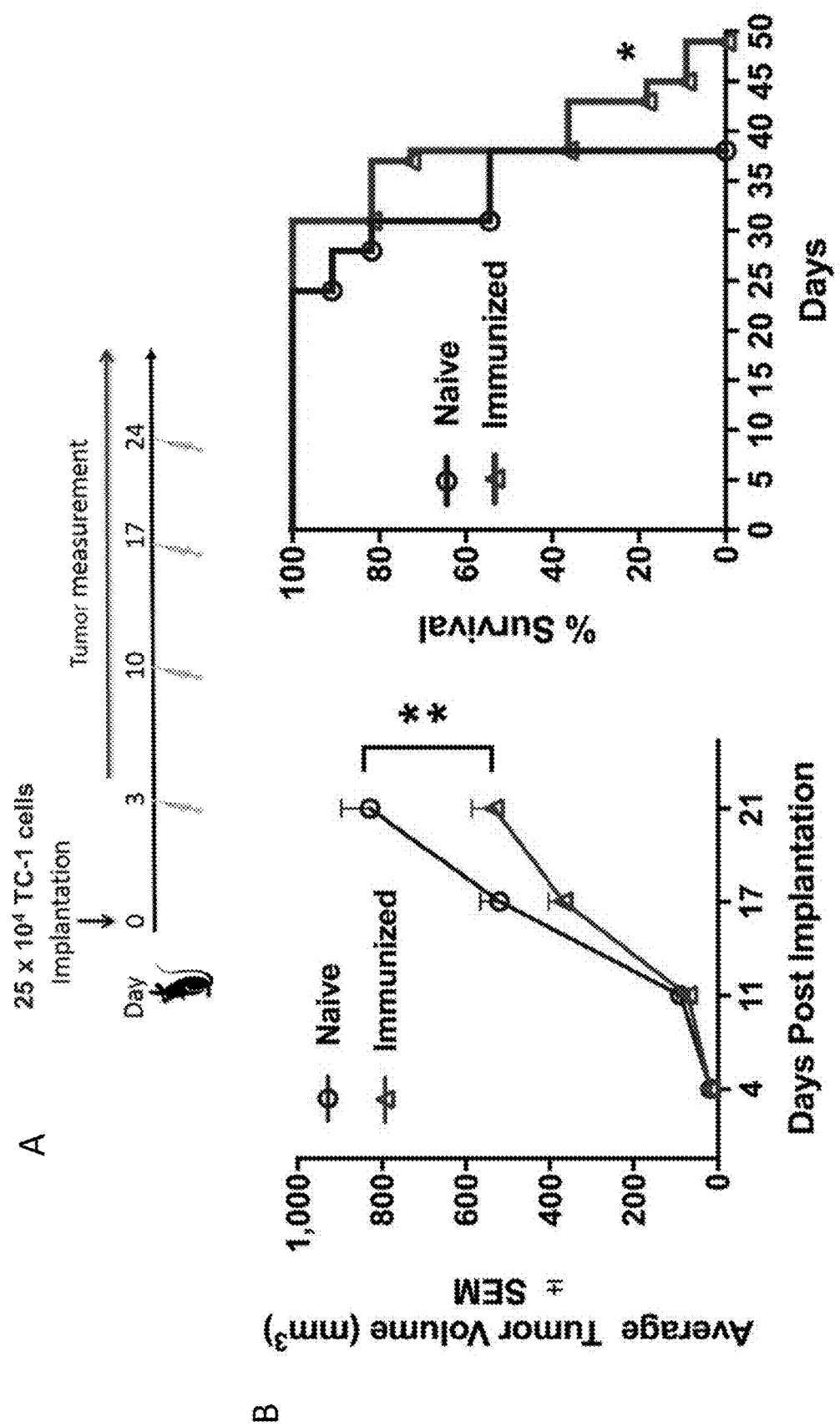
FIG. 28A through FIG. 28B, depicts the results of experiments demonstrating the multivalent SynCon vaccine reduces tumor burden and increases survival.

The multivalent formulation of WT-1, TERT, and PSMA induced robust immune responses in mice by IFNγ ELISpot and in the CD8+ T cell compartment (FIG. 27) and mice immunized with a combination of WT1, PSMA and consensus mTERT showed a reduced tumor burden and increased survival (FIG. 28).

The experiments presented herein demonstrate that synthetic consensus hTERT was able to break tolerance and induce a strong cellular immune response in non-human primates.

Example 15

Sequences

| SEQ ID NO: | Antigen | Type | Plasmid |
|---|---|---|---|
| 1 | Consensus Tyrosinase | Nucleic acid | |
| 2 | Consensus Tyrosinase | Amino acid | |
| 3 | Consensus Tyrosinase-related protein 1 | Nucleic acid | |
| 4 | Consensus Tyrosinase-related protein 1 | Amino acid | |
| 5 | Consensus Tyrosinase-related protein 2 | Nucleic acid | |
| 6 | Consensus Tyrosinase-related protein 2 | Amino acid | |
| 7 | Consensus Melanoma-associated antigen 4 | Nucleic acid | |
| 8 | Consensus Melanoma-associated antigen 4 | Amino acid | |
| 9 | Consensus Growth hormone releasing hormone | Nucleic acid | |
| 10 | Consensus Growth hormone releasing hormone | Amino acid | |
| 11 | Consensus Melan-A | Nucleic acid | |
| 12 | Consensus Melan-A | Amino acid | |
| 13 | Consensus NY-ESO-1 | Nucleic acid | |
| 14 | Consensus NY-ESO-1 | Amino acid | |
| 15 | Consensus NY-ESO-2 | Nucleic acid | |
| 16 | Consensus NY-ESO-2 | Amino acid | |
| 17 | Consensus PRAME | Nucleic acid | |
| 18 | Consensus PRAME | Amino acid | |
| 19 | Con WT1-L with modified Zinc Fingers | Nucleic acid | pGX1404 |
| 20 | Con WT1-L with modified Zinc Fingers | Amino acid | pGX1404 |
| 21 | Con WT1-S without Zinc fingers | Nucleic acid | |
| 22 | Con WT1-S without Zinc fingers | Amino acid | |
| 23 | hTERT operably linked to IgE | Nucleic acid | pGX1406 |
| 24 | hTERT operably linked to IgE | Amino acid | pGX1406 |
| 25 | gB consensus | Nucleic acid | |
| 26 | gB consensus | Amino acid | |
| 27 | gM consensus | Nucleic acid | |
| 28 | gM consensus | Amino acid | |
| 29 | gN consensus | Nucleic acid | |
| 30 | gN consensus | Amino acid | |
| 31 | gH consensus | Nucleic acid | |
| 32 | gH consensus | Amino acid | |
| 33 | gL consensus | Nucleic acid | |
| 34 | gL consensus | Amino acid | |
| 35 | gO consensus | Nucleic acid | |
| 36 | gO consensus | Amino acid | |
| 37 | UL128 consensus | Nucleic acid | |
| 38 | UL128 consensus | Amino acid | |
| 39 | UL130 consensus | Nucleic acid | |
| 40 | UL130 consensus | Amino acid | |
| 41 | UL131a consensus | Nucleic acid | |
| 42 | UL131a consensus | Amino acid | |
| 43 | UL83 consensus | Nucleic acid | |
| 44 | UL83 consensus | Amino acid | |
| 45 | Synthetic Consensus hTERT operably linked to IgE | Nucleic acid | pGX1434 |
| 46 | Synthetic Consensus hTERT operably linked to IgE | Amino acid | pGX1434 |
| 47 | Synthetic Consensus hTERT | Nucleic acid | pGX1434 |
| 48 | Synthetic Consensus hTERT | Amino acid | pGX1434 |
| 49 | Synthetic Consensus mTERT operably linked to IgE | Nucleic acid | pGX1418 |
| 50 | Synthetic Consensus mTERT operably linked to IgE | Amino acid | pGX1418 |
| 51 | Synthetic Consensus mTERT | Nucleic acid | pGX1418 |
| 52 | Synthetic Consensus mTERT | Amino acid | pGX1418 |
| 53 | Synthetic Consensus rhTERT operably linked to IgE | Nucleic acid | pGX1473 |
| 54 | Synthetic Consensus rhTERT operably linked to IgE | Amino acid | pGX1473 |
| 55 | Synthetic Consensus rhTERT | Nucleic acid | pGX1473 |
| 56 | Synthetic Consensus rhTERT | Amino acid | pGX1473 |
| 57 | mut rhTERT | Nucleic acid | pGX1447 |
| 58 | mut rhTERT | Amino acid | pGX1447 |
| 59 | Consensus FAP | Nucleic acid | |
| 60 | Consensus FAP | Amino acid | |
| 61 | Consensus FSHR | Nucleic acid | |
| 62 | Consensus FSHR | Amino acid | |
| 63 | Consensus PSA | Nucleic acid | |
| 64 | Consensus PSA | Amino acid | |
| 65 | Consensus PSMA | Nucleic acid | pGX1108 |
| 66 | Consensus PSMA | Amino acid | pGX1108 |
| 67 | Consensus STEAP | Nucleic acid | |
| 68 | Consensus STEAP | Amino acid | |
| 69 | Consensus PSCA | Nucleic acid | |
| 70 | Consensus PSCA | Amino acid | |

What is claimed is:

1. An immunogenic composition comprising a nucleic acid molecule encoding a consensus TERT antigen, wherein the nucleic acid encodes a peptide that comprises an amino acid sequence selected from the group consisting of:
   a) an amino acid sequence selected from the group consisting of SEQ ID NO: 46, SEQ ID NO:48, SEQ ID NO:50, SEQ ID NO:52, SEQ ID NO:54, and SEQ ID NO:56, and
   b) an amino acid sequence that is at least 96% identical to an amino acid sequence selected from the group consisting of SEQ ID NO: 46, SEQ ID NO:48, SEQ ID NO:50, SEQ ID NO:52, SEQ ID NO:54, and SEQ ID NO:56.

2. The immunogenic composition of claim 1, wherein the immunogenic composition further comprises one or more additional nucleotide sequences encoding one or more additional amino acid sequence selected from the group consisting of
   a) an amino acid sequence selected from the group consisting of: SEQ ID NO:2, SEQ ID NO:4, SEQ ID NO:6, SEQ ID NO:8, SEQ ID NO:10, SEQ ID NO:12, SEQ ID NO: 14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70;
   b) an amino acid sequence that is 95% identical or greater to the amino acid selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, and
   c) a fragment of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, wherein the fragment comprises at least 95% of the full length amino acid sequence.

3. The immunogenic composition of claim 2, wherein said one or more additional nucleotide sequences comprises one or more nucleotide sequences selected from the group consisting of:
   a) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69;
   b) a nucleotide sequence that is 95% identical or greater to a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, and
   c) a fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, wherein the fragment comprises at least 95% of the full length nucleotide sequence.

4. The immunogenic composition of claim 1 further comprising a nucleic acid encoding one or more antigens selected from the group consisting of: MAGE A1, gp100, a viral antigen, and combinations thereof.

5. The immunogenic composition of claim 4, wherein the viral antigen is selected from the group consisting of a Hepatitis B virus (HBV) antigen, a Hepatitis C virus (HCV) antigen, a Human Papilloma Virus (HPV) antigen, a HBV core antigen, a HBV surface antigen, a HCV NS34A antigen, a HCV NS5A antigen, a HCV NS5B antigen, an HCV NS4B antigen, a HPV type 6 E6 antigen, a HPV type 6 E7 antigen, a HPV type 11 E6 antigen, a HPV type 11 E7 antigen, a HPV type 16 E6 antigen, a HPV type 16 E7 antigen, a HPV type 18 E6 antigen, an HPV type 18 E7 antigen and combinations thereof.

6. The immunogenic composition of claim 1, further comprising an immune checkpoint inhibitor.

7. The immunogenic composition of claim 1, wherein the nucleic acid molecule comprises a nucleotide sequence selected from the group consisting of
   a) a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, and
   b) a nucleotide sequence that is at least 95% identical to a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55.

8. The immunogenic composition of claim 1, wherein the nucleic acid molecule is a plasmid.

9. The immunogenic composition of claim 1, further comprising an adjuvant.

10. The immunogenic composition of claim 9, wherein the adjuvant is IL-12, IL-15, IL-28, or RANTES.

11. A method of treating or preventing melanoma in a subject in need thereof, the method comprising administering the immunogenic composition of claim 1 to the subject.

12. The method of claim 11, further comprising administering an immune checkpoint inhibitor to the subject.

13. The method of claim 12, wherein the immunogenic composition and immune checkpoint inhibitor are combined in a single formulation for administration to the subject.

14. The method of claim 12, wherein the immunogenic composition and immune checkpoint inhibitor are administered separately to the subject.

15. A nucleic acid molecule comprising one or more nucleotide sequences selected from the group consisting of:
   a) a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55, and
   b) a nucleotide sequence that is 95% identical or greater to a nucleotide sequence selected from the group consisting of SEQ ID NO: 45, SEQ ID NO: 47, SEQ ID NO: 49, SEQ ID NO: 51, SEQ ID NO: 53 and SEQ ID NO: 55.

16. The nucleic acid molecule of claim 15, further comprising one or more nucleotide sequences selected from the group consisting of:
   a) a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69;
   b) a nucleotide sequence that is 95% identical or greater to a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, and
   c) a fragment of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:57, SEQ ID NO:59, SEQ ID NO:61, SEQ ID NO:63, SEQ ID NO:65, SEQ ID NO:67 and SEQ ID NO:69, wherein the fragment comprises at least 95% of the full length nucleotide sequence.

17. The nucleic acid molecule of claim 15, wherein the nucleic acid molecule is a plasmid.

18. An amino acid molecule comprising one or more amino acid sequence selected from the group consisting of:
   a) an amino acid sequence selected from the group consisting of SEQ ID NO: 46, SEQ ID NO:48, SEQ ID NO:50, SEQ ID NO:52, SEQ ID NO:54, and SEQ ID NO:56, and b) an amino acid sequence that is at least 96% identical to an amino acid sequence selected from the group consisting of SEQ ID NO: 46, SEQ ID NO:48, SEQ ID NO:50, SEQ ID NO:52, SEQ ID NO:54, and SEQ ID NO:56.

19. The amino acid molecule of claim 18, further comprising one or more amino acid sequence selected from the group consisting of: a) an amino acid sequence selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70;

b) an amino acid sequence that is 95% identical or greater to the amino acid selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, and c) a fragment of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO; 58, SEQ ID NO:60, SEQ ID NO:62, SEQ ID NO:64, SEQ ID NO:66, SEQ ID NO:68, SEQ ID NO:70, wherein the fragment comprises at least 95% of the full length amino acid sequence.

* * * * *

SEQUENCE LISTING

<160> NUMBER OF SEQ ID NOS: 70

<210> SEQ ID NO 1
<211> LENGTH: 1608
<212> TYPE: DNA
<213> ORGANISM: Artificial Sequence
<220> FEATURE:

<223> OTHER INFORMATION: Consensus Tyrosinase

<400> SEQUENCE: 1

```
atggattgga cttggatctt attttagtt gctgctgcta ctagagttca ttctgactgg     60
acttggattc tgttcctggt cgccgccgct acccgagtgc attccgaaaa agagtgttgc    120
ccaccttggt ctggagatcg aagcccatgc ggacagctga gtgggcgggg atcatgtcag    180
aacatcctgc tgagcaatgc cccctggga cctcagttcc ccttcaccgg cgtggacgat    240
agagagtctt ggcccagtgt cttttacaac aggacttgcc agtgtagcgg gaatttcatg    300
ggcttcaact gcggcaattg taagttcggc ttttgggggc aaactgcac cgagcggaga    360
ctgctggtga ggcgcaatat cttcgatctg tccgccccg aaaaggacaa attctttgcc    420
tatctgaccc tggctaagca cacaattagc tccgattatg tcatccccat ggaacatac    480
ggccagatga aaacggcag cactcctatg tttaacgata tcaatatcta cgacctgttc    540
gtgtggatgc attactatgt ctccatggac gctctgctgg gcgggtctga gatctggcgg    600
gacattgatt tcgcacacga agctccagca tttctgccct ggcataggct gttcctgctg    660
cgctgggagc aggaaatcca gaagctgact ggggacgaga actttaccat tccctattgg    720
gattggcggg acgccgagaa atgcgatatc tgtactgacg aatacatggg aggccagcac    780
cccaccaacc ctaatctgct gtcacctgcc agcttctttt ctagttggca gatcgtgtgc    840
agccggctgg aggaatacaa ctcccaccag agcctgtgca atgggactcc agagggacca    900
ctgcgacgaa accctggaaa tcatgataag agccgaaccc ctcgactgcc atcaagcgcc    960
gacgtggagt tttgcctgtc cctgacacag tatgaaagcg gcagcatgga taaagccgct   1020
aacttctctt ttaggaatac cctggaaggg ttcgcaagtc cactgacagg aatcgccgac   1080
gcttcacagt cctctatgca caacgctctg catatctaca tgaatggcac aatgtcacag   1140
gtgcagggga gcgcaaacga tcctatcttc ctgctgcacc atgccttcgt ggactccatt   1200
tttgagcagt ggctgagaag gcaccgccca ctgcaggagg tgtatcctga agcaaacgcc   1260
ccaatcggcc ataatcgcga atcttatatg gtccccttta tccctctgta ccgaaacgga   1320
gatttcttta ttagttcaaa ggatctggc tacgactata gttacctgca ggacagcgat   1380
cctgactcct tccaggacta tatcaaatct tacctggagc aggcctctag aatttggagt   1440
tggctgctgg gagcagcaat ggtgggagct gtcctgaccg ctctgctggc aggactggtg   1500
tccctgctgt gccggcacaa gagaaaacag ctgcccgagg aaaagcagcc actgctgatg   1560
gaaaagaag actaccactc actgctgtac cagacccacc tgtgataa               1608
```

<210> SEQ ID NO 2
<211> LENGTH: 517
<212> TYPE: PRT
<213> ORGANISM: Artificial Sequence
<220> FEATURE:
<223> OTHER INFORMATION: Consensus Tyrosinase

<400> SEQUENCE: 2

```
Met Asp Trp Thr Trp Ile Leu Phe Leu Val Ala Ala Ala Thr Arg Val
1               5                   10                  15

His Ser Glu Lys Glu Cys Cys Pro Pro Trp Ser Gly Asp Arg Ser Pro
            20                  25                  30

Cys Gly Gln Leu Ser Gly Arg Gly Ser Cys Gln Asn Ile Leu Leu Ser
        35                  40                  45

Asn Ala Pro Leu Gly Pro Gln Phe Pro Phe Thr Gly Val Asp Asp Arg
    50                  55                  60
```

-continued

```
Glu Ser Trp Pro Ser Val Phe Tyr Asn Arg Thr Cys Gln Cys Ser Gly
 65                  70                  75                  80

Asn Phe Met Gly Phe Asn Cys Gly Asn Cys Lys Phe Gly Phe Trp Gly
                 85                  90                  95

Pro Asn Cys Thr Glu Arg Arg Leu Leu Val Arg Arg Asn Ile Phe Asp
            100                 105                 110

Leu Ser Ala Pro Glu Lys Asp Lys Phe Phe Ala Tyr Leu Thr Leu Ala
        115                 120                 125

Lys His Thr Ile Ser Ser Asp Tyr Val Ile Pro Ile Gly Thr Tyr Gly
    130                 135                 140

Gln Met Lys Asn Gly Ser Thr Pro Met Phe Asn Asp Ile Asn Ile Tyr
145                 150                 155                 160

Asp Leu Phe Val Trp Met His Tyr Tyr Val Ser Met Asp Ala Leu Leu
                165                 170                 175

Gly Gly Ser Glu Ile Trp Arg Asp Ile Asp Phe Ala His Glu Ala Pro
            180                 185                 190

Ala Phe Leu Pro Trp His Arg Leu Phe Leu Leu Arg Trp Glu Gln Glu
        195                 200                 205

Ile Gln Lys Leu Thr Gly Asp Glu Asn Phe Thr Ile Pro Tyr Trp Asp
210                 215                 220

Trp Arg Asp Ala Glu Lys Cys Asp Ile Cys Thr Asp Glu Tyr Met Gly
225                 230                 235                 240

Gly Gln His Pro Thr Asn Pro Asn Leu Leu Ser Pro Ala Ser Phe Phe
                245                 250                 255

Ser Ser Trp Gln Ile Val Cys Ser Arg Leu Glu Glu Tyr Asn Ser His
            260                 265                 270

Gln Ser Leu Cys Asn Gly Thr Pro Glu Gly Pro Leu Arg Arg Asn Pro
        275                 280                 285

Gly Asn His Asp Lys Ser Arg Thr Pro Arg Leu Pro Ser Ser Ala Asp
290                 295                 300

Val Glu Phe Cys Leu Ser Leu Thr Gln Tyr Glu Ser Gly Ser Met Asp
305                 310                 315                 320

Lys Ala Ala Asn Phe Ser Phe Arg Asn Thr Leu Glu Gly Phe Ala Ser
                325                 330                 335

Pro Leu Thr Gly Ile Ala Asp Ala Ser Gln Ser Ser Met His Asn Ala
            340                 345                 350

Leu His Ile Tyr Met Asn Gly Thr Met Ser Gln Val Gln Gly Ser Ala
        355                 360                 365

Asn Asp Pro Ile Phe Leu Leu His His Ala Phe Val Asp Ser Ile Phe
370                 375                 380

Glu Gln Trp Leu Arg Arg His Arg Pro Leu Gln Glu Val Tyr Pro Glu
385                 390                 395                 400

Ala Asn Ala Pro Ile Gly His Asn Arg Glu Ser Tyr Met Val Pro Phe
                405                 410                 415

Ile Pro Leu Tyr Arg Asn Gly Asp Phe Phe Ile Ser Ser Lys Asp Leu
            420                 425                 430

Gly Tyr Asp Tyr Ser Tyr Leu Gln Asp Ser Asp Pro Asp Ser Phe Gln
        435                 440                 445

Asp Tyr Ile Lys Ser Tyr Leu Glu Gln Ala Ser Arg Ile Trp Ser Trp
450                 455                 460

Leu Leu Gly Ala Ala Met Val Gly Ala Val Leu Thr Ala Leu Leu Ala
465                 470                 475                 480
```

Gly Leu Val Ser Leu Leu Cys Arg His Lys Arg Lys Gln Leu Pro Glu
              485                 490                 495

Glu Lys Gln Pro Leu Leu Met Glu Lys Glu Asp Tyr His Ser Leu Leu
        500                 505                 510

Tyr Gln Thr His Leu
        515

<210> SEQ ID NO 3
<211> LENGTH: 1668
<212> TYPE: DNA
<213> ORGANISM: Artificial Sequence
<220> FEATURE:
<223> OTHER INFORMATION: Consensus Tyrosinase-related protein 1

<400> SEQUENCE: 3

```
atggactgga cctggattct gttcctggtc gccgccgcaa cccgcgtgca ttcctctgcc      60
ccaaaactgc tgtctctggg atgtatcttc tttccactgc tgctgttcca gcaggcacgc     120
gcccagtttc cacgacagtg cgcaaccgtc gaggccctga ggagcgggat gtgctgtcca     180
gacctgtcac ccgtgagcgg acctggcaca gatcgctgcg gaagctcctc tgggcgggga     240
agatgtgagg ccgtgactgc tgactcacgg ccccacagcc ctcagtaccc acatgatggc     300
agggacgatc gcgaagtgtg gcccctgcga ttctttaacc ggacttgcca ctgtaacggc     360
aatttctccg gcataattg cggaacctgt agacctggat ggaggggcgc cgcttgtgac     420
cagcgcgtgc tgatcgtccg gagaaacctg ctggatctgt caaggaggaa gaaccac       480
ttcgtccgag ctctggacat ggcaaagaga accacacatc ctctgtttgt gatcgccacc     540
aggcgcagcg aggaaattct ggggccagat ggaaacacac cccagttcga acatctca      600
atctacaatt atttcgtgtg gacccactac tatagcgtca agaaaacatt cctgggcgtg     660
gggcaggaga gtttcggaga gtggactttt tcacatgagg ccccgctttt tctgacatgg     720
caccggtacc atctgctgag actggaaaag gatatgcagg agatgctgca ggaacctagt     780
ttctcactgc catattggaa ctttgcaaca ggaaaaaacg tgtgcgacat ctgtactgac     840
gatctgatgg gcagcagatc caacttcgat tctacactga tttcccccaaa tagcgtgttc     900
agccagtgga gggtggtctg cgactccctg gaggactacg ataccctggg caccctgtgc     960
aattctactg aagatgggcc catccgacgg aaccctgccg gaaatgtggc taggccaatg    1020
gtccagcgcc tgcctgagcc acaggacgtg gcccagtgcc tggaagtcgg cctgttcgat    1080
actccccctt tttattctaa cagtacaaac tctttccgca acactgtcga gggctacagt    1140
gaccctaccg ggaaatatga tccagccgtg cggagtctgc acaacctggc tcatctgttc    1200
ctgaatggaa ctggcgggca gacccacctg tccccaaatg accctatttt tgtcctgctg    1260
catactttca ccgacgccgt gtttgatgag tggctgagaa ggtacaacgc agatatcagc    1320
acctttccac tggaaaatgc ccccattggc cacaaccggc agtataatat ggtgccttc     1380
tggccacccg tcacaaacac tgagatgttt gtgactgctc cagacaatct ggggtacacc    1440
tatgaaatcc agtggcccctc cagagagttc tctgtgcctg aaatcattgc tattgcagtg    1500
gtcggcgcac tgctgctggt ggccctgatc tttgggaccg ctagctacct gattagggca    1560
cgccgatcca tggacgaggc caaccagccc tgctgacaga tcagtacca gtgctatgcc    1620
gaagagtatg aaaagctgca gaaccctaac cagtccgtcg tgtgataa               1668
```

<210> SEQ ID NO 4
<211> LENGTH: 554
<212> TYPE: PRT

<213> ORGANISM: Artificial Sequence
<220> FEATURE:
<223> OTHER INFORMATION: Consensus Tyrosinase-related protein 1

<400> SEQUENCE: 4

```
Met Asp Trp Thr Trp Ile Leu Phe Leu Val Ala Ala Thr Arg Val
1               5                   10                  15

His Ser Ser Ala Pro Lys Leu Leu Ser Leu Gly Cys Ile Phe Phe Pro
            20                  25                  30

Leu Leu Leu Phe Gln Gln Ala Arg Ala Gln Phe Pro Arg Gln Cys Ala
            35                  40                  45

Thr Val Glu Ala Leu Arg Ser Gly Met Cys Cys Pro Asp Leu Ser Pro
        50                  55                  60

Val Ser Gly Pro Gly Thr Asp Arg Cys Gly Ser Ser Gly Arg Gly
65                  70                  75                  80

Arg Cys Glu Ala Val Thr Ala Asp Ser Arg Pro His Ser Pro Gln Tyr
                85                  90                  95

Pro His Asp Gly Arg Asp Asp Arg Glu Val Trp Pro Leu Arg Phe Phe
            100                 105                 110

Asn Arg Thr Cys His Cys Asn Gly Asn Phe Ser Gly His Asn Cys Gly
            115                 120                 125

Thr Cys Arg Pro Gly Trp Arg Gly Ala Ala Cys Asp Gln Arg Val Leu
        130                 135                 140

Ile Val Arg Arg Asn Leu Leu Asp Leu Ser Lys Glu Glu Lys Asn His
145                 150                 155                 160

Phe Val Arg Ala Leu Asp Met Ala Lys Arg Thr Thr His Pro Leu Phe
                165                 170                 175

Val Ile Ala Thr Arg Arg Ser Glu Glu Ile Leu Gly Pro Asp Gly Asn
            180                 185                 190

Thr Pro Gln Phe Glu Asn Ile Ser Ile Tyr Asn Tyr Phe Val Trp Thr
        195                 200                 205

His Tyr Tyr Ser Val Lys Lys Thr Phe Leu Gly Val Gly Gln Glu Ser
    210                 215                 220

Phe Gly Glu Val Asp Phe Ser His Glu Gly Pro Ala Phe Leu Thr Trp
225                 230                 235                 240

His Arg Tyr His Leu Leu Arg Leu Glu Lys Asp Met Gln Glu Met Leu
                245                 250                 255

Gln Glu Pro Ser Phe Ser Leu Pro Tyr Trp Asn Phe Ala Thr Gly Lys
            260                 265                 270

Asn Val Cys Asp Ile Cys Thr Asp Asp Leu Met Gly Ser Arg Ser Asn
        275                 280                 285

Phe Asp Ser Thr Leu Ile Ser Pro Asn Ser Val Phe Ser Gln Trp Arg
    290                 295                 300

Val Val Cys Asp Ser Leu Glu Asp Tyr Asp Thr Leu Gly Thr Leu Cys
305                 310                 315                 320

Asn Ser Thr Glu Asp Gly Pro Ile Arg Arg Asn Pro Ala Gly Asn Val
                325                 330                 335

Ala Arg Pro Met Val Gln Arg Leu Pro Glu Pro Gln Asp Val Ala Gln
            340                 345                 350

Cys Leu Glu Val Gly Leu Phe Asp Thr Pro Pro Phe Tyr Ser Asn Ser
        355                 360                 365

Thr Asn Ser Phe Arg Asn Thr Val Glu Gly Tyr Ser Asp Pro Thr Gly
    370                 375                 380

Lys Tyr Asp Pro Ala Val Arg Ser Leu His Asn Leu Ala His Leu Phe
```

```
                385                 390                 395                 400
Leu Asn Gly Thr Gly Gly Gln Thr His Leu Ser Pro Asn Asp Pro Ile
                    405                 410                 415

Phe Val Leu Leu His Thr Phe Thr Asp Ala Val Phe Asp Glu Trp Leu
                420                 425                 430

Arg Arg Tyr Asn Ala Asp Ile Ser Thr Phe Pro Leu Glu Asn Ala Pro
            435                 440                 445

Ile Gly His Asn Arg Gln Tyr Asn Met Val Pro Phe Trp Pro Pro Val
        450                 455                 460

Thr Asn Thr Glu Met Phe Val Thr Ala Pro Asp Asn Leu Gly Tyr Thr
465                 470                 475                 480

Tyr Glu Ile Gln Trp Pro Ser Arg Glu Phe Ser Val Pro Glu Ile Ile
                485                 490                 495

Ala Ile Ala Val Val Gly Ala Leu Leu Leu Val Ala Leu Ile Phe Gly
                500                 505                 510

Thr Ala Ser Tyr Leu Ile Arg Ala Arg Arg Ser Met Asp Glu Ala Asn
            515                 520                 525

Gln Pro Leu Leu Thr Asp Gln Tyr Gln Cys Tyr Ala Glu Glu Tyr Glu
        530                 535                 540

Lys Leu Gln Asn Pro Asn Gln Ser Val Val
545                 550
```

<210> SEQ ID NO 5
<211> LENGTH: 1614
<212> TYPE: DNA
<213> ORGANISM: Artificial Sequence
<220> FEATURE:
<223> OTHER INFORMATION: Consensus Tyrosinase-related protein 2

<400> SEQUENCE: 5

```
atggactgga cctggattct gttcctggtc gccgctgcta cccgcgtgca ttcatctcct    60
ctgtggtggg gatttctgct gtcttgcctg ggatgcaaga tcctgccagg agcacaggga   120
cagttccccc gggtgtgcat gaccgtcgac tctctggtga caaagagtg ctgtcctagg   180
ctgggagccg aaagcgccaa cgtgtgcggc tcccagcagg acgaggaca gtgtactgag   240
gtgcgcgcag ataccgacc atggagtgga ccctacattc tgaggaacca ggacgatcgc   300
gaactgtggc ccgaaagtt cttaccgg acatgcaaat gtactggaaa cttcgccggc   360
tataattgcg gggactgtaa gtttggctgg accgggccca actgcgagag aaagaaaccc   420
cctgtgatca ggcagaatat tcattctctg agtcctcagg agcgggaaca gttcctgggc   480
gcactggacc tggccaagaa aagagtccac ccagattacg tgatcaccac acagcattgg   540
ctgggactgc tgggccctaa cgggacacag ccacagtttg ccaattgctc cgtctatgac   600
ttcttcgtgt ggctgcacta ctattctgtg cgggatacac tgctgggacc aggccgaccc   660
taccgagcaa tcgacttcag ccatcaggga ccagcctttg tgacttggca cagatatcat   720
ctgctgtgcc tggagcggga tctgcagaga ctgattggca cgaatccttc gctctgccc   780
tactggaact tgcaaccgg gcggaatgag tgcgacgtgt gcacagatca gctgttcgga   840
gccgctagac ctgacgatcc aactctgatc tcaagaaata gcaggtttag ctcctgggag   900
accgtctgcg actctctgga cgattacaac cacctggtga ccctgtgcaa tggaacatat   960
gaaggcctgc tgcggagaaa ccagatgggc cgcaatagta tgaagctgcc caccctgaaa  1020
gacattcgag attgtctgtc actgcagaag ttcgacaacc cacccttctt tcagaattcc  1080
accttctctt ttaggaacgc cctggagggg tttgacaaag ctgatggaac actggatagt  1140
```

-continued

```
caggtcatgt cactgcacaa cctggtgcat tcattcctga acgggactaa tgccctgcct   1200
cacagcgcag ccaatgaccc aatctttgtg gtcctgcata gcttcaccga cgctattttt   1260
gatgagtgga tgaagaggtt caaccctcca gctgatgcat ggccccagga actggcacct   1320
atcggacaca accgcatgta caatatggtc cccttctttc cccctgtgac aaatgaggaa   1380
ctgtttctga cttctgacca gctgggctac agttatgcta ttgatctgcc cgtgagcgtc   1440
gaggaaacac ccgggtggcc tactaccctg ctggtggtca tgggcactct ggtggctctg   1500
gtcgggctgt tcgtgctgct ggcatttctg cagtataggc gcctgcgcaa aggatacacc   1560
ccactgatgg aaacccacct gtcctccaag agatacaccg aagaagcatg ataa         1614
```

<210> SEQ ID NO 6
<211> LENGTH: 536
<212> TYPE: PRT
<213> ORGANISM: Artificial Sequence
<220> FEATURE:
<223> OTHER INFORMATION: Consensus Tyrosinase-related protein 2

<400> SEQUENCE: 6

```
Met Asp Trp Thr Trp Ile Leu Phe Leu Val Ala Ala Thr Arg Val
1               5                   10                  15

His Ser Ser Pro Leu Trp Trp Gly Phe Leu Leu Ser Cys Leu Gly Cys
            20                  25                  30

Lys Ile Leu Pro Gly Ala Gln Gly Gln Phe Pro Arg Val Cys Met Thr
        35                  40                  45

Val Asp Ser Leu Val Asn Lys Glu Cys Cys Pro Arg Leu Gly Ala Glu
    50                  55                  60

Ser Ala Asn Val Cys Gly Ser Gln Gln Gly Arg Gly Gln Cys Thr Glu
65                  70                  75                  80

Val Arg Ala Asp Thr Arg Pro Trp Ser Gly Pro Tyr Ile Leu Arg Asn
                85                  90                  95

Gln Asp Asp Arg Glu Leu Trp Pro Arg Lys Phe His Arg Thr Cys
            100                 105                 110

Lys Cys Thr Gly Asn Phe Ala Gly Tyr Asn Cys Gly Asp Cys Lys Phe
        115                 120                 125

Gly Trp Thr Gly Pro Asn Cys Glu Arg Lys Lys Pro Val Ile Arg
    130                 135                 140

Gln Asn Ile His Ser Leu Ser Pro Gln Glu Arg Glu Gln Phe Leu Gly
145                 150                 155                 160

Ala Leu Asp Leu Ala Lys Lys Arg Val His Pro Asp Tyr Val Ile Thr
                165                 170                 175

Thr Gln His Trp Leu Gly Leu Leu Gly Pro Asn Gly Thr Gln Pro Gln
            180                 185                 190

Phe Ala Asn Cys Ser Val Tyr Asp Phe Phe Val Trp Leu His Tyr Tyr
        195                 200                 205

Ser Val Arg Asp Thr Leu Leu Gly Pro Gly Arg Pro Tyr Arg Ala Ile
    210                 215                 220

Asp Phe Ser His Gln Gly Pro Ala Phe Val Thr Trp His Arg Tyr His
225                 230                 235                 240

Leu Leu Cys Leu Glu Arg Asp Leu Gln Arg Leu Ile Gly Asn Glu Ser
                245                 250                 255

Phe Ala Leu Pro Tyr Trp Asn Phe Ala Thr Gly Arg Asn Glu Cys Asp
            260                 265                 270

Val Cys Thr Asp Gln Leu Phe Gly Ala Ala Arg Pro Asp Asp Pro Thr
```

```
              275                 280                 285
Leu Ile Ser Arg Asn Ser Arg Phe Ser Ser Trp Glu Thr Val Cys Asp
    290                 295                 300

Ser Leu Asp Asp Tyr Asn His Leu Val Thr Leu Cys Asn Gly Thr Tyr
305                 310                 315                 320

Glu Gly Leu Leu Arg Arg Asn Gln Met Gly Arg Asn Ser Met Lys Leu
                325                 330                 335

Pro Thr Leu Lys Asp Ile Arg Asp Cys Leu Ser Leu Gln Lys Phe Asp
            340                 345                 350

Asn Pro Pro Phe Phe Gln Asn Ser Thr Phe Ser Phe Arg Asn Ala Leu
        355                 360                 365

Glu Gly Phe Asp Lys Ala Asp Gly Thr Leu Asp Ser Gln Val Met Ser
    370                 375                 380

Leu His Asn Leu Val His Ser Phe Leu Asn Gly Thr Asn Ala Leu Pro
385                 390                 395                 400

His Ser Ala Ala Asn Asp Pro Ile Phe Val Val Leu His Ser Phe Thr
                405                 410                 415

Asp Ala Ile Phe Asp Glu Trp Met Lys Arg Phe Asn Pro Pro Ala Asp
            420                 425                 430

Ala Trp Pro Gln Glu Leu Ala Pro Ile Gly His Asn Arg Met Tyr Asn
        435                 440                 445

Met Val Pro Phe Phe Pro Pro Val Thr Asn Glu Glu Leu Phe Leu Thr
    450                 455                 460

Ser Asp Gln Leu Gly Tyr Ser Tyr Ala Ile Asp Leu Pro Val Ser Val
465                 470                 475                 480

Glu Glu Thr Pro Gly Trp Pro Thr Thr Leu Leu Val Val Met Gly Thr
                485                 490                 495

Leu Val Ala Leu Val Gly Leu Phe Val Leu Leu Ala Phe Leu Gln Tyr
            500                 505                 510

Arg Arg Leu Arg Lys Gly Tyr Thr Pro Leu Met Glu Thr His Leu Ser
        515                 520                 525

Ser Lys Arg Tyr Thr Glu Glu Ala
    530                 535

<210> SEQ ID NO 7
<211> LENGTH: 1008
<212> TYPE: DNA
<213> ORGANISM: Artificial Sequence
<220> FEATURE:
<223> OTHER INFORMATION: Consensus Melanoma-associated antigen 4

<400> SEQUENCE: 7
atggattgga catgattct gttcctggtc gccgccgcaa ctagagtgca ttcatcatca      60
gagcagaagt cacagcattg taaacctgag gaaggcgtcg aggctcagga ggaagcactg    120
ggactggtgg gagctcaggc accaaccaca gaggaacagg aggccgctgt gagctcctct    180
agtccactgg tccccggcac tctggaggaa gtgcctgcag cagagagcgc cggacccct    240 cagagtccac agggagcctc agctctgccc actaccatca gcttcacatg ctggaggcag    300
cctaacgagg gctcaagctc ccaggaggaa gaggggcctt ctactagtcc agacgcagag    360
agcctgttcc gggaagccct gtccaataag gtggatgagc tggcccactt tctgctgcgg    420
aagtacagag ctaaagaact ggtcaccaaa gcagagatgc tggaacgagt gatcaagaac    480
tataaacggt gcttccctgt gattttgga aaggcctcag agagcctgaa aatgatcttc    540
ggcattgacg tgaaggaagt cgatccagct tctaatacat acactctggt gacatgtctg    600
```

```
ggcctgagtt atgacggact gctgggcaac aatcagattt ttcccaaaac cgggctgctg    660
atcattgtgc tgggcacaat cgccatggag ggggattccg cttctgaaga ggaaatttgg    720
gaggaactgg gcgtgatggg agtctacgac gggcgcgagc acaccgtgta cggagaacca    780
cgaaagctgc tgacccagga ttgggtccag gagaactacc tggaatatcg gcaggtgccc    840
gggtccaatc ctgcaagata cgagtttctg tggggaccca gggcactggc cgagacatct    900
tatgtgaaag tcctggaaca tgtggtcagg gtgaacgctc gcgtgcgaat tgcctaccca    960
agcctgcgcg aagccgctct gctggaagaa gaggaaggag tgtgataa               1008
```

<210> SEQ ID NO 8
<211> LENGTH: 334
<212> TYPE: PRT
<213> ORGANISM: Artificial Sequence
<220> FEATURE:
<223> OTHER INFORMATION: Consensus Melanoma-associated antigen 4

<400> SEQUENCE: 8

```
Met Asp Trp Thr Trp Ile Leu Phe Leu Val Ala Ala Ala Thr Arg Val
1               5                   10                  15

His Ser Ser Glu Gln Lys Ser Gln His Cys Lys Pro Glu Glu Gly
            20                  25                  30

Val Glu Ala Gln Glu Glu Ala Leu Gly Leu Val Gly Ala Gln Ala Pro
        35                  40                  45

Thr Thr Glu Glu Gln Glu Ala Ala Val Ser Ser Ser Pro Leu Val
    50                  55                  60

Pro Gly Thr Leu Glu Glu Val Pro Ala Ala Glu Ser Ala Gly Pro Pro
65                  70                  75                  80

Gln Ser Pro Gln Gly Ala Ser Ala Leu Pro Thr Thr Ile Ser Phe Thr
                85                  90                  95

Cys Trp Arg Gln Pro Asn Glu Gly Ser Ser Ser Gln Glu Glu Glu Gly
            100                 105                 110

Pro Ser Thr Ser Pro Asp Ala Glu Ser Leu Phe Arg Glu Ala Leu Ser
        115                 120                 125

Asn Lys Val Asp Glu Leu Ala His Phe Leu Leu Arg Lys Tyr Arg Ala
    130                 135                 140

Lys Glu Leu Val Thr Lys Ala Glu Met Leu Glu Arg Val Ile Lys Asn
145                 150                 155                 160

Tyr Lys Arg Cys Phe Pro Val Ile Phe Gly Lys Ala Ser Glu Ser Leu
                165                 170                 175

Lys Met Ile Phe Gly Ile Asp Val Lys Glu Val Asp Pro Ala Ser Asn
            180                 185                 190

Thr Tyr Thr Leu Val Thr Cys Leu Gly Leu Ser Tyr Asp Gly Leu Leu
        195                 200                 205

Gly Asn Asn Gln Ile Phe Pro Lys Thr Gly Leu Leu Ile Ile Val Leu
    210                 215                 220

Gly Thr Ile Ala Met Glu Gly Asp Ser Ala Ser Glu Glu Glu Ile Trp
225                 230                 235                 240

Glu Glu Leu Gly Val Met Gly Val Tyr Asp Gly Arg Glu His Thr Val
                245                 250                 255

Tyr Gly Glu Pro Arg Lys Leu Leu Thr Gln Asp Trp Val Gln Glu Asn
            260                 265                 270

Tyr Leu Glu Tyr Arg Gln Val Pro Gly Ser Asn Pro Ala Arg Tyr Glu
        275                 280                 285
```

```
Phe Leu Trp Gly Pro Arg Ala Leu Ala Glu Thr Ser Tyr Val Lys Val
            290                 295                 300
Leu Glu His Val Val Arg Val Asn Ala Arg Val Arg Ile Ala Tyr Pro
305                 310                 315                 320
Ser Leu Arg Glu Ala Ala Leu Leu Glu Glu Glu Glu Gly Val
                325                 330

<210> SEQ ID NO 9
<211> LENGTH: 381
<212> TYPE: DNA
<213> ORGANISM: Artificial Sequence
<220> FEATURE:
<223> OTHER INFORMATION: Consensus Growth hormone releasing hormone

<400> SEQUENCE: 9
atggactgga cctggattct gttcctggtg gctgccgcaa ctcgcgtgca ttctcctctg    60
tgggtgttct tctttgtgat tctgactctg tctaacagct cccactgcag tccccctcca   120
cccctgaccc tgcgaatgcg gagatacgcc gacgctatct tcacaaattc ctatagaaag   180
gtgctgggac agctgtctgc taggaaactg ctgcaggata ttatgtcacg ccagcagggc   240
gagagcaacc aggaacgagg cgcaagggcc cgactgggc ggcaggtcga cagcatgtgg   300
gccgagcaga agcagatgga actggaaagc atcctggtcg cactgctgca gaaacatagc   360
cgaaatagcc agggatgata a                                             381

<210> SEQ ID NO 10
<211> LENGTH: 125
<212> TYPE: PRT
<213> ORGANISM: Artificial Sequence
<220> FEATURE:
<223> OTHER INFORMATION: Consensus Growth hormone releasing hormone

<400> SEQUENCE: 10

Met Asp Trp Thr Trp Ile Leu Phe Leu Val Ala Ala Ala Thr Arg Val
1               5                   10                  15

His Ser Pro Leu Trp Val Phe Phe Val Ile Leu Thr Leu Ser Asn
            20                  25                  30

Ser Ser His Cys Ser Pro Pro Pro Leu Thr Leu Arg Met Arg Arg
        35                  40                  45

Tyr Ala Asp Ala Ile Phe Thr Asn Ser Tyr Arg Lys Val Leu Gly Gln
    50                  55                  60

Leu Ser Ala Arg Lys Leu Leu Gln Asp Ile Met Ser Arg Gln Gln Gly
65                  70                  75                  80

Glu Ser Asn Gln Glu Arg Gly Ala Arg Ala Arg Leu Gly Arg Gln Val
                85                  90                  95

Asp Ser Met Trp Ala Glu Gln Lys Gln Met Glu Leu Glu Ser Ile Leu
            100                 105                 110

Val Ala Leu Leu Gln Lys His Ser Arg Asn Ser Gln Gly
        115                 120                 125

<210> SEQ ID NO 11
<211> LENGTH: 411
<212> TYPE: DNA
<213> ORGANISM: Artificial Sequence
<220> FEATURE:
<223> OTHER INFORMATION: Consensus Melan-A

<400> SEQUENCE: 11
atggactgga catggattct gttcctggtc gctgctgcta caagggtgca ttccccacgg    60
```

```
gaggacgccc acttcatcta tggatacccc aagaaaggcc acgggcattc ttacaccaca    120
gctgaggaag ccgctggaat cggcattctg acagtgatcc tgggggtcct gctgctgatt    180
ggatgctggt actgtcggag aaggaacggc tatagagcac tgatggacaa gagcctgcac    240
gtgggaactc agtgcgcact gacccgccga tgtccacagg agggattcga ccatcgggat    300
agcaaggtct ccctgcagga gaaaaattgc gaacccgtgg tccctaatgc cccacccgct    360
tacgaaaaac tgtccgcaga gcagagccca ccaccttatt caccttgata a              411
```

<210> SEQ ID NO 12
<211> LENGTH: 135
<212> TYPE: PRT
<213> ORGANISM: Artificial Sequence
<220> FEATURE:
<223> OTHER INFORMATION: Consensus Melan-A

<400> SEQUENCE: 12

```
Met Asp Trp Thr Trp Ile Leu Phe Leu Val Ala Ala Thr Arg Val
1               5                   10                  15

His Ser Pro Arg Glu Asp Ala His Phe Ile Tyr Gly Tyr Pro Lys Lys
            20                  25                  30

Gly His Gly His Ser Tyr Thr Thr Ala Glu Glu Ala Ala Gly Ile Gly
        35                  40                  45

Ile Leu Thr Val Ile Leu Gly Val Leu Leu Leu Ile Gly Cys Trp Tyr
    50                  55                  60

Cys Arg Arg Arg Asn Gly Tyr Arg Ala Leu Met Asp Lys Ser Leu His
65                  70                  75                  80

Val Gly Thr Gln Cys Ala Leu Thr Arg Arg Cys Pro Gln Glu Gly Phe
                85                  90                  95

Asp His Arg Asp Ser Lys Val Ser Leu Gln Glu Lys Asn Cys Glu Pro
            100                 105                 110

Val Val Pro Asn Ala Pro Pro Ala Tyr Glu Lys Leu Ser Ala Glu Gln
        115                 120                 125

Ser Pro Pro Pro Tyr Ser Pro
    130                 135
```

<210> SEQ ID NO 13
<211> LENGTH: 597
<212> TYPE: DNA
<213> ORGANISM: Artificial Sequence
<220> FEATURE:
<223> OTHER INFORMATION: Consensus NY-ESO-1

<400> SEQUENCE: 13

```
atggactgga catggattct gtttctggtg gctgccgcaa ctagagtgca ttcacaggcc     60
gctggacagg gaactggagg ctcaaccgga gacgcagatg ccctggcgg ccagggtg      120 cccgacggac ctggaggcaa cgctggggga cccggggagg ccggagctac aggcggggga    180
ggccctcagg gagccggcgc cgccagagcc agcggacccc ggggcgggc accccggggg     240 cctcacggcg ggcagcatc aggcctgaat ggatgctgtc gatgcggagc acggagacct     300
gagagcaggc tgctggaatt ctacctgact atgcctttg ccaccccaat ggaggcagaa     360
ctggcaaggc gctccctggc tcgggacgca ccccctctgc cagtgcccgg cgtcctgctg    420
aaggaattca ccgtctctgg caacatcctg accattaggc tgacagctgc agatcatcgc    480
cagctgcagc tgtctatcag ctcctgtctg cagcagctga gtctgctgat gtggattacc    540
cagtgctttc tgcccgtctt cctggctcag cctccttccg gacagcgccg atgataa       597
```

<210> SEQ ID NO 14
<211> LENGTH: 197
<212> TYPE: PRT
<213> ORGANISM: Artificial Sequence
<220> FEATURE:
<223> OTHER INFORMATION: Consensus NY-ESO-1

<400> SEQUENCE: 14

```
Met Asp Trp Thr Trp Ile Leu Phe Leu Val Ala Ala Thr Arg Val
 1               5                  10                  15

His Ser Gln Ala Ala Gly Gln Gly Thr Gly Gly Ser Thr Gly Asp Ala
                20                  25                  30

Asp Gly Pro Gly Gly Pro Gly Val Pro Asp Gly Pro Gly Gly Asn Ala
            35                  40                  45

Gly Gly Pro Gly Glu Ala Gly Ala Thr Gly Gly Gly Pro Gln Gly
        50                  55                  60

Ala Gly Ala Ala Arg Ala Ser Gly Pro Arg Gly Gly Ala Pro Arg Gly
 65                  70                  75                  80

Pro His Gly Gly Ala Ala Ser Gly Leu Asn Gly Cys Cys Arg Cys Gly
                85                  90                  95

Ala Arg Arg Pro Glu Ser Arg Leu Leu Glu Phe Tyr Leu Thr Met Pro
            100                 105                 110

Phe Ala Thr Pro Met Glu Ala Glu Leu Ala Arg Arg Ser Leu Ala Arg
        115                 120                 125

Asp Ala Pro Pro Leu Pro Val Pro Gly Val Leu Leu Lys Glu Phe Thr
130                 135                 140

Val Ser Gly Asn Ile Leu Thr Ile Arg Leu Thr Ala Ala Asp His Arg
145                 150                 155                 160

Gln Leu Gln Leu Ser Ile Ser Ser Cys Leu Gln Gln Leu Ser Leu Leu
                165                 170                 175

Met Trp Ile Thr Gln Cys Phe Leu Pro Val Phe Leu Ala Gln Pro Pro
            180                 185                 190

Ser Gly Gln Arg Arg
        195
```

<210> SEQ ID NO 15
<211> LENGTH: 687
<212> TYPE: DNA
<213> ORGANISM: Artificial Sequence
<220> FEATURE:
<223> OTHER INFORMATION: Consensus NY-ESO-2

<400> SEQUENCE: 15
atggactgga catggattct gtttctggtc gccgccgcaa cacgggtgca ttctcaggcc     60
gaggggcagg gaactggagg ctcaaccgga gacgcagatg gacctggcgg gccaggcatc    120
cccgacggac ctggaggcaa cgccgggga cctggggagg ccggagctac aggcgggaga    180
ggcccaaggg gcgcaggggc cgctagggcc agtggacccc gcggaggcgc cccacgaggc    240
ccacacgggg gagcagcctc cgcccaggac ggcagatgcc catgtggagc tcggagaccc    300
gattctaggc tgctgcagct gcatatcact atgcccttca gctcccctat ggaggctgaa    360
ctggtgaggc gcattctgtc ccgcgacgct gcacctctgc cacgaccagg ggccgtgctg    420
aaggatttca ccgtctcagg caatctgctg tttatgagcg tccgggacca ggatagagag    480
ggagcaggac gaatgcgagt ggtcggatgg ggactgggct ctgctagtcc tgaaggccag    540
aaagcacgcg atctgcgaac cccaagcac aaagtgagcg agcagcgccc tggcacacca    600

```
gggcccccctc cacccgaagg cgcccaggga gacggatgta gaggagtcgc cttcaatgtc    660
atgtttagtg caccccatat ttgataa                                         687
```

```
<210> SEQ ID NO 16
<211> LENGTH: 227
<212> TYPE: PRT
<213> ORGANISM: Artificial Sequence
<220> FEATURE:
<223> OTHER INFORMATION: Consensus NY-ESO-2

<400> SEQUENCE: 16
```

```
Met Asp Trp Thr Trp Ile Leu Phe Leu Val Ala Ala Thr Arg Val
1               5                   10                  15

His Ser Gln Ala Glu Gly Gln Gly Thr Gly Gly Ser Thr Gly Asp Ala
            20                  25                  30

Asp Gly Pro Gly Gly Pro Gly Ile Pro Asp Gly Pro Gly Gly Asn Ala
        35                  40                  45

Gly Gly Pro Gly Glu Ala Gly Ala Thr Gly Gly Arg Gly Pro Arg Gly
    50                  55                  60

Ala Gly Ala Ala Arg Ala Ser Gly Pro Arg Gly Gly Ala Pro Arg Gly
65                  70                  75                  80

Pro His Gly Gly Ala Ala Ser Ala Gln Asp Gly Arg Cys Pro Cys Gly
                85                  90                  95

Ala Arg Arg Pro Asp Ser Arg Leu Leu Gln Leu His Ile Thr Met Pro
            100                 105                 110

Phe Ser Ser Pro Met Glu Ala Glu Leu Val Arg Arg Ile Leu Ser Arg
        115                 120                 125

Asp Ala Ala Pro Leu Pro Arg Pro Gly Ala Val Leu Lys Asp Phe Thr
    130                 135                 140

Val Ser Gly Asn Leu Leu Phe Met Ser Val Arg Asp Gln Asp Arg Glu
145                 150                 155                 160

Gly Ala Gly Arg Met Arg Val Val Gly Trp Gly Leu Gly Ser Ala Ser
                165                 170                 175

Pro Glu Gly Gln Lys Ala Arg Asp Leu Arg Thr Pro Lys His Lys Val
            180                 185                 190

Ser Glu Gln Arg Pro Gly Thr Pro Gly Pro Pro Glu Gly Ala
        195                 200                 205

Gln Gly Asp Gly Cys Arg Gly Val Ala Phe Asn Val Met Phe Ser Ala
    210                 215                 220

Pro His Ile
225
```

```
<210> SEQ ID NO 17
<211> LENGTH: 1584
<212> TYPE: DNA
<213> ORGANISM: Artificial Sequence
<220> FEATURE:
<223> OTHER INFORMATION: Consensus PRAME

<400> SEQUENCE: 17
```

```
atggactgga catggattct gttcctggtc gctgctgcta cacgggtgca ttcagagaga    60
cgaagactgc ggggctcaat tcagagtagg tacatcagta tgtcagtctg gacctcacca   120
cggagactgg tggaactggc cgggcagagc ctgctgaagg atgaggccct ggctattgcc   180
gctctggaac tgctgccccg agagctgttc cctcccctgt tcatggcagc cttcgacgga   240
cgccacagcc agactctgaa ggctatggtc caggcatggc cctttacctg cctgcctctg   300
```

-continued

| | |
|---|---|
| ggcgtgctga tgaaggggca gcagctgcat ctggagactt tcaaagcagt gctggatggc | 360 |
| ctggacgtgc tgctggccca ggaagtgagg cctaggcgct ggaagctgga ggtcctggat | 420 |
| ctgcgcaaaa acagccacca ggacttttgg accgtgtggt ccgggaatcg ggccagtctg | 480 |
| tactcattcc cagaacccga ggctgcacag ccaatgcgga agaaaagaaa ggtggatgga | 540 |
| ctgtccaccg aagctgagca gccttttaca ccaatcgaag tgctggtcga tctgtccctg | 600 |
| aaagaaggcg catgcgacga gctgttctct tatctgatgg agaaggtcaa agacagaag | 660 |
| aacgtgctgc acctgtgctg taagaaactg aaaatctttg ctatgcccat gcaggacatc | 720 |
| aagatgattc tgaaaatggt ccagctggat tccattgaag acctggaggt cacttgtacc | 780 |
| tggaagctgc aacactggc caaattctct ccctacctgg acagatgat caatctgcga | 840 |
| cggctgctgc tgtctcacat ccatgctagc tcctctatta gtcctgagaa ggaggaagag | 900 |
| tacattgcac agtttacttc tcagttcctg agtctgcagt gcctgcaggc cctgtatgtg | 960 |
| gatagcctgt tctttctgag aggcaggctg gaccagctgc tgcgacacgt catgaacccc | 1020 |
| ctggaaacac tgagtgtgac taattgtaga ctgtcagagg gcgatgtgat gcatctgagc | 1080 |
| cagtccccta cgtgagcca gctgtccgtc ctgtctctga gtggcgtgat gctgacagac | 1140 |
| gtgagccctg aaccactgca ggccctgctg agcgagcat ctgccactct gcaggacctg | 1200 |
| gattttgacg agtgtgggat catggacgat cagctgctgg tgctgctgcc ttcactgagc | 1260 |
| cactgctccc agctgaccac actgtctttc tgtgggaacc caatctccat ttctgtgctg | 1320 |
| cagaatctgc tgcaccatct gattggactg agcaacctga cccatgtgct gtaccccgtc | 1380 |
| cctctggaaa gctatgagga tgtgcacgga acactgcatc tgggcaggct ggcctatctg | 1440 |
| cacgctcgcc tgcgagaact gctgtgcgag ctgggcagac cctcaatggt gtggctgagc | 1500 |
| gccaatccat gtccccattg cggcgaccgg acattctacg accccgaacc tattctgtgc | 1560 |
| ccctgcttca tgcctaactg ataa | 1584 |

<210> SEQ ID NO 18
<211> LENGTH: 526
<212> TYPE: PRT
<213> ORGANISM: Artificial Sequence
<220> FEATURE:
<223> OTHER INFORMATION: Consensus PRAME

<400> SEQUENCE: 18

Met Asp Trp Thr Trp Ile Leu Phe Leu Val Ala Ala Thr Arg Val
1               5                   10                  15

His Ser Glu Arg Arg Leu Arg Gly Ser Ile Gln Ser Arg Tyr Ile
                20                  25                  30

Ser Met Ser Val Trp Thr Ser Pro Arg Arg Leu Val Glu Leu Ala Gly
            35                  40                  45

Gln Ser Leu Leu Lys Asp Glu Ala Leu Ala Ile Ala Ala Leu Glu Leu
        50                  55                  60

Leu Pro Arg Glu Leu Phe Pro Pro Leu Phe Met Ala Ala Phe Asp Gly
65                  70                  75                  80

Arg His Ser Gln Thr Leu Lys Ala Met Val Gln Ala Trp Pro Phe Thr
                85                  90                  95

Cys Leu Pro Leu Gly Val Leu Met Lys Gly Gln Leu His Leu Glu
            100                 105                 110

Thr Phe Lys Ala Val Leu Asp Gly Leu Asp Val Leu Leu Ala Gln Glu
        115                 120                 125

Val Arg Pro Arg Arg Trp Lys Leu Glu Val Leu Asp Leu Arg Lys Asn

```
              130                 135                 140
Ser His Gln Asp Phe Trp Thr Val Trp Ser Gly Asn Arg Ala Ser Leu
145                 150                 155                 160

Tyr Ser Phe Pro Glu Pro Ala Ala Gln Pro Met Arg Lys Lys Arg
                165                 170                 175

Lys Val Asp Gly Leu Ser Thr Glu Ala Glu Gln Pro Phe Thr Pro Ile
                180                 185                 190

Glu Val Leu Val Asp Leu Ser Leu Lys Glu Gly Ala Cys Asp Glu Leu
                195                 200                 205

Phe Ser Tyr Leu Met Glu Lys Val Lys Arg Gln Lys Asn Val Leu His
                210                 215                 220

Leu Cys Cys Lys Lys Leu Lys Ile Phe Ala Met Pro Met Gln Asp Ile
225                 230                 235                 240

Lys Met Ile Leu Lys Met Val Gln Leu Asp Ser Ile Glu Asp Leu Glu
                245                 250                 255

Val Thr Cys Thr Trp Lys Leu Pro Thr Leu Ala Lys Phe Ser Pro Tyr
                260                 265                 270

Leu Gly Gln Met Ile Asn Leu Arg Arg Leu Leu Leu Ser His Ile His
                275                 280                 285

Ala Ser Ser Ser Ile Ser Pro Glu Lys Glu Glu Tyr Ile Ala Gln
                290                 295                 300

Phe Thr Ser Gln Phe Leu Ser Leu Gln Cys Leu Gln Ala Leu Tyr Val
305                 310                 315                 320

Asp Ser Leu Phe Phe Leu Arg Gly Arg Leu Asp Gln Leu Leu Arg His
                325                 330                 335

Val Met Asn Pro Leu Glu Thr Leu Ser Val Thr Asn Cys Arg Leu Ser
                340                 345                 350

Glu Gly Asp Val Met His Leu Ser Gln Ser Pro Asn Val Ser Gln Leu
                355                 360                 365

Ser Val Leu Ser Leu Ser Gly Val Met Leu Thr Asp Val Ser Pro Glu
                370                 375                 380

Pro Leu Gln Ala Leu Leu Glu Arg Ala Ser Ala Thr Leu Gln Asp Leu
385                 390                 395                 400

Asp Phe Asp Glu Cys Gly Ile Met Asp Asp Gln Leu Leu Val Leu Leu
                405                 410                 415

Pro Ser Leu Ser His Cys Ser Gln Leu Thr Thr Leu Ser Phe Cys Gly
                420                 425                 430

Asn Pro Ile Ser Ile Ser Val Leu Gln Asn Leu Leu His His Leu Ile
                435                 440                 445

Gly Leu Ser Asn Leu Thr His Val Leu Tyr Pro Val Pro Leu Glu Ser
450                 455                 460

Tyr Glu Asp Val His Gly Thr Leu His Leu Gly Arg Leu Ala Tyr Leu
465                 470                 475                 480

His Ala Arg Leu Arg Glu Leu Leu Cys Glu Leu Gly Arg Pro Ser Met
                485                 490                 495

Val Trp Leu Ser Ala Asn Pro Cys Pro His Cys Gly Asp Arg Thr Phe
                500                 505                 510

Tyr Asp Pro Glu Pro Ile Leu Cys Pro Cys Phe Met Pro Asn
                515                 520                 525

<210> SEQ ID NO 19
<211> LENGTH: 1332
<212> TYPE: DNA
<213> ORGANISM: Artificial Sequence
```

<220> FEATURE:
<223> OTHER INFORMATION: Con WT1-L with modified Zinc Fingers nucleic acid sequence

<400> SEQUENCE: 19

```
ggatccgcca ccatggactg gacctggatt ctgttcctgg tcgccgccgc aacacgggtg    60
catagtggga gtgatgtgag agacctgaac gccctgctgc cagcagtgcc atccctgcct   120
ggcgggggag gctgcgctct gccagtctct ggagcagctc agtgggctcc cgtgctggac   180
tttgcacccc ctgcagcccc ttacggaagt ctgggcggcc cacactcatt catcaaacag   240
gagccaagct ggggcgggc agatcctcat gaggaacagt gcctgtcagc cttcacagtc   300
cactttagcg ggcagttcac tggaaccgca ggagcttgta gatacggacc ctttggagca   360
ccaccccctt cccaggcacc ttctggacag gcacgcatgt ccccaaacgc tccctatctg   420
cctaattgtc tggaaagcca gcccgctatt aggaaccagg gctactccac agtggcattt   480
gacgggactc ctagctatgg acataccca tcccaccatg ctgcacagtt tcctaatcac   540
tccttcaagc atgaggaccc catgggacag caggggtccc tggagaaca gcagtactct   600
gtgccccctc ccgtgtacgg atgccacaca ccaactgaca gttgtacagg ctcacaggcc   660
ctgctgctgc gaactccata caacagtgat aatctgtatc agatgacctc acagctggag   720
tgcatgacat ggaaccagat gaatctgggc agcacactga aaggccatgc cactgggtac   780
gaatctgaca ccacaccac acctatgctg tacagttgtg gagcccagta tagaatccac   840
actcatggag tcttcagagg cattcaggat gtgcggagag tcccaggagt ggcaccaact   900
atcgtgcgga gcgcctccga gaccaacgaa aagcgcccct tatgggcgc ctaccctgga   960
ggcaataagc ggtatttcaa actgtctcac ctgcagatgg ggagtagaaa ggggaccgga  1020
gagaaacctt atcagggcga ctttaaagat ggggaaaggc gcttctctcg cagtgaccag  1080
ctgaagcgag acagcgacg aggaaccggg gtgaagccat tcagtgcaa acatgtcag    1140
agaaagttct caaggagcga tcacctgaag acccatacaa gaactcacac cggcaagacc  1200
agcgagaaac cattttcctg ccgatggccc tcttgtcaga gaaattcgc ccgctccgac  1260
gaactggtcc gacaccacaa tatgcatcag agaaatatga caaaactgca gctggctctg  1320
tgataactcg ag                                                       1332
```

<210> SEQ ID NO 20
<211> LENGTH: 436
<212> TYPE: PRT
<213> ORGANISM: Artificial Sequence
<220> FEATURE:
<223> OTHER INFORMATION: Con WT1-L with modified Zinc Fingers protein sequence

<400> SEQUENCE: 20

```
Met Asp Trp Thr Trp Ile Leu Phe Leu Val Ala Ala Ala Thr Arg Val
1               5                   10                  15

His Ser Gly Ser Asp Val Arg Asp Leu Asn Ala Leu Leu Pro Ala Val
            20                  25                  30

Pro Ser Leu Pro Gly Gly Gly Cys Ala Leu Pro Val Ser Gly Ala
        35                  40                  45

Ala Gln Trp Ala Pro Val Leu Asp Phe Ala Pro Pro Ala Ala Pro Tyr
    50                  55                  60

Gly Ser Leu Gly Gly Pro His Ser Phe Ile Lys Gln Glu Pro Ser Trp
65                  70                  75                  80

Gly Gly Ala Asp Pro His Glu Glu Gln Cys Leu Ser Ala Phe Thr Val
```

```
                85                  90                  95
His Phe Ser Gly Gln Phe Thr Gly Thr Ala Gly Ala Cys Arg Tyr Gly
            100                 105                 110

Pro Phe Gly Ala Pro Pro Ser Gln Ala Pro Ser Gly Gln Ala Arg
            115                 120                 125

Met Phe Pro Asn Ala Pro Tyr Leu Pro Asn Cys Leu Glu Ser Gln Pro
130                 135                 140

Ala Ile Arg Asn Gln Gly Tyr Ser Thr Val Ala Phe Asp Gly Thr Pro
145                 150                 155                 160

Ser Tyr Gly His Thr Pro Ser His His Ala Ala Gln Phe Pro Asn His
                165                 170                 175

Ser Phe Lys His Glu Asp Pro Met Gly Gln Gln Gly Ser Leu Gly Glu
                180                 185                 190

Gln Gln Tyr Ser Val Pro Pro Val Tyr Gly Cys His Thr Pro Thr
            195                 200                 205

Asp Ser Cys Thr Gly Ser Gln Ala Leu Leu Leu Arg Thr Pro Tyr Asn
        210                 215                 220

Ser Asp Asn Leu Tyr Gln Met Thr Ser Gln Leu Glu Cys Met Thr Trp
225                 230                 235                 240

Asn Gln Met Asn Leu Gly Ser Thr Leu Lys Gly His Ala Thr Gly Tyr
                    245                 250                 255

Glu Ser Asp Asn His Thr Thr Pro Met Leu Tyr Ser Cys Gly Ala Gln
                260                 265                 270

Tyr Arg Ile His Thr His Gly Val Phe Arg Gly Ile Gln Asp Val Arg
            275                 280                 285

Arg Val Pro Gly Val Ala Pro Thr Ile Val Arg Ser Ala Ser Glu Thr
        290                 295                 300

Asn Glu Lys Arg Pro Phe Met Gly Ala Tyr Pro Gly Asn Lys Arg
305                 310                 315                 320

Tyr Phe Lys Leu Ser His Leu Gln Met Gly Ser Arg Lys Gly Thr Gly
                325                 330                 335

Glu Lys Pro Tyr Gln Gly Asp Phe Lys Asp Gly Glu Arg Arg Phe Ser
            340                 345                 350

Arg Ser Asp Gln Leu Lys Arg Gly Gln Arg Gly Thr Gly Val Lys
        355                 360                 365

Pro Phe Gln Cys Lys Thr Cys Gln Arg Lys Phe Ser Arg Ser Asp His
        370                 375                 380

Leu Lys Thr His Thr Arg Thr His Thr Gly Lys Thr Ser Glu Lys Pro
385                 390                 395                 400

Phe Ser Cys Arg Trp Pro Ser Cys Gln Lys Lys Phe Ala Arg Ser Asp
                405                 410                 415

Glu Leu Val Arg His His Asn Met His Gln Arg Asn Met Thr Lys Leu
            420                 425                 430

Gln Leu Ala Leu
        435

<210> SEQ ID NO 21
<211> LENGTH: 954
<212> TYPE: DNA
<213> ORGANISM: Artificial Sequence
<220> FEATURE:
<223> OTHER INFORMATION: Con WT1-S without Zinc fingers nucleic acid
      sequence

<400> SEQUENCE: 21
```

```
ggatccgcca ccatggactg gacctggatt ctgtttctgg tggctgctgc tacacgggtg    60
cattctggga gcgatgtgag agacctgaac gccctgctgc cagctgtgcc aagtctgcct   120
ggcgggggag gctgcgcact gccagtgagc ggagcagctc agtgggctcc cgtcctggac   180
tttgcacccc ctgcagcacc ttacggctca ctgggcggcc acacagctt catcaagcag    240
gagccatctt ggggcggggc cgatcctcac gaggaacagt gcctgagtgc tttcacagtg   300
catttttcag gccagttcac tggaaccgca ggagcttgtc gatacggacc ctttggagcc   360
ccaccccta gccaggcacc ttccggacag gccagaatgt tcccaaacgc tccctatctg    420
cctaattgtc tggaatcaca gcctgcaatt cggaaccagg gctacagcac cgtcgccttt   480
gacgggacac atcctatgg acacactccc tctcaccatg ctgcacagtt tcctaatcac    540
agcttcaagc atgaggaccc catgggacag caggggagcc tgggagaaca gcagtactcc   600
gtgccaccc ctgtctatgg ctgccataca ccaactgact cttgtacagg gagtcaggcc    660
ctgctgctgc gaactccata caactctgat aatctgtatc agatgactag tcagctggag   720
tgcatgacct ggaaccagat gaatctgggg tccacccctga aaggccacgc cacagggtat  780
gaatccgaca accataccac acccatgctg tactcttgtg gcgcccagta tagaatccac   840
acccatggag tgttccgcgg cattcaggat gtgcggagag tcccaggagt cgctcccacc   900
atcgtgagat ccgccagtga gaccaatgaa aagagaccct tctgataact cgag         954
```

```
<210> SEQ ID NO 22
<211> LENGTH: 310
<212> TYPE: PRT
<213> ORGANISM: Artificial Sequence
<220> FEATURE:
<223> OTHER INFORMATION: Con WT1-S without Zinc fingers protein sequence

<400> SEQUENCE: 22

Met Asp Trp Thr Trp Ile Leu Phe Leu Val Ala Ala Thr Arg Val
1               5                   10                  15

His Ser Gly Ser Asp Val Arg Asp Leu Asn Ala Leu Leu Pro Ala Val
            20                  25                  30

Pro Ser Leu Pro Gly Gly Gly Gly Cys Ala Leu Pro Val Ser Gly Ala
        35                  40                  45

Ala Gln Trp Ala Pro Val Leu Asp Phe Ala Pro Pro Ala Ala Pro Tyr
    50                  55                  60

Gly Ser Leu Gly Gly Pro His Ser Phe Ile Lys Gln Glu Pro Ser Trp
65                  70                  75                  80

Gly Gly Ala Asp Pro His Glu Glu Gln Cys Leu Ser Ala Phe Thr Val
                85                  90                  95

His Phe Ser Gly Gln Phe Thr Gly Thr Ala Gly Ala Cys Arg Tyr Gly
            100                 105                 110

Pro Phe Gly Ala Pro Pro Ser Gln Ala Pro Ser Gly Gln Ala Arg
        115                 120                 125

Met Phe Pro Asn Ala Pro Tyr Leu Pro Asn Cys Leu Glu Ser Gln Pro
    130                 135                 140

Ala Ile Arg Asn Gln Gly Tyr Ser Thr Val Ala Phe Asp Gly Thr Pro
145                 150                 155                 160

Ser Tyr Gly His Thr Pro Ser His His Ala Ala Gln Phe Pro Asn His
                165                 170                 175

Ser Phe Lys His Glu Asp Pro Met Gly Gln Gln Gly Ser Leu Gly Glu
            180                 185                 190

Gln Gln Tyr Ser Val Pro Pro Pro Val Tyr Gly Cys His Thr Pro Thr
```

```
            195                 200                 205
Asp Ser Cys Thr Gly Ser Gln Ala Leu Leu Arg Thr Pro Tyr Asn
    210                 215                 220

Ser Asp Asn Leu Tyr Gln Met Thr Ser Gln Leu Glu Cys Met Thr Trp
225                 230                 235                 240

Asn Gln Met Asn Leu Gly Ser Thr Leu Lys Gly His Ala Thr Gly Tyr
                245                 250                 255

Glu Ser Asp Asn His Thr Thr Pro Met Leu Tyr Ser Cys Gly Ala Gln
            260                 265                 270

Tyr Arg Ile His Thr His Gly Val Phe Arg Gly Ile Gln Asp Val Arg
            275                 280                 285

Arg Val Pro Gly Val Ala Pro Thr Ile Val Arg Ser Ala Ser Glu Thr
    290                 295                 300

Asn Glu Lys Arg Pro Phe
305                 310

<210> SEQ ID NO 23
<211> LENGTH: 3447
<212> TYPE: DNA
<213> ORGANISM: Artificial Sequence
<220> FEATURE:
<223> OTHER INFORMATION: hTERT

<400> SEQUENCE: 23
atggactgga cctggatcct gttcctggtg ccgctgcca caagagtgca cagccccagg      60 gccccaggt gcagagccgt gcggagcctg ctgcggagcc actaccggga ggtgctgccc     120
ctggccacct tcgtgcggag ctgggccct caggggtggc ggctggtgca gagaggcgac     180
cctgccgcct tcagagccct ggtggcccag tgcctggtgt gcgtgccctg ggacgccaga     240
cctccccctg ccgcccctag cttccggcag gtgtcctgcc tgaaagaact ggtggcccgg     300
gtgctgcagc ggctgtgcga gaggggcgcc aagaacgtgc tggccttcgg cttcgccctg     360
ctggacggcg ccagaggcgg ccctcccgag gccttcacca cctccgtgag aagctacctg     420
cccaacaccg tgaccgacgc cctgagaggc agcggcgctt ggggcctgct gctgcgcaga     480
gtgggcgacg acgtgctggt gcacctgctg gccagatgcg ccctgttcgt gctggtcgcc     540
cccagctgcg cctaccaggt gtgcggccca ccctgtacc agctgggagc cgccacccag     600
gccagacccc tcctcacgc ctccggcccc aggcggagac tgggctgcga gcgggcctgg     660
aaccacagcg tgcggaggc cggcgtgccc ctgggcctgc agccctggg cgccagaaga     720 aggggcggca cgccagcag aagcctgccc ctgcccaagc ggcccagacg cggagccgcc     780
cctgagcccg agagaacccc cgtgggccag ggctcttggg cccaccctgg ccggaccaga     840
ggccccagca ccggggcttc tgcgtggtg tccccgcca gaccgccga ggaagccacc     900 tccctggaag gcgccctgag cggcaccagg cacagccacc ccagcgtggg ccgccagcac     960
cacgccggac cccccagcac ctccaggccc ccaggccct gggacaccc ttgcccccct    1020 gtgtacgccg agaccaagca cttcctgtac agcagcggcg acaaagagca gctgcggccc    1080
agcttcctgc tgtccagcct gaggccctcc ctgaccggcg ctaggcgcct ggtggagacc    1140
atctttctgg gcagccggcc ctggatgccc ggcaccccca gcggctgcc caggctgccc    1200 cagcggtact ggcagatgag gcctctgttc ctggaactgc tgggcaacca cgcccagtgc    1260
ccctacggcg tgctgctgaa aacccactgc ccctgagag ccgccgtgac ccagccgcc    1320 ggagtgtgcg ccagagagaa gcctcagggc agcgtggccg ctcccgagga agaggacacc    1380
```

-continued

| | | |
|---|---|---|
| gaccccagac gcctggtgca gctgctgcgg cagcacagca gcccttggca ggtgtacggc | 1440 | |
| ttcgtgcggg cctgcctgag aaggctggtg cccctggcc tgtggggcag caggcacaac | 1500 | |
| gagcggcggt ttctgcggaa caccaagaag ttcatcagcc tggggaagca cgccaagctg | 1560 | |
| tccctgcagg aactgacctg gaagatgagc gtgcggggct cgcctggct gagaagatcc | 1620 | |
| cctggcgtgg gctgcgtgcc tgccgccgag caccggctgc gggaggaaat cctggccaag | 1680 | |
| ttcctgcact ggctgatgag cgtgtacgtg gtggagctgc tgagatcctt cttctacgtg | 1740 | |
| accgagacca ccttccagaa gaactacctg ttcttctacc ggaagagcgt gtggagcaag | 1800 | |
| ctgcagagca tcggcatccg gcagcacctg aagcgggtgc agctgagaga gctgtccgag | 1860 | |
| gccgaagtga ggcagcaccg ggaggccaga cctgccctgc tgaccagccg gctgcggttc | 1920 | |
| atccccaagc ccgacggcct gcggcccatc gtgaacatgg actacgtggt gggcgccagg | 1980 | |
| accttccggc gggagaagcg ggccgagcgg ctgacctcga gggtgaaggc cctgttcagc | 2040 | |
| gtgctgaact acgagcgggc caggcggcca ggcctgctgg gcgccagcgt gctgggcctg | 2100 | |
| gacgacatcc accgggcctg gcggaccttc gtgctgagag tgcgggccca ggaccccct | 2160 | |
| cccgagctgt acttcgtgaa ggtggacgtg acaggcgcct acgacaccat cccccaggac | 2220 | |
| cggctgaccg aggtgatcgc cagcatcatc aagcccaga acacctactg cgtgcggaga | 2280 | |
| tacgccgtgg tgcagaaggc cgcccacggc cacgtgcgga aggccttcaa gagccacgtg | 2340 | |
| agcacctga ccgacctgca gccctacatg cggcagttcg tggcccacct gcaggaaacc | 2400 | |
| agcccctgc gggatgccgt ggtgatcgag cagagcagca gcctgaacga ggccagcagc | 2460 | |
| ggcctgttcg acgtgttcct gagattcatg tgccaccacg ccgtgcggat ccggggcaag | 2520 | |
| agctacgtgc agtgccaggg catcccacag ggcagcatcc tgtccaccct gctgtgctcc | 2580 | |
| ctgtgctacg gcgacatgga aaacaagctg ttcgccggca tcaggcggga cggactgctg | 2640 | |
| ctgagactgg tggacgactt cctgctggtg acccccacc tgacccacgc caagaccttt | 2700 | |
| ctgcggaccc tggtgcgcgg cgtgcccgag tacggctgcg tggtgaacct gagaaagacc | 2760 | |
| gtggtgaact ccccgtgga ggacgaggcc ctgggcggca cagccttcgt gcagatgcct | 2820 | |
| gcccatggac tgttcccttg gtgcgggctg ctgctggaca ccggaccct ggaagtgcag | 2880 | |
| agcgactaca gcagctacgc ccggaccagc atccgggcct ccctgacctt caacaggggc | 2940 | |
| ttcaaggccg caggaacat gcggcggaag ctgtttggcg tgctgcggct gaagtgccac | 3000 | |
| agcctgtttc tgtacctgca ggtgaacagc ctgcagaccg tgtgcaccaa catctacaag | 3060 | |
| atcctgctgc tgcaggccta ccggttccac gcctgcgtgc tgcagctgcc ctttcaccag | 3120 | |
| caggtgtgga agaaccctac cttcttcctg cgggtgatca gcgacaccgc cagcctgtgc | 3180 | |
| tacagcatcc tgaaggccaa gaacgccggc atgagcctgg cgccaaggg agccgccgga | 3240 | |
| cctctgccca gcgaggccgt gcagtggctg tgccaccagg cctttctgct gaagctgacc | 3300 | |
| cggcaccggg tgacctacgt gcccctgctg ggcagcctgc ggaccgccca gacccagctg | 3360 | |
| tcccggaagc tgcctggcac cacctgaca gccctggaag ccgccgccaa ccccgccctg | 3420 | |
| ccctccgact tcaagaccat cctggac | 3447 | |

<210> SEQ ID NO 24
<211> LENGTH: 1149
<212> TYPE: PRT
<213> ORGANISM: Artificial Sequence
<220> FEATURE:
<223> OTHER INFORMATION: hTERT

<400> SEQUENCE: 24

-continued

```
Met Asp Trp Thr Trp Ile Leu Phe Leu Val Ala Ala Thr Arg Val
1               5                   10                  15

His Ser Pro Arg Ala Pro Arg Cys Arg Ala Val Arg Ser Leu Leu Arg
            20                  25                  30

Ser His Tyr Arg Glu Val Leu Pro Leu Ala Thr Phe Val Arg Arg Leu
            35                  40                  45

Gly Pro Gln Gly Trp Arg Leu Val Gln Arg Gly Asp Pro Ala Ala Phe
50                  55                  60

Arg Ala Leu Val Ala Gln Cys Leu Val Cys Val Pro Trp Asp Ala Arg
65                  70                  75                  80

Pro Pro Pro Ala Ala Pro Ser Phe Arg Gln Val Ser Cys Leu Lys Glu
                85                  90                  95

Leu Val Ala Arg Val Leu Gln Arg Leu Cys Glu Arg Gly Ala Lys Asn
                100                 105                 110

Val Leu Ala Phe Gly Phe Ala Leu Leu Asp Gly Ala Arg Gly Gly Pro
            115                 120                 125

Pro Glu Ala Phe Thr Thr Ser Val Arg Ser Tyr Leu Pro Asn Thr Val
    130                 135                 140

Thr Asp Ala Leu Arg Gly Ser Gly Ala Trp Gly Leu Leu Leu Arg Arg
145                 150                 155                 160

Val Gly Asp Asp Val Leu Val His Leu Ala Arg Cys Ala Leu Phe
                165                 170                 175

Val Leu Val Ala Pro Ser Cys Ala Tyr Gln Val Cys Gly Pro Pro Leu
            180                 185                 190

Tyr Gln Leu Gly Ala Ala Thr Gln Ala Arg Pro Pro His Ala Ser
            195                 200                 205

Gly Pro Arg Arg Leu Gly Cys Glu Arg Ala Trp Asn His Ser Val
    210                 215                 220

Arg Glu Ala Gly Val Pro Leu Gly Leu Pro Ala Pro Gly Ala Arg Arg
225                 230                 235                 240

Arg Gly Gly Ser Ala Ser Arg Ser Leu Pro Leu Pro Lys Arg Pro Arg
            245                 250                 255

Arg Gly Ala Ala Pro Glu Pro Glu Arg Thr Pro Val Gly Gln Gly Ser
            260                 265                 270

Trp Ala His Pro Gly Arg Thr Arg Gly Pro Ser Asp Arg Gly Phe Cys
            275                 280                 285

Val Val Ser Pro Ala Arg Pro Ala Glu Glu Ala Thr Ser Leu Glu Gly
    290                 295                 300

Ala Leu Ser Gly Thr Arg His Ser His Pro Ser Val Gly Arg Gln His
305                 310                 315                 320

His Ala Gly Pro Pro Ser Thr Ser Arg Pro Pro Arg Pro Trp Asp Thr
                325                 330                 335

Pro Cys Pro Pro Val Tyr Ala Glu Thr Lys His Phe Leu Tyr Ser Ser
                340                 345                 350

Gly Asp Lys Glu Gln Leu Arg Pro Ser Phe Leu Leu Ser Ser Leu Arg
            355                 360                 365

Pro Ser Leu Thr Gly Ala Arg Arg Leu Val Glu Thr Ile Phe Leu Gly
    370                 375                 380

Ser Arg Pro Trp Met Pro Gly Thr Pro Arg Arg Leu Pro Arg Leu Pro
385                 390                 395                 400

Gln Arg Tyr Trp Gln Met Arg Pro Leu Phe Leu Glu Leu Leu Gly Asn
                405                 410                 415
```

```
His Ala Gln Cys Pro Tyr Gly Val Leu Leu Lys Thr His Cys Pro Leu
                420                 425                 430

Arg Ala Ala Val Thr Pro Ala Ala Gly Val Cys Ala Arg Glu Lys Pro
            435                 440                 445

Gln Gly Ser Val Ala Ala Pro Glu Glu Glu Asp Thr Asp Pro Arg Arg
        450                 455                 460

Leu Val Gln Leu Leu Arg Gln His Ser Ser Pro Trp Gln Val Tyr Gly
465                 470                 475                 480

Phe Val Arg Ala Cys Leu Arg Arg Leu Val Pro Pro Gly Leu Trp Gly
                485                 490                 495

Ser Arg His Asn Glu Arg Arg Phe Leu Arg Asn Thr Lys Lys Phe Ile
            500                 505                 510

Ser Leu Gly Lys His Ala Lys Leu Ser Leu Gln Glu Leu Thr Trp Lys
        515                 520                 525

Met Ser Val Arg Gly Cys Ala Trp Leu Arg Arg Ser Pro Gly Val Gly
        530                 535                 540

Cys Val Pro Ala Ala Glu His Arg Leu Arg Glu Glu Ile Leu Ala Lys
545                 550                 555                 560

Phe Leu His Trp Leu Met Ser Val Tyr Val Val Glu Leu Leu Arg Ser
                565                 570                 575

Phe Phe Tyr Val Thr Glu Thr Thr Phe Gln Lys Asn Tyr Leu Phe Phe
            580                 585                 590

Tyr Arg Lys Ser Val Trp Ser Lys Leu Gln Ser Ile Gly Ile Arg Gln
        595                 600                 605

His Leu Lys Arg Val Gln Leu Arg Glu Leu Ser Glu Ala Glu Val Arg
        610                 615                 620

Gln His Arg Glu Ala Arg Pro Ala Leu Leu Thr Ser Arg Leu Arg Phe
625                 630                 635                 640

Ile Pro Lys Pro Asp Gly Leu Arg Pro Ile Val Asn Met Asp Tyr Val
                645                 650                 655

Val Gly Ala Arg Thr Phe Arg Arg Glu Lys Arg Ala Glu Arg Leu Thr
            660                 665                 670

Ser Arg Val Lys Ala Leu Phe Ser Val Leu Asn Tyr Glu Arg Ala Arg
        675                 680                 685

Arg Pro Gly Leu Leu Gly Ala Ser Val Leu Gly Leu Asp Asp Ile His
        690                 695                 700

Arg Ala Trp Arg Thr Phe Val Leu Arg Val Arg Ala Gln Asp Pro Pro
705                 710                 715                 720

Pro Glu Leu Tyr Phe Val Lys Val Asp Val Thr Gly Ala Tyr Asp Thr
                725                 730                 735

Ile Pro Gln Asp Arg Leu Thr Glu Val Ile Ala Ser Ile Ile Lys Pro
            740                 745                 750

Gln Asn Thr Tyr Cys Val Arg Arg Tyr Ala Val Val Gln Lys Ala Ala
        755                 760                 765

His Gly His Val Arg Lys Ala Phe Lys Ser His Val Ser Thr Leu Thr
        770                 775                 780

Asp Leu Gln Pro Tyr Met Arg Gln Phe Val Ala His Leu Gln Glu Thr
785                 790                 795                 800

Ser Pro Leu Arg Asp Ala Val Val Ile Glu Gln Ser Ser Ser Leu Asn
                805                 810                 815

Glu Ala Ser Ser Gly Leu Phe Asp Val Phe Leu Arg Phe Met Cys His
            820                 825                 830

His Ala Val Arg Ile Arg Gly Lys Ser Tyr Val Gln Cys Gln Gly Ile
```

```
                  835                 840                 845
Pro Gln Gly Ser Ile Leu Ser Thr Leu Leu Cys Ser Leu Cys Tyr Gly
        850                 855                 860

Asp Met Glu Asn Lys Leu Phe Ala Gly Ile Arg Arg Asp Gly Leu Leu
865                 870                 875                 880

Leu Arg Leu Val Asp Asp Phe Leu Leu Val Thr Pro His Leu Thr His
                885                 890                 895

Ala Lys Thr Phe Leu Arg Thr Leu Val Arg Gly Val Pro Glu Tyr Gly
            900                 905                 910

Cys Val Val Asn Leu Arg Lys Thr Val Asn Phe Pro Val Glu Asp
            915                 920                 925

Glu Ala Leu Gly Gly Thr Ala Phe Val Gln Met Pro Ala His Gly Leu
        930                 935                 940

Phe Pro Trp Cys Gly Leu Leu Asp Thr Arg Thr Leu Glu Val Gln
945                 950                 955                 960

Ser Asp Tyr Ser Ser Tyr Ala Arg Thr Ser Ile Arg Ala Ser Leu Thr
                965                 970                 975

Phe Asn Arg Gly Phe Lys Ala Gly Arg Asn Met Arg Arg Lys Leu Phe
                980                 985                 990

Gly Val Leu Arg Leu Lys Cys His  Ser Leu Phe Leu Tyr  Leu Gln Val
            995                 1000                1005

Asn Ser Leu Gln Thr Val Cys  Thr Asn Ile Tyr Lys  Ile Leu Leu
    1010                1015                1020

Leu Gln Ala Tyr Arg Phe His  Ala Cys Val Leu Gln  Leu Pro Phe
    1025                1030                1035

His Gln Gln Val Trp Lys Asn  Pro Thr Phe Phe Leu  Arg Val Ile
    1040                1045                1050

Ser Asp Thr Ala Ser Leu Cys  Tyr Ser Ile Leu Lys  Ala Lys Asn
    1055                1060                1065

Ala Gly Met Ser Leu Gly Ala  Lys Gly Ala Ala Gly  Pro Leu Pro
    1070                1075                1080

Ser Glu Ala Val Gln Trp Leu  Cys His Gln Ala Phe  Leu Leu Lys
    1085                1090                1095

Leu Thr Arg His Arg Val Thr  Tyr Val Pro Leu Leu  Gly Ser Leu
    1100                1105                1110

Arg Thr Ala Gln Thr Gln Leu  Ser Arg Lys Leu Pro  Gly Thr Thr
    1115                1120                1125

Leu Thr Ala Leu Glu Ala Ala  Asn Pro Ala Leu Pro  Ser Asp
    1130                1135                1140

Phe Lys  Thr Ile Leu Asp
    1145

<210> SEQ ID NO 25
<211> LENGTH: 2724
<212> TYPE: DNA
<213> ORGANISM: Artificial Sequence
<220> FEATURE:
<223> OTHER INFORMATION: gB consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 25
nnngagagca gaatctggtg cctggtcgtg tgcgtgaacc tgtgcatcgt gtgcctggga       60
gccgccgtgt ccagcagcag cacccggggc acaagcgcca cacacagcca ccacagcagc      120
```

```
cacaccacca gcgccgccca cagccggagc ggaagcgtga gcagccagcg ggtgaccagc      180
agcgaggccg tgtcccaccg ggccaacgag acaatctaca acaccaccct gaagtacggc      240
gacgtcgtgg gagtgaacac caccaagtac ccctacagag tgtgcagcat ggcccagggc      300
accgacctga tcagattcga gcggaacatc gtgtgtacca gcatgaagcc catcaacgag      360
gacctggacg agggcatcat ggtggtgtac aagagaaaca tcgtggccca caccttcaaa      420
gtgcgggtgt accagaaggt gctgaccttc cggcggagct acgcctacat ccacaccacc      480
tacctgctgg gcagcaacac cgagtacgtg gcccctccca tgtgggagat ccaccacatc      540
aacagccaca gccagtgcta cagcagctac agccgcgtga tcgccggcac cgtgttcgtg      600
gcctaccacc gggacagcta cgagaacaag accatgcagc tgatgcccga cgactacagc      660
aacacccaca gcaccagata cgtgaccgtg aaggaccagt ggcacagccg ggaagcacc       720
tggctgtaca gagagacatg caacctgaac tgcatggtca ccatcaccac cgccagaagc      780
aagtaccctt accacttctt cgccaccagc accggcgacg tggtggacat cagcccttc       840
tacaacggca ccaaccggaa cgccagctac ttcggcgaga cgccgacaa gttcttcatc       900
ttccccaact acaccatcgt gtccgacttc ggcagcccca cagcgcccc tgagacacac       960
cggctggtgg cctttctgga acgggccgac agcgtgatca gctgggacat ccaggacgag     1020
aagaacgtga cctgccagct gaccttctgg gaggctagcg agcggaccat cagaagcgag     1080
gccgaggaca gctaccactt cagcagcgcc aagatgaccg ccaccttcct gagcaagaaa     1140
caggaagtga acatgagcga cagcgccctg gactgcgtgc gggatgaggc catcaacaag     1200
ctgcagcaga tcttcaacac cagctacaac cagacctacg agaagtatgg caacgtgtcc     1260
gtgttcgaga caacaggcgg cctggtggtg ttctggcagg gcatcaagca gaagtccctg     1320
gtcgagctgg aacggctggc caacagaagc agcctgaacc tgacccaccg gaccaagcgg     1380
agcaccgacg gcaacaatac cacccacctg agcaacatgg aaagcgtcca caacctggtg     1440
tacgcccagc tgcagttcac ctacgacacc ctgcggggct acatcaaccg ggccctggcc     1500
cagatcgccg aggcttggtg tgtggaccag cggcggaccc tggaagtgtt caaagagctg     1560
agcaagatca cccccagcgc catcctgagc gccatctaca caagcctat cgccgccaga      1620
ttcatgggcg acgtgctggg cctggccagc tgcgtgacca tcaaccagac cagcgtgaag     1680
gtgctgcggg acatgaacgt gaaagaaagc cccggcagat gctactccag acccgtggtc     1740
atcttcaact cgccaacag ctcctacgtg cagtacggcc agctgggcga ggacaacgag      1800
atcctgctgg aaaccaccg gaccgaggaa tgccagctgc ccagcctgaa gatctttatc      1860
gccggcaaca cgcctacga gtatgtggac tacctgttca gcggatgat cgacctgagc       1920
agcatcagca ccgtggacag catgatcgcc ctggacatcg accccctgga aaacaccgac     1980
ttccggtgc tggaactgta cagccagaaa gagctgcgga gcagcaacgt gttcgacctg      2040
gaagagatca tgcgcgagtt caacagctac aagcagcgct gaaatacgt cgaggacaag      2100
gtggtggacc ccctgccccc ctacctgaag ggcctggacg acctgatgag cggcctggga     2160
gctgctggca aggccgtggg agtggccatt ggagctgtgg gcggagccgt ggccagcgtg     2220
gtggaaggcg tggccacctt tctgaagaac cccttcggcg ccttcaccat catcctggtg     2280
gctatcgccg tcgtgatcat cacctacctg atctacaccc ggcagcggcg gctgtgtacc     2340
cagcctctgc agaacctgtt cccctacctg gtgtccgccg acggcaccac cgtgacaagc     2400
ggctccacca aggacaccag cctgcaggcc ccacccagct acgaggaatc cgtgtacaac     2460
```

-continued

```
agcggccgga agggcccagg ccctcctagc tctgacgcct ctacagccgc cccaccctac    2520
accaacgagc aggcctacca gatgctgctg ccctggcta gactggacgc cgagcagaga    2580
gcccagcaga acggaaccga cagcctggat ggccagaccg caccagga caagggccag     2640 aagcccaacc tgctggaccg gctgcggcac agaaagaacg gctaccggca cctgaaggac   2700
agcgacgaag aggaaaacgt gtga                                          2724
```

<210> SEQ ID NO 26
<211> LENGTH: 907
<212> TYPE: PRT
<213> ORGANISM: Artificial Sequence
<220> FEATURE:
<223> OTHER INFORMATION: gB consensus amino acid sequenc
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 26

```
Xaa Glu Ser Arg Ile Trp Cys Leu Val Val Cys Val Asn Leu Cys Ile
  1               5                  10                  15

Val Cys Leu Gly Ala Ala Val Ser Ser Ser Thr Arg Gly Thr Ser
             20                  25                  30

Ala Thr His Ser His His Ser Ser His Thr Thr Ser Ala Ala His Ser
         35                  40                  45

Arg Ser Gly Ser Val Ser Ser Gln Arg Val Thr Ser Ser Glu Ala Val
     50                  55                  60

Ser His Arg Ala Asn Glu Thr Ile Tyr Asn Thr Thr Leu Lys Tyr Gly
 65                  70                  75                  80

Asp Val Val Gly Val Asn Thr Thr Lys Tyr Pro Tyr Arg Val Cys Ser
                 85                  90                  95

Met Ala Gln Gly Thr Asp Leu Ile Arg Phe Glu Arg Asn Ile Val Cys
            100                 105                 110

Thr Ser Met Lys Pro Ile Asn Glu Asp Leu Asp Glu Gly Ile Met Val
        115                 120                 125

Val Tyr Lys Arg Asn Ile Val Ala His Thr Phe Lys Val Arg Val Tyr
    130                 135                 140

Gln Lys Val Leu Thr Phe Arg Arg Ser Tyr Ala Tyr Ile His Thr Thr
145                 150                 155                 160

Tyr Leu Leu Gly Ser Asn Thr Glu Tyr Val Ala Pro Pro Met Trp Glu
                165                 170                 175

Ile His His Ile Asn Ser His Ser Gln Cys Tyr Ser Ser Tyr Ser Arg
            180                 185                 190

Val Ile Ala Gly Thr Val Phe Val Ala Tyr His Arg Asp Ser Tyr Glu
        195                 200                 205

Asn Lys Thr Met Gln Leu Met Pro Asp Asp Tyr Ser Asn Thr His Ser
    210                 215                 220

Thr Arg Tyr Val Thr Val Lys Asp Gln Trp His Ser Arg Gly Ser Thr
225                 230                 235                 240

Trp Leu Tyr Arg Glu Thr Cys Asn Leu Asn Cys Met Val Thr Ile Thr
                245                 250                 255

Thr Ala Arg Ser Lys Tyr Pro Tyr His Phe Phe Ala Thr Ser Thr Gly
            260                 265                 270

Asp Val Val Asp Ile Ser Pro Phe Tyr Asn Gly Thr Asn Arg Asn Ala
        275                 280                 285

Ser Tyr Phe Gly Glu Asn Ala Asp Lys Phe Phe Ile Phe Pro Asn Tyr
```

```
            290                 295                 300
Thr Ile Val Ser Asp Phe Gly Arg Pro Asn Ser Ala Leu Glu Thr His
305                 310                 315                 320

Arg Leu Val Ala Phe Leu Glu Arg Ala Asp Ser Val Ile Ser Trp Asp
                325                 330                 335

Ile Gln Asp Glu Lys Asn Val Thr Cys Gln Leu Thr Phe Trp Glu Ala
                340                 345                 350

Ser Glu Arg Thr Ile Arg Ser Glu Ala Glu Asp Ser Tyr His Phe Ser
                355                 360                 365

Ser Ala Lys Met Thr Ala Thr Phe Leu Ser Lys Lys Gln Glu Val Asn
370                 375                 380

Met Ser Asp Ser Ala Leu Asp Cys Val Arg Asp Glu Ala Ile Asn Lys
385                 390                 395                 400

Leu Gln Gln Ile Phe Asn Thr Ser Tyr Asn Gln Thr Tyr Glu Lys Tyr
                405                 410                 415

Gly Asn Val Ser Val Phe Glu Thr Thr Gly Gly Leu Val Val Phe Trp
                420                 425                 430

Gln Gly Ile Lys Gln Lys Ser Leu Val Glu Leu Glu Arg Leu Ala Asn
                435                 440                 445

Arg Ser Ser Leu Asn Leu Thr His Arg Thr Lys Arg Ser Thr Asp Gly
450                 455                 460

Asn Asn Thr Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
                515                 520                 525

Leu Ser Ala Ile Tyr Asn Lys Pro Ile Ala Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
                595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
                675                 680                 685

Ser Tyr Lys Gln Arg Val Lys Tyr Val Glu Asp Lys Val Val Asp Pro
690                 695                 700

Leu Pro Pro Tyr Leu Lys Gly Leu Asp Asp Leu Met Ser Gly Leu Gly
705                 710                 715                 720
```

```
Ala Ala Gly Lys Ala Val Gly Val Ala Ile Gly Ala Val Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Asn Val
                900                 905

<210> SEQ ID NO 27
<211> LENGTH: 1119
<212> TYPE: DNA
<213> ORGANISM: Artificial Sequence
<220> FEATURE:
<223> OTHER INFORMATION: gM consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 27
nnngcaccca gccacgtgga caaagtgaac acccggactt ggagcgccag catcgtgttc      60
atggtgctga ccttcgtgaa tgtgtccgtc cacctggtgc tgagcaactt cccccacctg     120
ggctacccct gcgtgtacta ccacgtggtg gacttcgagc ggctgaacat gagcgcctac     180
aacgtgatgc atctgcacac ccccatgctg tttctggaca gcgtgcagct cgtgtgctac     240
gccgtgttta tgcagctggt gttcctggcc gtgaccatct actacctcgt gtgctggatc     300
aagatttcta tgcggaagga caagggcatg agcctgaacc agagcacccg ggacatcagc     360
tacatgggcg acagcctgac cgccttcctg ttcatcctga gcatggacac cttccagctg     420
ttcaccctga ccatgagctt ccggctgccc agcatgatcg cctttatggc cgccgtccac     480
ttcttctgtc tgaccatctt caacgtgtcc atggtcaccc agtacagaag ctacaagcgg     540
agcctgttct tcttcagtcg gctgcacccc aagctgaagg gcaccgtcca gttccggacc     600
ctgatcgtga acctggtgga agtggccctg gccttcaaca ccaccgtggt ggctatggct     660
ctgtgctacg gcttcggcaa caacttcttc gtgcggacag gccacatggt gctggccgtg     720
ttcgtggtgt acgccattat cagcatcatc tactttctgc tgatcgaggc cgtgttcttc     780
cagtacgtga aggtgcagtt cggctaccac ctgggcgcct ttttcggcct gtgcggcctg     840
```

```
atctacccca tcgtgcagta cgacaccttc ctgagcaacg agtaccggac cggcatcagc    900
tggtccttcg gcatgctgtt cttcatctgg gccatgttca ccacctgtcg ggccgtgcgg    960
tacttcagag gcagaggcag cggctccgtg aagtaccagg ccctggccac agccagcggc   1020
gaagaagtgg ccgccctgag ccaccacgac agcctggaaa gcagacggct gagagaggaa   1080
gaggacgacg acgacgatga ggacttcgag gacgcctga                          1119
```

```
<210> SEQ ID NO 28
<211> LENGTH: 372
<212> TYPE: PRT
<213> ORGANISM: Artificial Sequence
<220> FEATURE:
<223> OTHER INFORMATION: gM consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 28
```

Xaa Ala Pro Ser His Val Asp Lys Val Asn Thr Arg Thr Trp Ser Ala
 1               5                  10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly

```
            290                 295                 300
Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Ala Leu Ser His His Asp Ser Leu
            340                 345                 350

Glu Ser Arg Arg Leu Arg Glu Glu Asp Asp Asp Asp Asp Glu Asp
                355                 360                 365

Phe Glu Asp Ala
    370

<210> SEQ ID NO 29
<211> LENGTH: 411
<212> TYPE: DNA
<213> ORGANISM: Artificial Sequence
<220> FEATURE:
<223> OTHER INFORMATION: gN consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 29
nnngagtgga acaccctggt gctgggtctg ctggtgctgt ctgtggccgc cagcagcaac      60
aacaccagca ctgccagcac ccccagccct agcagcagca cccacacctc caccaccgtg     120
aaggccacca ccaccgccac cacaagcacc acaacagcca ccagcaccac ctcttccacc     180
accagcacaa agcccggcag caccactcac gaccccaacg tgatgaggcc ccacgcccac     240
aacgacttct acaaggccca ctgcaccagc catatgtacg agctgagcct gagcagcttc     300
gccgccggtg ggaccatgct gaacgccctg atcctgatgg gcgccttctg catcgtgctg     360
cggcactgct gcttccagaa cttcaccgcc acaaccacca agggctactg a              411

<210> SEQ ID NO 30
<211> LENGTH: 136
<212> TYPE: PRT
<213> ORGANISM: Artificial Sequence
<220> FEATURE:
<223> OTHER INFORMATION: N consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 30

Xaa Glu Trp Asn Thr Leu Val Leu Gly Leu Leu Val Leu Ser Val Ala
1               5                   10                  15

Ala Ser Ser Asn Asn Thr Ser Thr Ala Ser Thr Pro Ser Pro Ser Ser
                20                  25                  30

Ser Thr His Thr Ser Thr Thr Val Lys Ala Thr Thr Thr Ala Thr Thr
            35                  40                  45

Ser Thr Thr Thr Ala Thr Ser Thr Thr Ser Thr Thr Ser Thr Thr Lys
        50                  55                  60

Pro Gly Ser Thr Thr His Asp Pro Asn Val Met Arg Pro His Ala His
65                  70                  75                  80

Asn Asp Phe Tyr Lys Ala His Cys Thr Ser His Met Tyr Glu Leu Ser
                85                  90                  95

Leu Ser Ser Phe Ala Ala Trp Trp Thr Met Leu Asn Ala Leu Ile Leu
                100                 105                 110
```

Met Gly Ala Phe Cys Ile Val Leu Arg His Cys Cys Phe Gln Asn Phe
            115                 120                 125

Thr Ala Thr Thr Thr Lys Gly Tyr
        130                 135

<210> SEQ ID NO 31
<211> LENGTH: 2232
<212> TYPE: DNA
<213> ORGANISM: Artificial Sequence
<220> FEATURE:
<223> OTHER INFORMATION: gH consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 31

```
nnncgacccg gcctgcccag ctacctgacc gtgttcgccg tgtacctgct gagccatctg       60
cccagccaga gatacggcgc cgatgccgcc tctgaggccc tggatcctca cgccttccat      120
ctgctgctga acacctacgg cagacctatc cggttcctgc gcgagaacac caccccagtgc     180 acctacaaca gcagcctgcg gaacagcacc gtcgtgcgcg agaatgctat cagcttcaac     240
ttcttccaga gctacaacca gtactacgtg ttccacatgc ccggtgcct gttcgccgga      300 cctctggccg agcagttcct gaaccaggtg gacctgaccg agacactgga agataccag      360 cagcggctga atacctacgc cctggtgtcc aaggacctgg ccagctaccg gtccttcagc    420
cagcagctga aggctcagga cagcctgggc gagcagccta ccaccgtgcc ccctccaatc    480
gacctgagca tcccccacgt gtggatgccc cccagacca cacctcacgg ctggaaagag    540
agccacacca ccagcggcct gcacagaccc cacttcaacc agacctgcat tctgttcgac    600
ggccacgacc tgctgttcag caccgtgacc ccctgcctgc caccagggctt ctacctgatc    660 gacgagctga gatacgtgaa gatcaccctg accgaggatt tcttcgtggt caccgtgtcc    720
atcgacgacg acacccccat gctgctgatc ttcggccatc tgcctcgggt gctgttcaag    780 gcccccctacc agcgggacaa cttcatcctg cggcagaccg agaagcacga gctgctggtg    840
ctggtcaaga aggaccagct gaaccggcac tcctacctga aggaccccga cttcctggac    900
gccgccctgg acttcaacta cctggacctg agcgccctgc tgagaaacag cttccacaga    960
tacgccgtga cgtgctgaa gtccggccgg tgccagatgc tggacagacg accgtggaa     1020 atggccttcg cctatgccct ggccctgttt gccgccgctc ggcaggaaga ggctggcgct    1080
gaagtgtccg tgcccagagc cctggacaga caggccgctc tgctgcagat ccaggaattc    1140
atgatcacct gtctgagcca gacccccccct cggaccaccc tgctgctgta ccctaccgcc    1200
gtggatctgg ccaagcgggc cctgtggacc cccaaccaga tcaccgacat cacaagcctc    1260
gtgcggctgg tgtacatcct gagcaagcag aaccagcagc acctgatccc ccagtgggcc    1320
ctgagacaga tcgccgactt cgccctgaag ctgcacaaga cccacctggc tagctttctg    1380
agcgccttcg ctaggcagga actgtacctg atgggcagcc tggtgcactc catgctggtg    1440
cacaccaccg agaggcggga aatcttcatc gtggaaaccg gcctgtgcag cctggccgag    1500
ctgagccact tcacccagct gctggcccac cccaccacca gtacctgag cgacctgtac     1560 acccccctgca gctctagcgg cagacgggat cacagcctgg aacggctgac ccggctgttc    1620
cccgatgcca cagtgcctgc cactgtgcca gccgccctgt ccatcctgtc caccatgcag    1680
cccagcaccc tggaaaccct ccccgacctg ttctgcctgc cctgggcgcga gagcttcagc    1740
```

-continued

```
gccctgacag tgtccgagca cgtgtcctac gtggtcacca accagtacct gatcaagggc    1800
atcagctacc ccgtgtccac caccgtcgtg ggccagagcc tgatcatcac ccagaccgac    1860
agccagacca agtgcgagct gacccggaac atgcacacca cacacagcat cactgccgcc    1920
ctgaacatca gcctggaaaa ctgcgccttc tgccagtctg ccctgctgga atacgacgat    1980
acccagggcg tgatcaacat catgtacatg cacgacagcg acgacgtgct gttcgccctg    2040 gaccccctaca acgaggtggt ggtgtccagc ccccggaccc actacctgat gctgctgaag    2100
aacggcaccg tgctggaagt gaccgacgtg gtggtggacg ccaccgacag cagactgctg    2160
atgatgagcg tgtacgccct gagcgccatc atcggcatct acctgctgta ccggatgctg    2220
aaaacctgct ga                                                        2232
```

<210> SEQ ID NO 32
<211> LENGTH: 743
<212> TYPE: PRT
<213> ORGANISM: Artificial Sequence
<220> FEATURE:
<223> OTHER INFORMATION: gH consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 32

```
Xaa Arg Pro Gly Leu Pro Ser Tyr Leu Thr Val Phe Ala Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110

Thr Glu Thr Leu Glu Arg Tyr Gln Gln Arg Leu Asn Thr Tyr Ala Leu
        115                 120                 125

Val Ser Lys Asp Leu Ala Ser Tyr Arg Ser Phe Ser Gln Gln Leu Lys
    130                 135                 140

Ala Gln Asp Ser Leu Gly Glu Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Gly Trp Lys Glu Ser His Thr Thr Ser Gly Leu His Arg Pro His Phe
            180                 185                 190

Asn Gln Thr Cys Ile Leu Phe Asp Gly His Asp Leu Leu Phe Ser Thr
        195                 200                 205

Val Thr Pro Cys Leu His Gln Gly Phe Tyr Leu Ile Asp Glu Leu Arg
    210                 215                 220

Tyr Val Lys Ile Thr Leu Thr Glu Asp Phe Phe Val Val Thr Val Ser
225                 230                 235                 240

Ile Asp Asp Asp Thr Pro Met Leu Leu Ile Phe Gly His Leu Pro Arg
                245                 250                 255
```

```
Val Leu Phe Lys Ala Pro Tyr Gln Arg Asp Asn Phe Ile Leu Arg Gln
            260                 265                 270

Thr Glu Lys His Glu Leu Leu Val Leu Val Lys Lys Asp Gln Leu Asn
            275                 280                 285

Arg His Ser Tyr Leu Lys Asp Pro Asp Phe Leu Asp Ala Ala Leu Asp
            290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
                325                 330                 335

Arg Thr Val Glu Met Ala Phe Ala Tyr Ala Leu Ala Leu Phe Ala Ala
            340                 345                 350

Ala Arg Gln Glu Glu Ala Gly Ala Glu Val Ser Val Pro Arg Ala Leu
            355                 360                 365

Asp Arg Gln Ala Ala Leu Leu Gln Ile Gln Glu Phe Met Ile Thr Cys
            370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asn Gln Ile Thr Asp
                405                 410                 415

Ile Thr Ser Leu Val Arg Leu Val Tyr Ile Leu Ser Lys Gln Asn Gln
            420                 425                 430

Gln His Leu Ile Pro Gln Trp Ala Leu Arg Gln Ile Ala Asp Phe Ala
            435                 440                 445

Leu Lys Leu His Lys Thr His Leu Ala Ser Phe Leu Ser Ala Phe Ala
450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Ser Gly Arg
            515                 520                 525

Arg Asp His Ser Leu Glu Arg Leu Thr Arg Leu Phe Pro Asp Ala Thr
530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
            595                 600                 605

Val Val Gly Gln Ser Leu Ile Ile Thr Gln Thr Asp Ser Gln Thr Lys
            610                 615                 620

Cys Glu Leu Thr Arg Asn Met His Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670
```

```
Ser Asp Asp Val Leu Phe Ala Leu Asp Pro Tyr Asn Glu Val Val
        675                 680                 685

Ser Ser Pro Arg Thr His Tyr Leu Met Leu Leu Lys Asn Gly Thr Val
690                 695                 700

Leu Glu Val Thr Asp Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740

<210> SEQ ID NO 33
<211> LENGTH: 837
<212> TYPE: DNA
<213> ORGANISM: Artificial Sequence
<220> FEATURE:
<223> OTHER INFORMATION: gL consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 33
nnntgcaggc ggcccgactg cggcttcagc ttcagccctg gccccgtgat cctgctgtgg      60
tgctgcctgc tgctgcccat cgtgtcctct gccgccgtgt ctgtggcccc tacagccgcc     120
gagaaggtgc cagccgagtg ccctgagctg accagacggt gtctgctggg cgaggtgttc     180
cagggcgata agtacgagag ctggctgcgg cccctggtca acgtgaccgg cagagatggc     240
cccctgagcc agctgatccg gtacagaccc gtgacccctg aggccgccaa cagcgtgctg     300
ctggacgaag cctttctgga cacactggcc ctgctgtaca acaaccccga ccagctgcgg     360
gccctgctga cactgctgag cagcgatacc gcccccagat ggatgaccgt gatgcgggc     420 tacagcgagt gcggcgacgg atctcccgcc gtgtacacct gtgtggacga cctgtgccgg     480
ggctacgacc tgaccagact gagctacggc cggtccatct tcacagagca cgtgctgggc     540
ttcgagctgg tgcccccag cctgttcaat gtggtggtgg ccatccggaa cgaggccacc     600
cggaccaaca gagcagtgcg gctgcctgtg tccaccgctg ctgctccaga gggcatcacc     660
ctgttctacg gcctgtacaa cgccgtgaaa gagttctgcc tgagacacca gctggacccc     720
cccctgctgc ggcacctgga caagtactac gccggcctgc ctcccgagct gaagcagacc     780
agagtgaacc tgcccgccca cagcagatac ggccctcagg ccgtggacgc cagatga      837

<210> SEQ ID NO 34
<211> LENGTH: 278
<212> TYPE: PRT
<213> ORGANISM: Artificial Sequence
<220> FEATURE:
<223> OTHER INFORMATION: gL consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 34

Xaa Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45
```

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
                100                 105                 110

Tyr Asn Asn Pro Asp Gln Leu Arg Ala Leu Leu Thr Leu Leu Ser Ser
                115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
                180                 185                 190

Val Ala Ile Arg Asn Glu Ala Thr Arg Thr Asn Arg Ala Val Arg Leu
                195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
                260                 265                 270

Gln Ala Val Asp Ala Arg
        275

<210> SEQ ID NO 35
<211> LENGTH: 1419
<212> TYPE: DNA
<213> ORGANISM: Artificial Sequence
<220> FEATURE:
<223> OTHER INFORMATION: gO consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 35
nnnggcaaga aagaaatgat catggtcaag ggcatcccca agatcatgct gctgatcagc      60
atcacctttc tgctgctgag cctgatcaac tgcaacgtgc tggtcaacag caagggcaca     120
cggcggagct ggccctacac cgtgctgagc taccggggca agagatcct gaagaagcag      180 aaagaggaca tcctgaagcg gctgatgagc accagcagcg acggctaccg gttcctgatg     240 tacccccagcc agcagaaatt ccacgccatc gtgatcagca tggacaagtt ccccccaggac   300 tacatcctgg ccggacccat ccggaacgac agcatcaccc acatgtggtt cgacttctac     360
agcacccagc tgcggaagcc cgccaaatac gtgtacagcg agtacaacca caccgcccac     420
aagatcaccc tgcggcctcc cccttgcggc accgtgccca gcatgaactg cctgagcgag     480
atgctgaacg tgtccaagcg gaacgacacc ggcgagaagg gctgcggcaa cttcaccacc     540
ttcaacccca tgttcttcaa cgtgccccgg tggaacacca agctgtacat cggcagcaac     600

```
aaagtgaacg tggacagcca gaccatctac tttctgggcc tgaccgccct gctgctgcgc      660
tacgcccaga gaaactgcac ccggtccttc tacctggtca acgccatgag ccggaacctg      720
ttccgggtgc ccaagtacat caacggcacc aagctgaaga acaccatgcg gaagctgaag      780
cggaagcagg ccctggtcaa agagcagccc cagaagaaga caagaagtc ccagagcacc       840 accacccct acctgagcta caccaccagc accgccttca acgtgaccac caacgtgacc       900
tacagcgcca cagccgccgt gaccagagtg gccacctcca ccaccggcta ccggcccgac      960
agcaacttca tgaagtccat catggccacc cagctgaggg acctggccac ctgggtgtac     1020
accaccctgc ggtacagaaa cgagcccttc tgcaagcccg accggaacag aaccgccgtg     1080
tccgagttca tgaagaatac ccacgtgctg atccgcaacg agacaccta ccatctctac       1140 ggcaccctgg acatgagcag cctgtactac aacgagacaa tgagcgtcga gaacgagaca     1200
gccagcgaca acaacgaaac cacccccacc agccccagca cccggttcca gcggaccttc     1260
atcgaccccc tgtgggacta cctggacagc ctgctgttcc tggacaagat ccggaacttc     1320
agcctgcagc tgcccgccta cggcaacctg acccccctg aacacagaag ggccgccaac      1380
ctgagcaccc tgaacagcct gtggtggtgg ctgcagtga                            1419
```

<210> SEQ ID NO 36
<211> LENGTH: 472
<212> TYPE: PRT
<213> ORGANISM: Artificial Sequence
<220> FEATURE:
<223> OTHER INFORMATION: g0 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 36

```
Xaa Gly Lys Lys Glu Met Ile Met Val Lys Gly Ile Pro Lys Ile Met
1               5                   10                  15

Leu Leu Ile Ser Ile Thr Phe Leu Leu Leu Ser Leu Ile Asn Cys Asn
            20                  25                  30

Val Leu Val Asn Ser Lys Gly Thr Arg Arg Ser Trp Pro Tyr Thr Val
        35                  40                  45

Leu Ser Tyr Arg Gly Lys Glu Ile Leu Lys Lys Gln Lys Glu Asp Ile
    50                  55                  60

Leu Lys Arg Leu Met Ser Thr Ser Ser Asp Gly Tyr Arg Phe Leu Met
65                  70                  75                  80

Tyr Pro Ser Gln Gln Lys Phe His Ala Ile Val Ile Ser Met Asp Lys
                85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
        115                 120                 125

Lys Tyr Val Tyr Ser Glu Tyr Asn His Thr Ala His Lys Ile Thr Leu
    130                 135                 140

Arg Pro Pro Cys Gly Thr Val Pro Ser Met Asn Cys Leu Ser Glu
145                 150                 155                 160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190
```

Thr Lys Leu Tyr Ile Gly Ser Asn Lys Val Asn Val Asp Ser Gln Thr
    195                 200                 205

Ile Tyr Phe Leu Gly Leu Thr Ala Leu Leu Arg Tyr Ala Gln Arg
210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
            245                 250                 255

Arg Lys Leu Lys Arg Lys Gln Ala Leu Val Lys Glu Gln Pro Gln Lys
        260                 265                 270

Lys Asn Lys Lys Ser Gln Ser Thr Thr Thr Pro Tyr Leu Ser Tyr Thr
    275                 280                 285

Thr Ser Thr Ala Phe Asn Val Thr Thr Asn Val Thr Tyr Ser Ala Thr
290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
            325                 330                 335

Thr Trp Val Tyr Thr Thr Leu Arg Tyr Arg Asn Glu Pro Phe Cys Lys
        340                 345                 350

Pro Asp Arg Asn Arg Thr Ala Val Ser Glu Phe Met Lys Asn Thr His
    355                 360                 365

Val Leu Ile Arg Asn Glu Thr Pro Tyr Thr Ile Tyr Gly Thr Leu Asp
370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
            405                 410                 415

Gln Arg Thr Phe Ile Asp Pro Leu Trp Asp Tyr Leu Asp Ser Leu Leu
        420                 425                 430

Phe Leu Asp Lys Ile Arg Asn Phe Ser Leu Gln Leu Pro Ala Tyr Gly
    435                 440                 445

Asn Leu Thr Pro Pro Glu His Arg Arg Ala Ala Asn Leu Ser Thr Leu
450                 455                 460

Asn Ser Leu Trp Trp Trp Leu Gln
465                 470

<210> SEQ ID NO 37
<211> LENGTH: 516
<212> TYPE: DNA
<213> ORGANISM: Artificial Sequence
<220> FEATURE:
<223> OTHER INFORMATION: UL128 consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 37
nnnagcccca aggatctgac ccctttcctg accgccctgt ggctgctcct gggccacagc      60
agagtgccta gagtgcgggc cgaggaatgc tgcgagttca tcaacgtgaa ccaccccccc     120
gagcggtgct acgacttcaa gatgtgcaac cggttcaccg tggctctgag atgccccgac     180
ggcgaagtgt gctacagccc cgagaaaacc gccgagatcc ggggcatcgt gaccaccatg     240
acccacagcc tgaccagaca ggtggtgcat aacaagctga ccagttgcaa ctacaacccc     300
ctgtacctgg aagccgacgg ccggatcaga tgcggcaaag tgaacgacaa ggcccagtac     360

```
ctgctgggcg ctgcaggcag tgtgccctac agatggatca acctggaata cgacaagatc    420
acccggatcg tgggcctgga ccagtacctg gaaagcgtga agaagcacaa gcggctggac    480
gtgtgccggg ccaagatggg ctacatgctg cagtga                              516
```

```
<210> SEQ ID NO 38
<211> LENGTH: 171
<212> TYPE: PRT
<213> ORGANISM: Artificial Sequence
<220> FEATURE:
<223> OTHER INFORMATION: UL128 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 38

Xaa Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 39
<211> LENGTH: 646
<212> TYPE: DNA
<213> ORGANISM: Artificial Sequence
<220> FEATURE:
<223> OTHER INFORMATION: UL130 consensus amino acid sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (1)..(3)
<223> OTHER INFORMATION: n is a, c, g, or t

<400> SEQUENCE: 39
nnngctgcgg ctgctgctgc ggcaccactt ccactgcctg ctgctgtgtg ccgtgtgggc    60 cacccttgt ctggccagcc cttggagcac cctgaccgcc aaccagaacc ctagccccc    120 ctggtccaag ctgacctaca gcaagcccca cgacgccgct accttctact gcccattcct    180
gtaccccagc cctcccagaa gcccccctgca gttcagcggc ttccagcggg tgtccaccgg    240
```

```
cccctgagtgc cggaacgaga cactgtacct gctgtacaac cgcgagggcc agaccctggt    300
ggaacggtct agcacctggg tcaagaaagt gatctggtat ctgagcggcc ggaaccagac    360
catcctgcag cggatgcctc ggaccgccag caagcctagc gacggcaacg tgcagatcag    420
cgtggaagat gccaaaatct tcggcgccca catggtgccc aagcagacca agctgctgag    480
attcgtggtc aacgacggca ccagatacca gatgtgcgtg atgaagctgg aaagctgggc    540
ccacgtgttc cgggactaca gcgtgtcatt ccaggtccga ctgaccttca ccgaggccaa    600
caaccagacc tacaccttct gcacccaccc caacctgatc gtctga                   646
```

<210> SEQ ID NO 40
<211> LENGTH: 214
<212> TYPE: PRT
<213> ORGANISM: Artificial Sequence
<220> FEATURE:
<223> OTHER INFORMATION: UL130 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 40

```
Xaa Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210
```

<210> SEQ ID NO 41
<211> LENGTH: 390
<212> TYPE: DNA

```
<213> ORGANISM: Artificial Sequence
<220> FEATURE:
<223> OTHER INFORMATION: UL131a consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 41
nnnagactgt gcagagtgtg gctgagcgtg tgcctgtgcg ccgtggtgct gggccagtgc      60
cagagagaga cagccgagaa gaacgactac taccgggtgc cccactactg ggacgcctgc     120
tctagagccc tgcccgacca gacccggtac aaatacgtgg aacagctggt ggacctgacc     180
ctgaactacc actacgacgc cagccacggc ctggacaact tcgacgtgct gaagcggatc     240
aacgtgaccg aggtgtccct gctgatcagc gacttccggc ggcagaacag aagaggcggc     300
accaacaagc ggactacctt caacgccgct ggcagcctgg cccctcacgc cagatccctg     360
gaattcagcg tgcggctgtt cgccaactga                                      390

<210> SEQ ID NO 42
<211> LENGTH: 129
<212> TYPE: PRT
<213> ORGANISM: Artificial Sequence
<220> FEATURE:
<223> OTHER INFORMATION: UL131a consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 42

Xaa Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 43
<211> LENGTH: 1687
<212> TYPE: DNA
<213> ORGANISM: Artificial Sequence
<220> FEATURE:
<223> OTHER INFORMATION: UL83 consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 43
nnntgagagt cgcgggcgga gatgccctga aatgatcagc gtgctgggcc caatttccgg      60
```

```
gcatgtgctg aaggccgtct tctcccgcgg agacaccccc gtgctgcctc acgagacaag    120
actgctgcag actggcatcc atgtgagggt ctcccagcca tctctgattc tggtgtctca    180
gtacacccca gatagtacac cctgccacag aggggacaac cagctgcagg tgcagcatac    240
ctacttcacc ggatcagagg tcgaaaatgt gagcgtcaac gtgcacaatc ccacaggcag    300
gagtatctgt ccttcacagg agccaatgag catctacgtg tacgccctgc ccctgaaaat    360
gctgaacatc cctagcatta atgtgcacca ttacccctcc gccgtgaac gaaagcaccg    420 gcatctgcct gtggcagatg ccgtcatcca tgcttcaggc aaacagatgt ggcaggcacg    480
actgaccgtg agcggactgg catggacacg acagcagaac cagtggaagg agccagacgt    540
gtactatact agcgccttcg tgttccccac caaagacgtg gccctgcgac acgtggtctg    600
cgcacatgag ctggtgtgct ctatggaaaa tactcgggcc accaagatgc aggtcattgg    660
cgatcagtac gtcaaagtgt atctggagtc cttttgtgaa gacgtgccct ctgggaagct    720
gttcatgcac gtgaccctgg gaagcgatgt cgaggaagac ctgactatga cccggaaccc    780
acagcccttt atgagacctc acgagaggaa cggcttcact gtgctgtgcc caaagaatat    840
gatcattaag cccgggaaaa tctctctatat tatgctggat gtggcctta caagtcacga    900 gcatttcgga ctgctgtgcc ccaaaagcat ccctgggctg tcaattagcg gaaacctgct    960
gatgaatggc cagcagatct ttctggaagt gcaggccatt cgagagaccg tcgaactgcg    1020
acagtacgac ccagtggcag ccctgttctt tttcgatatc gacctgctgc tgcagagagg    1080
ccctcagtat agtgagcacc caacattcac ttcacagtac aggattcagg ggaagctgga    1140
gtatcggcac acttgggata gacatgacga aggagctgca cagggcgacg atgacgtgtg    1200
gacctccggc tctgatagtg acgaggaact ggtgaccaca gagcgaaaaa ctccccgggt    1260
gaccggagga ggagctatgg caggagcatc aaccagcgcc ggacgaaaga gaaaaagcgc    1320
cagcagcgcc acagcatgca ctgcaggcgt gatgacaagg gggcgcctga aggcagaatc    1380
cacagtcgcc cctgaggaag atactgacga ggattctgac aacgaaatcc acaatccagc    1440
cgtgttcacc tggccacctt ggcaggcagg aattctggct cgcaatctgg tccctatggt    1500
ggccactgtc cagggacaga acctgaagta ccaggagttt ttctgggatg ctaatgacat    1560
ctatcggatt ttcgcagagc tggaaggcgt gtggcagcca gcagctcagc caaaaaggcg    1620
ccgacacaga caggacgcac tgcctggacc atgtatcgcc tccaccccaa agaaacatag    1680
gggctga                                                              1687
```

<210> SEQ ID NO 44
<211> LENGTH: 561
<212> TYPE: PRT
<213> ORGANISM: Artificial Sequence
<220> FEATURE:
<223> OTHER INFORMATION: UL83 consensus amino acid sequence
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 44

Xaa Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

```
Arg Val Ser Gln Pro Ser Leu Ile Leu Val Ser Gln Tyr Thr Pro Asp
 50                  55                  60

Ser Thr Pro Cys His Arg Gly Asp Asn Gln Leu Gln Val Gln His Thr
 65                  70                  75                  80

Tyr Phe Thr Gly Ser Glu Val Glu Asn Val Ser Val Asn Val His Asn
                     85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
            115                 120                 125

His His Tyr Pro Ser Ala Ala Glu Arg Lys His Arg His Leu Pro Val
        130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
            195                 200                 205

Glu Asn Thr Arg Ala Thr Lys Met Gln Val Ile Gly Asp Gln Tyr Val
210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Asp Leu Thr Met
                245                 250                 255

Thr Arg Asn Pro Gln Pro Phe Met Arg Pro His Glu Arg Asn Gly Phe
                260                 265                 270

Thr Val Leu Cys Pro Lys Asn Met Ile Ile Lys Pro Gly Lys Ile Ser
            275                 280                 285

His Ile Met Leu Asp Val Ala Phe Thr Ser His Glu His Phe Gly Leu
        290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
                340                 345                 350

Ile Asp Leu Leu Leu Gln Arg Gly Pro Gln Tyr Ser Glu His Pro Thr
            355                 360                 365

Phe Thr Ser Gln Tyr Arg Ile Gln Gly Lys Leu Glu Tyr Arg His Thr
        370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
                420                 425                 430

Ala Gly Arg Lys Arg Lys Ser Ala Ser Ser Thr Ala Cys Thr Ala
            435                 440                 445

Gly Val Met Thr Arg Gly Arg Leu Lys Ala Glu Ser Thr Val Ala Pro
450                 455                 460
```

```
Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 45
<211> LENGTH: 3447
<212> TYPE: DNA
<213> ORGANISM: Artificial Sequence
<220> FEATURE:
<223> OTHER INFORMATION: Synthetic Consensus hTERT nucleic acid sequence
      operably linked to IgE (pgx1434)

<400> SEQUENCE: 45
atggattgga catgattct gttcctggtc gcagccgcca cacgagtgca tagccctaga      60
gccccacggt gtagagcagt ccgcagcctg ctgcgcagcc gataccggga agtgctgcct    120
ctggccacct ttgtccggag actgggacca caggcaggc gcctggtgca gcgcggcgac     180
cccgcagctt tccgagcact ggtggcacag tgcctggtgt gcgtgccatg ggatgcacgg    240
cccctccag cagcccctag ctttagacag gtgtcctgcc tgaaagaact ggtcgcaagg     300
gtggtccagc ggctgtgcga gagaggcgcc aggaacgtgc tggcattcgg ctttgcactg    360
ctggacggag ctaggggcgg gccccctgag gcattcacca aagcgtgcg ctcctacctg     420
ccaaatacag tcactgatac cctgcgaggc tccggagcat ggggactgct gctgcgacgg    480
gtggggacg atgtgctggt ccacctgctg ctagatgcg cactgtatgt gctggtcgct     540
ccctcttgcg cataccaggt gtgcggacca ccctgtatg acctgggcgc tgcaacccag    600
gcaagacctc cacccacgc ctctggcact agaaggggac tgggcaccga caggcatgg     660
aaccatagtg tcagggaggc aggagtgcca ctggactgc agcacctgg ggtcgcga      720
cggagaggga gtgccggacg gtcactgcca ctggctaaga gaccaaggcg cggagccgct    780
ccagaaccag agaggacacc tgtgggacag ggaagctggg cacaccctgg aagaactagg    840
gggccaagtg atagggggctt ctgcgtggtc tcaccagcac gaccagcaga ggaagctact    900
tctctggagg gagctctgag tggcacccgg cactctcatc ctagtgtggg aagacagcac    960
catgcaggcc ctccaagcac cagccggcct cccggcccat gggacactcc ttgtccaccc   1020
gtgtacgctg aaaccaaaca ctttctgtat agctccggag ataaggagca gctgcggccc   1080
tcttttcctgc tgtctagtct gagacctagt ctgaccggag cacgacggct ggtggaaaca   1140
atctttctgg gtcccgccc ttggatgcca ggaaccccca aaggacacc tcgactgcca    1200
cagcggtact ggcagatgcg gccactgttc ctggagctgc tgggcaatca cgctcagtgc   1260
ccctatgggg cactgctgcg aacacattgt cctctgcggg cagccgtgac tccagctgca   1320
ggagtctgcg ccaggaaaaa gccacagggc agcgtggcag ctcctgagga agaggacacc   1380
gatccacgcc gactggtgca gctgctgaga cagcactcaa gccccctggca ggtgtacgga   1440
```

```
tttctgaggg cctgtctgcg gagactggtg cctccaggac tgtggggtc caggcacaac      1500
gaaaggcgct ttctgcgcaa tactaagaaa ttcatcagcc tgggcaagca tgctaaactg      1560
tccctgcagg agctgacctg gaaaatgagt gtgcgcgact gcgcatggct gcgacggtca      1620
ccaggagtcg ggtgcgtgcc tgcagccgag caccgcctgc gagaagagat tctggccaag      1680
tttctgcatt ggctgatgtc agtgtacgtg gtcgaactgc tgcggagctt cttttatgtg      1740
acagagacta ccttccagaa aaactacctg ttcttttatc gcaagtcagt gtggagcaaa      1800
ctgcagtcaa tcggcattcg gcagcacctg aagagagtgc agctgaggga actgagtgaa      1860
gccgaggtcc ggcagcatag agaggcaagg cctgccctgc tgacctcccg gctgagattc      1920
ctgcctaagc cagacgggct gagaccaatc gtgaacatgg attacgtggt cggagcacgg      1980
accttccgga gggaaaaacg cgctgagcga ctgacatccc gcgtgaagac tctgttctct      2040
gtcctgaatt atgagcgagc tcgccgaccc ggactgctgg agcatctgt gctgggactg      2100
gacgatattc accgggcttg gagagcattt gtcctgaggg tgcgcgcaca ggaccctccc      2160
ccagaactgt acttcgtgaa agtcgccgtg accggggctt atgacacaat ccctcaggat      2220
cggctgactg aagtgatcgc ctccatcatt aagccacaga ataccactg cgtgcggaga      2280
tatgctgtgg tcaggcgcgc tgcacacggc catgtgagga gagcttcaa cgccacgtc      2340
agcacactga ctgatctgca gccctacatg agacagttcg tggctcatct gcaggagacc      2400
agccctctga gggacgcagt ggtcatcgaa cagtcctcta gtctgaacga ggcatcaagc      2460
gggctgttcg atgtctttct gcggttcgtg tgccaccatg ccgtcagaat tggaggcaaa      2520
tcttacgtgc agtgtcaggg catcccccag ggcagcattc tgtctaccct gctgtgcagc      2580
ctgtgctatg gcgacatgga aaataagctg tttgccggaa tccgacggga tggcctgctg      2640
ctgagactgg tggccgcttt tctgctggtc actccacacc tgacccatgc caaagctttc      2700
ctgcgcacac tggtccgagg ggtgccagag tacggatgcg tggtcaacct gaggaagacc      2760
gtggtcaatt cccagtgga agacgaggcc ctgggcggca cagcatttgt ccagctgcca      2820
gcacacggac tgttcccatg tgtggactg ctgctggaca cccgcacact ggaggtgcag      2880
tccgattact cctcttatgc ccggacaagc atcagagctt ccctgacttt taacagaggc      2940
ttcaaggccg ggaggaatat gagaaggaaa ctgtttggcg tgctgcgcct gaagtgccat      3000
tccctgttcc tgtatctgca ggtgaactct ctgcagactg tctgtaccaa cgtgtacaaa      3060
attttttctgc tgcaggccta tcggttccac gcttgcgtgc tgcagctgcc attccatcag      3120
caggtcagga agaaccccac cttctttctg cgcgtgatct ctgatacagc tagtctgtgc      3180
tactcaattc tgaaggccaa aaatgctggc atgagcctgg agcaaaagg agcagcagga      3240
ccatttcctt ccgaggctgc acagtggctg tgccaccagg cattcctgct gaagctggcc      3300
cgacatcggg tgacatatag gtgcctgctg ggcgcactgc gaacagcaca gactcagctg      3360
tgcagaaagc tgcccgggc cactctggct gccctggaag ccgctgccga ccctgccctg      3420
acctccgatt tcaagactat tctggac                                            3447
```

<210> SEQ ID NO 46
<211> LENGTH: 1149
<212> TYPE: PRT
<213> ORGANISM: Artificial Sequence
<220> FEATURE:
<223> OTHER INFORMATION: Synthetic consensus hTERT amino acid sequence
      operably linked to IgE (pgx 1434)

<400> SEQUENCE: 46

-continued

```
Met Asp Trp Thr Trp Ile Leu Phe Leu Val Ala Ala Thr Arg Val
1               5                   10                  15

His Ser Pro Arg Ala Pro Arg Cys Arg Ala Val Arg Ser Leu Leu Arg
            20                  25                  30

Ser Arg Tyr Arg Glu Val Leu Pro Leu Ala Thr Phe Val Arg Arg Leu
            35                  40                  45

Gly Pro Gln Gly Arg Arg Leu Val Gln Arg Gly Asp Pro Ala Ala Phe
        50                  55                  60

Arg Ala Leu Val Ala Gln Cys Leu Val Cys Val Pro Trp Asp Ala Arg
65                  70                  75                  80

Pro Pro Pro Ala Ala Pro Ser Phe Arg Gln Val Ser Cys Leu Lys Glu
                85                  90                  95

Leu Val Ala Arg Val Val Gln Arg Leu Cys Glu Arg Gly Ala Arg Asn
            100                 105                 110

Val Leu Ala Phe Gly Phe Ala Leu Leu Asp Gly Ala Arg Gly Gly Pro
        115                 120                 125

Pro Glu Ala Phe Thr Thr Ser Val Arg Ser Tyr Leu Pro Asn Thr Val
    130                 135                 140

Thr Asp Thr Leu Arg Gly Ser Gly Ala Trp Gly Leu Leu Arg Arg
145                 150                 155                 160

Val Gly Asp Asp Val Leu Val His Leu Leu Ala Arg Cys Ala Leu Tyr
                165                 170                 175

Val Leu Val Ala Pro Ser Cys Ala Tyr Gln Val Cys Gly Pro Pro Leu
            180                 185                 190

Tyr Asp Leu Gly Ala Ala Thr Gln Ala Arg Pro Pro His Ala Ser
        195                 200                 205

Gly Thr Arg Arg Gly Leu Gly Thr Glu Gln Ala Trp Asn His Ser Val
    210                 215                 220

Arg Glu Ala Gly Val Pro Leu Gly Leu Pro Ala Pro Gly Ala Arg Arg
225                 230                 235                 240

Arg Arg Gly Ser Ala Gly Arg Ser Leu Pro Leu Ala Lys Arg Pro Arg
                245                 250                 255

Arg Gly Ala Ala Pro Glu Pro Glu Arg Thr Pro Val Gly Gln Gly Ser
            260                 265                 270

Trp Ala His Pro Gly Arg Thr Arg Gly Pro Ser Asp Arg Gly Phe Cys
        275                 280                 285

Val Val Ser Pro Ala Arg Pro Ala Glu Glu Ala Thr Ser Leu Glu Gly
    290                 295                 300

Ala Leu Ser Gly Thr Arg His Ser His Pro Ser Val Gly Arg Gln His
305                 310                 315                 320

His Ala Gly Pro Pro Ser Thr Ser Arg Pro Pro Arg Pro Trp Asp Thr
                325                 330                 335

Pro Cys Pro Pro Val Tyr Ala Glu Thr Lys His Phe Leu Tyr Ser Ser
            340                 345                 350

Gly Asp Lys Glu Gln Leu Arg Pro Ser Phe Leu Leu Ser Ser Leu Arg
        355                 360                 365

Pro Ser Leu Thr Gly Ala Arg Arg Leu Val Glu Thr Ile Phe Leu Gly
    370                 375                 380

Ser Arg Pro Trp Met Pro Gly Thr Pro Arg Arg Thr Pro Arg Leu Pro
385                 390                 395                 400

Gln Arg Tyr Trp Gln Met Arg Pro Leu Phe Leu Glu Leu Leu Gly Asn
                405                 410                 415

His Ala Gln Cys Pro Tyr Gly Ala Leu Leu Arg Thr His Cys Pro Leu
```

```
            420               425               430
Arg Ala Ala Val Thr Pro Ala Ala Gly Val Cys Ala Arg Glu Lys Pro
            435               440               445
Gln Gly Ser Val Ala Ala Pro Glu Glu Asp Thr Asp Pro Arg Arg
        450               455               460
Leu Val Gln Leu Leu Arg Gln His Ser Ser Pro Trp Gln Val Tyr Gly
465                 470               475               480
Phe Leu Arg Ala Cys Leu Arg Arg Leu Val Pro Pro Gly Leu Trp Gly
                485               490               495
Ser Arg His Asn Glu Arg Arg Phe Leu Arg Asn Thr Lys Lys Phe Ile
            500               505               510
Ser Leu Gly Lys His Ala Lys Leu Ser Leu Gln Glu Leu Thr Trp Lys
            515               520               525
Met Ser Val Arg Asp Cys Ala Trp Leu Arg Arg Ser Pro Gly Val Gly
            530               535               540
Cys Val Pro Ala Ala Glu His Arg Leu Arg Glu Glu Ile Leu Ala Lys
545                 550               555               560
Phe Leu His Trp Leu Met Ser Val Tyr Val Val Glu Leu Leu Arg Ser
                565               570               575
Phe Phe Tyr Val Thr Glu Thr Thr Phe Gln Lys Asn Tyr Leu Phe Phe
                580               585               590
Tyr Arg Lys Ser Val Trp Ser Lys Leu Gln Ser Ile Gly Ile Arg Gln
            595               600               605
His Leu Lys Arg Val Gln Leu Arg Glu Leu Ser Glu Ala Glu Val Arg
            610               615               620
Gln His Arg Glu Ala Arg Pro Ala Leu Leu Thr Ser Arg Leu Arg Phe
625                 630               635               640
Leu Pro Lys Pro Asp Gly Leu Arg Pro Ile Val Asn Met Asp Tyr Val
                645               650               655
Val Gly Ala Arg Thr Phe Arg Arg Glu Lys Arg Ala Glu Arg Leu Thr
                660               665               670
Ser Arg Val Lys Thr Leu Phe Ser Val Leu Asn Tyr Glu Arg Ala Arg
            675               680               685
Arg Pro Gly Leu Leu Gly Ala Ser Val Leu Gly Leu Asp Asp Ile His
            690               695               700
Arg Ala Trp Arg Ala Phe Val Leu Arg Val Arg Ala Gln Asp Pro Pro
705                 710               715               720
Pro Glu Leu Tyr Phe Val Lys Val Ala Val Thr Gly Ala Tyr Asp Thr
                725               730               735
Ile Pro Gln Asp Arg Leu Thr Glu Val Ile Ala Ser Ile Ile Lys Pro
            740               745               750
Gln Asn Thr Tyr Cys Val Arg Arg Tyr Ala Val Val Arg Arg Ala Ala
            755               760               765
His Gly His Val Arg Lys Ser Phe Lys Arg His Val Ser Thr Leu Thr
            770               775               780
Asp Leu Gln Pro Tyr Met Arg Gln Phe Val Ala His Leu Gln Glu Thr
785                 790               795               800
Ser Pro Leu Arg Asp Ala Val Val Ile Glu Gln Ser Ser Ser Leu Asn
                805               810               815
Glu Ala Ser Ser Gly Leu Phe Asp Val Phe Leu Arg Phe Val Cys His
                820               825               830
His Ala Val Arg Ile Gly Gly Lys Ser Tyr Val Gln Cys Gln Gly Ile
            835               840               845
```

-continued

```
Pro Gln Gly Ser Ile Leu Ser Thr Leu Leu Cys Ser Leu Cys Tyr Gly
    850                 855                 860
Asp Met Glu Asn Lys Leu Phe Ala Gly Ile Arg Arg Asp Gly Leu Leu
865                 870                 875                 880
Leu Arg Leu Val Ala Ala Phe Leu Leu Val Thr Pro His Leu Thr His
                885                 890                 895
Ala Lys Ala Phe Leu Arg Thr Leu Val Arg Gly Val Pro Glu Tyr Gly
            900                 905                 910
Cys Val Val Asn Leu Arg Lys Thr Val Val Asn Phe Pro Val Glu Asp
        915                 920                 925
Glu Ala Leu Gly Gly Thr Ala Phe Val Gln Leu Pro Ala His Gly Leu
    930                 935                 940
Phe Pro Trp Cys Gly Leu Leu Asp Thr Arg Thr Leu Glu Val Gln
945                 950                 955                 960
Ser Asp Tyr Ser Ser Tyr Ala Arg Thr Ser Ile Arg Ala Ser Leu Thr
                965                 970                 975
Phe Asn Arg Gly Phe Lys Ala Gly Arg Asn Met Arg Arg Lys Leu Phe
            980                 985                 990
Gly Val Leu Arg Leu Lys Cys His Ser Leu Phe Leu Tyr Leu Gln Val
        995                 1000                1005
Asn Ser Leu Gln Thr Val Cys Thr Asn Val Tyr Lys Ile Phe Leu
    1010                1015                1020
Leu Gln Ala Tyr Arg Phe His Ala Cys Val Leu Gln Leu Pro Phe
    1025                1030                1035
His Gln Gln Val Arg Lys Asn Pro Thr Phe Phe Leu Arg Val Ile
    1040                1045                1050
Ser Asp Thr Ala Ser Leu Cys Tyr Ser Ile Leu Lys Ala Lys Asn
    1055                1060                1065
Ala Gly Met Ser Leu Gly Ala Lys Gly Ala Ala Gly Pro Phe Pro
    1070                1075                1080
Ser Glu Ala Ala Gln Trp Leu Cys His Gln Ala Phe Leu Leu Lys
    1085                1090                1095
Leu Ala Arg His Arg Val Thr Tyr Arg Cys Leu Leu Gly Ala Leu
    1100                1105                1110
Arg Thr Ala Gln Thr Gln Leu Cys Arg Lys Leu Pro Gly Ala Thr
    1115                1120                1125
Leu Ala Ala Leu Glu Ala Ala Asp Pro Ala Leu Thr Ser Asp
    1130                1135                1140
Phe Lys Thr Ile Leu Asp
    1145

<210> SEQ ID NO 47
<211> LENGTH: 3393
<212> TYPE: DNA
<213> ORGANISM: Artificial Sequence
<220> FEATURE:
<223> OTHER INFORMATION: Synthetic Consensus hTERT nucleic acid sequence
      (pgx1434)

<400> SEQUENCE: 47
cctagagccc cacggtgtag agcagtccgc agcctgctgc gcagccgata ccgggaagtg      60
ctgcctctgg ccacctttgt ccggagactg ggaccacagg gcaggcgcct ggtgcagcgc     120
ggcgaccccg cagctttccg agcactggtg gcacagtgcc tggtgtgcgt gccatgggat     180
gcacggcccc ctccagcagc ccctagcttt agacaggtgt cctgcctgaa agaactggtc     240
```

```
gcaagggtgg tccagcggct gtgcgagaga ggcgccagga acgtgctggc attcggcttt    300
gcactgctgg acggagctag gggcgggccc cctgaggcat tcaccacaag cgtgcgctcc    360
tacctgccaa atacagtcac tgatacccty cgaggctccg gagcatgggg actgctgctg    420
cgacgggtgg gggacgatgt gctggtccac ctgctggcta gatgcgcact gtatgtgctg    480
gtcgctccct cttgcgcata ccaggtgtgc ggaccacccc tgtatgacct gggcgctgca    540
acccaggcaa gacctccacc ccacgcctct ggcactagaa ggggactggg caccgaacag    600
gcatggaacc atagtgtcag ggaggcagga gtgccactgg gactgccagc acctggggct    660
cgccgacgga gagggagtgc cggacggtca ctgccactgg ctaagagacc aaggcgcgga    720
gccgctccag aaccagagag gacacctgtg ggacagggaa gctgggcaca ccctggaaga    780
actagggggc caagtgatag gggcttctgc gtggtctcac cagcacgacc agcagaggaa    840
gctacttctc tggagggagc tctgagtggc acccggcact ctcatcctag tgtgggaaga    900
cagcaccatg caggccctcc aagcaccagc cggcctcccc ggccatggga cactccttgt    960
ccacccgtgt acgctgaaac caaacacttt ctgtatagct ccggagataa ggagcagctg   1020
cggccctctt tcctgctgtc tagtctgaga cctagtctga ccggagcacg acggctggtg   1080
gaaacaatct ttctggggtc ccgcccttgg atgccaggaa cccccagaag gacacctcga   1140
ctgccacagc ggtactggca gatgcggcca ctgttcctgg agctgctggg caatcacgct   1200
cagtgcccct atggggcact gctgcgaaca cattgtcctc tgcgggcagc cgtgactcca   1260
gctgcaggag tctgcgccag ggaaaagcca cagggcagcg tggcagctcc tgaggaagag   1320
gacaccgatc cacgccgact ggtgcagctg ctgagacagc actcaagccc ctggcaggtg   1380
tacggatttc tgagggcctg tctgcggaga ctggtgcctc caggactgtg ggggtccagg   1440
cacaacgaaa ggcgctttct gcgcaatact aagaaattca tcagcctggg caagcatgct   1500
aaactgtccc tgcaggagct gacctggaaa atgagtgtgc gcgactgcgc atggctgcga   1560
cggtcaccag gagtcgggtg cgtgcctgca gccgagcacc gcctgcgaga agagattctg   1620
gccaagtttc tgcattggct gatgtcagtg tacgtggtcg aactgctgcg gagcttcttt   1680
tatgtgacag agactacctt ccagaaaaac tacctgttct tttatcgcaa gtcagtgtgg   1740 agcaaaactgc agtcaatcgg cattcggcag cacctgaaga gagtgcagct gagggaactg   1800
agtgaagccg aggtccggca gcatagagag gcaaggcctg ccctgctgac ctcccggctg   1860
agattcctgc ctaagccaga cgggctgaga ccaatcgtga acatggatta cgtggtcgga   1920
gcacggacct tccggaggga aaaacgcgct gagcgactga catcccgcgt gaagactctg   1980
ttctctgtcc tgaattatga gcagctcgc cgacccggac tgctgggagc atctgtgctg   2040
ggactggacg atattcaccg ggcttggaga gcatttgtcc tgagggtgcg cgcacaggac   2100 cctccccag aactgtactt cgtgaaagtc gccgtgaccg gggcttatga cacaatccct   2160
caggatcggt tgactgaagt gatcgcctcc atcattaagc cacagaatac ctactgcgtg   2220
cggagatatg ctgtggtcag gcgcgctgca cacggccatg tgaggaagag cttcaagcgc   2280
cacgtcagca cactgactga tctgcagccc tacatgagac agttcgtggc tcatctgcag   2340
gagaccagcc ctctgaggga cgcagtggtc atcgaacagt cctctagtct gaacgaggca   2400
tcaagcgggc tgttcgatgt ctttctgcgg ttcgtgtgcc accatgccgt cagaattgga   2460
ggcaaatctt acgtgcagtg tcagggcatc ccccagggca gcattctgtc taccctgctg   2520
tgcagcctgt gctatggcga catggaaaat aagctgtttg ccggaatccg acgggatggc   2580
```

```
ctgctgctga gactggtggc cgcttttctg ctggtcactc cacacctgac ccatgccaaa    2640
gctttcctgc gcacactggt ccgaggggtg ccagagtacg gatgcgtggt caacctgagg    2700
aagaccgtgg tcaatttccc agtggaagac gaggccctgg gcggcacagc atttgtccag    2760
ctgccagcac acggactgtt cccatggtgt ggactgctgc tggacacccg cacactggag    2820
gtgcagtccg attactcctc ttatgcccgg acaagcatca gagcttccct gacttttaac    2880
agaggcttca aggccgggag gaatatgaga aggaaactgt ttggcgtgct gcgcctgaag    2940
tgccattccc tgttcctgta tctgcaggtg aactctctgc agactgtctg taccaacgtg    3000
tacaaaattt ttctgctgca ggcctatcgg ttccacgctt gcgtgctgca gctgccattc    3060
catcagcagg tcaggaagaa ccccaccttc tttctgcgcg tgatctctga tacagctagt    3120
ctgtgctact caattctgaa ggccaaaaat gctggcatga gcctgggagc aaaaggagca    3180
gcaggaccat ttccttccga ggctgcacag tggctgtgcc accaggcatt cctgctgaag    3240
ctggcccgac atcgggtgac atataggtgc ctgctgggcg cactgcgaac agcacagact    3300
cagctgtgca gaaagctgcc cggggccact ctggctgccc tggaagccgc tgccgaccct    3360
gccctgacct ccgatttcaa gactattctg gac                                 3393
```

<210> SEQ ID NO 48
<211> LENGTH: 1131
<212> TYPE: PRT
<213> ORGANISM: Artificial Sequence
<220> FEATURE:
<223> OTHER INFORMATION: Synthetic Consensus hTERT amino acid sequence (pgx1434)

<400> SEQUENCE: 48

```
Pro Arg Ala Pro Arg Cys Arg Ala Val Arg Ser Leu Leu Arg Ser Arg
1               5                   10                  15

Tyr Arg Glu Val Leu Pro Leu Ala Thr Phe Val Arg Arg Leu Gly Pro
            20                  25                  30

Gln Gly Arg Arg Leu Val Gln Arg Gly Asp Pro Ala Ala Phe Arg Ala
        35                  40                  45

Leu Val Ala Gln Cys Leu Val Cys Val Pro Trp Asp Ala Arg Pro Pro
    50                  55                  60

Pro Ala Ala Pro Ser Phe Arg Gln Val Ser Cys Leu Lys Glu Leu Val
65                  70                  75                  80

Ala Arg Val Val Gln Arg Leu Cys Glu Arg Gly Ala Arg Asn Val Leu
                85                  90                  95

Ala Phe Gly Phe Ala Leu Leu Asp Gly Ala Arg Gly Gly Pro Pro Glu
            100                 105                 110

Ala Phe Thr Thr Ser Val Arg Ser Tyr Leu Pro Asn Thr Val Thr Asp
        115                 120                 125

Thr Leu Arg Gly Ser Gly Ala Trp Gly Leu Leu Leu Arg Arg Val Gly
    130                 135                 140

Asp Asp Val Leu Val His Leu Leu Ala Arg Cys Ala Leu Tyr Val Leu
145                 150                 155                 160

Val Ala Pro Ser Cys Ala Tyr Gln Val Cys Gly Pro Pro Leu Tyr Asp
                165                 170                 175

Leu Gly Ala Ala Thr Gln Ala Arg Pro Pro His Ala Ser Gly Thr
            180                 185                 190

Arg Arg Gly Leu Gly Thr Glu Gln Ala Trp Asn His Ser Val Arg Glu
        195                 200                 205

Ala Gly Val Pro Leu Gly Leu Pro Ala Pro Gly Ala Arg Arg Arg Arg
```

-continued

```
            210                 215                 220
Gly Ser Ala Gly Arg Ser Leu Pro Leu Ala Lys Arg Pro Arg Gly
225                 230                 235                 240

Ala Ala Pro Glu Pro Glu Arg Thr Pro Val Gly Gln Gly Ser Trp Ala
                245                 250                 255

His Pro Gly Arg Thr Arg Gly Pro Ser Asp Arg Gly Phe Cys Val Val
                260                 265                 270

Ser Pro Ala Arg Pro Ala Glu Glu Ala Thr Ser Leu Glu Gly Ala Leu
                275                 280                 285

Ser Gly Thr Arg His Ser His Pro Ser Val Gly Arg Gln His His Ala
                290                 295                 300

Gly Pro Pro Ser Thr Ser Arg Pro Pro Arg Pro Trp Asp Thr Pro Cys
305                 310                 315                 320

Pro Pro Val Tyr Ala Glu Thr Lys His Phe Leu Tyr Ser Ser Gly Asp
                325                 330                 335

Lys Glu Gln Leu Arg Pro Ser Phe Leu Leu Ser Ser Leu Arg Pro Ser
                340                 345                 350

Leu Thr Gly Ala Arg Arg Leu Val Glu Thr Ile Phe Leu Gly Ser Arg
                355                 360                 365

Pro Trp Met Pro Gly Thr Pro Arg Arg Thr Pro Arg Leu Pro Gln Arg
370                 375                 380

Tyr Trp Gln Met Arg Pro Leu Phe Leu Glu Leu Leu Gly Asn His Ala
385                 390                 395                 400

Gln Cys Pro Tyr Gly Ala Leu Leu Arg Thr His Cys Pro Leu Arg Ala
                405                 410                 415

Ala Val Thr Pro Ala Ala Gly Val Cys Ala Arg Glu Lys Pro Gln Gly
                420                 425                 430

Ser Val Ala Ala Pro Glu Glu Asp Thr Asp Pro Arg Arg Leu Val
                435                 440                 445

Gln Leu Leu Arg Gln His Ser Ser Pro Trp Gln Val Tyr Gly Phe Leu
                450                 455                 460

Arg Ala Cys Leu Arg Arg Leu Val Pro Pro Gly Leu Trp Gly Ser Arg
465                 470                 475                 480

His Asn Glu Arg Arg Phe Leu Arg Asn Thr Lys Lys Phe Ile Ser Leu
                485                 490                 495

Gly Lys His Ala Lys Leu Ser Leu Gln Glu Leu Thr Trp Lys Met Ser
                500                 505                 510

Val Arg Asp Cys Ala Trp Leu Arg Arg Ser Pro Gly Val Gly Cys Val
                515                 520                 525

Pro Ala Ala Glu His Arg Leu Arg Glu Glu Ile Leu Ala Lys Phe Leu
530                 535                 540

His Trp Leu Met Ser Val Tyr Val Val Glu Leu Leu Arg Ser Phe Phe
545                 550                 555                 560

Tyr Val Thr Glu Thr Thr Phe Gln Lys Asn Tyr Leu Phe Phe Tyr Arg
                565                 570                 575

Lys Ser Val Trp Ser Lys Leu Gln Ser Ile Gly Ile Arg Gln His Leu
                580                 585                 590

Lys Arg Val Gln Leu Arg Glu Leu Ser Glu Ala Glu Val Arg Gln His
                595                 600                 605

Arg Glu Ala Arg Pro Ala Leu Leu Thr Ser Arg Leu Arg Phe Leu Pro
610                 615                 620

Lys Pro Asp Gly Leu Arg Pro Ile Val Asn Met Asp Tyr Val Val Gly
625                 630                 635                 640
```

```
Ala Arg Thr Phe Arg Arg Glu Lys Arg Ala Glu Arg Leu Thr Ser Arg
            645                 650                 655

Val Lys Thr Leu Phe Ser Val Leu Asn Tyr Glu Arg Ala Arg Arg Pro
            660                 665                 670

Gly Leu Leu Gly Ala Ser Val Leu Gly Leu Asp Asp Ile His Arg Ala
            675                 680                 685

Trp Arg Ala Phe Val Leu Arg Val Arg Ala Gln Asp Pro Pro Pro Glu
        690                 695                 700

Leu Tyr Phe Val Lys Val Ala Val Thr Gly Ala Tyr Asp Thr Ile Pro
705                 710                 715                 720

Gln Asp Arg Leu Thr Glu Val Ile Ala Ser Ile Lys Pro Gln Asn
            725                 730                 735

Thr Tyr Cys Val Arg Arg Tyr Ala Val Val Arg Arg Ala His Gly
            740                 745                 750

His Val Arg Lys Ser Phe Lys Arg His Val Ser Thr Leu Thr Asp Leu
            755                 760                 765

Gln Pro Tyr Met Arg Gln Phe Val Ala His Leu Gln Glu Thr Ser Pro
770                 775                 780

Leu Arg Asp Ala Val Val Ile Glu Gln Ser Ser Ser Leu Asn Glu Ala
785                 790                 795                 800

Ser Ser Gly Leu Phe Asp Val Phe Leu Arg Phe Val Cys His His Ala
                805                 810                 815

Val Arg Ile Gly Gly Lys Ser Tyr Val Gln Cys Gln Gly Ile Pro Gln
                820                 825                 830

Gly Ser Ile Leu Ser Thr Leu Leu Cys Ser Leu Cys Tyr Gly Asp Met
            835                 840                 845

Glu Asn Lys Leu Phe Ala Gly Ile Arg Arg Asp Gly Leu Leu Leu Arg
        850                 855                 860

Leu Val Ala Ala Phe Leu Leu Val Thr Pro His Leu Thr His Ala Lys
865                 870                 875                 880

Ala Phe Leu Arg Thr Leu Val Arg Gly Val Pro Glu Tyr Gly Cys Val
                885                 890                 895

Val Asn Leu Arg Lys Thr Val Val Asn Phe Pro Val Glu Asp Glu Ala
                900                 905                 910

Leu Gly Gly Thr Ala Phe Val Gln Leu Pro Ala His Gly Leu Phe Pro
            915                 920                 925

Trp Cys Gly Leu Leu Leu Asp Thr Arg Thr Leu Glu Val Gln Ser Asp
930                 935                 940

Tyr Ser Ser Tyr Ala Arg Thr Ser Ile Arg Ala Ser Leu Thr Phe Asn
945                 950                 955                 960

Arg Gly Phe Lys Ala Gly Arg Asn Met Arg Arg Lys Leu Phe Gly Val
                965                 970                 975

Leu Arg Leu Lys Cys His Ser Leu Phe Leu Tyr Leu Gln Val Asn Ser
            980                 985                 990

Leu Gln Thr Val Cys Thr Asn Val Tyr Lys Ile Phe Leu Leu Gln Ala
            995                 1000                1005

Tyr Arg Phe His Ala Cys Val Leu Gln Leu Pro Phe His Gln Gln
    1010                1015                1020

Val Arg Lys Asn Pro Thr Phe Phe Leu Arg Val Ile Ser Asp Thr
    1025                1030                1035

Ala Ser Leu Cys Tyr Ser Ile Leu Lys Ala Lys Asn Ala Gly Met
    1040                1045                1050
```

```
Ser Leu Gly Ala Lys Gly Ala Ala Gly Pro Phe Pro Ser Glu Ala
    1055                1060                1065

Ala Gln Trp Leu Cys His Gln Ala Phe Leu Leu Lys Leu Ala Arg
    1070                1075                1080

His Arg Val Thr Tyr Arg Cys Leu Leu Gly Ala Leu Arg Thr Ala
    1085                1090                1095

Gln Thr Gln Leu Cys Arg Lys Leu Pro Gly Ala Thr Leu Ala Ala
    1100                1105                1110

Leu Glu Ala Ala Ala Asp Pro Ala Leu Thr Ser Asp Phe Lys Thr
    1115                1120                1125

Ile Leu Asp
    1130

<210> SEQ ID NO 49
<211> LENGTH: 3417
<212> TYPE: DNA
<213> ORGANISM: Artificial Sequence
<220> FEATURE:
<223> OTHER INFORMATION: Synthetic Consensus mTERT nucleic acid sequence
      operably linked to IgE (pgx1418)

<400> SEQUENCE: 49
atggactgga catggattct gtttctcgtc gccgccgcta caagagtgca ttccccaaga      60
gcccccaggt gccctgctgt gaggtcactg ctccgaagca ggtacagaga agtgtggccc     120
ctggccacat tcgtcaggag actgggacct gaagggcggc gcctggtgca gccaggtgac     180
cccaaggtgt ttagaactct ggtcgctcag tgcctggtgt gcgtgccatg ggggtctcag     240 cccccctccag cagatctgag tttccaccag gtgagctccc tgaaggagct cgtcgcccga     300
gtggtccaga ggctgtgcga gagaggcgaa cggaacgtgc tggctttcgg ttttgcactg     360
ctcaatggag cccgcggcgg accccctatg gctttcacca catctgtgag gagttacctg     420
cccaactctg tgaccgagag tctgagagtc tcaggagctt ggatgctgct cctgagccgg     480
gtgggggacg atctcctggt ctacctcctg gctcattgcg cactgtatct cctggtgcca     540
ccctcatgcg cctaccaggt ctgtggaagc ccactgtatc agatctgtgc cactaccgac     600
acctggccaa gcgtgagcgc cagctaccga cctacccgac cagtcggacg gaacttcaca     660
aatctggggt ccctccacca gattaagaat tctagtcatc aggaggcccc taaaccactc     720
gctctgccct ccagagggac aaagcggcac ctctctctga cctccacatc tgtgcctagt     780
gccaagaaag ctcgatgcta tcccgcccct agggtcgaaa agggtcctca tcgccaggtg     840
gtcccaacac cctctggcaa aacttgggtg cctagcccag caaggtcccc agaggtccct     900
actgccgaaa aggacctgtc aagcaagggt aaagctagcg atctcagtct gtcaggcagc     960
gtgtgctgta agcacaaacc atcctctacc tcactcctga gccctccaag gcagaacgcc    1020
ttccagctga gaccctttac tgagacccgg catttcctgt acagccgcgg gggtggccag    1080
gaacgactga atccttcctt tctcctgaac aatctgcagc catctctcac cggcgctcga    1140
aggctggtgg agatcatttt cctcggttcc cggccacgca catctggacc tctgtgcaga    1200
actagacggc tctcccgccg atactggcag atgcggccac tgttccagca gctcctggtg    1260
aaccacgccg aatgccagta tgtcaggctc ctgagatctc attgtaggtt caggactgca    1320
aaccagcagg tgaccgacgc cctgaataca agccctcccc acctgatgga tctcctgcgc    1380
ctccatagtt caccatggca ggtgtacgga ttcctgcgag cttgcctgcg aaagctcgtc    1440
ccagcaggtc tgtggggcac aaggcacaac gagaggagat tctttaaaaa cgtgaagaag    1500
```

| | |
|---|---|
| ttcatctcac tgggaaagta tgggaaactc agcctgcagg agctgatgtg aagatgaaa | 1560 |
| gtggaagact gtcactggct gaggagctcc ccaggcaagg atagagtgcc cgccgctgag | 1620 |
| catagactgc gggaacgcat cctcgccatg ttcctgtttt ggctcatgga cacatacgtg | 1680 |
| gtccagctcc tgcgcagctt cttttatatt actgagacaa cttccagaa gaacaggctg | 1740 |
| ttcttttaca gaaagtccgt gtggtctaaa ctgcagtcta tcggggtgag acagcacctg | 1800 |
| gagcgagtca ggctgagaga actcagtcag gaggaagtgc ggcaccatca ggatacatgg | 1860 |
| ctggccatgc ctatctgccg gctgcgcttc attcccaagc taacggcct gaggccaatt | 1920 |
| gtgaatatgt cctattctat gggaactcgg gcttttggga agcgcaaaca ggcacagcac | 1980 |
| ttcactcagc gcctgaagac cctctttagc gtgctgaact acgagaggac taaacatccc | 2040 |
| aatctgatgg gtgcttccgt gctcggcatg aacgacatct atcgaacctg gcgagccttc | 2100 |
| gtgctgcgag tcagggctct cgaccagacc cctagaatgt actttgtgaa ggccgatgtc | 2160 |
| acaggagcat atgacgccat tccacaggat aaactggtgg aggtggtcgc taatatgatc | 2220 |
| cggcacagtg aatcaaccta ctgtattcgg cagtatgcag tggtccagcg agacagccag | 2280 |
| ggacaggtgc ataagtcctt ccggcgccag gtcagtacac tgtcagatct ccagccctac | 2340 |
| atgggacagt ttctgaaaca cctccaggac agcgatgcct ccgctctgag aaacagcgtg | 2400 |
| gtcatcgagc agagcatttc catgaatgaa tctagttcaa gcctgttcga cttctttctc | 2460 |
| cactttgtgc gccattccgt ggtcaagatc ggagggcgat gctatgtcca gtgtcagggt | 2520 |
| attcctcagg gctcctctct gagtaccctc ctgtgctcac tgtgcttcgg agacatggag | 2580 |
| aacaagctgt ttgctgaagt gcagcaggat gggctcctgc tccggttcgt ggcagccttt | 2640 |
| ctgctcgtca ctccccacct ggatcaggca aaggccttcc tgtccaccct cgtgcatgga | 2700 |
| gtccctgagt acgggtgcat gatcaacctg cagaaaactg tggtcaattt tccagtggaa | 2760 |
| ccaggcaccc tgggtggcgc tgcacctcac cagctgccag cccattgcct cttcccttgg | 2820 |
| tgtggtctgc tcctggacac acagactctg gaggtgtttt gtgattactc cggctatgcc | 2880 |
| aggacctcta tcaagactag tctgaccttc cagagcgtgt caaggctgg aaaaacaatg | 2940 |
| cgatacaagc tcctgtcagt gctcaggctg aaatgccacg ggctcttcct ggacctccag | 3000 |
| gtgaactctc tgcagaccgt ctgtatcaat atctacaaga tcttcctcct gcaggcatat | 3060 |
| agatttcacg cctgcgtgat tcagctgcct ttcgatcagc atgtccggaa aaacctggcc | 3120 |
| ttctttctcg gaatcatttc aaatcaggct agctgctgtt atgcaatcct gaaggtgaaa | 3180 |
| aacccaggaa tgacactgaa ggcaaaaggg tccttcccac ccgaggccgc tagatggctg | 3240 |
| tgctaccagg ccttctcct gaagctggca gcccactctg tgacatataa atgcctcctg | 3300 |
| ggccctctga aactgcaca gaagcagctg tgccggaaac tcccagaagc caccatgaca | 3360 |
| atcctgaaga ccgctgcaga ccccgctctc tccactgatt tccagaccat tctcgac | 3417 |

<210> SEQ ID NO 50
<211> LENGTH: 1139
<212> TYPE: PRT
<213> ORGANISM: Artificial Sequence
<220> FEATURE:
<223> OTHER INFORMATION: Synthetic Consensus mTERT amino acid sequence
      operably linked to IgE (pgx1418)

<400> SEQUENCE: 50

Met Asp Trp Thr Trp Ile Leu Phe Leu Val Ala Ala Ala Thr Arg Val
1               5                   10                  15

His Ser Pro Arg Ala Pro Arg Cys Pro Ala Val Arg Ser Leu Leu Arg

```
                    20                  25                  30
Ser Arg Tyr Arg Glu Val Trp Pro Leu Ala Thr Phe Val Arg Arg Leu
                35                  40                  45
Gly Pro Glu Gly Arg Arg Leu Val Gln Pro Gly Asp Pro Lys Val Phe
            50                  55                  60
Arg Thr Leu Val Ala Gln Cys Leu Val Cys Val Pro Trp Gly Ser Gln
65                  70                  75                  80
Pro Pro Pro Ala Asp Leu Ser Phe His Gln Val Ser Ser Leu Lys Glu
                85                  90                  95
Leu Val Ala Arg Val Val Gln Arg Leu Cys Glu Arg Gly Glu Arg Asn
                100                 105                 110
Val Leu Ala Phe Gly Phe Ala Leu Leu Asn Gly Ala Arg Gly Gly Pro
            115                 120                 125
Pro Met Ala Phe Thr Thr Ser Val Arg Ser Tyr Leu Pro Asn Ser Val
            130                 135                 140
Thr Glu Ser Leu Arg Val Ser Gly Ala Trp Met Leu Leu Leu Ser Arg
145                 150                 155                 160
Val Gly Asp Asp Leu Leu Val Tyr Leu Leu Ala His Cys Ala Leu Tyr
                165                 170                 175
Leu Leu Val Pro Pro Ser Cys Ala Tyr Gln Val Cys Gly Ser Pro Leu
            180                 185                 190
Tyr Gln Ile Cys Ala Thr Thr Asp Thr Trp Pro Ser Val Ser Ala Ser
            195                 200                 205
Tyr Arg Pro Thr Arg Pro Val Gly Arg Asn Phe Thr Asn Leu Gly Ser
            210                 215                 220
Leu His Gln Ile Lys Asn Ser Ser His Gln Glu Ala Pro Lys Pro Leu
225                 230                 235                 240
Ala Leu Pro Ser Arg Gly Thr Lys Arg His Leu Ser Leu Thr Ser Thr
                245                 250                 255
Ser Val Pro Ser Ala Lys Lys Ala Arg Cys Tyr Pro Ala Pro Arg Val
                260                 265                 270
Glu Lys Gly Pro His Arg Gln Val Val Pro Thr Pro Ser Gly Lys Thr
            275                 280                 285
Trp Val Pro Ser Pro Ala Arg Ser Pro Glu Val Pro Thr Ala Glu Lys
            290                 295                 300
Asp Leu Ser Ser Lys Gly Lys Ala Ser Asp Leu Ser Leu Ser Gly Ser
305                 310                 315                 320
Val Cys Cys Lys His Lys Pro Ser Ser Thr Ser Leu Leu Ser Pro Pro
                325                 330                 335
Arg Gln Asn Ala Phe Gln Leu Arg Pro Phe Thr Glu Thr Arg His Phe
            340                 345                 350
Leu Tyr Ser Arg Gly Gly Gly Gln Glu Arg Leu Asn Pro Ser Phe Leu
            355                 360                 365
Leu Asn Asn Leu Gln Pro Ser Leu Thr Gly Ala Arg Arg Leu Val Glu
            370                 375                 380
Ile Ile Phe Leu Gly Ser Arg Pro Arg Thr Ser Gly Pro Leu Cys Arg
385                 390                 395                 400
Thr Arg Arg Leu Ser Arg Arg Tyr Trp Gln Met Arg Pro Leu Phe Gln
                405                 410                 415
Gln Leu Leu Val Asn His Ala Glu Cys Gln Tyr Val Arg Leu Leu Arg
                420                 425                 430
Ser His Cys Arg Phe Arg Thr Ala Asn Gln Gln Val Thr Asp Ala Leu
            435                 440                 445
```

```
Asn Thr Ser Pro Pro His Leu Met Asp Leu Leu Arg Leu His Ser Ser
    450                 455                 460

Pro Trp Gln Val Tyr Gly Phe Leu Arg Ala Cys Leu Arg Lys Leu Val
465                 470                 475                 480

Pro Ala Gly Leu Trp Gly Thr Arg His Asn Glu Arg Arg Phe Phe Lys
                485                 490                 495

Asn Val Lys Lys Phe Ile Ser Leu Gly Lys Tyr Gly Lys Leu Ser Leu
            500                 505                 510

Gln Glu Leu Met Trp Lys Met Lys Val Glu Asp Cys His Trp Leu Arg
        515                 520                 525

Ser Ser Pro Gly Lys Asp Arg Val Pro Ala Ala Glu His Arg Leu Arg
    530                 535                 540

Glu Arg Ile Leu Ala Met Phe Leu Phe Trp Leu Met Asp Thr Tyr Val
545                 550                 555                 560

Val Gln Leu Leu Arg Ser Phe Phe Tyr Ile Thr Glu Thr Thr Phe Gln
                565                 570                 575

Lys Asn Arg Leu Phe Phe Tyr Arg Lys Ser Val Trp Ser Lys Leu Gln
            580                 585                 590

Ser Ile Gly Val Arg Gln His Leu Glu Arg Val Arg Leu Arg Glu Leu
        595                 600                 605

Ser Gln Glu Glu Val Arg His His Gln Asp Thr Trp Leu Ala Met Pro
    610                 615                 620

Ile Cys Arg Leu Arg Phe Ile Pro Lys Pro Asn Gly Leu Arg Pro Ile
625                 630                 635                 640

Val Asn Met Ser Tyr Ser Met Gly Thr Arg Ala Phe Gly Lys Arg Lys
                645                 650                 655

Gln Ala Gln His Phe Thr Gln Arg Leu Lys Thr Leu Phe Ser Val Leu
            660                 665                 670

Asn Tyr Glu Arg Thr Lys His Pro Asn Leu Met Gly Ala Ser Val Leu
        675                 680                 685

Gly Met Asn Asp Ile Tyr Arg Thr Trp Arg Ala Phe Val Leu Arg Val
    690                 695                 700

Arg Ala Leu Asp Gln Thr Pro Arg Met Tyr Phe Val Lys Ala Asp Val
705                 710                 715                 720

Thr Gly Ala Tyr Asp Ala Ile Pro Gln Asp Lys Leu Val Glu Val Val
                725                 730                 735

Ala Asn Met Ile Arg His Ser Glu Ser Thr Tyr Cys Ile Arg Gln Tyr
            740                 745                 750

Ala Val Val Gln Arg Asp Ser Gln Gly Gln Val His Lys Ser Phe Arg
        755                 760                 765

Arg Gln Val Ser Thr Leu Ser Asp Leu Gln Pro Tyr Met Gly Gln Phe
    770                 775                 780

Leu Lys His Leu Gln Asp Ser Asp Ala Ser Ala Leu Arg Asn Ser Val
785                 790                 795                 800

Val Ile Glu Gln Ser Ile Ser Met Asn Glu Ser Ser Ser Ser Leu Phe
                805                 810                 815

Asp Phe Phe Leu His Phe Val Arg His Ser Val Val Lys Ile Gly Gly
            820                 825                 830

Arg Cys Tyr Val Gln Cys Gln Gly Ile Pro Gln Gly Ser Ser Leu Ser
        835                 840                 845

Thr Leu Leu Cys Ser Leu Cys Phe Gly Asp Met Glu Asn Lys Leu Phe
    850                 855                 860
```

```
Ala Glu Val Gln Gln Asp Gly Leu Leu Leu Arg Phe Val Ala Ala Phe
865                 870                 875                 880

Leu Leu Val Thr Pro His Leu Asp Gln Ala Lys Ala Phe Leu Ser Thr
                885                 890                 895

Leu Val His Gly Val Pro Glu Tyr Gly Cys Met Ile Asn Leu Gln Lys
            900                 905                 910

Thr Val Asn Phe Pro Val Glu Pro Gly Thr Leu Gly Gly Ala Ala
        915                 920                 925

Pro His Gln Leu Pro Ala His Cys Leu Phe Pro Trp Cys Gly Leu Leu
    930                 935                 940

Leu Asp Thr Gln Thr Leu Glu Val Phe Cys Asp Tyr Ser Gly Tyr Ala
945                 950                 955                 960

Arg Thr Ser Ile Lys Thr Ser Leu Thr Phe Gln Ser Val Phe Lys Ala
                965                 970                 975

Gly Lys Thr Met Arg Tyr Lys Leu Leu Ser Val Leu Arg Leu Lys Cys
            980                 985                 990

His Gly Leu Phe Leu Asp Leu Gln  Val Asn Ser Leu Gln  Thr Val Cys
        995                 1000                1005

Ile Asn  Ile Tyr Lys Ile Phe  Leu Leu Gln Ala Tyr  Arg Phe His
1010                 1015                 1020

Ala Cys  Val Ile Gln Leu Pro  Phe Asp Gln His Val  Arg Lys Asn
    1025                 1030                 1035

Leu Ala  Phe Phe Leu Gly Ile  Ile Ser Asn Gln Ala  Ser Cys Cys
    1040                 1045                 1050

Tyr Ala  Ile Leu Lys Val Lys  Asn Pro Gly Met Thr  Leu Lys Ala
    1055                 1060                 1065

Lys Gly  Ser Phe Pro Pro Glu  Ala Ala Arg Trp Leu  Cys Tyr Gln
    1070                 1075                 1080

Ala Phe  Leu Leu Lys Leu Ala  Ala His Ser Val Thr  Tyr Lys Cys
    1085                 1090                 1095

Leu Leu  Gly Pro Leu Arg Thr  Ala Gln Lys Gln Leu  Cys Arg Lys
    1100                 1105                 1110

Leu Pro  Glu Ala Thr Met Thr  Ile Leu Lys Thr Ala  Ala Asp Pro
    1115                 1120                 1125

Ala Leu  Ser Thr Asp Phe Gln  Thr Ile Leu Asp
    1130                 1135

<210> SEQ ID NO 51
<211> LENGTH: 3363
<212> TYPE: DNA
<213> ORGANISM: Artificial Sequence
<220> FEATURE:
<223> OTHER INFORMATION: Synthetic Consensus mTERT nucleic acid sequence
      (pgx1418)

<400> SEQUENCE: 51
ccaagagccc ccaggtgccc tgctgtgagg tcactgctcc gaagcaggta cagagaagtg      60
tggcccctgg ccacattcgt caggagactg ggacctgaag ggcggcgcct ggtgcagcca     120
ggtgacccca aggtgtttag aactctggtc gctcagtgcc tggtgtgcgt gccatggggg     180
tctcagcccc ctccagcaga tctgagtttc caccaggtga gctccctgaa ggagctcgtc     240
gcccgagtgg tccagaggct gtgcgagaga ggcgaacgga acgtgctggc tttcggtttt     300
gcactgctca atgagcccg cggcggaccc cctatggctt tcaccacatc tgtgaggagt     360
tacctgccca actctgtgac cgagagtctg agagtctcag gagcttggat gctgctcctg     420
```

| | |
|---|---|
| agccgggtgg gggacgatct cctggtctac ctcctggctc attgcgcact gtatctcctg | 480 |
| gtgccaccct catgcgccta ccaggtctgt ggaagcccac tgtatcagat ctgtgccact | 540 |
| accgacacct ggccaagcgt gagcgccagc taccgaccta cccgaccagt cggacggaac | 600 |
| ttcacaaatc tggggtccct ccaccagatt aagaattcta gtcatcagga ggcccctaaa | 660 |
| ccactcgctc tgccctccag agggacaaag cggcacctct ctctgacctc acatctgtg | 720 |
| cctagtgcca agaaagctcg atgctatccc gcccctaggg tcgaaaaggg tcctcatcgc | 780 |
| caggtggtcc caacaccctc tggcaaaact tgggtgccta gcccagcaag gtccccagag | 840 |
| gtccctactg ccgaaaagga cctgtcaagc aagggtaaag ctagcgatct cagtctgtca | 900 |
| ggcagcgtgt gctgtaagca caaaccatcc tctacctcac tcctgagccc tccaaggcag | 960 |
| aacgccttcc agctgagacc ctttactgag acccggcatt tcctgtacag ccgcgggggt | 1020 |
| ggccaggaac gactgaatcc ttcctttctc ctgaacaatc tgcagccatc tctcaccggc | 1080 |
| gctcgaaggc tggtggagat cattttcctc ggttcccggc cacgcacatc tggacctctg | 1140 |
| tgcagaacta cggctctc ccgccgatac tggcagatgc ggccactgtt ccagcagctc | 1200 |
| ctggtgaacc acgccgaatg ccagtatgtc aggctcctga gatctcattg taggttcagg | 1260 |
| actgcaaacc agcaggtgac cgacgccctg aatacaagcc ctccccacct gatggatctc | 1320 |
| ctgcgcctcc atagttcacc atggcaggtg tacggattcc tgcgagcttg cctgcgaaag | 1380 |
| ctcgtcccag caggtctgtg ggcacaagg cacaacgaga ggagattctt taaaaacgtg | 1440 |
| aagaagttca tctcactggg aaagtatggg aaactcagcc tgcaggagct gatgtggaag | 1500 |
| atgaaagtgg aagactgtca ctggctgagg agctccccag gcaaggatag agtgcccgcc | 1560 |
| gctgagcata gactgcggga acgcatcctc gccatgttcc tgttttggct catggacaca | 1620 |
| tacgtggtcc agctcctgcg cagcttcttt tatattactg agacaacttt ccagaagaac | 1680 |
| aggctgttct tttacagaaa gtccgtgtgg tctaaactgc agtctatcgg ggtgagacag | 1740 |
| cacctggagc gagtcaggct gagagaactc agtcaggagg aagtgcggca ccatcaggat | 1800 |
| acatggctgg ccatgcctat ctgccggctg cgcttcattc ccaagcctaa cggcctgagg | 1860 |
| ccaattgtga atatgtccta ttctatggga actcgggctt tgggaagcg caaacaggca | 1920 |
| cagcacttca ctcagcgcct gaagaccctc tttagcgtgc tgaactacga gaggactaaa | 1980 |
| catcccaatc tgatgggtgc ttccgtgctc ggcatgaacg acatctatcg aacctggcga | 2040 |
| gccttcgtgc tgcgagtcag ggctctcgac cagaccccta gaatgtactt tgtgaaggcc | 2100 |
| gatgtcacag gagcatatga cgccattcca caggataaac tggtggaggt ggtcgctaat | 2160 |
| atgatccggc acagtgaatc aacctactgt attcggcagt atgcagtggt ccagcgagac | 2220 |
| agccagggac aggtgcataa gtccttccgg cgccaggtca gtacactgtc agatctccag | 2280 |
| ccctacatgg gacagtttct gaaacacctc caggacagcg atgcctccgc tctgagaaac | 2340 |
| agcgtggtca tcgagcagag catttccatg aatgaatcta gttcaagcct gttcgacttc | 2400 |
| tttctccact tgtgcgcca ttccgtggtc aagatcggag ggcgatgcta tgtccagtgt | 2460 |
| cagggtattc ctcagggctc ctctctgagt accctcctgt gctcactgtg cttcggagac | 2520 |
| atggagaaca agctgtttgc tgaagtgcag caggatgggc tcctgctccg gttcgtggca | 2580 |
| gcctttctgc tcgtcactcc ccacctggat caggcaaagg ccttcctgtc caccctcgtg | 2640 |
| catggagtcc ctgagtacgg gtgcatgatc aacctgcaga aaactgtggt caattttcca | 2700 |
| gtggaaccag gcaccctggg tggcgctgca cctcaccagc tgccagccca ttgcctcttc | 2760 |
| ccttggtgtg gtctgctcct ggacacacag actctggagg tgttttgtga ttactccggc | 2820 |

```
tatgccagga cctctatcaa gactagtctg accttccaga gcgtgttcaa ggctggaaaa   2880
acaatgcgat acaagctcct gtcagtgctc aggctgaaat gccacgggct cttcctggac   2940
ctccaggtga actctctgca gaccgtctgt atcaatatct acaagatctt cctcctgcag   3000
 
gcatatagat ttcacgcctg cgtgattcag ctgcctttcg atcagcatgt ccggaaaaac   3060
ctggccttct ttctcggaat catttcaaat caggctagct gctgttatgc aatcctgaag   3120
gtgaaaaacc caggaatgac actgaaggca aaagggtcct tcccacccga ggccgctaga   3180
tggctgtgct accaggcctt tctcctgaag ctggcagccc actctgtgac atataaatgc   3240
ctcctgggcc ctctgagaac tgcacagaag cagctgtgcc ggaaactccc agaagccacc   3300
atgacaatcc tgaagaccgc tgcagacccc gctctctcca ctgatttcca gaccattctc   3360
gac                                                                 3363
```

<210> SEQ ID NO 52
<211> LENGTH: 1121
<212> TYPE: PRT
<213> ORGANISM: Artificial Sequence
<220> FEATURE:
<223> OTHER INFORMATION: Synthetic Consensus mTERT amino acid sequence (pgx1418)

<400> SEQUENCE: 52

```
Pro Arg Ala Pro Arg Cys Pro Ala Val Arg Ser Leu Leu Arg Ser Arg
1               5                   10                  15

Tyr Arg Glu Val Trp Pro Leu Ala Thr Phe Val Arg Arg Leu Gly Pro
            20                  25                  30

Glu Gly Arg Arg Leu Val Gln Pro Gly Asp Pro Lys Val Phe Arg Thr
        35                  40                  45

Leu Val Ala Gln Cys Leu Val Cys Val Pro Trp Gly Ser Gln Pro Pro
    50                  55                  60

Pro Ala Asp Leu Ser Phe His Gln Val Ser Ser Leu Lys Glu Leu Val
65                  70                  75                  80

Ala Arg Val Val Gln Arg Leu Cys Glu Arg Gly Glu Arg Asn Val Leu
                85                  90                  95

Ala Phe Gly Phe Ala Leu Leu Asn Gly Ala Arg Gly Gly Pro Pro Met
            100                 105                 110

Ala Phe Thr Thr Ser Val Arg Ser Tyr Leu Pro Asn Ser Val Thr Glu
        115                 120                 125

Ser Leu Arg Val Ser Gly Ala Trp Met Leu Leu Leu Ser Arg Val Gly
    130                 135                 140

Asp Asp Leu Leu Val Tyr Leu Leu Ala His Cys Ala Leu Tyr Leu Leu
145                 150                 155                 160

Val Pro Pro Ser Cys Ala Tyr Gln Val Cys Gly Ser Pro Leu Tyr Gln
                165                 170                 175

Ile Cys Ala Thr Thr Asp Thr Trp Pro Ser Val Ser Ala Ser Tyr Arg
            180                 185                 190

Pro Thr Arg Pro Val Gly Arg Asn Phe Thr Asn Leu Gly Ser Leu His
        195                 200                 205

Gln Ile Lys Asn Ser Ser His Gln Glu Ala Pro Lys Pro Leu Ala Leu
    210                 215                 220

Pro Ser Arg Gly Thr Lys Arg His Leu Ser Leu Thr Ser Thr Ser Val
225                 230                 235                 240

Pro Ser Ala Lys Lys Ala Arg Cys Tyr Pro Ala Pro Arg Val Glu Lys
                245                 250                 255
```

```
Gly Pro His Arg Gln Val Val Pro Thr Pro Ser Gly Lys Thr Trp Val
            260                 265                 270

Pro Ser Pro Ala Arg Ser Pro Glu Val Pro Thr Ala Glu Lys Asp Leu
        275                 280                 285

Ser Ser Lys Gly Lys Ala Ser Asp Leu Ser Leu Ser Gly Ser Val Cys
    290                 295                 300

Cys Lys His Lys Pro Ser Ser Thr Ser Leu Leu Ser Pro Pro Arg Gln
305                 310                 315                 320

Asn Ala Phe Gln Leu Arg Pro Phe Thr Glu Thr Arg His Phe Leu Tyr
                325                 330                 335

Ser Arg Gly Gly Gly Gln Glu Arg Leu Asn Pro Ser Phe Leu Leu Asn
            340                 345                 350

Asn Leu Gln Pro Ser Leu Thr Gly Ala Arg Arg Leu Val Glu Ile Ile
        355                 360                 365

Phe Leu Gly Ser Arg Pro Arg Thr Ser Gly Pro Leu Cys Arg Thr Arg
    370                 375                 380

Arg Leu Ser Arg Arg Tyr Trp Gln Met Arg Pro Leu Phe Gln Gln Leu
385                 390                 395                 400

Leu Val Asn His Ala Glu Cys Gln Tyr Val Arg Leu Leu Arg Ser His
                405                 410                 415

Cys Arg Phe Arg Thr Ala Asn Gln Gln Val Thr Asp Ala Leu Asn Thr
            420                 425                 430

Ser Pro Pro His Leu Met Asp Leu Leu Arg Leu His Ser Ser Pro Trp
        435                 440                 445

Gln Val Tyr Gly Phe Leu Arg Ala Cys Leu Arg Lys Leu Val Pro Ala
    450                 455                 460

Gly Leu Trp Gly Thr Arg His Asn Glu Arg Arg Phe Phe Lys Asn Val
465                 470                 475                 480

Lys Lys Phe Ile Ser Leu Gly Lys Tyr Gly Lys Leu Ser Leu Gln Glu
                485                 490                 495

Leu Met Trp Lys Met Lys Val Glu Asp Cys His Trp Leu Arg Ser Ser
            500                 505                 510

Pro Gly Lys Asp Arg Val Pro Ala Ala Glu His Arg Leu Arg Glu Arg
        515                 520                 525

Ile Leu Ala Met Phe Leu Phe Trp Leu Met Asp Thr Tyr Val Val Gln
    530                 535                 540

Leu Leu Arg Ser Phe Phe Tyr Ile Thr Glu Thr Thr Phe Gln Lys Asn
545                 550                 555                 560

Arg Leu Phe Phe Tyr Arg Lys Ser Val Trp Ser Lys Leu Gln Ser Ile
                565                 570                 575

Gly Val Arg Gln His Leu Glu Arg Val Arg Leu Arg Glu Leu Ser Gln
            580                 585                 590

Glu Glu Val Arg His His Gln Asp Thr Trp Leu Ala Met Pro Ile Cys
        595                 600                 605

Arg Leu Arg Phe Ile Pro Lys Pro Asn Gly Leu Arg Pro Ile Val Asn
    610                 615                 620

Met Ser Tyr Ser Met Gly Thr Arg Ala Phe Gly Lys Arg Lys Gln Ala
625                 630                 635                 640

Gln His Phe Thr Gln Arg Leu Lys Thr Leu Phe Ser Val Leu Asn Tyr
                645                 650                 655

Glu Arg Thr Lys His Pro Asn Leu Met Gly Ala Ser Val Leu Gly Met
            660                 665                 670
```

```
Asn Asp Ile Tyr Arg Thr Trp Arg Ala Phe Val Leu Arg Val Arg Ala
            675                 680                 685

Leu Asp Gln Thr Pro Arg Met Tyr Phe Val Lys Ala Asp Val Thr Gly
    690                 695                 700

Ala Tyr Asp Ala Ile Pro Gln Asp Lys Leu Val Glu Val Val Ala Asn
705                 710                 715                 720

Met Ile Arg His Ser Glu Ser Thr Tyr Cys Ile Arg Gln Tyr Ala Val
            725                 730                 735

Val Gln Arg Asp Ser Gln Gly Gln Val His Lys Ser Phe Arg Arg Gln
            740                 745                 750

Val Ser Thr Leu Ser Asp Leu Gln Pro Tyr Met Gly Gln Phe Leu Lys
            755                 760                 765

His Leu Gln Asp Ser Asp Ala Ser Ala Leu Arg Asn Ser Val Val Ile
            770                 775                 780

Glu Gln Ser Ile Ser Met Asn Glu Ser Ser Ser Leu Phe Asp Phe
785                 790                 795                 800

Phe Leu His Phe Val Arg His Ser Val Val Lys Ile Gly Gly Arg Cys
                805                 810                 815

Tyr Val Gln Cys Gln Gly Ile Pro Gln Gly Ser Ser Leu Ser Thr Leu
            820                 825                 830

Leu Cys Ser Leu Cys Phe Gly Asp Met Glu Asn Lys Leu Phe Ala Glu
            835                 840                 845

Val Gln Gln Asp Gly Leu Leu Leu Arg Phe Val Ala Ala Phe Leu Leu
            850                 855                 860

Val Thr Pro His Leu Asp Gln Ala Lys Ala Phe Leu Ser Thr Leu Val
865                 870                 875                 880

His Gly Val Pro Glu Tyr Gly Cys Met Ile Asn Leu Gln Lys Thr Val
                885                 890                 895

Val Asn Phe Pro Val Glu Pro Gly Thr Leu Gly Gly Ala Ala Pro His
                900                 905                 910

Gln Leu Pro Ala His Cys Leu Phe Pro Trp Cys Gly Leu Leu Leu Asp
            915                 920                 925

Thr Gln Thr Leu Glu Val Phe Cys Asp Tyr Ser Gly Tyr Ala Arg Thr
            930                 935                 940

Ser Ile Lys Thr Ser Leu Thr Phe Gln Ser Val Phe Lys Ala Gly Lys
945                 950                 955                 960

Thr Met Arg Tyr Lys Leu Leu Ser Val Leu Arg Leu Lys Cys His Gly
                965                 970                 975

Leu Phe Leu Asp Leu Gln Val Asn Ser Leu Gln Thr Val Cys Ile Asn
            980                 985                 990

Ile Tyr Lys Ile Phe Leu Leu Gln Ala Tyr Arg Phe His Ala Cys Val
            995                 1000                1005

Ile Gln Leu Pro Phe Asp Gln His Val Arg Lys Asn Leu Ala Phe
    1010            1015                1020

Phe Leu Gly Ile Ile Ser Asn Gln Ala Ser Cys Cys Tyr Ala Ile
    1025            1030                1035

Leu Lys Val Lys Asn Pro Gly Met Thr Leu Lys Ala Lys Gly Ser
    1040            1045                1050

Phe Pro Pro Glu Ala Ala Arg Trp Leu Cys Tyr Gln Ala Phe Leu
    1055            1060                1065

Leu Lys Leu Ala Ala His Ser Val Thr Tyr Lys Cys Leu Leu Gly
    1070            1075                1080

Pro Leu Arg Thr Ala Gln Lys Gln Leu Cys Arg Lys Leu Pro Glu
```

```
                1085              1090               1095
Ala Thr Met Thr Ile Leu Lys  Thr Ala Ala Asp Pro  Ala Leu Ser
           1100              1105              1110

Thr Asp Phe Gln Thr Ile Leu  Asp
           1115              1120

<210> SEQ ID NO 53
<211> LENGTH: 3447
<212> TYPE: DNA
<213> ORGANISM: Artificial Sequence
<220> FEATURE:
<223> OTHER INFORMATION: Synthetic Consensus rhTERT nucleic acid
      sequence operably linked to IgE (pGX1473)

<400> SEQUENCE: 53
atggactgga cctggattct gttcctcgtc gccgccgcaa ctagagtgca tagcccaaga      60
gccccacgct gtagagctgt gagagccctg ctgaggtcca gatacaggga ggtgctgcca     120
ctggccacct tcgtgaggag actgggacct gagggccggc gcctggtgca gaggggcgac     180
cccgcagcct ccgcgccct ggtggcccag tgcctggtgt gcgtgccatg ggacgccagg      240 cccctccag cagcaccatc cttcagacag gtgagctgcc tgaaggagct ggtgccagg      300 gtggtgcaga gactgtgcga gaggggcgcc aggaacgtgc tggccttcgg cttcgcactg     360
ctggacggag ccaggggcgg gcccctgag gccttcacca cctccgtgag aagctacctg      420
cctaacaccg tgaccgacac cctgaggggc tccggagcat ggggcctgct gctgaggaga     480 gtggggacg acgtgctggt gcacctgctg caaggtgcg ccctgtacgt gctggtggca      540
ccaagctgcg cataccaggt gtgcggccca ccctgtacg agctgtgcgc agcaacccag     600
gccagaccag cccctcacgc atccggaacc aggagggac tgggctgcga gagggcctgg     660
aacggaagcg tgagagaggc aggagtgcca ctggactgc ctgcaccagg ggccaggaga     720
cggcgcgggt ctgccggacg gtcccctcca ctggcaaagc gccctaggag aggagccgca     780
ccagagcctg agaggacccc agtggggcag ggaagctggg cacaccctgg aaggaccagg     840
gggccatccg acaggggatt ctgcgtggtg agcccagcca ggcccgcaga ggaggccacc     900
tctctggagg gagccctgtc cggaaccagg cactctcacc catccgtggg aagacagcac     960
cacgcaggcc ctcccagcac ctctaggcca ccctcccat gggacacccc atgcccactg    1020
gtgtacgcag agacaaagca cttcctgtac tgcagcggga caaggagag actgcggcca    1080 tctttcctgc tgtccagcct gcgccctcc ctgaccggag cacggcgcct ggtggagaca    1140
atcttcctgg gaagcaggcc ttggatgcca ggaaccccca ggaggcctcc caggctgcca    1200
cagaggtact ggcagatgcg ccctctgttc ctggagctgc tgggaaaacca cgcaaggtgc    1260 ccatacggag ccctgctgcg gacccactgc cctctgaggg cagcagcaac ccagcagca    1320 ggcgtgtgcg ccagggagaa gcccaggggg agcgtggccg cccctgagga ggaggacacc    1380
gacccacggc gcctggtgca gctgctgaga cagcactctt ccccctggca ggtgtacgga    1440
ttcctgaggg catgcctgag gagactggtg ccccctggcc tgtggggctc caggcacaac    1500
gagcggcgct tcctgcgcaa caccaagaag ttcatctctc tgggcaagca cgccaagctg    1560
tccctgcagg agctgacctg gaagatgtct gtgagggact cgcctggct gaggagatcc    1620 cccggagtgg gatgcgtgcc tgcagcagag cacaggctga gggaggagat cctggccaag    1680
ttcctgcact ggctgatggg ggtgtacgtg gtggagctgc tgaggtcttt cttctacgtg    1740
accgagacaa ccttccagaa gaactacctg ttcttctacc gcaagagcgt gtggtctaag    1800
```

|   |   |   |
|---|---|---|
| ctgcagtcta tcggaatcag gcagcacctg aagagggtgc agctgagaga gctgtccgag | 1860 |
| gccgaggtga cacagcacag ggaggcccgc cccgccctgc tgacctccag actgcggttc | 1920 |
| ctgcctaagc cagacggcct gaggcccatc gtgaacatgg actacgtggt gggagcacgg | 1980 |
| accttccgga gggagaagag ggccgagaga ctgaccagcc gcgtgaagac cctgttctct | 2040 |
| gtgctgaact acgagagggc aaggaggccc ggactgctgg agccagcgt gctgggcctg | 2100 |
| gacgacatcc acagggcatg gagggccttc gtgctgcgcg tgagggcaca ggacccaccc | 2160 |
| cctgagctgt acttcgtgaa ggtggcagtg accggagcat acgacaccat cccacaggac | 2220 |
| aggctgaccg aggtcatcgc ctctatcatc aagcctcaga cacctactg cgtgcggcgc | 2280 |
| tacgcagtgg tgcagaaggc agcacacgga cacgtgagga agaccttcaa gaagcacgtg | 2340 |
| tccaccctga ccgacctgca gccctacatg agacagttcg tggcccacct gcaggagaca | 2400 |
| tcctccctga gggacgcagt ggtcatcgag cagtccagct ctctgaacga ggcctccagc | 2460 |
| ggcctgttcg acgtgttcct gaggttcgtg tgcaaccacg tggtgagaat cggaggcaag | 2520 |
| agctacgtgc agtgccaggg catccccag ggctccatcc tgagcaccct gctgtgctct | 2580 |
| ctgtgctacg ggacatggaa gaacaagctg ttcgccggaa tcaggagaga cggcctgctg | 2640 |
| ctgagactgg tggcagcctt cctgctggtg accctcacc tgacccacgc aaaggccttc | 2700 |
| ctgcggaccc tggtgcgcgg ggtgccagag tacggatgcg tggtgaacct gcggaagacc | 2760 |
| gtggtgaact tccagtggaa ggacgaggcc ctgggcggcg ccgccttcgt gcagctgcca | 2820 |
| gcacacgggc tgttcccatg gtgcggactg ctgctggaca ccagaaccct ggaggtgcag | 2880 |
| tccgactact cttcctacgc caggaccagc atcagagcct ctctgacctt caacaggggc | 2940 |
| ttcaaggccg ggagaaacat gcggcgcaag ctgttcgggg tgctgaggct gaagtgccac | 3000 |
| agcctgttcc tgtacctgca ggtgaactct ctgcagaccg tgtgcactaa cgtgtacaag | 3060 |
| atcttcctgc tgcaggccta cagattccac gcctgcgtgc tgcagctgcc tttcaaccag | 3120 |
| caagtgtgga gaacccagc cttcttcctg agagtgatct ccgacaccgc cagcctgtgc | 3180 |
| tactctatcc tgaaggcaaa gaacgcagga atgagcctgg agcaaaggg agcagcagga | 3240 |
| ccactgcctt ctgaggcagt gcagtggctg tgccaccagg ccttcctgct gaagctgacc | 3300 |
| agacaccggg tgacctacgt gcctctgctg ggctccctga ggaccgcaca gacccagctg | 3360 |
| agccgcaagc tgccagggac caccctggcc gctctggaag ccgccgccaa ccccgccctc | 3420 |
| ccatccgatt tcaaaaccat tctggac | 3447 |

<210> SEQ ID NO 54
<211> LENGTH: 1149
<212> TYPE: PRT
<213> ORGANISM: Artificial Sequence
<220> FEATURE:
<223> OTHER INFORMATION: Synthetic Consensus rhTERT amino acid sequence
      operably linked to IgE (pGX1473)

<400> SEQUENCE: 54

Met Asp Trp Thr Trp Ile Leu Phe Leu Val Ala Ala Thr Arg Val
1               5                   10                  15

His Ser Pro Arg Ala Pro Arg Cys Arg Ala Val Arg Ala Leu Leu Arg
                20                  25                  30

Ser Arg Tyr Arg Glu Val Leu Pro Leu Ala Thr Phe Val Arg Arg Leu
            35                  40                  45

Gly Pro Glu Gly Arg Arg Leu Val Gln Arg Gly Asp Pro Ala Ala Phe
        50                  55                  60

-continued

```
Arg Ala Leu Val Ala Gln Cys Leu Val Cys Val Pro Trp Asp Ala Arg
 65                  70                  75                  80

Pro Pro Pro Ala Ala Pro Ser Phe Arg Gln Val Ser Cys Leu Lys Glu
                 85                  90                  95

Leu Val Ala Arg Val Val Gln Arg Leu Cys Glu Arg Gly Ala Arg Asn
            100                 105                 110

Val Leu Ala Phe Gly Phe Ala Leu Leu Asp Gly Ala Arg Gly Gly Pro
            115                 120                 125

Pro Glu Ala Phe Thr Thr Ser Val Arg Ser Tyr Leu Pro Asn Thr Val
            130                 135                 140

Thr Asp Thr Leu Arg Gly Ser Gly Ala Trp Gly Leu Leu Arg Arg
145                 150                 155                 160

Val Gly Asp Asp Val Leu Val His Leu Leu Ala Arg Cys Ala Leu Tyr
                165                 170                 175

Val Leu Val Ala Pro Ser Cys Ala Tyr Gln Val Cys Gly Pro Pro Leu
                180                 185                 190

Tyr Glu Leu Cys Ala Ala Thr Gln Ala Arg Pro Ala Pro His Ala Ser
            195                 200                 205

Gly Thr Arg Arg Gly Leu Gly Cys Glu Arg Ala Trp Asn Gly Ser Val
210                 215                 220

Arg Glu Ala Gly Val Pro Leu Gly Leu Pro Ala Pro Gly Ala Arg Arg
225                 230                 235                 240

Arg Arg Gly Ser Ala Gly Arg Ser Pro Pro Leu Ala Lys Arg Pro Arg
                245                 250                 255

Arg Gly Ala Ala Pro Glu Pro Glu Arg Thr Pro Val Gly Gln Gly Ser
            260                 265                 270

Trp Ala His Pro Gly Arg Thr Arg Gly Pro Ser Asp Arg Gly Phe Cys
            275                 280                 285

Val Val Ser Pro Ala Arg Pro Ala Glu Glu Ala Thr Ser Leu Glu Gly
            290                 295                 300

Ala Leu Ser Gly Thr Arg His Ser His Pro Ser Val Gly Arg Gln His
305                 310                 315                 320

His Ala Gly Pro Pro Ser Thr Ser Arg Pro Pro Ser Pro Trp Asp Thr
                325                 330                 335

Pro Cys Pro Leu Val Tyr Ala Glu Thr Lys His Phe Leu Tyr Cys Ser
            340                 345                 350

Gly Asp Lys Glu Arg Leu Arg Pro Ser Phe Leu Leu Ser Ser Leu Arg
            355                 360                 365

Pro Ser Leu Thr Gly Ala Arg Arg Leu Val Glu Thr Ile Phe Leu Gly
            370                 375                 380

Ser Arg Pro Trp Met Pro Gly Thr Pro Arg Arg Pro Arg Leu Pro
385                 390                 395                 400

Gln Arg Tyr Trp Gln Met Arg Pro Leu Phe Leu Glu Leu Leu Gly Asn
            405                 410                 415

His Ala Arg Cys Pro Tyr Gly Ala Leu Leu Arg Thr His Cys Pro Leu
            420                 425                 430

Arg Ala Ala Thr Pro Ala Ala Gly Val Cys Ala Arg Glu Lys Pro
            435                 440                 445

Gln Gly Ser Val Ala Ala Pro Glu Glu Asp Thr Asp Pro Arg Arg
            450                 455                 460

Leu Val Gln Leu Leu Arg Gln His Ser Ser Pro Trp Gln Val Tyr Gly
465                 470                 475                 480

Phe Leu Arg Ala Cys Leu Arg Arg Leu Val Pro Pro Gly Leu Trp Gly
```

```
                485                 490                 495
Ser Arg His Asn Glu Arg Arg Phe Leu Arg Asn Thr Lys Lys Phe Ile
                500                 505                 510

Ser Leu Gly Lys His Ala Lys Leu Ser Leu Gln Glu Leu Thr Trp Lys
                515                 520                 525

Met Ser Val Arg Asp Cys Ala Trp Leu Arg Arg Ser Pro Gly Val Gly
                530                 535                 540

Cys Val Pro Ala Ala Glu His Arg Leu Arg Glu Glu Ile Leu Ala Lys
545                 550                 555                 560

Phe Leu His Trp Leu Met Gly Val Tyr Val Glu Leu Leu Arg Ser
                565                 570                 575

Phe Phe Tyr Val Thr Glu Thr Thr Phe Gln Lys Asn Tyr Leu Phe Phe
                580                 585                 590

Tyr Arg Lys Ser Val Trp Ser Lys Leu Gln Ser Ile Gly Ile Arg Gln
                595                 600                 605

His Leu Lys Arg Val Gln Leu Arg Glu Leu Ser Glu Ala Glu Val Arg
                610                 615                 620

Gln His Arg Glu Ala Arg Pro Ala Leu Leu Thr Ser Arg Leu Arg Phe
625                 630                 635                 640

Leu Pro Lys Pro Asp Gly Leu Arg Pro Ile Val Asn Met Asp Tyr Val
                645                 650                 655

Val Gly Ala Arg Thr Phe Arg Arg Glu Lys Arg Ala Glu Arg Leu Thr
                660                 665                 670

Ser Arg Val Lys Thr Leu Phe Ser Val Leu Asn Tyr Glu Arg Ala Arg
                675                 680                 685

Arg Pro Gly Leu Leu Gly Ala Ser Val Leu Gly Leu Asp Asp Ile His
                690                 695                 700

Arg Ala Trp Arg Ala Phe Val Leu Arg Val Arg Ala Gln Asp Pro Pro
705                 710                 715                 720

Pro Glu Leu Tyr Phe Val Lys Val Ala Val Thr Gly Ala Tyr Asp Thr
                725                 730                 735

Ile Pro Gln Asp Arg Leu Thr Glu Val Ile Ala Ser Ile Ile Lys Pro
                740                 745                 750

Gln Asn Thr Tyr Cys Val Arg Arg Tyr Ala Val Val Gln Lys Ala Ala
                755                 760                 765

His Gly His Val Arg Lys Thr Phe Lys Lys His Val Ser Thr Leu Thr
                770                 775                 780

Asp Leu Gln Pro Tyr Met Arg Gln Phe Val Ala His Leu Gln Glu Thr
785                 790                 795                 800

Ser Ser Leu Arg Asp Ala Val Val Ile Glu Gln Ser Ser Ser Leu Asn
                805                 810                 815

Glu Ala Ser Ser Gly Leu Phe Asp Val Phe Leu Arg Phe Val Cys Asn
                820                 825                 830

His Val Val Arg Ile Gly Gly Lys Ser Tyr Val Gln Cys Gln Gly Ile
                835                 840                 845

Pro Gln Gly Ser Ile Leu Ser Thr Leu Leu Cys Ser Leu Cys Tyr Gly
                850                 855                 860

Asp Met Glu Asn Lys Leu Phe Ala Gly Ile Arg Arg Asp Gly Leu Leu
865                 870                 875                 880

Leu Arg Leu Val Ala Ala Phe Leu Leu Val Thr Pro His Leu Thr His
                885                 890                 895

Ala Lys Ala Phe Leu Arg Thr Leu Val Arg Gly Val Pro Glu Tyr Gly
                900                 905                 910
```

```
Cys Val Val Asn Leu Arg Lys Thr Val Val Asn Phe Pro Val Glu Asp
        915                 920                 925

Glu Ala Leu Gly Gly Ala Ala Phe Val Gln Leu Pro Ala His Gly Leu
        930                 935                 940

Phe Pro Trp Cys Gly Leu Leu Leu Asp Thr Arg Thr Leu Glu Val Gln
945                 950                 955                 960

Ser Asp Tyr Ser Ser Tyr Ala Arg Thr Ser Ile Arg Ala Ser Leu Thr
        965                 970                 975

Phe Asn Arg Gly Phe Lys Ala Gly Arg Asn Met Arg Arg Lys Leu Phe
        980                 985                 990

Gly Val Leu Arg Leu Lys Cys His Ser Leu Phe Leu Tyr Leu Gln Val
        995                 1000                1005

Asn Ser Leu Gln Thr Val Cys Thr Asn Val Tyr Lys Ile Phe Leu
    1010                1015                1020

Leu Gln Ala Tyr Arg Phe His Ala Cys Val Leu Gln Leu Pro Phe
    1025                1030                1035

Asn Gln Gln Val Trp Lys Asn Pro Ala Phe Phe Leu Arg Val Ile
    1040                1045                1050

Ser Asp Thr Ala Ser Leu Cys Tyr Ser Ile Leu Lys Ala Lys Asn
    1055                1060                1065

Ala Gly Met Ser Leu Gly Ala Lys Gly Ala Ala Gly Pro Leu Pro
    1070                1075                1080

Ser Glu Ala Val Gln Trp Leu Cys His Gln Ala Phe Leu Leu Lys
    1085                1090                1095

Leu Thr Arg His Arg Val Thr Tyr Val Pro Leu Leu Gly Ser Leu
    1100                1105                1110

Arg Thr Ala Gln Thr Gln Leu Ser Arg Lys Leu Pro Gly Thr Thr
    1115                1120                1125

Leu Ala Ala Leu Glu Ala Ala Asn Pro Ala Leu Pro Ser Asp
    1130                1135                1140

Phe Lys Thr Ile Leu Asp
    1145

<210> SEQ ID NO 55
<211> LENGTH: 3393
<212> TYPE: DNA
<213> ORGANISM: Artificial Sequence
<220> FEATURE:
<223> OTHER INFORMATION: Synthetic Consensus rhTERT nucleic acid
      sequence (pGX1473)

<400> SEQUENCE: 55
ccaagagccc cacgctgtag agctgtgaga gccctgctga ggtccagata cagggaggtg      60
ctgccactgg ccaccttcgt gaggagactg ggacctgagg gccggcgcct ggtgcagagg     120
ggcgaccccg cagccttccg cgccctggtg cccagtgcc tggtgtgcgt gccatgggac      180
gccaggcccc ctccagcagc accatccttc agacaggtga gctgcctgaa ggagctggtg     240
gccagggtgg tgcagagact gtgcgagagg ggcgccagga acgtgctggc cttcggcttc     300
gcactgctgg acggagccag ggcgggccc cctgaggcct tcaccacctc cgtgagaagc      360
tacctgccta acaccgtgac cgacaccctg aggggctccg agcatggggg cctgctgctg     420
aggagagtgg gggacgacgt gctggtgcac ctgctggcaa ggtgcgccct gtacgtgctg     480
gtggcaccaa gctgcgcata ccaggtgtgc ggccccaccc ctgtacgagct gtgcgcagca    540 acccaggcca gaccagcccc tcacgcatcc ggaaccagga ggggactggg ctgcgagagg    600
```

-continued

```
gcctggaacg gaagcgtgag agaggcagga gtgccactgg gactgcctgc accaggggcc      660
aggagacggc gcgggtctgc cggacggtcc cctccactgg caaagcgccc taggagagga      720
gccgcaccag agcctgagag acccccagtg gggcagggaa gctgggcaca ccctggaagg      780
accaggggcc catccgacag gggattctgc gtggtgagcc cagccaggcc cgcagaggag      840
gccacctctc tggagggagc cctgtccgga accaggcact ctcacccatc cgtgggaaga      900
cagcaccacg caggccctcc cagcacctct aggccaccct ccccatggga caccccatgc      960
ccactggtgt acgcagagac aaagcacttc ctgtactgca gcggagacaa ggagagactg     1020
cggccatctt tcctgctgtc cagcctgcgc ccctccctga ccgagcacg cgcctggtg      1080 gagacaatct tcctgggaag caggccttgg atgccaggaa ccccaggag gcctcccagg      1140 ctgccacaga ggtactggca gatgcgccct ctgttcctgg agctgctggg aaaccacgca     1200
aggtgcccat acggagccct gctgcggacc cactgccctc tgagggcagc agcaaccccA     1260
gcagcaggcg tgtgcgccag ggagaagccc aggggagcg tggccgcccc tgaggaggag     1320
gacaccgacc cacggcgcct ggtgcagctg ctgagacagc actcttcccc ctggcaggtg     1380
tacggattcc tgagggcatg cctgaggaga ctggtgcccc ctggcctgtg ggctccagg      1440 cacaacgagc ggcgcttcct gcgcaacacc aagaagttca tctctctggg caagcacgcc     1500
aagctgtccc tgcaggagct gacctggaag atgtctgtga gggactgcgc ctggctgagg     1560 agatccccg gagtgggatg cgtgcctgca gcagagcaca ggctgaggga ggagatcctg     1620
gccaagttcc tgcactggct gatggggtg tacgtggtgg agctgctgag gtctttcttc     1680
tacgtgaccg agacaacctt ccagaagaac tacctgttct ctaccgcaa gagcgtgtgg     1740 tctaagctgc agtctatcgg aatcaggcag cacctgaaga gggtgcagct gagagagctg     1800
tccgaggccg aggtgagaca gcacagggag gcccgccccg ccctgctgac ctccagactg     1860
cggttcctgc ctaagccaga cggcctgagg cccatcgtga acatggacta cgtggtggga     1920
gcacggacct tccggaggga aagagggcc gagagactga ccagccgcgt gaagaccctg     1980
ttctctgtgc tgaactacga gagggcaagg aggcccggac tgctgggagc cagcgtgctg     2040
ggcctggacg acatccacag ggcatggagg gccttcgtgc tgcgcgtgag ggcacaggac     2100
ccaccccctg agctgtactt cgtgaaggtg gcagtgaccg gagcatacga caccatccca     2160
caggacaggc tgaccgaggt catcgcctct atcatcaagc tcagaacac ctactgcgtg     2220 cggcgctacg cagtggtgca gaaggcagca cacggacacg tgaggaagac cttcaagaag     2280
cacgtgtcca ccctgaccga cctgcagccc tacatggaca gttcgtggc ccacctgcag     2340 gagacatcct ccctgaggga cgcagtggtc atcgagcagt ccagctctct gaacgaggcc     2400
tccagcggcc tgttcgacgt gttcctgagg ttcgtgtgca accacgtggt gagaatcgga     2460
ggcaagagct acgtgcagtg ccagggcatc ccccagggct ccatcctgag caccctgctg     2520
tgctctctgt gctacgggga catggagaac aagctgttcg ccggaatcag agagacggc      2580 ctgctgctga gactggtggc agccttcctg ctggtgaccc ctcacctgac ccacgcaaag     2640
gccttcctgc ggaccctggt gcgcggggtg ccagagtacg gatgcgtggt gaacctgcgg     2700
aagaccgtgg tgaacttccc agtggaggac gaggccctgg gcgcgccgc cttcgtgcag     2760 ctgccagcac acgggctgtt cccatggtgc ggactgctgc tggacaccag aaccctggag     2820
gtgcagtccg actactcttc ctacgccagg accagcatca gagcctctct gaccttcaac     2880 agggcttca aggccgggag aaacatgcgg cgcaagctgt cgggtgct gaggctgaag      2940
```

-continued

```
tgccacagcc tgttcctgta cctgcaggtg aactctctgc agaccgtgtg cactaacgtg    3000
tacaagatct tcctgctgca ggcctacaga ttccacgcct gcgtgctgca gctgcctttc    3060
aaccagcaag tgtggaagaa cccagccttc ttcctgagag tgatctccga caccgccagc    3120
ctgtgctact ctatcctgaa ggcaaagaac gcaggaatga gcctgggagc aaagggagca    3180
gcaggaccac tgccttctga ggcagtgcag tggctgtgcc accaggcctt cctgctgaag    3240
ctgaccagac accgggtgac ctacgtgcct ctgctgggct ccctgaggac cgcacagacc    3300
cagctgagcc gcaagctgcc agggaccacc ctggccgctc tggaagccgc cgccaacccc    3360
gccctcccat ccgatttcaa aaccattctg gac                                 3393
```

<210> SEQ ID NO 56
<211> LENGTH: 1131
<212> TYPE: PRT
<213> ORGANISM: Artificial Sequence
<220> FEATURE:
<223> OTHER INFORMATION: Synthetic Consensus rhTERT amino acid sequence (pGX1473)

<400> SEQUENCE: 56

```
Pro Arg Ala Pro Arg Cys Arg Ala Val Arg Ala Leu Leu Arg Ser Arg
1               5                   10                  15

Tyr Arg Glu Val Leu Pro Leu Ala Thr Phe Val Arg Arg Leu Gly Pro
            20                  25                  30

Glu Gly Arg Arg Leu Val Gln Arg Gly Asp Pro Ala Ala Phe Arg Ala
        35                  40                  45

Leu Val Ala Gln Cys Leu Val Cys Val Pro Trp Asp Ala Arg Pro Pro
    50                  55                  60

Pro Ala Ala Pro Ser Phe Arg Gln Val Ser Cys Leu Lys Glu Leu Val
65                  70                  75                  80

Ala Arg Val Val Gln Arg Leu Cys Glu Arg Gly Ala Arg Asn Val Leu
                85                  90                  95

Ala Phe Gly Phe Ala Leu Leu Asp Gly Ala Arg Gly Gly Pro Pro Glu
            100                 105                 110

Ala Phe Thr Thr Ser Val Arg Ser Tyr Leu Pro Asn Thr Val Thr Asp
        115                 120                 125

Thr Leu Arg Gly Ser Gly Ala Trp Gly Leu Leu Leu Arg Arg Val Gly
    130                 135                 140

Asp Asp Val Leu Val His Leu Leu Ala Arg Cys Ala Leu Tyr Val Leu
145                 150                 155                 160

Val Ala Pro Ser Cys Ala Tyr Gln Val Cys Gly Pro Pro Leu Tyr Glu
                165                 170                 175

Leu Cys Ala Ala Thr Gln Ala Arg Pro Ala Pro His Ala Ser Gly Thr
            180                 185                 190

Arg Arg Gly Leu Gly Cys Glu Arg Ala Trp Asn Gly Ser Val Arg Glu
        195                 200                 205

Ala Gly Val Pro Leu Gly Leu Pro Ala Pro Gly Ala Arg Arg Arg Arg
    210                 215                 220

Gly Ser Ala Gly Arg Ser Pro Leu Ala Lys Arg Pro Arg Arg Gly
225                 230                 235                 240

Ala Ala Pro Glu Pro Glu Arg Thr Pro Val Gly Gln Gly Ser Trp Ala
                245                 250                 255

His Pro Gly Arg Thr Arg Gly Pro Ser Asp Arg Gly Phe Cys Val Val
            260                 265                 270

Ser Pro Ala Arg Pro Ala Glu Glu Ala Thr Ser Leu Glu Gly Ala Leu
```

```
            275                 280                 285
Ser Gly Thr Arg His Ser His Pro Ser Val Gly Arg Gln His His Ala
290                 295                 300
Gly Pro Pro Ser Thr Ser Arg Pro Pro Ser Pro Trp Asp Thr Pro Cys
305                 310                 315                 320
Pro Leu Val Tyr Ala Glu Thr Lys His Phe Leu Tyr Cys Ser Gly Asp
                325                 330                 335
Lys Glu Arg Leu Arg Pro Ser Phe Leu Leu Ser Ser Leu Arg Pro Ser
            340                 345                 350
Leu Thr Gly Ala Arg Arg Leu Val Glu Thr Ile Phe Leu Gly Ser Arg
        355                 360                 365
Pro Trp Met Pro Gly Thr Pro Arg Arg Pro Pro Arg Leu Pro Gln Arg
    370                 375                 380
Tyr Trp Gln Met Arg Pro Leu Phe Leu Glu Leu Leu Gly Asn His Ala
385                 390                 395                 400
Arg Cys Pro Tyr Gly Ala Leu Leu Arg Thr His Cys Pro Leu Arg Ala
                405                 410                 415
Ala Ala Thr Pro Ala Ala Gly Val Cys Ala Arg Glu Lys Pro Gln Gly
            420                 425                 430
Ser Val Ala Ala Pro Glu Glu Asp Thr Asp Pro Arg Arg Leu Val
        435                 440                 445
Gln Leu Leu Arg Gln His Ser Ser Pro Trp Gln Val Tyr Gly Phe Leu
    450                 455                 460
Arg Ala Cys Leu Arg Arg Leu Val Pro Pro Gly Leu Trp Gly Ser Arg
465                 470                 475                 480
His Asn Glu Arg Arg Phe Leu Arg Asn Thr Lys Lys Phe Ile Ser Leu
                485                 490                 495
Gly Lys His Ala Lys Leu Ser Leu Gln Glu Leu Thr Trp Lys Met Ser
            500                 505                 510
Val Arg Asp Cys Ala Trp Leu Arg Arg Ser Pro Gly Val Gly Cys Val
        515                 520                 525
Pro Ala Ala Glu His Arg Leu Arg Glu Glu Ile Leu Ala Lys Phe Leu
    530                 535                 540
His Trp Leu Met Gly Val Tyr Val Val Glu Leu Leu Arg Ser Phe Phe
545                 550                 555                 560
Tyr Val Thr Glu Thr Thr Phe Gln Lys Asn Tyr Leu Phe Phe Tyr Arg
                565                 570                 575
Lys Ser Val Trp Ser Lys Leu Gln Ser Ile Gly Ile Arg Gln His Leu
            580                 585                 590
Lys Arg Val Gln Leu Arg Glu Leu Ser Glu Ala Glu Val Arg Gln His
        595                 600                 605
Arg Glu Ala Arg Pro Ala Leu Leu Thr Ser Arg Leu Arg Phe Leu Pro
    610                 615                 620
Lys Pro Asp Gly Leu Arg Pro Ile Val Asn Met Asp Tyr Val Val Gly
625                 630                 635                 640
Ala Arg Thr Phe Arg Arg Glu Lys Arg Ala Glu Arg Leu Thr Ser Arg
                645                 650                 655
Val Lys Thr Leu Phe Ser Val Leu Asn Tyr Glu Arg Ala Arg Arg Pro
            660                 665                 670
Gly Leu Leu Gly Ala Ser Val Leu Gly Leu Asp Asp Ile His Arg Ala
        675                 680                 685
Trp Arg Ala Phe Val Leu Arg Val Arg Ala Gln Asp Pro Pro Pro Glu
    690                 695                 700
```

```
Leu Tyr Phe Val Lys Val Ala Val Thr Gly Ala Tyr Asp Thr Ile Pro
705                 710                 715                 720

Gln Asp Arg Leu Thr Glu Val Ile Ala Ser Ile Ile Lys Pro Gln Asn
            725                 730                 735

Thr Tyr Cys Val Arg Arg Tyr Ala Val Val Gln Lys Ala Ala His Gly
        740                 745                 750

His Val Arg Lys Thr Phe Lys Lys His Val Ser Thr Leu Thr Asp Leu
    755                 760                 765

Gln Pro Tyr Met Arg Gln Phe Val Ala His Leu Gln Glu Thr Ser Ser
770                 775                 780

Leu Arg Asp Ala Val Val Ile Glu Gln Ser Ser Leu Asn Glu Ala
785                 790                 795                 800

Ser Ser Gly Leu Phe Asp Val Phe Leu Arg Phe Val Cys Asn His Val
                805                 810                 815

Val Arg Ile Gly Gly Lys Ser Tyr Val Gln Cys Gln Gly Ile Pro Gln
            820                 825                 830

Gly Ser Ile Leu Ser Thr Leu Leu Cys Ser Leu Cys Tyr Gly Asp Met
            835                 840                 845

Glu Asn Lys Leu Phe Ala Gly Ile Arg Arg Asp Gly Leu Leu Leu Arg
850                 855                 860

Leu Val Ala Ala Phe Leu Leu Val Thr Pro His Leu Thr His Ala Lys
865                 870                 875                 880

Ala Phe Leu Arg Thr Leu Val Arg Gly Val Pro Glu Tyr Gly Cys Val
                885                 890                 895

Val Asn Leu Arg Lys Thr Val Val Asn Phe Pro Val Glu Asp Glu Ala
            900                 905                 910

Leu Gly Gly Ala Ala Phe Val Gln Leu Pro Ala His Gly Leu Phe Pro
            915                 920                 925

Trp Cys Gly Leu Leu Leu Asp Thr Arg Thr Leu Glu Val Gln Ser Asp
    930                 935                 940

Tyr Ser Ser Tyr Ala Arg Thr Ser Ile Arg Ala Ser Leu Thr Phe Asn
945                 950                 955                 960

Arg Gly Phe Lys Ala Gly Arg Asn Met Arg Arg Lys Leu Phe Gly Val
                965                 970                 975

Leu Arg Leu Lys Cys His Ser Leu Phe Leu Tyr Leu Gln Val Asn Ser
            980                 985                 990

Leu Gln Thr Val Cys Thr Asn Val Tyr Lys Ile Phe Leu Leu Gln Ala
            995                 1000                1005

Tyr Arg Phe His Ala Cys Val Leu Gln Leu Pro Phe Asn Gln Gln
    1010                1015                1020

Val Trp Lys Asn Pro Ala Phe Phe Leu Arg Val Ile Ser Asp Thr
    1025                1030                1035

Ala Ser Leu Cys Tyr Ser Ile Leu Lys Ala Lys Asn Ala Gly Met
    1040                1045                1050

Ser Leu Gly Ala Lys Gly Ala Gly Pro Leu Pro Ser Glu Ala
    1055                1060                1065

Val Gln Trp Leu Cys His Gln Ala Phe Leu Leu Lys Leu Thr Arg
    1070                1075                1080

His Arg Val Thr Tyr Val Pro Leu Leu Gly Ser Leu Arg Thr Ala
    1085                1090                1095

Gln Thr Gln Leu Ser Arg Lys Leu Pro Gly Thr Thr Leu Ala Ala
    1100                1105                1110
```

| Leu | Glu | Ala | Ala | Ala | Asn | Pro | Ala | Leu | Pro | Ser | Asp | Phe | Lys | Thr |
|---|---|---|---|---|---|---|---|---|---|---|---|---|---|---|
| 1115 | | | | | 1120 | | | | | 1125 | | | | |

| Ile | Leu | Asp |
|---|---|---|
| 1130 | | |

<210> SEQ ID NO 57
<211> LENGTH: 3393
<212> TYPE: DNA
<213> ORGANISM: Artificial Sequence
<220> FEATURE:
<223> OTHER INFORMATION: mut rhTERT nucelic acid sequence (pGX1447)

<400> SEQUENCE: 57

| | | | | | |
|---|---|---|---|---|---|
| cctcgcgccc | cacgctgtag | agccgtcagg | tctctgctgc | gcagccggta | cagagaggtg | 60 |
| ctgccactgg | ccacctttgt | gcagcggctg | ggacctgagg | gatggagact | ggtgcagagg | 120 |
| ggcgaccctg | cagccttcag | agccctggtg | gcacagtgcc | tggtgtgcgt | gccatgggat | 180 |
| gccagacccc | ctccagcagc | accatctttt | aggcaggtga | gctgcctgaa | ggagctggtg | 240 |
| gcccgcgtgc | tgcagcggct | gtgcgagagg | ggcgcccgca | acgtgctggc | cttcggcttt | 300 |
| gccctgctgg | acggagcccg | ggcggcccct | cccgaggcct | tcaccacatc | cgtgcggtct | 360 |
| tatctgccca | ataccgtgac | agatgccctg | agaggcagcg | agcatggggg | cctgctgctg | 420 |
| aggagagtgg | gcgacgatgt | gctggtgcac | ctgctggcaa | ggtgcgcact | gtttgtgctg | 480 |
| gtggcaccct | cctgcgcata | ccaggtgtgc | ggcccacccc | tgtatgagct | gggagcagca | 540 |
| acacagggcc | gcccagcagc | ccacgcctcc | ggcaccaggc | gcggcctggg | ctgtgagctg | 600 |
| gcctggaacc | ggtctgtgag | agaggcagga | gtgccaatgg | gcctgccagc | acctggcgcc | 660 |
| cggagaaggc | gcggctctgc | caatcgcagc | ctgccactgc | caaagcggcc | taggagaggc | 720 |
| gccgcacctg | agccagagag | gacaccagtg | ggacagggca | gctgggcaca | cccagacagg | 780 |
| acccgcggcc | cttctgatag | gggattctgc | gtggtgagcc | ctgcccggcc | agcagaggag | 840 |
| gccacctccc | tggagggcgc | cctgtctggc | acaagacaca | gccacccatc | cgtgggcagg | 900 |
| cagcaccacg | caggccctcc | aagcaccagc | cggcctccct | ccccatggga | cacacggtgt | 960 |
| cccctggtgt | acgccgagac | aaagcacttt | ctgtatagct | ccggcgataa | ggagcagctg | 1020 |
| cggccctcct | tcctgctgaa | ctccctgagg | ccctctctga | ccggagcaag | gcgcctggtg | 1080 |
| gagacaatct | ttctgggctc | taggccctgg | atgcctggaa | cccccagacg | gcctccccgg | 1140 |
| ctgccacaga | ggtactggca | gatgcgccct | ctgttcctgg | agctgctggg | caatcacgcc | 1200 |
| cagtgcccat | atggcgccct | gctgaagaca | cactgtccac | tgagggcagc | agtgaccccca | 1260 |
| gcagcaggcg | tgtgcgcccg | cgagaagcct | cagggctctg | tggcagcacc | agaggaggag | 1320 |
| gacaccgata | ggcgccggct | ggtgcagctg | ctgaggcagc | actctagccc | ctggcaggtg | 1380 |
| tacggcttcg | tgagagcctg | tctgagaagg | ctggtgcctc | caggcctgtg | ggctccaga | 1440 |
| cacaaccagc | gccggtttct | gaggaataca | aagaagttca | tctccctggg | caagcacgcc | 1500 |
| aagctgtctc | tgagggagct | gacctggaag | atgagcgtgc | gcgactgcgc | ctggctgcgg | 1560 |
| aagtcccctg | gagtgggatg | cgtgccagca | gcagagcacc | ggctgagaga | ggagatcctg | 1620 |
| gccaagtttc | tgcactggct | gatgagcgtg | tacgtggtgg | agctgctgcg | gtccttcttt | 1680 |
| tatgtgaccg | agacaacctt | ccagaagaac | tacctgttct | tttataggaa | gagcgtgtgg | 1740 |
| agcaagctgc | agagcatcgg | catcagacag | cacctgaagc | gcgtgcagct | gcgggagctg | 1800 |
| tccgaggcag | aggcaaggca | gcacagggag | gcccggccaa | cactgctggc | cagcaggctg | 1860 |
| cgcttcctgc | caaagcctga | cggcctgcgg | cccatcgtga | atatggatta | cgtggtgggc | 1920 |

```
gccagaacct ttagaaggga aagagagca gagaggctgg ccagcagggt gaaggccctg   1980
ttctccgtgc tgaactatga gagggcaaga cggcccggcc tgctgggagc cagcgtgctg   2040
ggcctggacg atatccacag ggcatggcgg aattttgtgc tgcgggtgag agcacaggac   2100
cctcccccaa agctgtactt cgtgaaggtg gatgtgatgg gcgcctatga caccatcccc   2160
caggatcgcc tgacagaagt gatcgcctcc atcatcaagc ctcagaacac atactgcgtg   2220
agaaggtatg cagtggtgcg caaggcagca cacggacacg tgcggaagac ctttaagtcc   2280
cacgtgtcta ccctgacaga cctgcagcca tacatgagc agttcgtggc acacctgcag   2340
gagacaagcc ccctgaggga cgcagtggtc atcgagcagt cctctagcct gaacgagaca   2400
agcagcggcc tgttcgacgt gttcctgaga ttcgtgtgcc accacgccgt gaggatcggc   2460
ggcaagtctt acgtgcagtg tcagggcatc ccccagggca gcatcctgtc caccctgctg   2520
tgcagcctgt gctatggcga catggagaat aagctgttcg caggaatgag gagggatggc   2580
ctgctgctga ggctggtgga cgattttctg ctggtgaccc ctcacctgac acacgccaag   2640
gccttcctga gaacactggt gaggggcgtg cctgagtacg gctgcgtggt gaacctgcgc   2700
aagaccgtgg tgaattttcc agtggaggat gaggccctgg gcggcgccgc ctttgtgcag   2760
ctgccagcac acggcctgtt cccttggtgt ggcctgctgc tggacacccg gacactggag   2820
gtgcagtccg attacagctc ctatgcacgc accagcatca gggcatccct gaccttcaac   2880
agaggcttca aggccggcag gaatatgaga aggaagctgt ttggcgtgct gagactgaag   2940
tgccactctc tgttcctgta cctgcaggtg aacagcctgc agaccgtgtg cacaaacgtg   3000
tacaagatcc tgctgctgca ggcctatcgg tttcacgcct gcgtgctgca gctgcctttc   3060
caccagcaag tgtggaagaa cccagccttc tttctgagag tgatctctga taccgccagc   3120
ctgtgctact ccatcctgaa ggccaagaat gccggcatgt ctctgggagc aaagggagca   3180
gcaggaccac tgccaagcga ggcagtgcag tggctgtgcc accaggcctt cctgctgaag   3240
ctgacccagc acagagtgac atatgtgcca ctgctgggct ccctgaggac cgcacagaca   3300
cagctgtctc ggaagctgcc tggcaccaca ctggccgctc tggaggctgc tgctaatccc   3360
gccctgccat ccgacttcaa aacaatcctg gac                                 3393
```

<210> SEQ ID NO 58
<211> LENGTH: 1131
<212> TYPE: PRT
<213> ORGANISM: Artificial Sequence
<220> FEATURE:
<223> OTHER INFORMATION: mut rhTERT amino acid sequence (pGX1447)

<400> SEQUENCE: 58

```
Pro Arg Ala Pro Arg Cys Arg Ala Val Arg Ser Leu Leu Arg Ser Arg
 1               5                  10                  15

Tyr Arg Glu Val Leu Pro Leu Ala Thr Phe Val Gln Arg Leu Gly Pro
                20                  25                  30

Glu Gly Trp Arg Leu Val Gln Arg Gly Asp Pro Ala Ala Phe Arg Ala
            35                  40                  45

Leu Val Ala Gln Cys Leu Val Cys Val Pro Trp Asp Ala Arg Pro Pro
        50                  55                  60

Pro Ala Ala Pro Ser Phe Arg Gln Val Ser Cys Leu Lys Glu Leu Val
    65                  70                  75                  80

Ala Arg Val Leu Gln Arg Leu Cys Glu Arg Gly Ala Arg Asn Val Leu
                85                  90                  95
```

```
Ala Phe Gly Phe Ala Leu Leu Asp Gly Ala Arg Gly Gly Pro Pro Glu
                100                 105                 110

Ala Phe Thr Thr Ser Val Arg Ser Tyr Leu Pro Asn Thr Val Thr Asp
            115                 120                 125

Ala Leu Arg Gly Ser Gly Ala Trp Gly Leu Leu Arg Arg Val Gly
        130                 135                 140

Asp Asp Val Leu Val His Leu Leu Ala Arg Cys Ala Leu Phe Val Leu
145                 150                 155                 160

Val Ala Pro Ser Cys Ala Tyr Gln Val Cys Gly Pro Pro Leu Tyr Glu
                165                 170                 175

Leu Gly Ala Ala Thr Gln Gly Arg Pro Ala Ala His Ala Ser Gly Thr
            180                 185                 190

Arg Arg Gly Leu Gly Cys Glu Leu Ala Trp Asn Arg Ser Val Arg Glu
        195                 200                 205

Ala Gly Val Pro Met Gly Leu Pro Ala Pro Gly Ala Arg Arg Arg Arg
        210                 215                 220

Gly Ser Ala Asn Arg Ser Leu Pro Leu Pro Lys Arg Pro Arg Arg Gly
225                 230                 235                 240

Ala Ala Pro Glu Pro Glu Arg Thr Pro Val Gly Gln Gly Ser Trp Ala
                245                 250                 255

His Pro Asp Arg Thr Arg Gly Pro Ser Asp Arg Gly Phe Cys Val Val
            260                 265                 270

Ser Pro Ala Arg Pro Ala Glu Glu Ala Thr Ser Leu Glu Gly Ala Leu
        275                 280                 285

Ser Gly Thr Arg His Ser His Pro Ser Val Gly Arg Gln His His Ala
        290                 295                 300

Gly Pro Pro Ser Thr Ser Arg Pro Pro Ser Pro Trp Asp Thr Arg Cys
305                 310                 315                 320

Pro Leu Val Tyr Ala Glu Thr Lys His Phe Leu Tyr Ser Ser Gly Asp
                325                 330                 335

Lys Glu Gln Leu Arg Pro Ser Phe Leu Leu Asn Ser Leu Arg Pro Ser
            340                 345                 350

Leu Thr Gly Ala Arg Arg Leu Val Glu Thr Ile Phe Leu Gly Ser Arg
        355                 360                 365

Pro Trp Met Pro Gly Thr Pro Arg Arg Pro Arg Leu Pro Gln Arg
        370                 375                 380

Tyr Trp Gln Met Arg Pro Leu Phe Leu Glu Leu Gly Asn His Ala
385                 390                 395                 400

Gln Cys Pro Tyr Gly Ala Leu Leu Lys Thr His Cys Pro Leu Arg Ala
                405                 410                 415

Ala Val Thr Pro Ala Ala Gly Val Cys Ala Arg Glu Lys Pro Gln Gly
            420                 425                 430

Ser Val Ala Ala Pro Glu Glu Glu Asp Thr Asp Arg Arg Leu Val
        435                 440                 445

Gln Leu Leu Arg Gln His Ser Ser Pro Trp Gln Val Tyr Gly Phe Val
        450                 455                 460

Arg Ala Cys Leu Arg Arg Leu Val Pro Gly Leu Trp Gly Ser Arg
465                 470                 475                 480

His Asn Gln Arg Arg Phe Leu Arg Asn Thr Lys Lys Phe Ile Ser Leu
                485                 490                 495

Gly Lys His Ala Lys Leu Ser Leu Arg Glu Leu Thr Trp Lys Met Ser
            500                 505                 510

Val Arg Asp Cys Ala Trp Leu Arg Lys Ser Pro Gly Val Gly Cys Val
```

-continued

```
            515                 520                 525
Pro Ala Ala Glu His Arg Leu Arg Glu Glu Ile Leu Ala Lys Phe Leu
530                     535                 540

His Trp Leu Met Ser Val Tyr Val Val Glu Leu Leu Arg Ser Phe Phe
545                     550                 555                 560

Tyr Val Thr Glu Thr Thr Phe Gln Lys Asn Tyr Leu Phe Phe Tyr Arg
                    565                 570                 575

Lys Ser Val Trp Ser Lys Leu Gln Ser Ile Gly Ile Arg Gln His Leu
                580                 585                 590

Lys Arg Val Gln Leu Arg Glu Leu Ser Glu Ala Glu Ala Arg Gln His
            595                 600                 605

Arg Glu Ala Arg Pro Thr Leu Leu Ala Ser Arg Leu Arg Phe Leu Pro
610                 615                 620

Lys Pro Asp Gly Leu Arg Pro Ile Val Asn Met Asp Tyr Val Val Gly
625                 630                 635                 640

Ala Arg Thr Phe Arg Arg Glu Lys Arg Ala Glu Arg Leu Ala Ser Arg
                    645                 650                 655

Val Lys Ala Leu Phe Ser Val Leu Asn Tyr Glu Arg Ala Arg Arg Pro
                660                 665                 670

Gly Leu Leu Gly Ala Ser Val Leu Gly Leu Asp Asp Ile His Arg Ala
            675                 680                 685

Trp Arg Asn Phe Val Leu Arg Val Arg Ala Gln Asp Pro Pro Lys
690                 695                 700

Leu Tyr Phe Val Lys Val Asp Val Met Gly Ala Tyr Asp Thr Ile Pro
705                 710                 715                 720

Gln Asp Arg Leu Thr Glu Val Ile Ala Ser Ile Ile Lys Pro Gln Asn
                    725                 730                 735

Thr Tyr Cys Val Arg Arg Tyr Ala Val Val Arg Lys Ala Ala His Gly
                740                 745                 750

His Val Arg Lys Thr Phe Lys Ser His Val Ser Thr Leu Thr Asp Leu
            755                 760                 765

Gln Pro Tyr Met Arg Gln Phe Val Ala His Leu Gln Glu Thr Ser Pro
770                 775                 780

Leu Arg Asp Ala Val Val Ile Glu Gln Ser Ser Ser Leu Asn Glu Thr
785                 790                 795                 800

Ser Ser Gly Leu Phe Asp Val Phe Leu Arg Phe Val Cys His His Ala
                    805                 810                 815

Val Arg Ile Gly Gly Lys Ser Tyr Val Gln Cys Gln Gly Ile Pro Gln
                820                 825                 830

Gly Ser Ile Leu Ser Thr Leu Leu Cys Ser Leu Cys Tyr Gly Asp Met
            835                 840                 845

Glu Asn Lys Leu Phe Ala Gly Met Arg Arg Asp Gly Leu Leu Leu Arg
850                 855                 860

Leu Val Asp Asp Phe Leu Leu Val Thr Pro His Leu Thr His Ala Lys
865                 870                 875                 880

Ala Phe Leu Arg Thr Leu Val Arg Gly Val Pro Glu Tyr Gly Cys Val
                    885                 890                 895

Val Asn Leu Arg Lys Thr Val Val Asn Phe Pro Val Glu Asp Glu Ala
                900                 905                 910

Leu Gly Gly Ala Ala Phe Val Gln Leu Pro Ala His Gly Leu Phe Pro
            915                 920                 925

Trp Cys Gly Leu Leu Leu Asp Thr Arg Thr Leu Glu Val Gln Ser Asp
930                 935                 940
```

```
Tyr Ser Ser Tyr Ala Arg Thr Ser Ile Arg Ala Ser Leu Thr Phe Asn
945                 950                 955                 960

Arg Gly Phe Lys Ala Gly Arg Asn Met Arg Arg Lys Leu Phe Gly Val
                965                 970                 975

Leu Arg Leu Lys Cys His Ser Leu Phe Leu Tyr Leu Gln Val Asn Ser
            980                 985                 990

Leu Gln Thr Val Cys Thr Asn Val Tyr Lys Ile Leu Leu Leu Gln Ala
        995                 1000                1005

Tyr Arg Phe His Ala Cys Val Leu Gln Leu Pro Phe His Gln Gln
    1010                1015                1020

Val Trp Lys Asn Pro Ala Phe Phe Leu Arg Val Ile Ser Asp Thr
    1025                1030                1035

Ala Ser Leu Cys Tyr Ser Ile Leu Lys Ala Lys Asn Ala Gly Met
    1040                1045                1050

Ser Leu Gly Ala Lys Gly Ala Gly Pro Leu Pro Ser Glu Ala
    1055                1060                1065

Val Gln Trp Leu Cys His Gln Ala Phe Leu Leu Lys Leu Thr Gln
    1070                1075                1080

His Arg Val Thr Tyr Val Pro Leu Leu Gly Ser Leu Arg Thr Ala
    1085                1090                1095

Gln Thr Gln Leu Ser Arg Lys Leu Pro Gly Thr Thr Leu Ala Ala
    1100                1105                1110

Leu Glu Ala Ala Ala Asn Pro Ala Leu Pro Ser Asp Phe Lys Thr
    1115                1120                1125

Ile Leu Asp
    1130

<210> SEQ ID NO 59
<211> LENGTH: 2202
<212> TYPE: DNA
<213> ORGANISM: Artificial Sequence
<220> FEATURE:
<223> OTHER INFORMATION: Synthetic Consensus FAP nucleic acid sequence

<400> SEQUENCE: 59
ctgaggcctt ctagagtgca caactccgag ggcccaacca gagccctgac actgaaggac      60
atcctgaatg gcacctttc ttacaagaca ttctttccca actggatctc tggccaggag     120
tatctgcacc agagcgccga taacaacatc atcctgtaca acatcgagac aggcgagagc     180
tacacaatcc tgtccaactc taccatgaag agcgtgaacg cctccaatta cggcctgagc     240
cctgacaggc agttcgccta cctggagtct gattatagca agctgtggag atactcctat     300
accgccacat accacatcta tgatctgatc aatggcgagt tgtgcggga gaacgagctg     360 ccccgcccta tccagtacct gtgctggagc ccgtgggca gcaagctggc atacgtgtat     420
cagaacaata tctatctgaa gcagaggccc agggaccctc ccttccagat cacatccaac     480
ggcaaggaga ataagatctt aacggcatc cccgattggg tgtacgagga ggagatgctg     540
gccaccaagt atgccctgtg gtggagccct aatggcaagt tcctggccta cgccgagttt     600
aacgacacag atatcccagt gatcgcctat tcctactatg cgacgagca gtaccccgg     660 accatcaata tcccatatcc caaggcagga gcaaagaacc caacagtgcg cgtgttcatc     720
atcgatacca catcccaga gcacgtggga ccaaaggagg tgcctgtgcc agccatgatc     780
gccagctccg actactactt cagctggctg acctgggtga cagatgagag gatctgtctg     840
cagtggctga agagaatcca gaacgtgagc gtgctgtcta tctgcgactt cagggaggat     900
```

```
tggaacacct gggactgtcc taagacacag gagcacatcg aggagagcag aaccggatgg    960
gccggcggct tcttcgtgag cacaccagtg ttctctagcg acgccatcag ctactataag   1020
atcttttccg acaaggatgg ctacaagcac atccactata tcaaggatac cgtggagaat   1080
gccatccaga tcacatctgg caagtgggag gccatcaaca tcttcagggt gacccaggac   1140
agcctgttct actcctctaa tgagtttgag ggctacccag caggagaaa catctataga   1200
atcagcatcg gctcctaccc acccagcaag aagtgcgtga cctgtcacct gcggaaggag   1260
aggtgccagt actatacagc cagcttttcc gattacgcca agtactatgc cctgatctgt   1320
tatgccccg gcatccctat ctccaccctg cacgacggcc ggacagatca ggagatcaag   1380
atcctggagg agaataagga gctggagaat gccctgaaga acatccagct gcctaaggag   1440
gagatcaaga gctggaggt ggacggcatc accctgtggt acaagatgat cctgcctcca   1500
cagttcgatc ggtctaagaa gtatcccctg ctgatccagg tgtacggcgg accttgctct   1560
cagagcgtgc gcagcgtgtt ttccatctct tggatctcct acctggcctc taaggagggc   1620
atcgtggtgg ccctggtgga cggaagggga accgccttcc agggcgataa gctgctgtac   1680
gccgtgtatc gcaagctggg cgtgtacgag gtggaggacc agatcacagc cgtgcggaag   1740
ttcatcgaga tgggctttat cgatgagaag aggatcgcaa tctggggatg gcatacggc   1800
ggatatgtga gctccctggc cctggcatct ggaaccggcc tgttcaagtg tggcatcgcc   1860
gtggccccag tgtctagctg ggagtactat gcctccatct acaccgagag gttcatgggc   1920
ctgcccacaa agtccgacaa tctggagcac tataagaact ctaccgtgat ggccagggcc   1980
gagtacttca gaaacgtgga ttatctgctg atccacggca cagccgacga taatgtgcac   2040
ttccagaact ccgcccagat cgccaaggcc ctggtgaatg cccaggtgga ctttcaggcc   2100
atgtggtact ctgatcagaa ccacggcatc tctggcctga gcaccaagca cctgtatacc   2160
cacatgacac acttcctgaa gcagtgcttt agcctgtccg ac                      2202
```

<210> SEQ ID NO 60
<211> LENGTH: 734
<212> TYPE: PRT
<213> ORGANISM: Artificial Sequence
<220> FEATURE:
<223> OTHER INFORMATION: Synthetic Consensus FAP amino acid sequence

<400> SEQUENCE: 60

```
Leu Arg Pro Ser Arg Val His Asn Ser Glu Gly Pro Thr Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Ile Leu Tyr Asn Ile Glu Thr Gly Glu Ser Tyr Thr Ile Leu
    50                  55                  60

Ser Asn Ser Thr Met Lys Ser Val Asn Ala Ser Asn Tyr Gly Leu Ser
65                  70                  75                  80

Pro Asp Arg Gln Phe Ala Tyr Leu Glu Ser Asp Tyr Ser Lys Leu Trp
                85                  90                  95

Arg Tyr Ser Tyr Thr Ala Thr Tyr His Ile Tyr Asp Leu Ile Asn Gly
            100                 105                 110

Glu Phe Val Arg Glu Asn Glu Leu Pro Arg Pro Ile Gln Tyr Leu Cys
        115                 120                 125
```

Trp Ser Pro Val Gly Ser Lys Leu Ala Tyr Val Tyr Gln Asn Asn Ile
    130             135                 140

Tyr Leu Lys Gln Arg Pro Arg Asp Pro Phe Gln Ile Thr Ser Asn
145                 150                 155                 160

Gly Lys Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Thr Val Arg Val Phe Ile
225                 230                 235                 240

Ile Asp Thr Thr Tyr Pro Glu His Val Gly Pro Lys Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Ile Cys Leu Gln Trp Leu Lys Arg Ile Gln Asn
    275                 280                 285

Val Ser Val Leu Ser Ile Cys Asp Phe Arg Glu Asp Trp Asn Thr Trp
    290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Ser Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
        355                 360                 365

Trp Glu Ala Ile Asn Ile Phe Arg Val Thr Gln Asp Ser Leu Phe Tyr
    370                 375                 380

Ser Ser Asn Glu Phe Glu Gly Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Ile Cys Tyr Gly Pro Gly Ile Pro Ile Ser
        435                 440                 445

Thr Leu His Asp Gly Arg Thr Asp Gln Glu Ile Lys Ile Leu Glu Glu
    450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Gly Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ser
        515                 520                 525

Ile Ser Trp Ile Ser Tyr Leu Ala Ser Lys Glu Gly Ile Val Val Ala
    530                 535                 540

Leu Val Asp Gly Arg Gly Thr Ala Phe Gln Gly Asp Lys Leu Leu Tyr

```
                  545                 550                 555                 560
Ala Val Tyr Arg Lys Leu Gly Val Tyr Glu Val Glu Asp Gln Ile Thr
                565                 570                 575
Ala Val Arg Lys Phe Ile Glu Met Gly Phe Ile Asp Glu Lys Arg Ile
                580                 585                 590
Ala Ile Trp Gly Trp Ala Tyr Gly Gly Tyr Val Ser Ser Leu Ala Leu
                595                 600                 605
Ala Ser Gly Thr Gly Leu Phe Lys Cys Gly Ile Ala Val Ala Pro Val
                610                 615                 620
Ser Ser Trp Glu Tyr Tyr Ala Ser Ile Tyr Thr Glu Arg Phe Met Gly
625                 630                 635                 640
Leu Pro Thr Lys Ser Asp Asn Leu Glu His Tyr Lys Asn Ser Thr Val
                645                 650                 655
Met Ala Arg Ala Glu Tyr Phe Arg Asn Val Asp Tyr Leu Leu Ile His
                660                 665                 670
Gly Thr Ala Asp Asp Asn Val His Phe Gln Asn Ser Ala Gln Ile Ala
                675                 680                 685
Lys Ala Leu Val Asn Ala Gln Val Asp Phe Gln Ala Met Trp Tyr Ser
                690                 695                 700
Asp Gln Asn His Gly Ile Ser Gly Leu Ser Thr Lys His Leu Tyr Thr
705                 710                 715                 720
His Met Thr His Phe Leu Lys Gln Cys Phe Ser Leu Ser Asp
                725                 730

<210> SEQ ID NO 61
<211> LENGTH: 2034
<212> TYPE: DNA
<213> ORGANISM: Artificial Sequence
<220> FEATURE:
<223> OTHER INFORMATION: Synthetic Consensus FSHR nucleic acid sequence

<400> SEQUENCE: 61
tgtcatcata ggatttgtca ttgctctaat agggtgttcc tgtgccagga gtccaaggtc     60
actgaaatcc catctgacct gccccggaat gctgtggagc tgagatttgt cctgaccaag    120
ctgagagtga tccctaaagg cgcattcagt ggctttgggg acctgagaa atcgaaatt    180 tcacagaacg atgtgctgga ggtcatcgaa gctaacgtgt tcagcaacct gccaaagctg    240
cacgagatcc gcattgaaaa agctaacaat ctgctgtaca ttgatcccga agcatttcag    300
aatctgccta acctgcgata tctgctgatc agcaataccg gcattaagca cctgcccgcc    360
gtgcataaga ttcagtccct gcagaaagtc ctgctggaca tccaggataa tatcaacatt    420
cacacagtgg agagaaacag cttcatgggg ctgtcctttg aatctgtcat cctgtggctg    480
aataagaacg gcatccagga gattcataat gcgcattca cgggacaca gctggacgaa    540 ctgaatctgt ccgataacaa taacctggag gaactgccta cgacgtgtt tcaggggcc    600 agcggaccag tcatcctgga tatttcccga caagaatcc acagtctgcc ttcatacggc    660
ctggagaatc tgaagaaact gagagccagg tcaacttata acctgaagaa actgccaagc    720
ctggagaagt tcgtggccct gatggaagct tcactgacct accccagcca ctgctgtgct    780
tttgcaaatt ggcggagaca gatctccgag ctgcatccaa tctgtaacaa atctattctg    840
cggcaggaag tggacgatat gacccaggca cgcgggcagc gagtctccct ggccgaggac    900
gatgaaagct cctactctag aggattcgac atgatgtata gtgagttcga ctttgatctg    960
tgcaatgaag tggtcgatgt gacttgttct cccaagcctg acgccttcaa tcctgcgag    1020
```

-continued

```
gatatcatgg gctataacat tctgagggtg ctgatctggt ttatctctat tctggctatc    1080
accgggaata tcattgtgct ggtcatcctg attactagtc agtacaagct gaccgtgcct    1140
cgcttcctga tgtgcaacct ggcctttgct gacctgtgca tcgggatcta cctgctgctg    1200
attgccagtg tggatatcca cacaaaatca cagtaccata actatgccat cgactggcag    1260
acaggagctg gctgtgatgc cgctggattc tttaccgtgt tcgccagcga gctgtccgtc    1320
tacaccctga cagctattac tctggcaaga gcccacacta tcacccatgc catgcagctg    1380
gactgcaagg tgcagctgag gcacgcagcc agcgtgatgc tggtcggatg gatcttcgct    1440
tttgcagtgg ccctgttccc aatctttggc atttctagtt acatgaaagt gagcatttgt    1500
ctgcctatgg acatcgattc tccactgagt cagctgtatg tgatgtccct gctggtgctg    1560
aacgtcctgg cttttgtggt catttgcggc tgttacaccc atatctatct gacagtgcga    1620
aatcccaaca tcgtctcaag ctcctctgac accaagattg caaaacggat ggccatgctg    1680
atcttcacag attttctgtg catggccccc attagcttct ttgctatctc tgcaagtctg    1740
aaggtgcctc tgattacagt ctcaaagagc aaaatcctgc tggtgctgtt ctacccaatt    1800
aattcttgcg ctaaccccct tctgtatgca atcttcacta agaactttag gcgcgacttc    1860
tttattctgc tgagcaaatt cggatgttac gagatgcagg cacagatcta taggacagaa    1920
actagttcaa ccgcccacaa tagccatcct cgcaacggcc actgcagctc cgccccaaga    1980
gtcactaatg gaagcaacta caccctggtc ccactgtctc acctggctca gaac          2034
```

<210> SEQ ID NO 62
<211> LENGTH: 678
<212> TYPE: PRT
<213> ORGANISM: Artificial Sequence
<220> FEATURE:
<223> OTHER INFORMATION: Synthetic Consensus FSHR amino acid sequence

<400> SEQUENCE: 62

```
Cys His His Arg Ile Cys His Cys Ser Asn Arg Val Phe Leu Cys Gln
1               5                   10                  15

Glu Ser Lys Val Thr Glu Ile Pro Ser Asp Leu Pro Arg Asn Ala Val
            20                  25                  30

Glu Leu Arg Phe Val Leu Thr Lys Leu Arg Val Ile Pro Lys Gly Ala
        35                  40                  45

Phe Ser Gly Phe Gly Asp Leu Glu Lys Ile Glu Ile Ser Gln Asn Asp
    50                  55                  60

Val Leu Glu Val Ile Glu Ala Asn Val Phe Ser Asn Leu Pro Lys Leu
65                  70                  75                  80

His Glu Ile Arg Ile Glu Lys Ala Asn Asn Leu Leu Tyr Ile Asp Pro
                85                  90                  95

Glu Ala Phe Gln Asn Leu Pro Asn Leu Arg Tyr Leu Leu Ile Ser Asn
            100                 105                 110

Thr Gly Ile Lys His Leu Pro Ala Val His Lys Ile Gln Ser Leu Gln
        115                 120                 125

Lys Val Leu Leu Asp Ile Gln Asp Asn Ile Asn Ile His Thr Val Glu
    130                 135                 140

Arg Asn Ser Phe Met Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Asn Leu Glu Glu Leu
            180                 185                 190
```

```
Pro Asn Asp Val Phe Gln Gly Ala Ser Gly Pro Val Ile Leu Asp Ile
    195                 200                 205

Ser Arg Thr Arg Ile His Ser Leu Pro Ser Tyr Gly Leu Glu Asn Leu
210             215                 220

Lys Lys Leu Arg Ala Arg Ser Thr Tyr Asn Leu Lys Lys Leu Pro Ser
225             230                 235                 240

Leu Glu Lys Phe Val Ala Leu Met Glu Ala Ser Leu Thr Tyr Pro Ser
                245                 250                 255

His Cys Cys Ala Phe Ala Asn Trp Arg Arg Gln Ile Ser Glu Leu His
            260                 265                 270

Pro Ile Cys Asn Lys Ser Ile Leu Arg Gln Glu Val Asp Asp Met Thr
        275                 280                 285

Gln Ala Arg Gly Gln Arg Val Ser Leu Ala Glu Asp Asp Glu Ser Ser
290                 295                 300

Tyr Ser Arg Gly Phe Asp Met Met Tyr Ser Glu Phe Asp Phe Asp Leu
305                 310                 315                 320

Cys Asn Glu Val Val Asp Val Thr Cys Ser Pro Lys Pro Asp Ala Phe
                325                 330                 335

Asn Pro Cys Glu Asp Ile Met Gly Tyr Asn Ile Leu Arg Val Leu Ile
            340                 345                 350

Trp Phe Ile Ser Ile Leu Ala Ile Thr Gly Asn Ile Ile Val Leu Val
        355                 360                 365

Ile Leu Ile Thr Ser Gln Tyr Lys Leu Thr Val Pro Arg Phe Leu Met
        370                 375                 380

Cys Asn Leu Ala Phe Ala Asp Leu Cys Ile Gly Ile Tyr Leu Leu Leu
385                 390                 395                 400

Ile Ala Ser Val Asp Ile His Thr Lys Ser Gln Tyr His Asn Tyr Ala
                405                 410                 415

Ile Asp Trp Gln Thr Gly Ala Gly Cys Asp Ala Ala Gly Phe Phe Thr
            420                 425                 430

Val Phe Ala Ser Glu Leu Ser Val Tyr Thr Leu Thr Ala Ile Thr Leu
        435                 440                 445

Ala Arg Ala His Thr Ile Thr His Ala Met Gln Leu Asp Cys Lys Val
        450                 455                 460

Gln Leu Arg His Ala Ala Ser Val Met Leu Val Gly Trp Ile Phe Ala
465                 470                 475                 480

Phe Ala Val Ala Leu Phe Pro Ile Phe Gly Ile Ser Ser Tyr Met Lys
                485                 490                 495

Val Ser Ile Cys Leu Pro Met Asp Ile Asp Ser Pro Leu Ser Gln Leu
            500                 505                 510

Tyr Val Met Ser Leu Leu Val Leu Asn Val Leu Ala Phe Val Val Ile
        515                 520                 525

Cys Gly Cys Tyr Thr His Ile Tyr Leu Thr Val Arg Asn Pro Asn Ile
        530                 535                 540

Val Ser Ser Ser Ser Asp Thr Lys Ile Ala Lys Arg Met Ala Met Leu
545                 550                 555                 560

Ile Phe Thr Asp Phe Leu Cys Met Ala Pro Ile Ser Phe Phe Ala Ile
                565                 570                 575

Ser Ala Ser Leu Lys Val Pro Leu Ile Thr Val Ser Lys Ser Lys Ile
            580                 585                 590

Leu Leu Val Leu Phe Tyr Pro Ile Asn Ser Cys Ala Asn Pro Phe Leu
        595                 600                 605
```

```
Tyr Ala Ile Phe Thr Lys Asn Phe Arg Arg Asp Phe Phe Ile Leu Leu
    610                 615                 620
Ser Lys Phe Gly Cys Tyr Glu Met Gln Ala Gln Ile Tyr Arg Thr Glu
625                 630                 635                 640
Thr Ser Ser Thr Ala His Asn Ser His Pro Arg Asn Gly His Cys Ser
                645                 650                 655
Ser Ala Pro Arg Val Thr Asn Gly Ser Asn Tyr Thr Leu Val Pro Leu
            660                 665                 670
Ser His Leu Ala Gln Asn
        675
```

<210> SEQ ID NO 63
<211> LENGTH: 780
<212> TYPE: DNA
<213> ORGANISM: Artificial Sequence
<220> FEATURE:
<223> OTHER INFORMATION: Synthetic Consensus PSA nucleic acid sequence

<400> SEQUENCE: 63

```
tgggtcctgg tggtgttcct gactctgagc gtcacatgga tcggcgccgc tccactgatt      60
ctgagccgcc tggtgggcgg gtgggagtgc gaaaagcact cccagccatg gcaggtgctg     120
gtcgcttcta ggggccgagc agtgtgcgga ggcgtgctgg tccaccctca gtgggtcctg     180
accgcagccc attgtatccg acagaagagc gtgattctgc tggggcgaca ccagccattc     240
taccccgagg acacaggaca ggtgttccag gtctctcaca gttttcccca tcctctgtac     300
aacatgagcc tgctgaaaaa cagatatctg ggacctggcg acgatagctc ccatgatctg     360
atgctgctga ggctgtccga gccagccgaa ctgactgacg ctgtgcaggt cctggatctg     420
cccacccagg agcctgccct gggaaccaca tgttatgctt caggctgggg gagcatcgaa     480
ccagaggaac atctgactcc caagaaactg cagtgcgtgg acctgcacct gattagtaac     540
gatgtgtgtg cacaggtcca ttcacagaag gtgacaaagt tcatgctgtg cgccggctct     600
tggatgggcg gcaagtcaac ttgcagcggg gactccggcg ggccactggt gtgtgatgga     660
gtcctgcagg gcatcacctc ttggggcagt cagccttgtg ccctgcctcg gagaccaagt     720
ctgtacacta aggtggtccg gtataggaaa tggattcagg acactattgc cgctaacccc     780
```

<210> SEQ ID NO 64
<211> LENGTH: 260
<212> TYPE: PRT
<213> ORGANISM: Artificial Sequence
<220> FEATURE:
<223> OTHER INFORMATION: Synthetic Consensus PSA amino acid sequence

<400> SEQUENCE: 64

```
Trp Val Leu Val Val Phe Leu Thr Leu Ser Val Thr Trp Ile Gly Ala
1               5                   10                  15
Ala Pro Leu Ile Leu Ser Arg Leu Val Gly Gly Trp Glu Cys Glu Lys
            20                  25                  30
His Ser Gln Pro Trp Gln Val Leu Val Ala Ser Arg Gly Arg Ala Val
        35                  40                  45
Cys Gly Gly Val Leu Val His Pro Gln Trp Val Leu Thr Ala Ala His
    50                  55                  60
Cys Ile Arg Gln Lys Ser Val Ile Leu Leu Gly Arg His Gln Pro Phe
65                  70                  75                  80
Tyr Pro Glu Asp Thr Gly Gln Val Phe Gln Val Ser His Ser Phe Pro
                85                  90                  95
```

-continued

```
His Pro Leu Tyr Asn Met Ser Leu Leu Lys Asn Arg Tyr Leu Gly Pro
            100                 105                 110

Gly Asp Asp Ser Ser His Asp Leu Met Leu Leu Arg Leu Ser Glu Pro
        115                 120                 125

Ala Glu Leu Thr Asp Ala Val Gln Val Leu Asp Leu Pro Thr Gln Glu
    130                 135                 140

Pro Ala Leu Gly Thr Thr Cys Tyr Ala Ser Gly Trp Gly Ser Ile Glu
145                 150                 155                 160

Pro Glu Glu His Leu Thr Pro Lys Lys Leu Gln Cys Val Asp Leu His
                165                 170                 175

Leu Ile Ser Asn Asp Val Cys Ala Gln Val His Ser Gln Lys Val Thr
            180                 185                 190

Lys Phe Met Leu Cys Ala Gly Ser Trp Met Gly Gly Lys Ser Thr Cys
        195                 200                 205

Ser Gly Asp Ser Gly Gly Pro Leu Val Cys Asp Gly Val Leu Gln Gly
    210                 215                 220

Ile Thr Ser Trp Gly Ser Gln Pro Cys Ala Leu Pro Arg Arg Pro Ser
225                 230                 235                 240

Leu Tyr Thr Lys Val Val Arg Tyr Arg Lys Trp Ile Gln Asp Thr Ile
                245                 250                 255

Ala Ala Asn Pro
            260

<210> SEQ ID NO 65
<211> LENGTH: 2274
<212> TYPE: DNA
<213> ORGANISM: Artificial Sequence
<220> FEATURE:
<223> OTHER INFORMATION: Synthetic Consensus PSMA nucleic acid sequence

<400> SEQUENCE: 65
tggaacgcac tgcatgagac tgattctgct gtcgcactgg gacggagacc ccggtggctg      60
tgcgctggag cactggtgct ggccggcggg ggattcctgc tgggattcct gtttggctgg     120
tttatcaaaa gctccagcga ggctaccaat attaccccta gcacaataa gaaagcattc      180 ctggatgaac tgaaagccga gaacatcaag aaattcctgt acaacttcac aagaattcca     240
catctggctg cactgagca gaacttccag ctggcaaaac agatccagag tcagtggaag      300
gaatttgggc tggactcagt ggagctgacc cactacgatg tcctgctgtc ctatccaaat     360
aagactcatc ccaactacat ctctatcatt aacgaagacg gaatgagat tttcaacacc      420 tctctgtttg aaccccctcc acccggctat gagaatgtca gtgacgtggt ccctccattc     480
tcagccttca gcccccaggg gatgcctgag ggagatctgg tgtacgtcaa ttatgctaga     540
acagaagact ctttaagct ggagagggat atgaaaatca actgttccgg caagatcgtg      600
attgcccggt acgggaaggt gttcagagga aataaggtca aaacgctca gctggccgga     660 gctaccggcg tgatcctgta cagcgacccc gctgattatt ttgcacctgg cgtgaagtcc     720
tatccagacg gatggaatct gcccggcggg ggagtgcaga ggggaaacat cctgaacctg     780
aatggagccg cgatcctct gactccagga taccccgcca acgaatacgc ttatcgccgg      840
ggaattgcag aggccgtggg cctgcctagc atcccagtcc atccattgg ctattacgat      900 gcccagaagc tgctggagaa atgggcggg agcgctcccc ctgactctag ttggaagggc      960
tccctgaaag tgccttacaa tgtcgggcca ggattcactg gaaactttc tacccagaag     1020 gtgaaaatgc acatccatag taccagcgag gtgacacgaa tctacaacgt cattggcacc     1080
```

```
ctgagaggcg ccgtggagcc tgatcgctat gtcattctgg gaggccacag agactcatgg    1140
gtgttcgggg gaatcgatcc acagagcgga gcagctgtgg tccatgaaat tgtgcgcagc    1200
tttgggaccc tgaagaaaga gggatggcga cccaggcgca caatcctgtt cgcatcctgg    1260
gacgccgagg aatttgggct gctgggcagc acagaatggg ccgaggaaaa ttctcgcctg    1320
ctgcaggagc gaggggtggc ttacatcaat gcagactcaa gcattgaagg aaactatacc    1380
ctgcgggtgg attgcacacc cctgatgtac agtctggtct ataacctgac aaaggagctg    1440
aaatcacctg acgagggctt cgaagggaaa agcctgtacg aatcctggac tgagaagagc    1500
ccatcccccg aattcagcgg catgcctagg atctctaagc tgggcagtgg aacgattttt    1560
gaggtgttct ttcagcgcct gggaattgcc tctggccgag ctcggtacac aaaaaattgg    1620
gagactaaca agttctcctc ttacccactg tatcacagcg tgtacgagac ttatgaactg    1680
gtcgagaaat tctacgaccc cacttttaag tatcatctga ccgtggcaca ggtcaggggc    1740
gggatggtgt tcgaactggc caatagcatc gtcctgccat tgactgtcg agattacgct     1800 gtggtcctgc ggaagtacgc agacaagatc tataacatct ccatgaagca ccccaggag     1860 atgaaggcct attctgtgag tttcgattcc ctgttttctg ccgtcaaaaa tttcaccgaa    1920
atcgctagta agttttcaga gcgcctgcag gacctggata gtccaatcc catcctgctg      1980 cggattatga acgatcagct gatgttcctg gaaagagcct ttatcgaccc tctgggcctg    2040
cctgatagac cattctacag gcacgtgatc tacgcaccta gttcacataa caagtacgcc    2100
ggcgagtctt tcccagggat ctatgacgct ctgtttgata ttgaatcaaa ggtggacccc    2160
agcaaagcat ggggcgaggt caagagacag atcagcattg cagcctttac agtgcaggcc    2220
gccgccgaaa ccctgtccga agtcgcttac ccatacgatg tccccgatta cgca          2274
```

<210> SEQ ID NO 66
<211> LENGTH: 749
<212> TYPE: PRT
<213> ORGANISM: Artificial Sequence
<220> FEATURE:
<223> OTHER INFORMATION: Synthetic Consensus PSMA amino acid sequence

<400> SEQUENCE: 66

```
Trp Asn Ala Leu His Glu Thr Asp Ser Ala Val Ala Leu Gly Arg Arg
1               5                   10                  15

Pro Arg Trp Leu Cys Ala Gly Ala Leu Val Leu Ala Gly Gly Gly Phe
            20                  25                  30

Leu Leu Gly Phe Leu Phe Gly Trp Phe Ile Lys Ser Ser Ser Glu Ala
        35                  40                  45

Thr Asn Ile Thr Pro Lys His Asn Lys Lys Ala Phe Leu Asp Glu Leu
    50                  55                  60

Lys Ala Glu Asn Ile Lys Lys Phe Leu Tyr Asn Phe Thr Arg Ile Pro
65                  70                  75                  80

His Leu Ala Gly Thr Glu Gln Asn Phe Gln Leu Ala Lys Gln Ile Gln
                85                  90                  95

Ser Gln Trp Lys Glu Phe Gly Leu Asp Ser Val Glu Leu Thr His Tyr
            100                 105                 110

Asp Val Leu Leu Ser Tyr Pro Asn Lys Thr His Pro Asn Tyr Ile Ser
        115                 120                 125

Ile Ile Asn Glu Asp Gly Asn Glu Ile Phe Asn Thr Ser Leu Phe Glu
    130                 135                 140

Pro Pro Pro Pro Gly Tyr Glu Asn Val Ser Asp Val Val Pro Pro Phe
145                 150                 155                 160
```

-continued

Ser Ala Phe Ser Pro Gln Gly Met Pro Glu Gly Asp Leu Val Tyr Val
                165                 170                 175

Asn Tyr Ala Arg Thr Glu Asp Phe Phe Lys Leu Glu Arg Asp Met Lys
            180                 185                 190

Ile Asn Cys Ser Gly Lys Ile Val Ile Ala Arg Tyr Gly Lys Val Phe
        195                 200                 205

Arg Gly Asn Lys Val Lys Asn Ala Gln Leu Ala Gly Ala Thr Gly Val
    210                 215                 220

Ile Leu Tyr Ser Asp Pro Ala Asp Tyr Phe Ala Pro Gly Val Lys Ser
225                 230                 235                 240

Tyr Pro Asp Gly Trp Asn Leu Pro Gly Gly Val Gln Arg Gly Asn
                245                 250                 255

Ile Leu Asn Leu Asn Gly Ala Gly Asp Pro Leu Thr Pro Gly Tyr Pro
            260                 265                 270

Ala Asn Glu Tyr Ala Tyr Arg Arg Gly Ile Ala Glu Ala Val Gly Leu
        275                 280                 285

Pro Ser Ile Pro Val His Pro Ile Gly Tyr Tyr Asp Ala Gln Lys Leu
    290                 295                 300

Leu Glu Lys Met Gly Gly Ser Ala Pro Pro Asp Ser Ser Trp Lys Gly
305                 310                 315                 320

Ser Leu Lys Val Pro Tyr Asn Val Gly Pro Gly Phe Thr Gly Asn Phe
                325                 330                 335

Ser Thr Gln Lys Val Lys Met His Ile His Ser Thr Ser Glu Val Thr
            340                 345                 350

Arg Ile Tyr Asn Val Ile Gly Thr Leu Arg Gly Ala Val Glu Pro Asp
        355                 360                 365

Arg Tyr Val Ile Leu Gly Gly His Arg Asp Ser Trp Val Phe Gly Gly
    370                 375                 380

Ile Asp Pro Gln Ser Gly Ala Ala Val Val His Glu Ile Val Arg Ser
385                 390                 395                 400

Phe Gly Thr Leu Lys Lys Glu Gly Trp Arg Pro Arg Arg Thr Ile Leu
                405                 410                 415

Phe Ala Ser Trp Asp Ala Glu Glu Phe Gly Leu Leu Gly Ser Thr Glu
            420                 425                 430

Trp Ala Glu Glu Asn Ser Arg Leu Leu Gln Glu Arg Gly Val Ala Tyr
        435                 440                 445

Ile Asn Ala Asp Ser Ser Ile Glu Gly Asn Tyr Thr Leu Arg Val Asp
    450                 455                 460

Cys Thr Pro Leu Met Tyr Ser Leu Val Tyr Asn Leu Thr Lys Glu Leu
465                 470                 475                 480

Lys Ser Pro Asp Glu Gly Phe Glu Gly Lys Ser Leu Tyr Glu Ser Trp
                485                 490                 495

Thr Glu Lys Ser Pro Ser Pro Glu Phe Ser Gly Met Pro Arg Ile Ser
            500                 505                 510

Lys Leu Gly Ser Gly Asn Asp Phe Glu Val Phe Phe Gln Arg Leu Gly
        515                 520                 525

Ile Ala Ser Gly Arg Ala Arg Tyr Thr Lys Asn Trp Glu Thr Asn Lys
    530                 535                 540

Phe Ser Ser Tyr Pro Leu Tyr His Ser Val Tyr Glu Thr Tyr Glu Leu
545                 550                 555                 560

Val Glu Lys Phe Tyr Asp Pro Thr Phe Lys Tyr His Leu Thr Val Ala
                565                 570                 575

```
Gln Val Arg Gly Gly Met Val Phe Glu Leu Ala Asn Ser Ile Val Leu
                580                 585                 590

Pro Phe Asp Cys Arg Asp Tyr Ala Val Val Leu Arg Lys Tyr Ala Asp
            595                 600                 605

Lys Ile Tyr Asn Ile Ser Met Lys His Pro Gln Glu Met Lys Ala Tyr
        610                 615                 620

Ser Val Ser Phe Asp Ser Leu Phe Ser Ala Val Lys Asn Phe Thr Glu
625                 630                 635                 640

Ile Ala Ser Lys Phe Ser Glu Arg Leu Gln Asp Leu Asp Lys Ser Asn
                645                 650                 655

Pro Ile Leu Leu Arg Ile Met Asn Asp Gln Leu Met Phe Leu Glu Arg
            660                 665                 670

Ala Phe Ile Asp Pro Leu Gly Leu Pro Asp Arg Pro Phe Tyr Arg His
        675                 680                 685

Val Ile Tyr Ala Pro Ser Ser His Asn Lys Tyr Ala Gly Glu Ser Phe
690                 695                 700

Pro Gly Ile Tyr Asp Ala Leu Phe Asp Ile Glu Ser Lys Val Asp Pro
705                 710                 715                 720

Ser Lys Ala Trp Gly Glu Val Lys Arg Gln Ile Ser Ile Ala Ala Phe
                725                 730                 735

Thr Val Gln Ala Ala Ala Glu Thr Leu Ser Glu Val Ala
            740                 745

<210> SEQ ID NO 67
<211> LENGTH: 1014
<212> TYPE: DNA
<213> ORGANISM: Artificial Sequence
<220> FEATURE:
<223> OTHER INFORMATION: Synthetic Consensus STEAP nucleic acid sequence

<400> SEQUENCE: 67
gagagccgca aggacatcac aaatcaggaa gagctgtgga agatgaaacc acggagaaac      60
ctggaggaag acgattacct gcacaaggac accggcgaaa caagtatgct gaaaagacca     120
gtgctgctgc acctgcatca gactgctcat gcagacgagt ttgattgccc ctctgaactg     180
cagcacaccc aggagctgtt cccacagtgg catctgccca tcaagattgc cgctatcatt     240
gcttcactga catttctgta tactctgctg agagaagtga tccaccctct ggccaccagc     300
catcagcagt acttctataa gatccctatt ctggtcatca acaaggtcct gccaatggtg     360
agcatcacac tgctggccct ggtctacctg cctggcgtga tcgcagccat tgtccagctg     420
cacaacggaa caaagtacaa gaagttccca cattggctgg ataagtggat gctgactagg     480
aaacagttcg gctgctgtc cttctttttc gccgtgctgc acgctatcta cagcctgtcc     540
tatcccatga gcgctctta ccgatataag ctgctgaact gggcttacca gcaggtgcag     600
cagaacaagg aggacgcatg gattgaacac gatgtgtggc ggatggaaat ctatgtgtct     660
ctgggcattg tcgggctggc catcctggct ctgctggcag tgaccagtat cccttctgtc     720
agtgactcac tgacatggcg cgagtttcac tacattcaga gcaagctggg aatcgtgtcc     780
ctgctgctgg gcaccatcca tgcactgatt tttgcctgga ataagtggat cgatatcaag     840
cagttcgtgt ggtatactcc ccctaccttt atgattgccg tcttcctgcc catcgtggtc     900
ctgatttta agtccatcct gttcctgcct tgtctgcgaa agaaaatcct gaaaatccga     960
catgggtggg aagacgtgac aaaaatcaat aagaccgaaa tctcaagcca gctg           1014

<210> SEQ ID NO 68
```

<211> LENGTH: 338
<212> TYPE: PRT
<213> ORGANISM: Artificial Sequence
<220> FEATURE:
<223> OTHER INFORMATION: Synthetic Consensus STEAP amino acid sequence

<400> SEQUENCE: 68

Glu Ser Arg Lys Asp Ile Thr Asn Gln Glu Leu Trp Lys Met Lys
1               5                   10                  15

Pro Arg Arg Asn Leu Glu Glu Asp Asp Tyr Leu His Lys Asp Thr Gly
                20                  25                  30

Glu Thr Ser Met Leu Lys Arg Pro Val Leu Leu His Leu His Gln Thr
            35                  40                  45

Ala His Ala Asp Glu Phe Asp Cys Pro Ser Glu Leu Gln His Thr Gln
        50                  55                  60

Glu Leu Phe Pro Gln Trp His Leu Pro Ile Lys Ile Ala Ala Ile Ile
65                  70                  75                  80

Ala Ser Leu Thr Phe Leu Tyr Thr Leu Leu Arg Glu Val Ile His Pro
                85                  90                  95

Leu Ala Thr Ser His Gln Gln Tyr Phe Tyr Lys Ile Pro Ile Leu Val
            100                 105                 110

Ile Asn Lys Val Leu Pro Met Val Ser Ile Thr Leu Leu Ala Leu Val
        115                 120                 125

Tyr Leu Pro Gly Val Ile Ala Ala Ile Val Gln Leu His Asn Gly Thr
130                 135                 140

Lys Tyr Lys Lys Phe Pro His Trp Leu Asp Lys Trp Met Leu Thr Arg
145                 150                 155                 160

Lys Gln Phe Gly Leu Leu Ser Phe Phe Phe Ala Val Leu His Ala Ile
                165                 170                 175

Tyr Ser Leu Ser Tyr Pro Met Arg Arg Ser Tyr Arg Tyr Lys Leu Leu
            180                 185                 190

Asn Trp Ala Tyr Gln Gln Val Gln Gln Asn Lys Glu Asp Ala Trp Ile
        195                 200                 205

Glu His Asp Val Trp Arg Met Glu Ile Tyr Val Ser Leu Gly Ile Val
210                 215                 220

Gly Leu Ala Ile Leu Ala Leu Leu Ala Val Thr Ser Ile Pro Ser Val
225                 230                 235                 240

Ser Asp Ser Leu Thr Trp Arg Glu Phe His Tyr Ile Gln Ser Lys Leu
                245                 250                 255

Gly Ile Val Ser Leu Leu Leu Gly Thr Ile His Ala Leu Ile Phe Ala
            260                 265                 270

Trp Asn Lys Trp Ile Asp Ile Lys Gln Phe Val Trp Tyr Thr Pro Pro
        275                 280                 285

Thr Phe Met Ile Ala Val Phe Leu Pro Ile Val Val Leu Ile Phe Lys
        290                 295                 300

Ser Ile Leu Phe Leu Pro Cys Leu Arg Lys Lys Ile Leu Lys Ile Arg
305                 310                 315                 320

His Gly Trp Glu Asp Val Thr Lys Ile Asn Lys Thr Glu Ile Ser Ser
                325                 330                 335

Gln Leu

<210> SEQ ID NO 69
<211> LENGTH: 390
<212> TYPE: DNA
<213> ORGANISM: Artificial Sequence
<220> FEATURE:

```
<223> OTHER INFORMATION: Synthetic Consensus PSCA nucleic acid sequence

<400> SEQUENCE: 69
gactggacat ggattctgtt tctggtcgcc gccgcaaccc gcgtgcattc tgctggcctg      60
gcactgcagc ctggaaccgc cctgctgtgc tactcttgta aggcccaggt gagtaacgag     120
gactgcctgc aggtcgaaaa ttgtactcag ctgggagagc agtgctggac cgcacggatc     180
agagcagtgg gactgctgac agtcattagc aaagggtgct ccctgaactg tgtggacgat     240
agccaggatt actatgtcgg aaagaaaaac atcacctgct gtgacacaga tctgtgtaat     300
gcttctggcg cccacgctct gcagcccgca gccgctattc tggctctgct gcccgctctg     360
ggactgctgc tgtggggacc cggacagctg                                      390

<210> SEQ ID NO 70
<211> LENGTH: 130
<212> TYPE: PRT
<213> ORGANISM: Artificial Sequence
<220> FEATURE:
<223> OTHER INFORMATION: Synthetic Consensus PSCA amino acid sequence

<400> SEQUENCE: 70

Asp Trp Thr Trp Ile Leu Phe Leu Val Ala Ala Ala Thr Arg Val His
1               5                   10                  15

Ser Ala Gly Leu Ala Leu Gln Pro Gly Thr Ala Leu Leu Cys Tyr Ser
            20                  25                  30

Cys Lys Ala Gln Val Ser Asn Glu Asp Cys Leu Gln Val Glu Asn Cys
        35                  40                  45

Thr Gln Leu Gly Glu Gln Cys Trp Thr Ala Arg Ile Arg Ala Val Gly
    50                  55                  60

Leu Leu Thr Val Ile Ser Lys Gly Cys Ser Leu Asn Cys Val Asp Asp
65                  70                  75                  80

Ser Gln Asp Tyr Tyr Val Gly Lys Lys Asn Ile Thr Cys Cys Asp Thr
                85                  90                  95

Asp Leu Cys Asn Ala Ser Gly Ala His Ala Leu Gln Pro Ala Ala Ala
            100                 105                 110

Ile Leu Ala Leu Leu Pro Ala Leu Gly Leu Leu Leu Trp Gly Pro Gly
        115                 120                 125

Gln Leu
    130
```